(12) United States Patent  
Kawano et al.

(10) Patent No.: US 8,084,898 B2
(45) Date of Patent: Dec. 27, 2011

(54) MAGNETIC ACTUATOR, MAGNETIC ACTUATOR OPERATING METHOD, AND CAPSULE ENDOSCOPE USING THE SAME

(75) Inventors: Hironao Kawano, Machida (JP); Miho Katayama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/547,083

(22) Filed: Aug. 25, 2009

(65) Prior Publication Data
US 2010/0001592 A1    Jan. 7, 2010

Related U.S. Application Data

(63) Continuation of application No. PCT/JP2008/053256, filed on Feb. 26, 2008.

(30) Foreign Application Priority Data

Feb. 26, 2007  (JP) .................................. 2007-046013
Jul. 31, 2007  (JP) .................................. 2007-199999

(51) Int. Cl.
*H02K 7/06*    (2006.01)
(52) U.S. Cl. .................................. 310/12.14; 310/152
(58) Field of Classification Search ............... 310/12.14, 310/152, 156.01, 90.5, 112–113; 600/101, 600/106
See application file for complete search history.

(56) References Cited

U.S. PATENT DOCUMENTS

| | | | | |
|---|---|---|---|---|
| 6,084,326 A | * | 7/2000 | Nagai et al. | 310/80 |
| 6,232,685 B1 | * | 5/2001 | Swetish et al. | 310/71 |
| 6,420,810 B1 | * | 7/2002 | Jeong | 310/90.5 |
| 6,771,000 B2 | * | 8/2004 | Kim et al. | 310/209 |
| 6,975,055 B2 | * | 12/2005 | Joong et al. | 310/156.01 |
| 7,578,788 B2 | * | 8/2009 | Yokoi et al. | 600/160 |
| 2005/0200207 A1 | | 9/2005 | Hasegawa et al. | |
| 2009/0281387 A1 | * | 11/2009 | Takizawa et al. | 600/117 |

FOREIGN PATENT DOCUMENTS

| | | |
|---|---|---|
| JP | 2002-119035 | 4/2002 |
| JP | 2002-270423 | 9/2002 |
| JP | 2003-325438 | 11/2003 |
| JP | 2004-120818 | 4/2004 |
| JP | 2004-194499 | 7/2004 |
| JP | 2006-305695 | 11/2006 |

* cited by examiner

*Primary Examiner* — Dang D Le
(74) *Attorney, Agent, or Firm* — Scully, Scott, Murphy & Presser, P.C.

(57) ABSTRACT

A magnetic actuator includes a housing; a first permanent magnet and a second permanent magnet placed in the housing and being relatively rotatable in a plane including a magnetization direction; a magnetic-field generating unit outside of the housing, the magnetic-field generating unit generating a magnetic field that relatively rotates the first permanent magnet and/or the second permanent magnet in a direction such that the first permanent magnet and the second permanent magnet generate a repulsive force against each other; and a first guiding portion provided in the housing to regulate a direction in which the first permanent magnet and the second permanent magnet relatively move by the generated repulsive force.

12 Claims, 75 Drawing Sheets

MAGNETIC ACTUATOR 21

(1)　　　　(2)　　　　(3)

(1)                         (2)

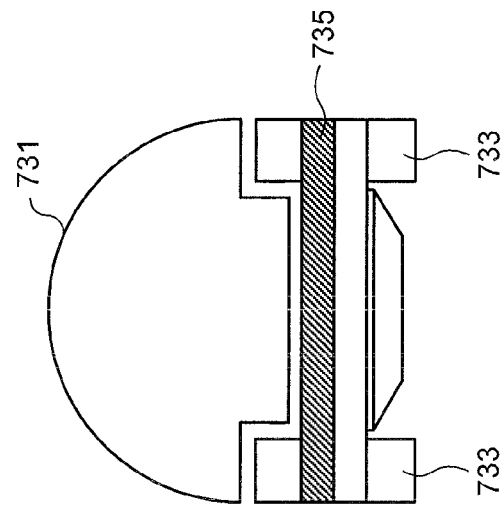
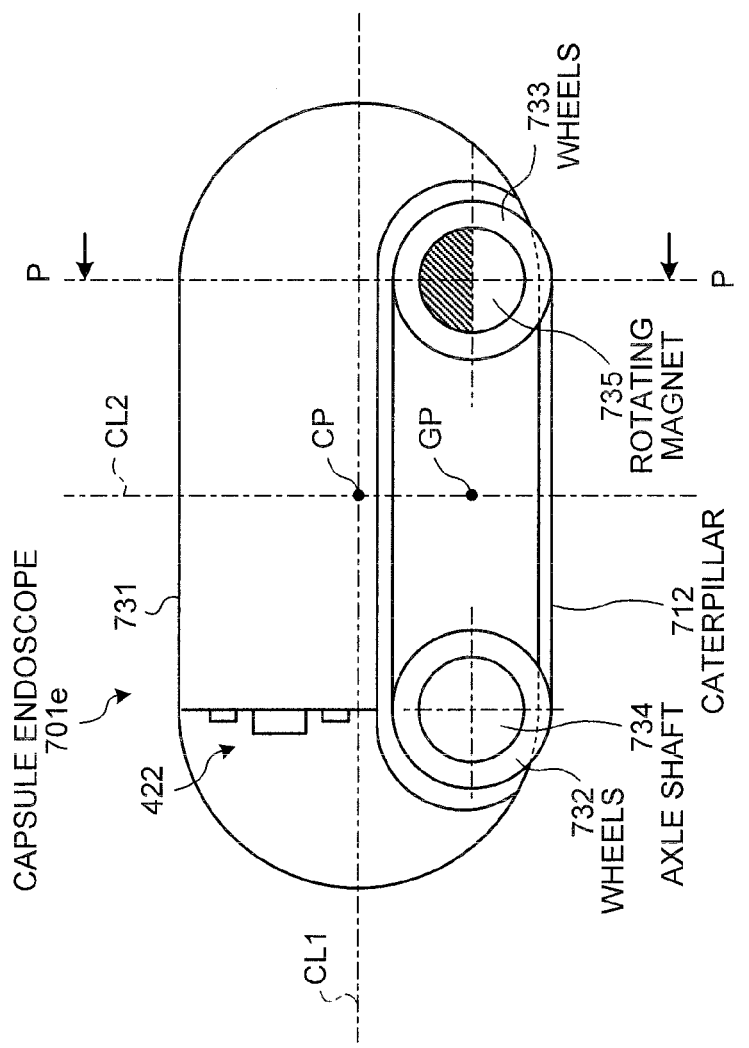

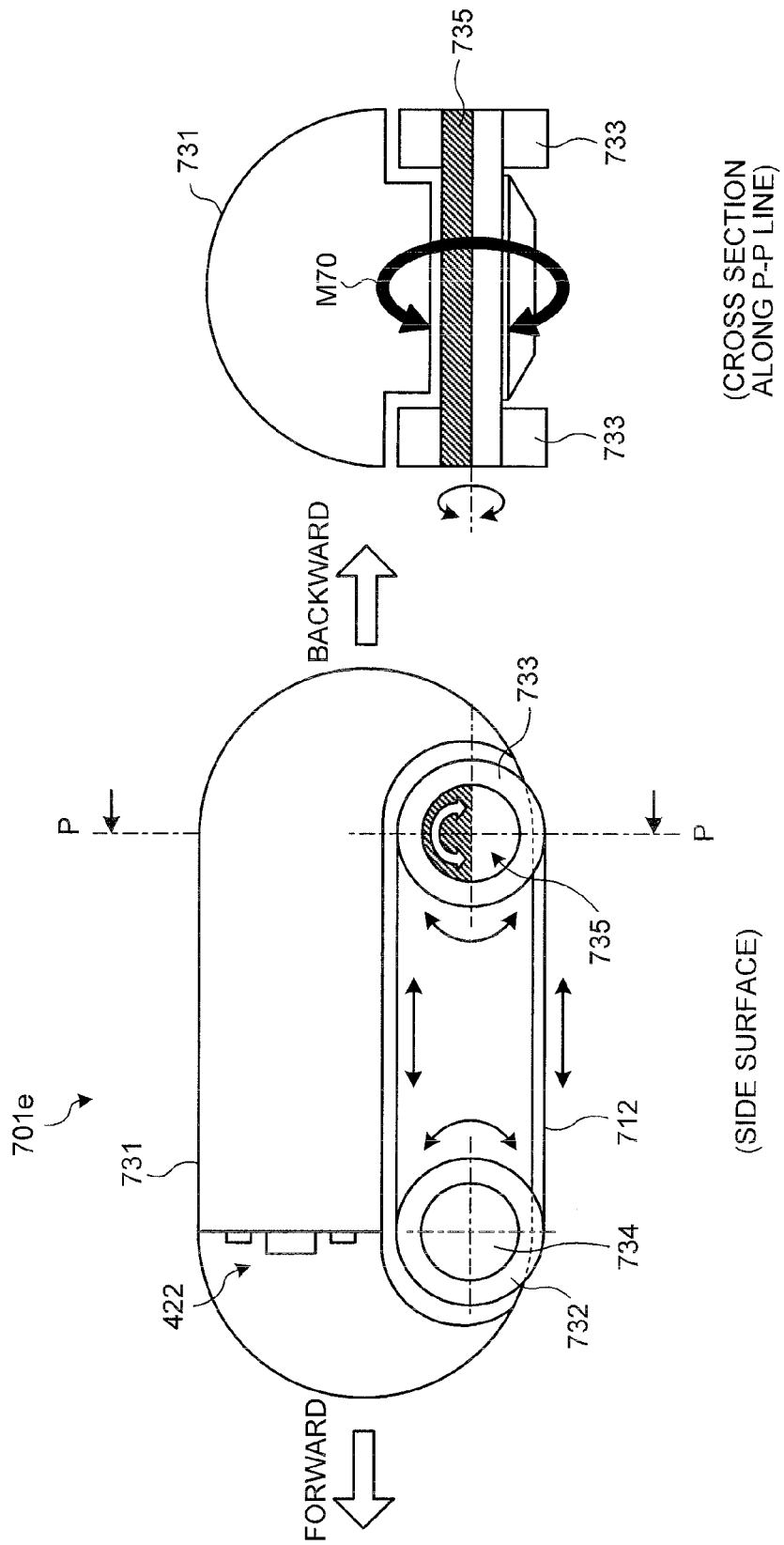

(CROSS SECTION ALONG Q-Q LINE)

(SIDE SURFACE)

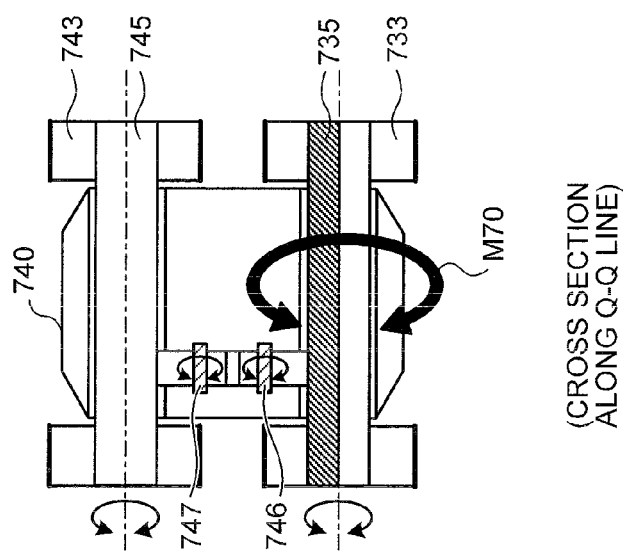
FIG. 94B (CROSS SECTION ALONG Q-Q LINE)
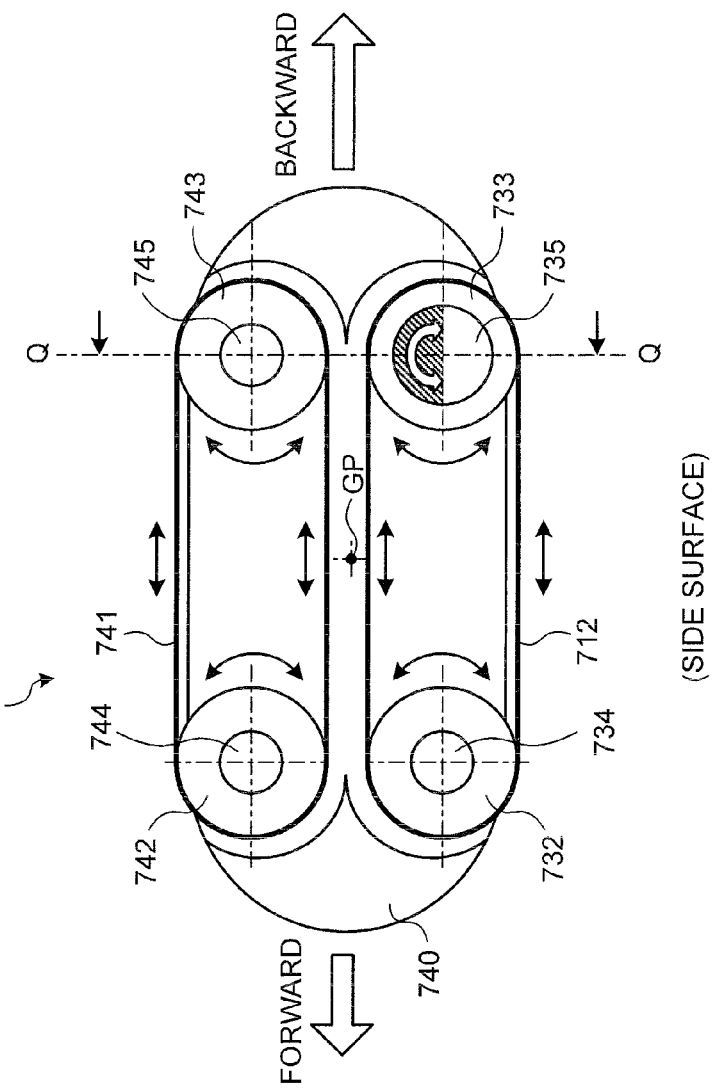
FIG. 94A (SIDE SURFACE)

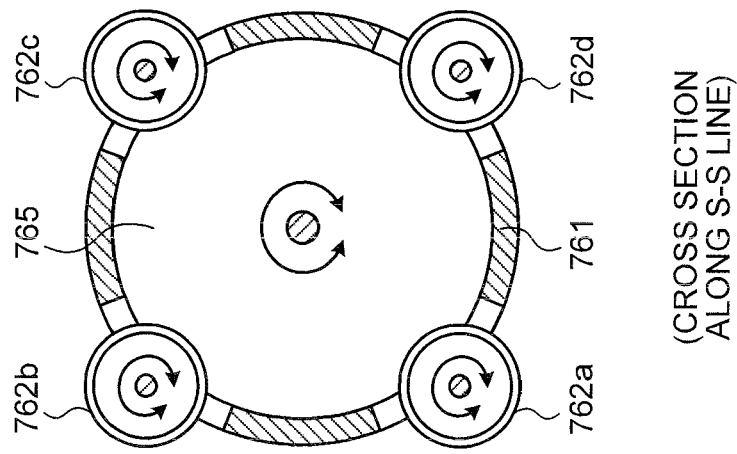
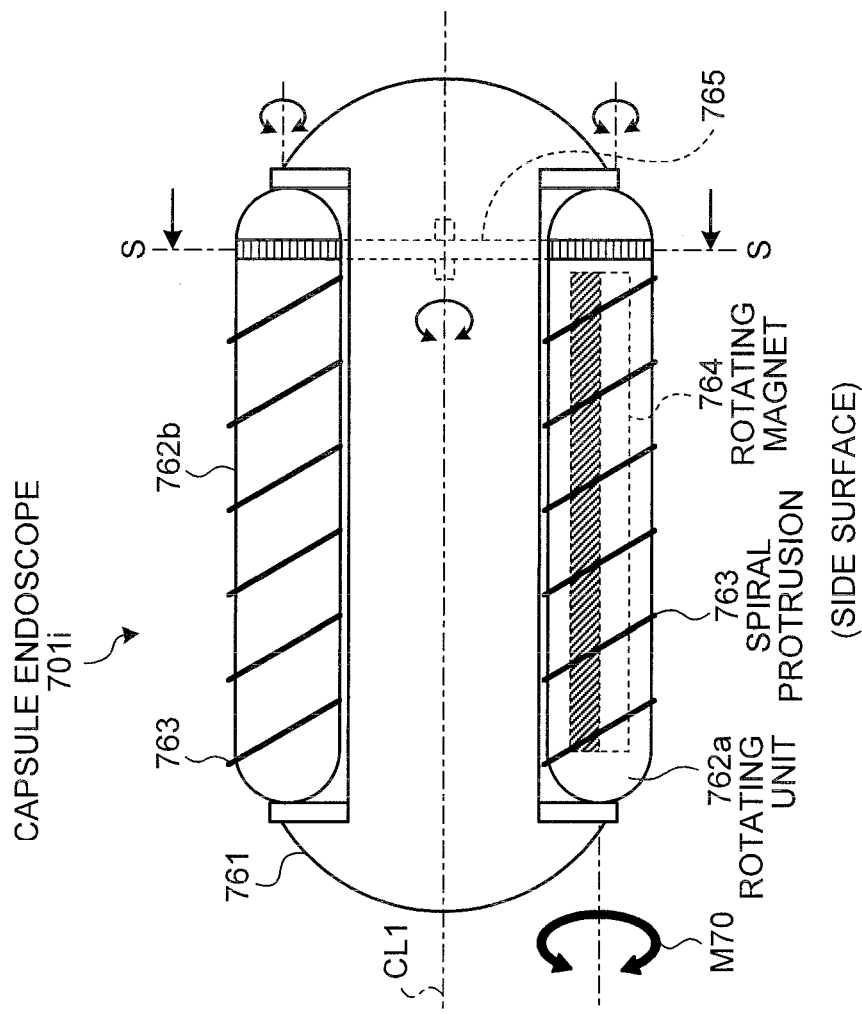

MAGNETIC ACTUATOR, MAGNETIC ACTUATOR OPERATING METHOD, AND CAPSULE ENDOSCOPE USING THE SAME

CROSS-REFERENCE TO RELATED APPLICATIONS

This application is a continuation of PCT international application Ser. No. PCT/JP2008/053256 filed on Feb. 26, 2008 which designates the United States, incorporated herein by reference, and which claims the benefit of priority from Japanese Patent Applications No. 2007-046013, filed on Feb. 26, 2007, and No. 2007-199999, filed on Jul. 31, 2007, incorporated herein by reference.

BACKGROUND OF THE INVENTION

1. Field of the Invention

The present invention relates to magnetic actuators driven by using magnetic force, magnetic actuator operating methods, and capsule endoscopes using the same.

2. Description of the Related Art

Conventionally, an actuator has been proposed which magnetizes, for example, a solenoid coil to move a magnet or ferromagnet in an axial direction of the solenoid coil (for example, refer to Japanese Patent Application Laid-open No. 2002-270423). Also, as an actuator for use in a capsule medical device, an actuator has been proposed which moves in an axial direction with a rotating magnetic field being applied by a combination of a rotatable magnet and a screw mechanism (for example, refer to Japanese Patent Application Laid-open No. 2003-325438).

SUMMARY OF THE INVENTION

A magnetic actuator according to an aspect of the present invention includes a housing; a first permanent magnet and a second permanent magnet placed in the housing and being relatively rotatable in a plane including a magnetization direction; a magnetic-field generating unit outside of the housing, the magnetic-field generating unit generating a magnetic field that relatively rotates the first permanent magnet and/or the second permanent magnet in a direction such that the first permanent magnet and the second permanent magnet generate a repulsive force against each other; and a first guiding portion provided in the housing to regulate a direction in which the first permanent magnet and the second permanent magnet relatively move by the generated repulsive force.

A capsule endoscope according to another aspect of the present invention includes a capsule-shaped casing insertable into a subject; a permanent magnet rotatable independently from the casing; and a propulsion-force converting unit that converts a rotary force of the permanent magnet rotating by following an external rotating magnetic field to a propulsion force.

A method according to still another aspect of the present invention of operating a magnetic actuator having a first permanent magnet and a second permanent magnet in a housing which contribute to operations, includes changing a magnetic field to be applied to the first permanent magnet and the second permanent magnet; relatively rotating the first permanent magnet and the second permanent magnet; and changing a relative distance between the first permanent magnet and the second permanent magnet.

A method according to still another aspect of the present invention of operating a magnetic actuator having a first permanent magnet, a second permanent magnet and a third permanent magnet in a housing which contribute to operations, includes changing a magnetic field to be applied to the first permanent magnet and the second permanent magnet; relatively rotating the first permanent magnet and the second permanent magnet; changing a relative distance between the first permanent magnet and the second permanent magnet; changing a magnetic field to be applied to the second permanent magnet and the third permanent magnet; relatively rotating the second permanent magnet and the third permanent magnet; and changing a relative distance between the second permanent magnet and the third permanent magnet.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 90A and 90B show schematic diagrams depicting a configuration example of a capsule endoscope according to a fifth modification example in the seventh embodiment;

FIGS. 91A and 91B show schematic diagrams depicting a state in which a caterpillar mechanism of the capsule endoscope operates with an external rotating magnetic field;

FIGS. 94A and 94B show schematic diagrams depicting a state in which caterpillar mechanisms on both sides of the capsule endoscope operate with an external rotating magnetic field;

FIGS. 97A and 97B show schematic diagrams depicting a configuration example of a capsule endoscope according to a ninth modification example of the seventh embodiment.

DETAILED DESCRIPTION OF THE PREFERRED EMBODIMENTS

Figure 1:
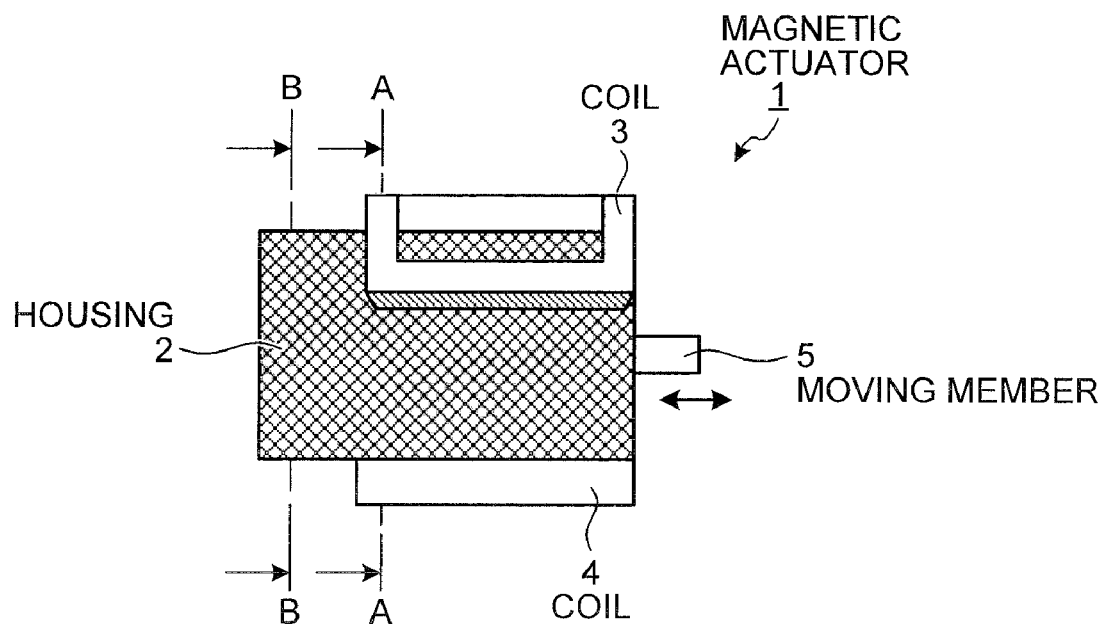
FIG. 1 shows a front view of a magnetic actuator according to a first embodiment.

Exemplary embodiments of the present invention will be described below with reference to the drawings. Note that these embodiments are not meant to restrict the present invention. Also, in the drawings depicted, the same portions are denoted with the same reference numerals. Furthermore, the drawings are merely schematic, and the relation between the thickness and the width of each portion, and the ratio of each portion, and others are different from those in actual ones. Still further, in the drawings, the relation and ratio among dimensions are partially different.

First Embodiment

Figure 2:
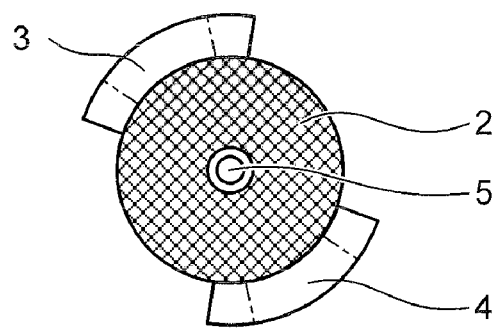
FIG. 2 shows a right side view of the magnetic actuator depicted in FIG. 1.

Now, a first embodiment is described. FIG. 1 is a front view of the magnetic actuator according to a first embodiment, and FIG. 2 is a right side view of the magnetic actuator depicted in FIG. 1. As depicted in FIG. 1 and FIG. 2, in a magnetic actuator 1 according to the first embodiment, outside of a housing 2, which is an exterior component in an approximately cylindrical shape with its ends closed, a coil 3 and a coil 4 disposed opposite to the coil 3 are fixed. The coils 3, 4 are capable of generating a magnetic field. Also, as depicted in FIG. 1 and FIG. 2, the magnetic actuator 1 has a moving member 5 movable in an axial direction of the housing 2. At a right end of the housing 2, a pass hole is provided so as to allow the moving member 5 to move in an axial direction. As indicated by an arrow in FIG. 1, the moving member 5 moves in and out relative to the housing 2. With this movement of the moving member 5 in an axial direction, driving of a predetermined operation in a driven device is controlled.

Figure 3:
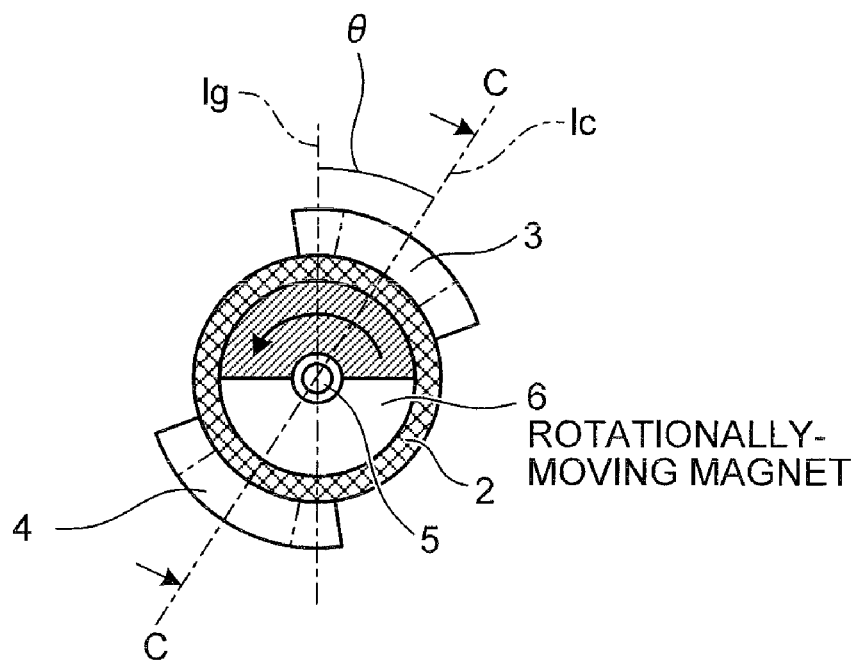
FIG. 3 shows a sectional view of the magnetic actuator depicted in FIG. 1 cut along an A-A line 1 in a radial direction depicted in FIG. 1.
Figure 4:
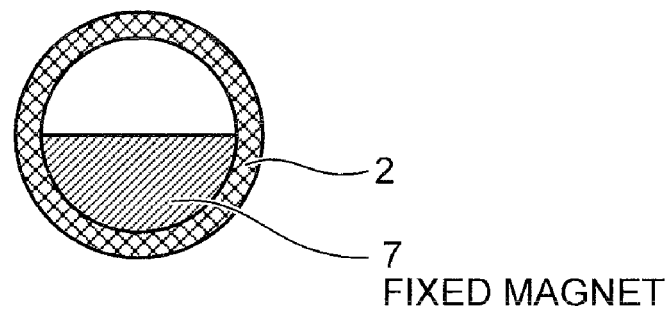
FIG. 4 shows a sectional view of the magnetic actuator depicted in FIG. 1 cut along a B-B line in a radial direction depicted in FIG. 1.
Figure 5:
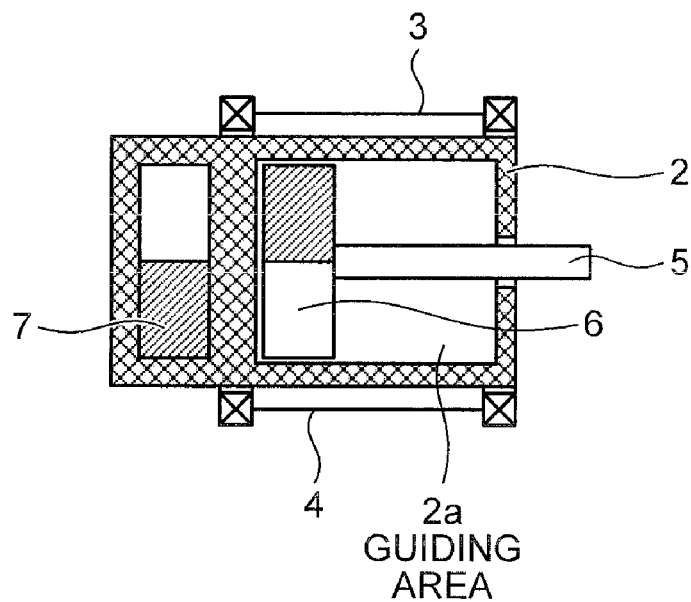
FIG. 5 shows a sectional view of the magnetic actuator depicted in FIG. 1 cut along a C-C line in an axial direction depicted in FIG. 3.

Next, the inside of the magnetic actuator 1 is described. FIG. 3 is a sectional view of the magnetic actuator 1 cut along an A-A line in a radial direction depicted in FIG. 1, and FIG. 4 is a sectional view of the magnetic actuator 1 cut along a B-B line in a radial direction depicted in FIG. 1. FIG. 5 is a sectional view of the magnetic actuator 1 cut along a C-C line in an axial direction depicted in FIG. 3.

As depicted in FIG. 3 and FIG. 5, a rotationally-moving magnet 6 having a cylindrical column shape and connected to the moving member 5 is provided in the housing 2. As an inner space of the housing 2, a guiding area 2a is provided in the housing 2. The guiding area 2a has an inner diameter corresponding to a diameter size of the rotationally-moving magnet 6 and a certain length in an axial direction. The length in the axial direction of the guiding area 2a is set such that the right end of the moving member 5 does not protrude when the moving member 5 is retracted toward the inside of the magnetic actuator 1. The rotationally-moving magnet 6 is provided in the guiding area 2a. Also, as depicted in FIG. 4 and FIG. 5, a fixed magnet 7 is provided in the housing 2 in a state of being fixed to the housing 2 and facing to the rotationally-moving magnet 6 via a partition that partitions the inner space. The fixed magnet 7 is fixed such that a magnetization direction thereof is in a radial direction relative to the magnetic actuator 1. Also, the rotationally-moving magnet 6 is rotatable about a central axis of the magnetic actuator 1.

The rotationally-moving magnet 6 and the moving member 5 connected to the right end of the rotationally-moving magnet 6 are movable horizontally in FIG. 5 in the guiding area 2a along the axial direction of the housing 2. The guiding area 2a regulates the rotationally-moving magnet 6 to move by repulsion, described later, along the axial direction of the housing 2. The rotationally-moving magnet 6, as depicted in FIG. 3 and FIG. 5, is rotatable in a plane including the magnetization direction of the rotationally-moving magnet 6. The rotationally-moving magnet 6 is rotatable, as indicated by an arrow in FIG. 3, in a radial direction of the magnetic actuator 1 by a magnetic field generated in the guiding area 2a by the coils 3, 4 fixedly disposed on the housing 2 correspondingly to the position of the guiding area 2a.

Supplied with predetermined power from a connected power supply unit not shown, the coils 3, 4 provided outside of the housing 2 generate a magnetic field with a predetermined magnetic field strength in the guiding area 2a. The housing 2 is fixed to the coils 3, 4. The coils 3, 4 are disposed such that the generated magnetic-field direction has a predetermined angle relative to the magnetization direction of the fixed magnet 7, of which rotation relative to the housing 2 in the plane including the magnetization direction is restrained. That is, as indicated by a straight line lc in FIG. 3, the coils 3, 4 are placed so as to have a predetermined angle $\theta$ relative to a straight line lg indicative of the magnetization direction of the fixed magnet 7.

Figure 6:
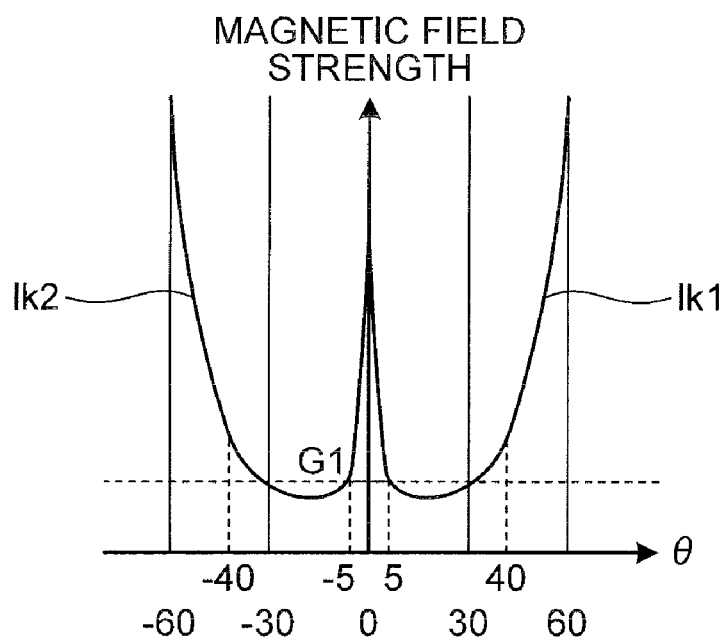
FIG. 6 shows a diagram explaining a magnetic field strength allowing a rotationally-moving magnet depicted in FIG. 1 to rotatably operate.

Now, magnetic field strengths of the coils 3, 4 disposed at the angle $\theta$ ranging from −60 degrees to 60 degrees are indicated by curves lk1, lk2 of FIG. 6, which allow the rotationally-moving magnet 6 to perform a rotating operation. As indicated by the curves lk1, lk2 of FIG. 6, when the absolute value of the angle $\theta$ exceeds 60 degrees, the magnetic field strength allowing the rotationally-moving magnet 6 to rotate significantly increases, and therefore the rotationally-moving magnet 6 cannot move. When the absolute value of the angle $\theta$ is greater than 0 degree and equal to or smaller than 60 degrees, the rotationally-moving magnet 6 can rotate. Therefore, for the rotationally-moving magnet 6 to rotate, the absolute value of the angle $\theta$ formed by the coils 3, 4 and the straight line lg indicative of the magnetization direction of the fixed magnet 7 is preferably greater than 0 degree and equal to or smaller than 60 degrees. Also, as indicated by the curves lk1, lk2 of FIG. 6, when the angle $\theta$ is equal to or greater than 5 degrees and equal to or smaller than 40 degrees, bottom portions of the curves lk1, lk2 each in a concave shape are included, and therefore the rotationally-moving magnet 6 is rotatable with a magnetic filed strength smaller compared with other angles. Therefore, it is further preferable that the angle $\theta$ formed by the coils 3, 4 and the straight line lg indicative of the magnetization direction of the fixed magnet 7 is equal to or greater than 5 degrees and equal to or smaller than 40 degrees. Furthermore, with the angle $\theta$ formed by the coils 3, 4 and the straight line lg indicative of the magnetization direction being equal to or greater than 5 degrees and equal to or smaller than 30 degrees, the rotationally-moving magnet 6 can be stably rotated with a relatively small magnetic field strength, on the order of "G1", of the magnetic field applied by the coils 3, 4.

Figure 7:
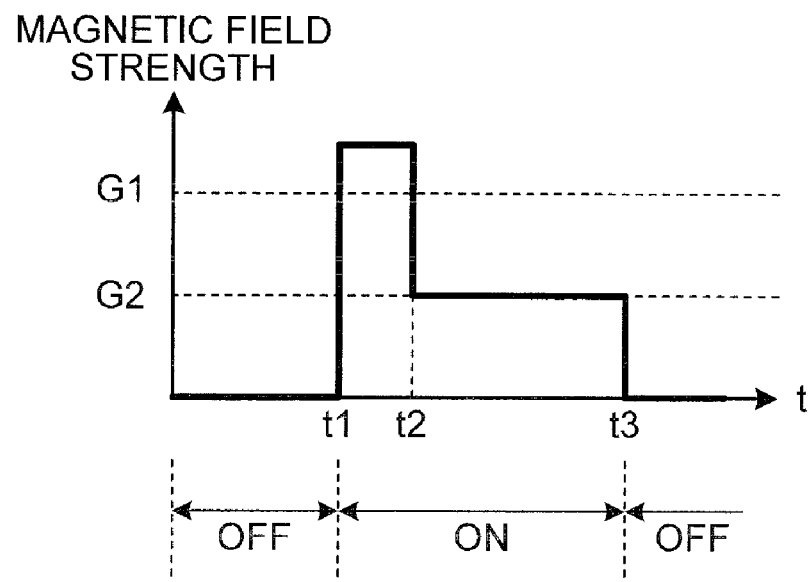
FIG. 7 shows a diagram depicting time dependency of the magnetic field strength applied by coils depicted in FIG. 1.
Figure 8:
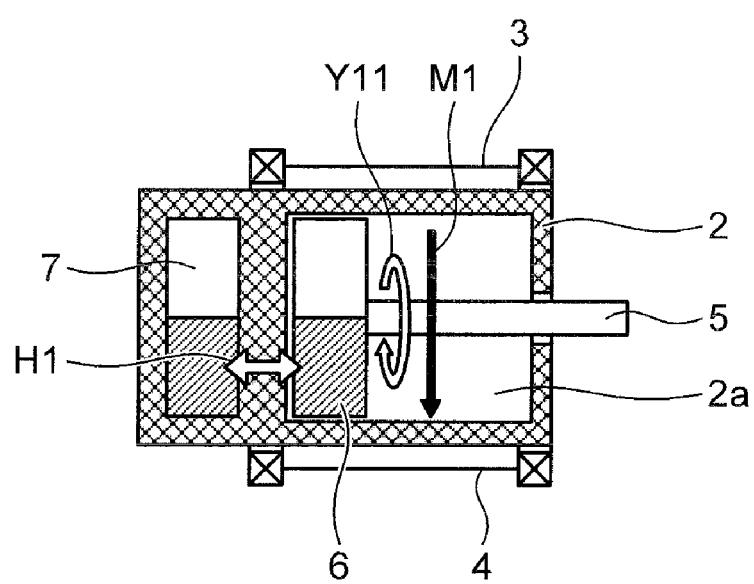
FIG. 8 shows a sectional view of the magnetic actuator depicted in FIG. 1 cut along an axial direction.
Figure 9:
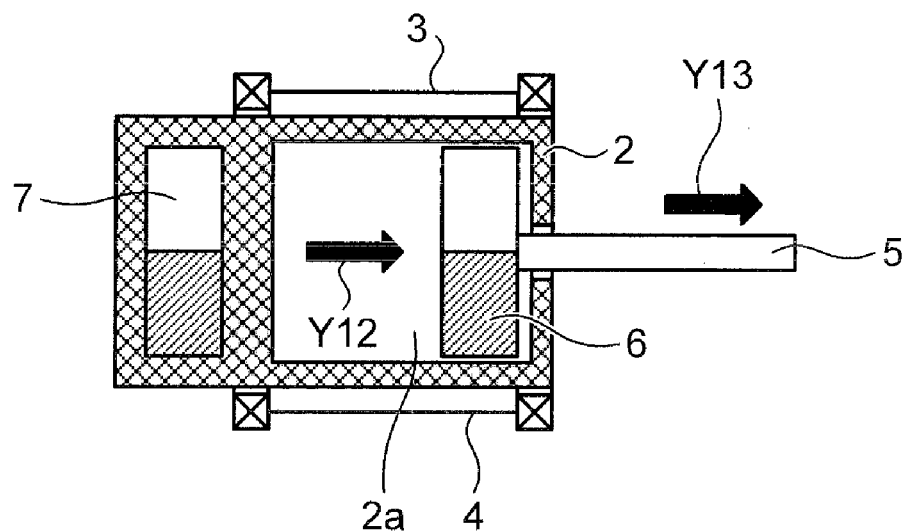
FIG. 9 shows a sectional view of the magnetic actuator depicted in FIG. 1 cut along an axial direction.

Next, with reference to FIG. 7 to FIG. 9, the operation of the magnetic actuator 1 is described. FIG. 7 is a diagram depicting time dependency of the magnetic field strength applied by the coils 3, 4, FIG. 8 is a sectional view of the magnetic actuator 1 cut along an axial direction at a time t1 depicted in FIG. 7, and FIG. 9 is a sectional view of the magnetic actuator 1 cut along an axial direction at a time t2 depicted in FIG. 7. Note that the angle $\theta$ in the magnetic actuator 1 is any from approximately 5 degrees to approximately 30 degrees.

First, as depicted in FIG. 7 and FIG. 8, at the time t1, to the magnetic actuator 1 in an OFF state depicted in FIG. 5, a magnetic field M1 equal to or greater than the magnetic strength G1 at which the rotationally-moving magnet 6 is rotatable is applied. The magnetic field M1 is oriented in a radial direction in the guiding area 2a. The direction of the magnetic field M1 is, as depicted in FIG. 8, a downward direction in FIG. 8. For this reason, with the magnetic field M1, as indicated by an arrow Y11, the rotationally-moving magnet 6 rotates a half turn in the downward direction in FIG. 8 according to the magnetic-field orientation of the magnetic field M1. In this case, since the orientation of the magnetic field of the rotationally-moving magnet 6 and the orientation of the magnetic field of the fixed magnet 7 are matched, a repulsive force H1 occurs between the rotationally-moving magnet 6 and the fixed magnet 7. In other words, the coils 3, 4 generate a magnetic field that causes the rotationally-moving magnet 6 to relatively rotate in a direction so that the rotationally-moving magnet 6 and the fixed magnet 7 generate a repulsive force.

As indicated by an arrow Y12 in FIG. 9, the rotationally-moving magnet 6 moves, with the repulsive force H1 occurring between the fixed magnet 7 and itself, in a right direction in FIG. 9 along the guiding area 2a. According to the movement of the rotationally-moving magnet 6 in the right direction, as indicated by an arrow Y13 in FIG. 9, the moving member 5 connected to the rotationally-moving magnet 6 protrudes from the right-side surface of the magnetic actuator 1 in the right direction in FIG. 9. As a result of this, the magnetic actuator 1 is turned to an ON state.

Then, to keep the magnetic actuator 1 in the ON state depicted in FIG. 9, at the time t2 indicated in FIG. 7, the position of the rotationally-moving magnet 6 is kept at the right end of the guiding area 2a, and the state is kept in which the orientation of the magnetic field of the rotationally-moving magnet 6 is matched with the orientation of the magnetic field generated by the coils 3, 4, that is, the rotationally-moving magnet 6 is prevented from being rotated again. Here, since the rotationally-moving magnet 6 is away from the fixed magnet 7 when the magnetic actuator 1 is in a driving state, the orientation of the magnetic field of the rotationally-moving magnet 6 can be kept the same as that of the magnetic field M1 with a magnetic field strength G2 smaller than the magnetic field strength G1. Therefore, to keep the magnetic actuator 1 in the ON state depicted in FIG. 9, at the time t2 after the ON state depicted in FIG. 7, it is sufficient to apply a magnetic field in the same direction as that of the magnetic field M1 with the magnetic field strength G2, at which the rotationally-moving magnet 6 does not rotate a half turn again.

To turn the magnetic actuator 1 to an OFF state, at a time t3 indicated in FIG. 7, application of the magnetic field by the coils 3, 4 is stopped. In this case, since the magnetic field that keeps the rotationally-moving magnet 6 oriented in the downward direction in FIG. 8 and FIG. 9 disappears, the rotationally-moving magnet 6 rotates in an upward direction in FIG. 8 and FIG. 9 and is retracted toward the inside of the housing 2 by an attractive force occurring between the fixed magnet 7 and itself. As a result, the moving member 5 connected to the rotationally-moving magnet 6 is also retracted toward the inside of the housing 2, and therefore the magnetic actuator 1 is turned to an OFF state depicted in FIG. 5.

As described above, the magnetic actuator 1 according to the first embodiment uses a repulsive force occurring between the rotationally-moving magnet 6 and the fixed magnet 7 to protrude the moving member 5 toward the outside of the magnetic actuator 1 to drive the magnetic actuator 1, thereby making a quick operation possible compared with the magnetic actuator according to the conventional technology. Also, according to the first embodiment, once the state becomes an ON state, the ON state can be kept even when the magnetic field strength is decreased, and therefore a magnetic actuator with high energy efficiency can be achieved.

In the first embodiment, a magnetic sensor, such as a pressure sensor, contact sensor, passage sensor, rotation sensor, or coil, may be further provided to detect the operation of the magnetic actuator 1.

First Modification Example

Figure 10:
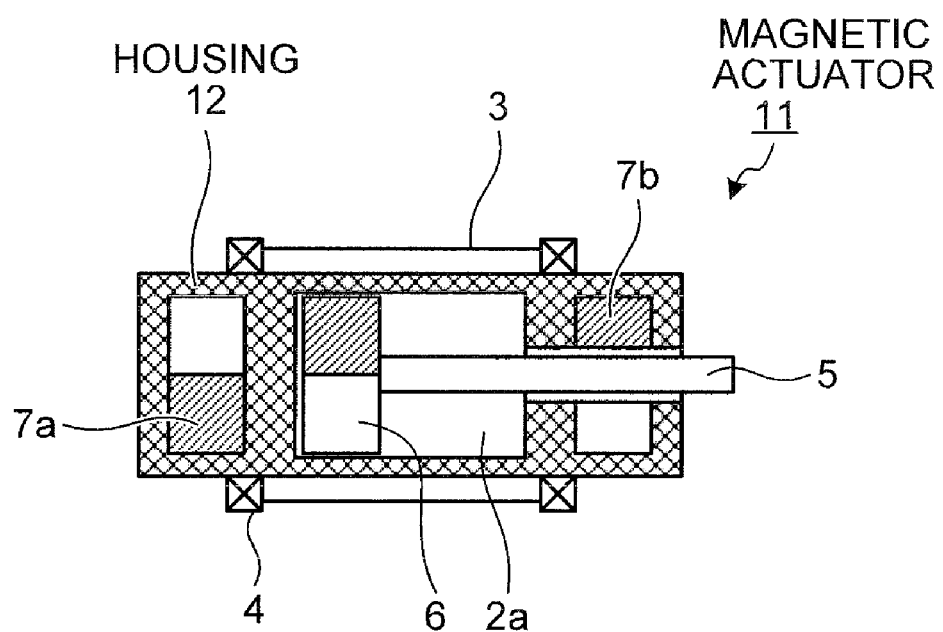
FIG. 10 shows a sectional view of a magnetic actuator according to a first modification example in the first embodiment cut along an axial direction.

Next, a first modification example in the first embodiment is described. FIG. 10 is a sectional view of a magnetic actuator according to the first modification example cut along an axial direction. As depicted in FIG. 10, a magnetic actuator 11 according to the first modification example has, in contrast to the magnetic actuator 1, two fixed magnets: a fixed magnet 7a disposed on a left side of the rotationally-moving magnet 6 in FIG. 10 and also a fixed magnet 7b fixedly disposed on a right side of the rotationally-moving magnet 6 placed in the guiding area 2a in FIG. 10. In other words, the guiding area 2a in which the rotationally-moving magnet 6 is disposed is placed between the fixed magnets 7a, 7b. The fixed magnet 7b and the fixed magnet 7a are fixedly disposed in the housing 12 so that their magnetization directions are differently oriented. The guiding area 2a is placed between the fixed magnet 7a and the fixed magnet 7b. The rotationally-moving magnet 6 is rotatabe relative to the housing 12 in a plane including the magnetization direction of the rotationally-moving magnet 6.

Figure 11:
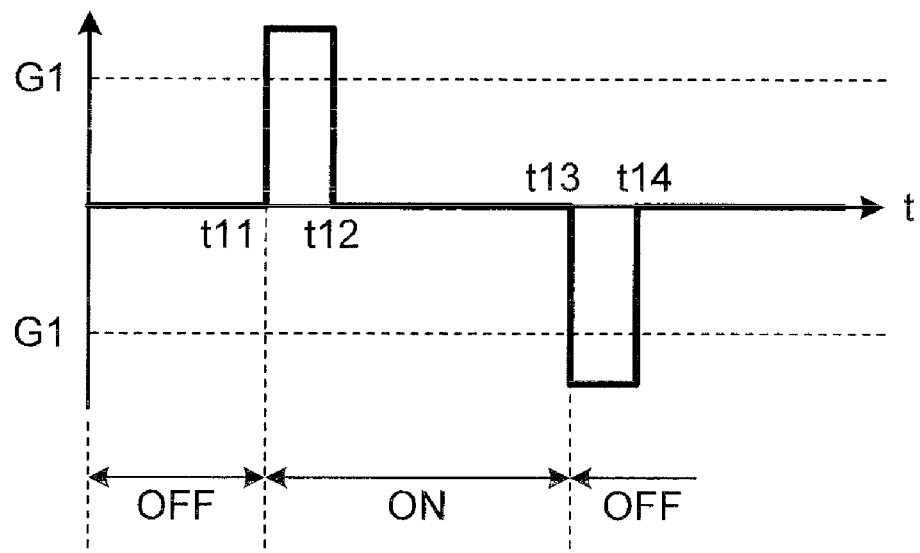
FIG. 11 shows a diagram depicting time dependency of the magnetic field strength applied by coils depicted in FIG. 10.
Figure 12:
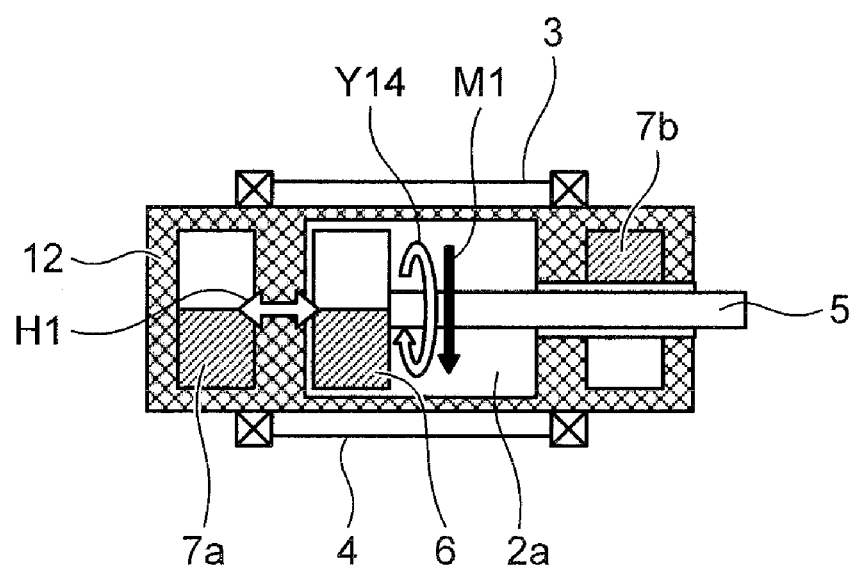
FIG. 12 shows a sectional view of the magnetic actuator depicted in FIG. 10 cut along an axial direction.
Figure 13:
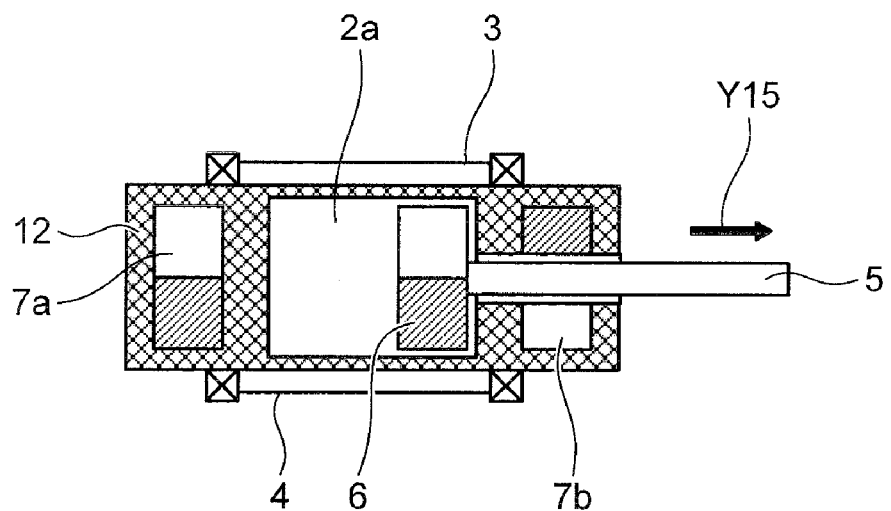
FIG. 13 shows a sectional view of the magnetic actuator depicted in FIG. 10 cut along an axial direction.
Figure 14:
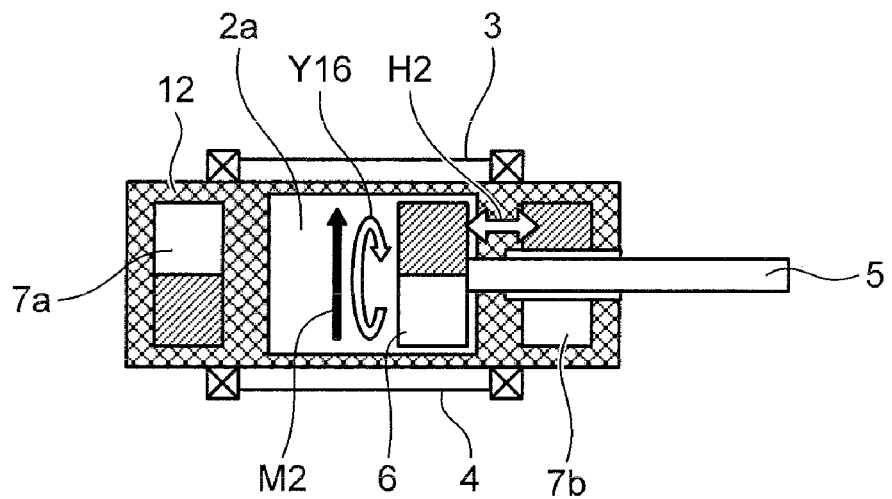
FIG. 14 shows a sectional view of the magnetic actuator depicted in FIG. 10 cut along an axial direction.
Figure 15:
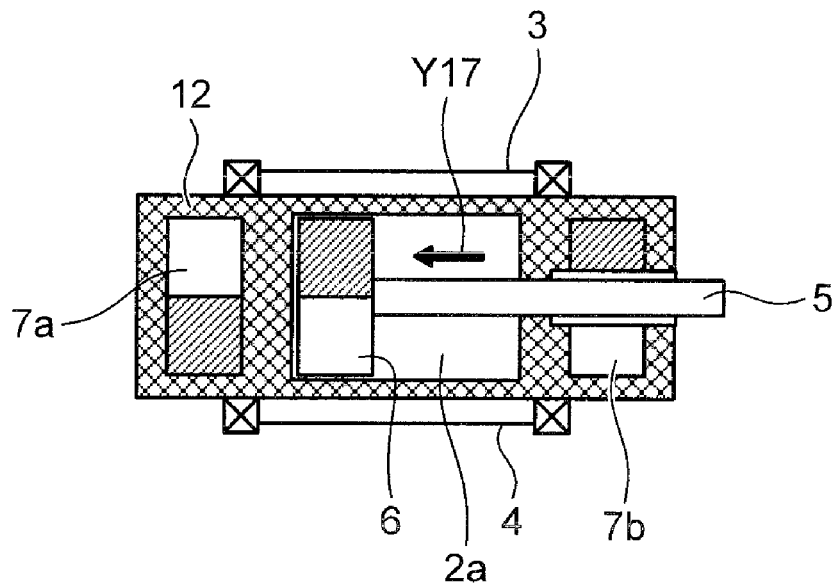
FIG. 15 shows a sectional view of the magnetic actuator depicted in FIG. 10 cut along an axial direction.

Next, with reference to FIG. 11 to FIG. 15, the operation of the magnetic actuator 11 is described. FIG. 11 is a diagram depicting time dependency of the magnetic field strength applied by the coils 3, 4. FIG. 12 is a sectional view of the magnetic actuator 11 cut along an axial direction at a time t11 depicted in FIG. 11. FIG. 13 is a sectional view of the magnetic actuator 11 cut along an axial direction at a time t12 depicted in FIG. 11. FIG. 14 is a sectional view of the magnetic actuator 11 cut along an axial direction at a time t13 depicted in FIG. 11. FIG. 15 is a sectional view of the magnetic actuator 11 cut along an axial direction at a time t14 depicted in FIG. 11. Note that the angle θ in the magnetic actuator 11 is any from approximately 5 degrees to approximately 30 degrees in the same manner as that in the magnetic actuator 1.

First, a case is described in which the magnetic actuator 11 is changed from an OFF state to an ON state. As depicted in FIG. 11 and FIG. 12, at the time t11, to the magnetic actuator 11 in an OFF state depicted in FIG. 10, the coils 3, 4 apply a magnetic field M1 oriented in a radial direction in the guiding area 2a. The magnetic field M1 has a magnetic field strength G1 that allows the rotationally-moving magnet 6 to rotate and is oriented in a downward direction in FIG. 12. Therefore, the rotationally-moving magnet 6, as indicated by an arrow Y14, rotates a half turn in the downward direction in FIG. 12 according to the magnetic-field orientation of the magnetic field M1 and. As a result, a repulsive force H1 occurs between the rotationally-moving magnet 6 and the fixed magnet 7a.

Then, as indicated by an arrow Y15 in FIG. 13, the rotationally-moving magnet 6 moves, with the repulsive force H1 occurring between the fixed magnet 7 and itself, in a right direction in FIG. 13 along the guiding area 2a to protrude the moving member 5 from the magnetic actuator 11, thereby bringing the magnetic actuator 11 into an ON state. The rotationally-moving magnet 6 moving in the right direction along the inside of the guiding area 2a is then attracted to a partition between the fixed magnet 7b and the rotationally-moving magnet 6 by an attractive force occurring between the fixed magnet 7b and the rotationally-moving magnet 6. Therefore, as depicted in FIG. 11, after the time t12 when the magnetic actuator 11 is brought into an ON state, the magnetic actuator 11 can keep the ON state even when the application of the magnetic field by the coils 3, 4 is stopped.

Next, a case is described in which the magnetic actuator 11 is changed from an ON state to an OFF state. At the time t13 in FIG. 11, as depicted in FIG. 14, a magnetic field M2 oriented in a radial direction in the guiding area 2a is applied with the magnetic field strength G1 that allows the rotationally-moving magnet 6 to rotate and is oriented in an upward direction, which is an orientation opposite to that of the magnetic field M1 applied at the time t11. Therefore, the rotationally-moving magnet 6 rotates a half turn, as indicated by an arrow Y16, in an upward direction in FIG. 14 according to the magnetic-field orientation of the magnetic field M2. As a result, a repulsive force H2 occurs between the rotationally-moving magnet 6 and the fixed magnet 7b. Then, as indicated by an arrow Y17 in FIG. 15, the rotationally-moving magnet 6 moves, with a repulsive force H2 occurring between the fixed magnet 7b and itself, in a left direction in FIG. 15 along the guiding area 2a to cause the moving member 5 to be retracted toward the inside of the housing 12, thereby bringing the magnetic actuator 11 into an OFF state. The rotationally-moving magnet 6 moving in the left direction along the inside of the guiding area 2a is then attracted to a partition between the fixed magnet 7a and the rotationally-moving magnet 6 by an attractive force occurring between the fixed magnet 7a and the rotationally-moving magnet 6. Therefore, as depicted in FIG. 11, after the time t14 when the magnetic actuator 11 is brought into an OFF state, the magnetic actuator 11 can keep the OFF state even when the application of the magnetic field by the coils 3, 4 is stopped.

According to the first modification example, by providing fixed magnets with their magnetic fields differently oriented on both sides of the rotationally-moving magnet 6, it is sufficient to generate a magnetic field only when the ON state or the OFF state is changed. With this, a magnetic actuator with further improved energy efficiency can be achieved. Furthermore, according to the first modification example, in each of the ON state and the OFF state, the rotationally-moving magnet 6 is attracted to a fixed magnet. Therefore, in either of the ON state and the OFF state, a strong keeping force in the ON state or the OFF state can be generated.

Second Modification Example

Figure 16:
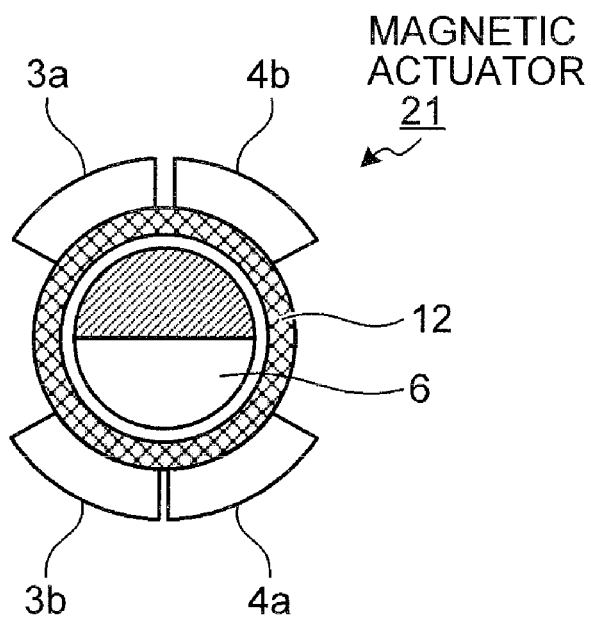
FIG. 16 shows a sectional view of a magnetic actuator according to a second modification example in the first embodiment cut along a radial direction.

Next, a second modification example in the first embodiment is described. FIG. 16 is a sectional view of a magnetic actuator according to the second modification example cut along a radial direction at a portion where coils are provided. As depicted in FIG. 16, a magnetic actuator 21 according to the second modification example has two sets of coils 3a, 3b, 4a, 4b that generate magnetic fields, in contrast to the magnetic actuator 11 having one set of coils 3, 4 that generate a magnetic field. The coil 3a and the coil 4a as one set generate a magnetic field, and the coil 3b and the coil 4b as one set generate a magnetic field in a direction opposite to that of the magnetic field generated by the coils 3a, 4a. As depicted in FIG. 16, the coils 3a, 4a are placed so as to have a predetermined angle equal to or smaller than 60 degrees relative to a straight line indicative of a magnetization direction of the fixed magnet 7, as in the magnetic actuator 11. The coils 3b, 4b are placed so as to have a predetermined angle equal to or smaller than −60 degrees relative to the straight line indicative of the magnetization direction of the fixed magnet 7.

Figure 17:
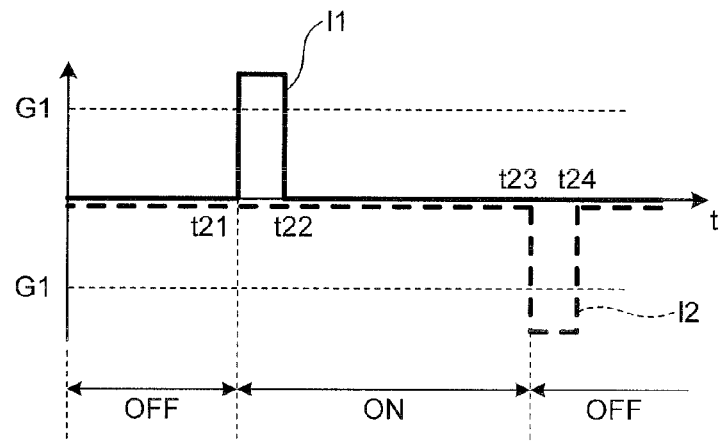
FIG. 17 shows a diagram depicting time dependency of the magnetic field strength applied by coils depicted in FIG. 16.
Figure 18:
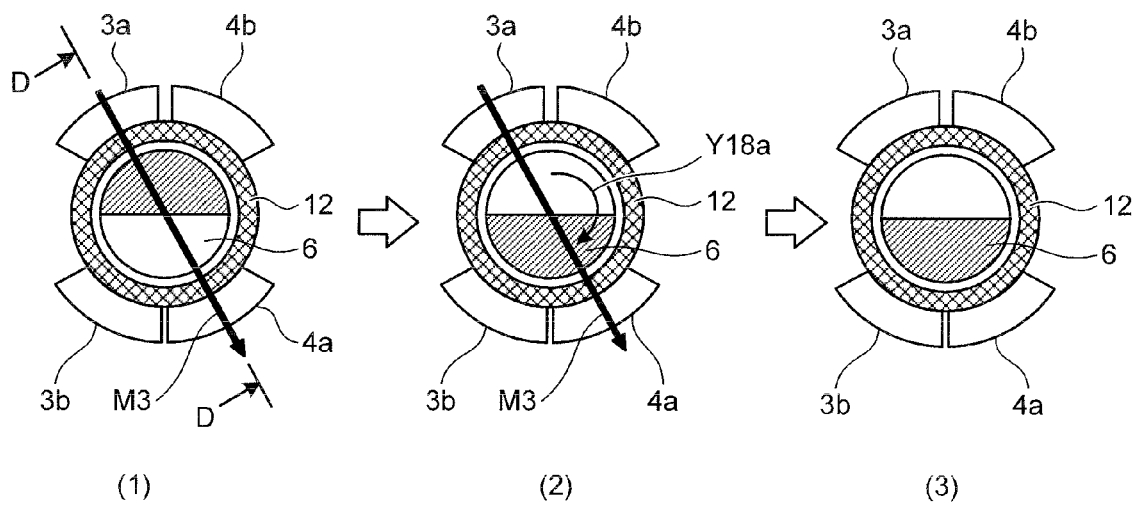
FIG. 18 shows sectional views of the magnetic actuator depicted in FIG. 16 cut along a radial direction.
Figure 19:
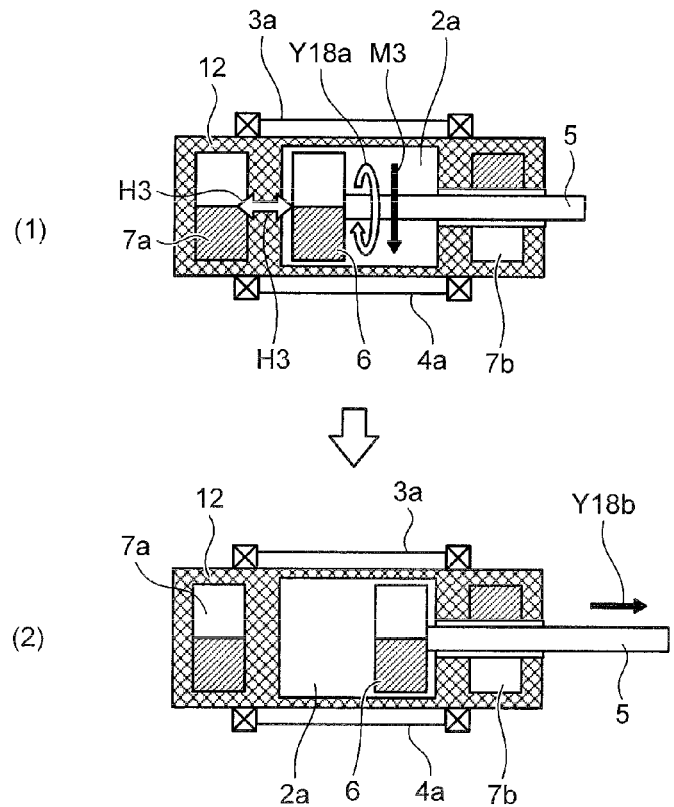
FIG. 19 shows sectional views of the magnetic actuator depicted in FIG. 16 cut along an axial direction.
Figure 20:
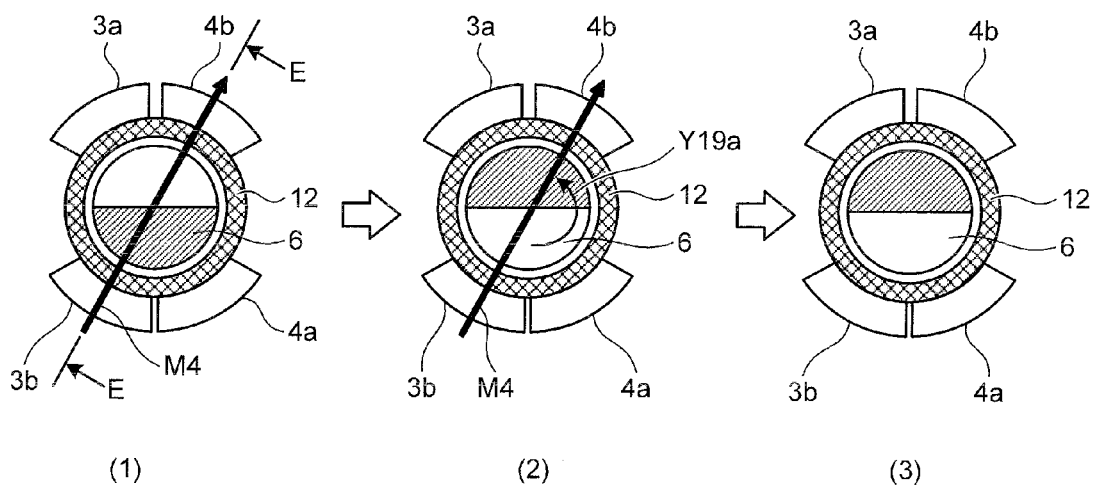
FIG. 20 shows sectional views of the magnetic actuator depicted in FIG. 16 cut along a radial direction.
Figure 21:
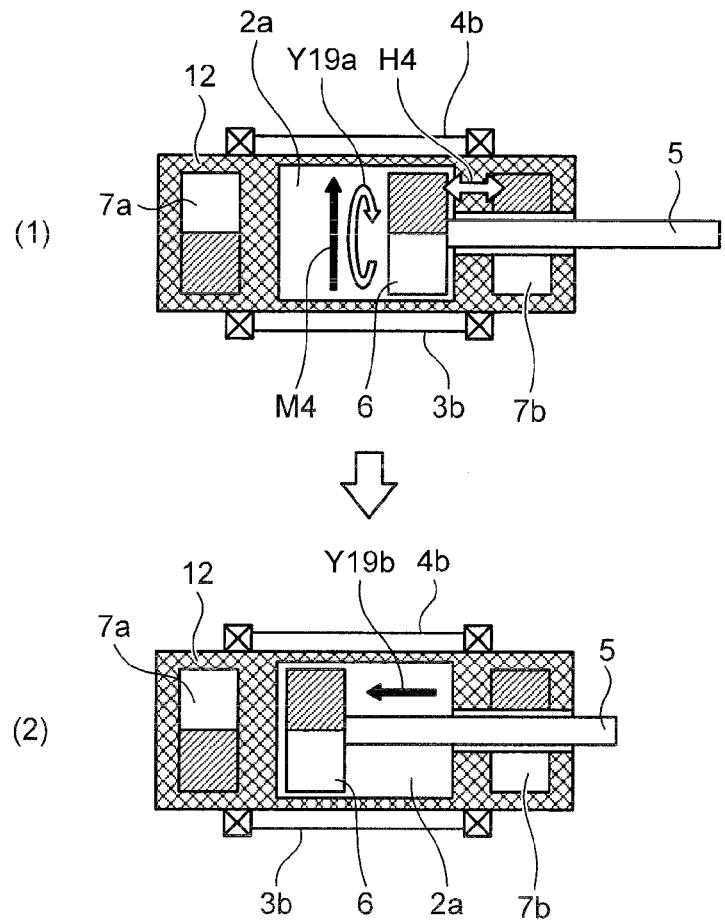
FIG. 21 shows sectional views of the magnetic actuator depicted in FIG. 16 cut along an axial direction.

Next, with reference to FIG. 17 to FIG. 21, the operation of the magnetic actuator 21 is described. FIG. 17 is a diagram depicting time dependency of the magnetic field strength applied by the coils 3a, 3b, 4a, 4b. FIG. 18 shows sectional views of the magnetic actuator 21 cut along a radial direction at times t21 to t22 depicted in FIG. 17. FIG. 19 shows sectional views of the magnetic actuator 21 cut along an axial direction at times t21 to t22 depicted in FIG. 17. FIG. 20 shows sectional views of the magnetic actuator 21 cut along a radial direction at times t23 to t24 depicted in FIG. 17. FIG. 21 shows sectional views of the magnetic actuator 21 cut along an axial direction at times t23 to t24 depicted in FIG. 17. A curve 11 in FIG. 17 represents a magnetic field strength of a magnetic field applied by the coils 3a, 4a, and a curve 12 represents a magnetic field strength of a magnetic field applied by the coils 3b, 4b. FIG. 19 corresponds to sectional views cut along a D-D line in FIG. 18, and FIG. 21 corresponds to sectional views cut along an E-E line in FIG. 20.

First, a case is described in which the magnetic actuator 21 is changed from an OFF state to an ON state. In this case, of the two sets of coils, the coils 3a, 4a generate a magnetic field. As indicated by the curve 11 in FIG. 17 and FIG. 18(1), at the time t21, to the magnetic actuator 21 in an OFF state, the coils 3a, 4a apply a magnetic field M3 oriented in a radial direction in the guiding area 2a. The magnetic field M3 has the magnetic field strength G1 that allows the rotationally-moving magnet 6 to rotate and is oriented in a lower-right direction in FIG. 18. Therefore, as indicated by an arrow Y18a in FIG. 18(2) and FIG. 19(1), the rotationally-moving magnet 6 rotates a half turn clockwise in a downward direction in FIG. 18(2) and FIG. 19(1) according to the magnetic-field orientation of the magnetic field M3. As a result, as depicted in FIG. 19(1), a repulsive force H3 occurs between the rotationally-moving magnet 6 and the fixed magnet 7a, and the rotationally-moving magnet 6 moves, as indicated by an arrow Y18b in FIG. 19(2), in a right direction in FIG. 19(2) along the guiding area 2a, thereby bringing the magnetic actuator 21 into an ON state. Thereafter, the rotationally-moving magnet 6 is attracted to a partition between the fixed magnet 7b and the rotationally-moving magnet 6 by an attractive force occurring between the fixed magnet 7b and the rotationally-moving magnet 6. Therefore, as depicted in FIG. 17 and FIG. 18(3), after the time t22 when the magnetic actuator 21 is brought into an ON state, the magnetic actuator 21 can keep the ON state even if the application of the magnetic field in the coils 3a, 4a is stopped.

Next, a case is described in which the magnetic actuator 21 is changed from an ON state to an OFF state. In this case, of the two sets of coils, the coils 3b, 4b generate a magnetic field. At the time t23 in FIG. 17, as depicted in a curve 12 in FIG. 17 and FIG. 20(1), to the magnetic actuator 21 in an ON state, the coils 3b, 4b apply a magnetic field M4 oriented in a radial direction in the guiding area 2a. The magnetic field M4 has a magnetic field strength equal to or greater than the magnetic field strength G1 that allows the rotationally-moving magnet 6 to rotate and is oriented in an upper-right direction in FIG. 20. Therefore, as indicated by an arrow Y19a in FIG. 20(2) and FIG. 21(1), the rotationally-moving magnet 6 rotates a half turn counter-clockwise in an upper direction in FIG. 20(2) and FIG. 21(1) according to the magnetic-field orientation of the magnet field M4. That is, the rotationally-moving magnet 6 rotates in a direction opposite to that when a magnetic field is applied by the coils 3a, 4a. As a result, as depicted in FIG. 21(1), a repulsive force H4 occurs between the rotationally-moving magnet 6 and the fixed magnet 7b, and the rotationally-moving magnet 6 moves, as indicated by an arrow Y19b in FIG. 21(2), in a left direction in FIG. 21(2) along the guiding area 2a, thereby causing the moving member 5 to be retracted toward the inside of the housing 12 of the magnetic actuator 21 and causing the magnetic actuator 21 to be in an OFF state. Thereafter, the rotationally-moving magnet 6 is attracted to a partition between the fixed magnet 7a and the rotationally-moving magnet 6 by an attractive force occurring between the fixed magnet 7a and the rotationally-moving magnet 6. Therefore, as depicted in FIG. 17 and FIG. 20(3), after the time t24 when the magnetic actuator 21 is brought into an OFF state, the magnetic actuator 21 can keep the OFF state even if the application of the magnetic field by the coils 3b, 4b is stopped.

According to the second modification example, two sets of coils are provided and, when the ON state or OFF state is changed, a magnetic field differently oriented is applied. Therefore, the rotating direction of the rotationally-moving magnet 6 in an ON state and the rotating direction of the rotationally-moving magnet 6 in an OFF state are opposite. Therefore, the second modification example can be applied to a case in which the moving member 5 should not be rotated in the same direction.

Third Modification Example

Figure 22:
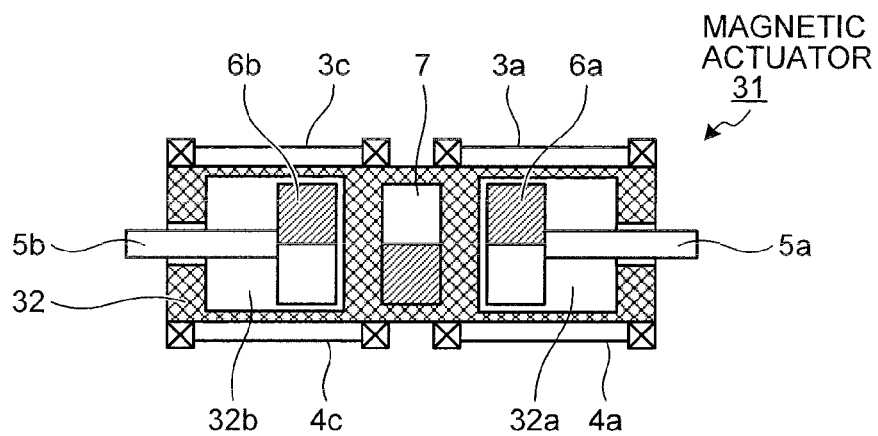
FIG. 22 shows a sectional view of a magnetic actuator according to a third modification example in the first embodiment cut along an axial direction.

Next, a third modification example in the first embodiment is described. FIG. 22 is a sectional view of a magnetic actuator according to the third modification example cut along an axial direction. As depicted in FIG. 22, a magnetic actuator 31 according to the third modification example has, in addition to the fixed magnet 7, plural rotationally-moving magnets 6a, 6b connected to moving members 5a, 5b, respectively, in contrast to the magnetic actuator 1. The fixed magnet 7 is placed between the rotationally-moving magnets 6a, 6b. The magnetic actuator 31 includes a housing 32 having a guiding area 32a corresponding to the rotationally-moving magnet 6a, coils 3a, 4a, a guiding area 32b corresponding to the rotationally-moving magnet 6b, and coils 3c, 4c. The guiding area 32a regulates a direction in which the rotationally-moving magnet 6a moves. The rotationally-moving magnet 6a is placed in the guiding area 32a while being rotatable in a plane including a magnetization direction. The guiding area 32b is provided at a position corresponding to the fixed magnet 7 and regulates a direction in which the rotationally-moving magnet 6b moves. The rotationally-moving magnet 6b is placed in the guiding area 32b while being rotatable in a plane including a magnetization direction. The coils 3a, 4a and the coils 3c, 4c generate magnetic fields not only in the guiding area 32a but also in the guiding area 32b in which the rotationally-moving magnet 6b is placed. The coils 3a, 4a, generate a magnetic field in the guiding area 32a, and are connected to a first external device not shown so as to be supplied with power. The magnetic-field generation of the coils 3a, 4a is controlled by the first external device. The coils 3c, 4c generate a magnetic field in the guiding area 32b, and are connected to a second external device different from the first external device so as to be supplied with power. The magnetic-field generation of the coils 3c, 4c is controlled by the second external device.

Figure 23:
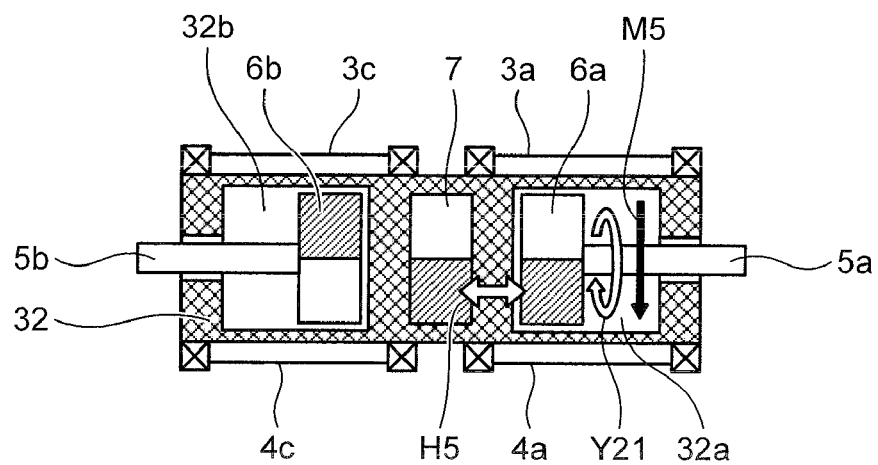
FIG. 23 shows a diagram explaining the operation of the magnetic actuator depicted in FIG. 22.
Figure 24:
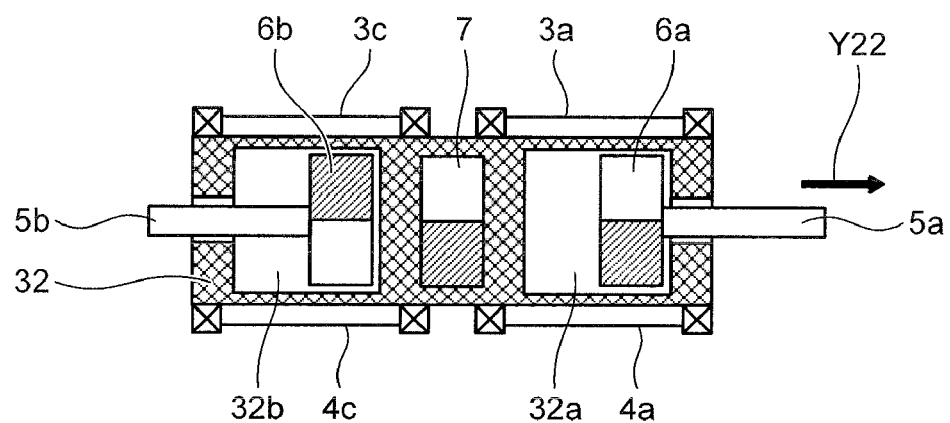
FIG. 24 shows a diagram explaining the operation of the magnetic actuator depicted in FIG. 22.
Figure 25:
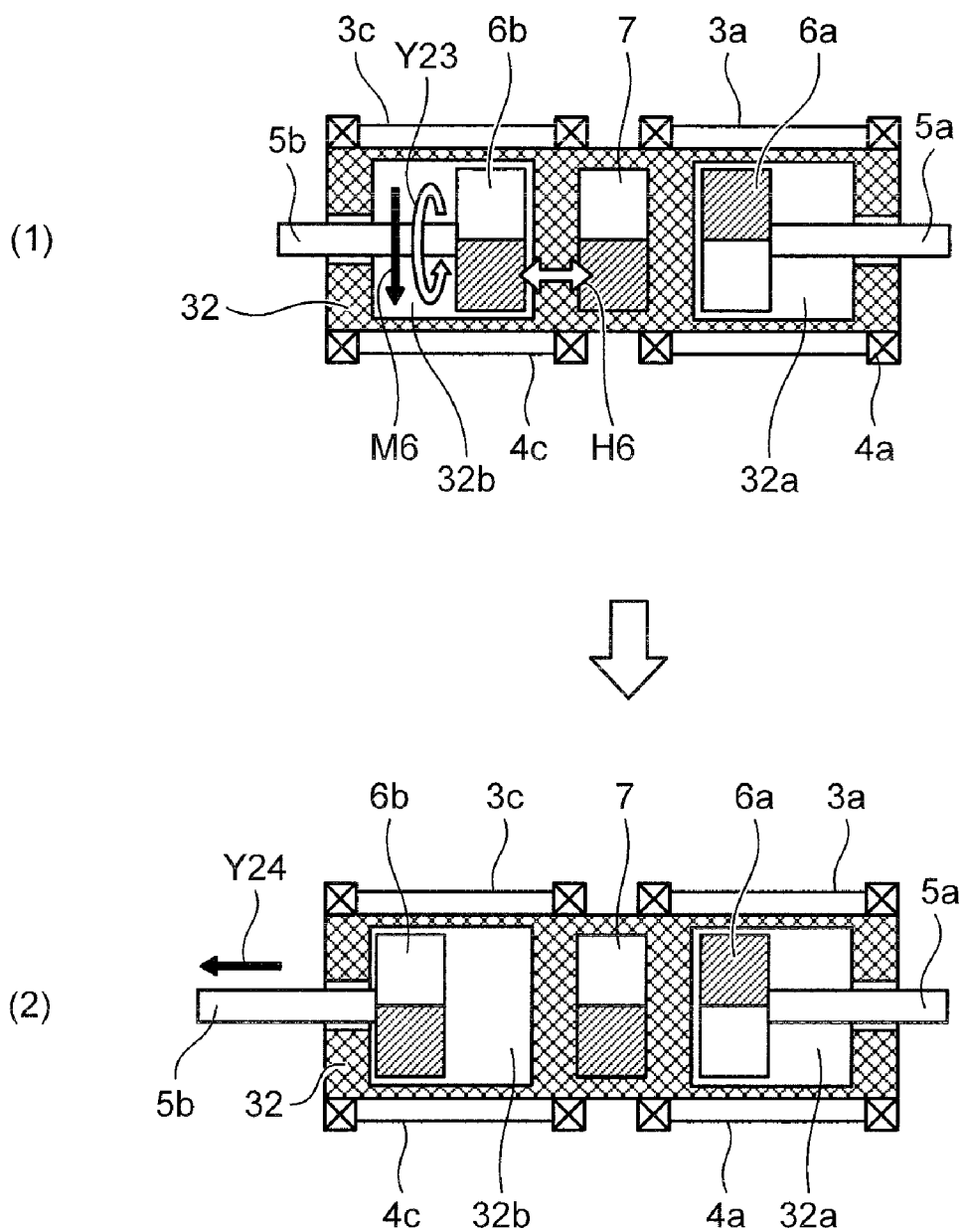
FIG. 25 shows diagrams explaining the operation of the magnetic actuator depicted in FIG. 22.

Next, with reference to FIG. 23 to FIG. 25, the operation of the magnetic actuator 31 is described. First, a case is described in which the moving member 5a connected to the rotationally-moving magnet 6a protrudes from the magnetic actuator 31 to be brought into an ON state. In this case, the coils 3a, 4a corresponding to the moving member 5a generate a magnetic field and apply a magnetic field M5 oriented in a radial direction in the guiding area 32a. The magnetic field M5 has the magnetic field strength G1 that allows the rotationally-moving magnet 6a to rotate and is oriented in a downward direction in FIG. 23. Therefore, as indicated by an arrow Y21 in FIG. 23, the rotationally-moving magnet 6a rotates a half turn in the downward direction in FIG. 23 according to the magnetic-field orientation of the magnetic field M5. As a result, as depicted in FIG. 23, a repulsive force H5 occurs between the rotationally-moving magnet 6a and the fixed magnet 7, the rotationally-moving magnet 6a moves, as indicated by an arrow Y22 in FIG. 24, in a right direction in FIG. 24 along the guiding area 32a, and the moving member 5a protrudes, thereby causing an ON state. In the magnetic actuator 31, in the same manner as the magnetic actuator 1, after the moving member 5a protrudes to achieve an ON state, the coils 3a, 4a apply the magnetic field strength G2 lower in strength than the magnetic field strength G1 to a degree that the rotationally-moving magnet 6a does not rotate a half turn again, thereby allowing the ON state to be kept.

Also, as depicted in FIG. 25(1), when the moving member 5b connected to the rotationally-moving magnet 6b is to be protruded from the magnetic actuator 31 to achieve an ON state, the coils 3c, 4c corresponding to the moving member 5b apply a magnetic field M6 oriented in a radial direction in the guiding area 32b. The magnetic field M6 has the magnetic field strength G1 that allows the rotationally-moving magnet 6b to rotate and is oriented in a downward direction in FIG. 25(1). Therefore, as indicated by an arrow Y23 in FIG. 25(1), the rotationally-moving magnet 6b rotates a half turn in the downward direction in FIG. 25(1) according to the magnetic-field orientation of the magnetic field M6, and a repulsive force H6 occurs between the rotationally-moving magnet 6b and the fixed magnet 7. As a result, the rotationally-moving magnet 6b moves, as indicated by an arrow Y24 in FIG. 25(2), in a left direction in FIG. 25(2) along the guiding area 32b, and the moving member 5b protrudes, thereby causing an ON state. In the magnetic actuator 31, in the same manner as the magnetic actuator 1, after the moving member 5b protrudes to achieve an ON state, the coils 3c, 4c apply the magnetic field strength G2 lower in strength than the magnetic field strength G1 to a degree that the rotationally-moving magnet 6b does not rotate a half turn again, thereby allowing the ON state to be kept.

As described above, according to the third modification example, one fixed magnet 7 can drive two rotationally-moving magnets. Therefore, compared with the magnetic actuator 1, further space saving can be achieved. Furthermore, according to the third modification example, the coils 3a, 4a and the coils 3c, 4c are caused to generate magnetic fields at different timings by different external devices, thereby causing the moving members 5a, 5b to operate at different timings. Alternatively, the coils 3a, 4a and the coils 3c, 4c may be caused to generate magnetic fields by the same external device, thereby causing the moving members 5a, 5b to operate at the same time.

Figure 26:
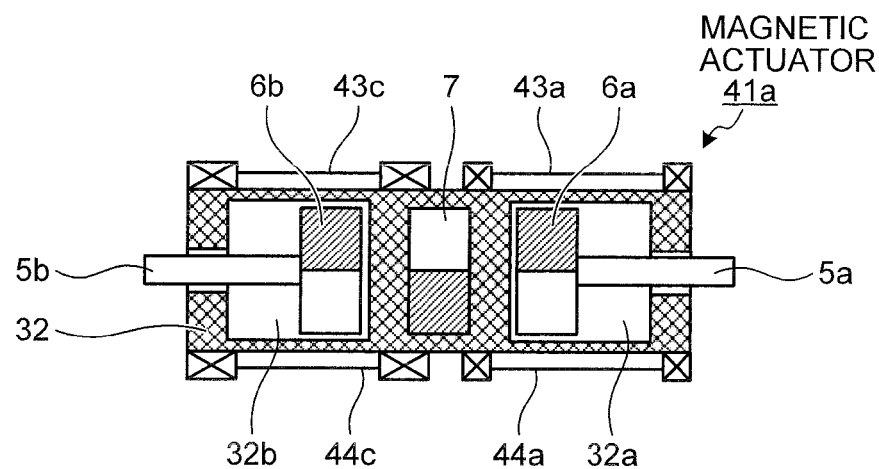
FIG. 26 shows a diagram depicting another configuration of the magnetic actuator depicted in FIG. 22.

In the third modification example, different magnetic fields may be given to move the rotationally-moving magnets 6a, 6b to switch the operation between the moving members 5a, 5b. For example, a magnetic actuator 41a will be described which has, as depicted in FIG. 26, coils 43a, 43c, 44a, 44c with different numbers of winding in place of the coils 3a, 3c, 4a, 4c in the magnetic actuator 31. In the magnetic actuator 41a, the coil 43a and the coil 43c are connected together in series, and the coil 44a and the coil 44c are connected together in series. Also, the coils 43a, 43c, 44a, 44c generate magnetic fields with power supply from the same external device. Furthermore, since the coils 43c, 44c have a larger number of winding compared with the coils 43a, 44a, they can generate a magnetic field larger than that of the coils 43a, 44a when supplied with the same power supply.

Figure 27:
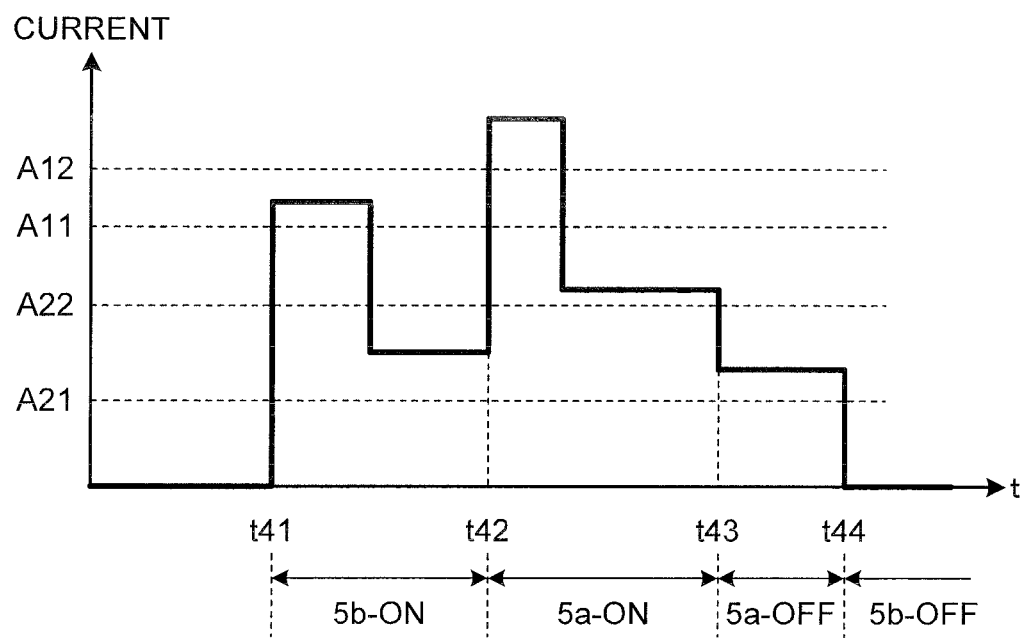
FIG. 27 shows a diagram depicting time dependency of a current value supplied to coils depicted in FIG. 26.
Figure 28:
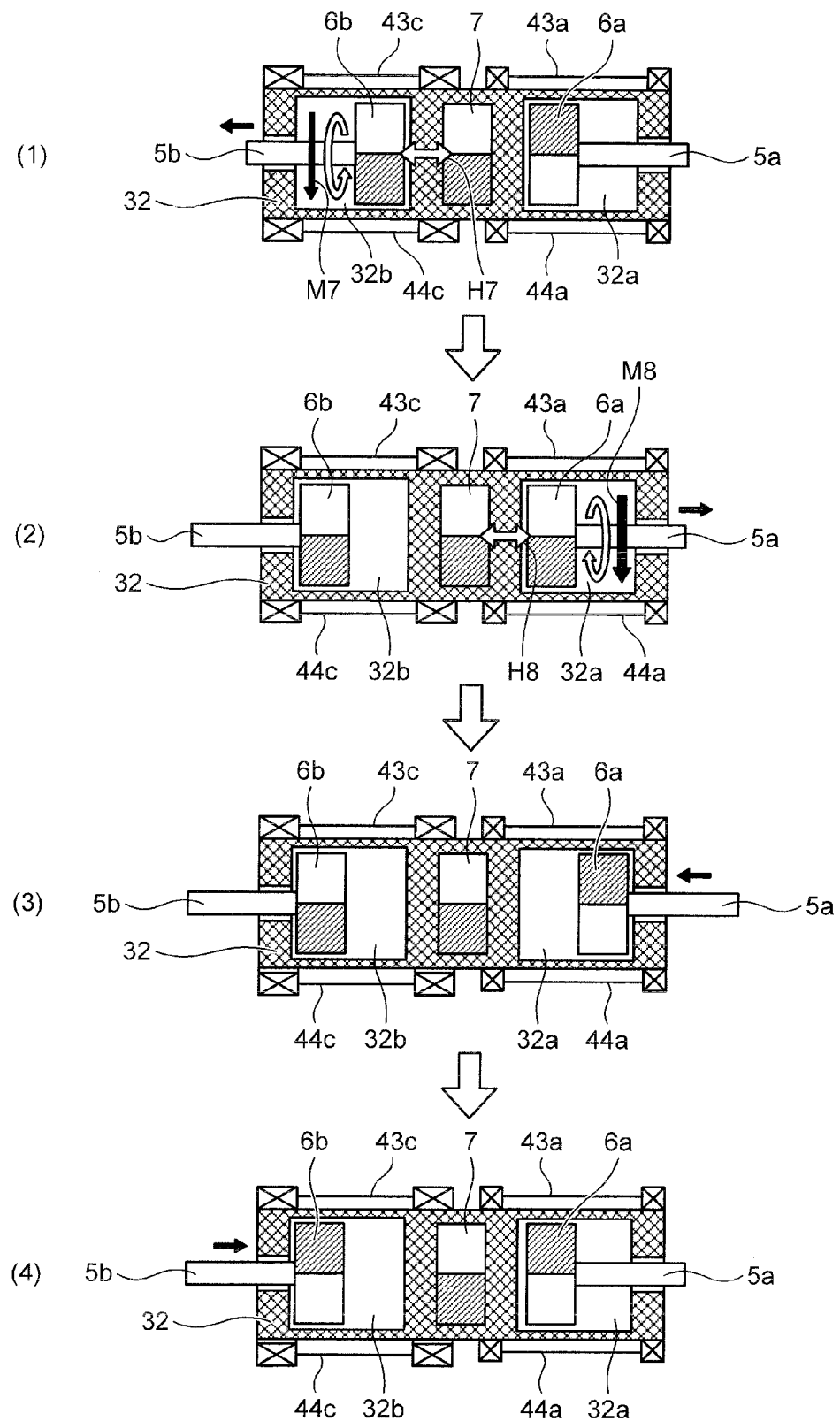
FIG. 28 shows sectional views explaining the operation of the magnetic actuator depicted in FIG. 26.

Next, with reference to FIG. 27 and FIG. 28, the operation of the magnetic actuator 41a is described. FIG. 27 is a diagram depicting time dependency of a current value supplied to the coils 43a, 43c, 44a, 44c, and FIG. 28 shows sectional views of the magnetic actuator 41a cut along an axial direction at times t41 to t44 depicted in FIG. 27. First, a case is described when the moving member 5b is brought into an ON state. In this case, as depicted in FIG. 27, at the time t41, a current is supplied to the coils 43a, 43c, 44a, 44c, the current being equal to or greater than a current value All allowing the coils 43c, 44c to generate a magnetic field with the magnetic field strength G1 allowing the rotationally-moving magnet 6b to rotate. As a result, as depicted in FIG. 28(1), the coils 43c, 44c apply a magnetic field M7 with the magnetic field strength G1 oriented in a radial direction of the guiding area 32b. Therefore, as depicted in FIG. 28(1), the rotationally-moving magnet 6b rotates a half turn according to the magnetic-field orientation of the magnetic field M7, and a repulsive force H7 occurs between the rotationally-moving magnet 6b and the fixed magnet 7. As a result, the rotationally-moving magnet 6b moves, as depicted in FIG. 28(2), in a left direction in FIG. 28(2) along the guiding area 32b, thereby causing the moving member 5b to be an ON state. Then, to keep the moving member 5b in the ON state, it is sufficient to supply the coils 43a, 43c, 44a, 44c with a current equal to or greater than a current value A21 that allows the coils 43c, 44c to generate a magnetic field with the magnetic field strength G2 allowing the moving member 5b to be kept in the ON state.

Next, a case is described in which the moving member 5a is turned to an ON state. In this case, as depicted in FIG. 27, at the time t42, the coils 43a, 43c, 44a, 44c are supplied with the current value A12 that allows the coils 43a, 44a to generate a magnetic field with a magnetic field strength greater than the magnetic field strength G1 allowing the rotationally-moving magnet 6a to rotate. As a result, as depicted in FIG. 28(2), the coils 43a, 44a apply a magnetic field M8 with the magnetic field strength G1 in a radial direction of the guiding area 32a. With this, as depicted in FIG. 28(2), the rotationally-moving magnet 6a rotates a half turn according to the magnetic-field orientation of the magnetic field M8, and a repulsive force H8 occurs between the rotationally-moving magnet 6a and the fixed magnet 7. As a result, the rotationally-moving magnet 6a moves, as depicted in FIG. 28(3), in a left direction in FIG. 28(3) along the guiding area 32a, thereby causing the moving member 5a to be in an ON state. Then, to keep the moving member 5a in the ON state, it is sufficient to supply the coils 43a, 43c, 44a, 44c with a current value A22 that allows the coils 43a, 44a to generate a magnetic field with a magnetic field strength greater than the magnetic field strength G2 allowing the moving member 5a to be kept in the ON state.

Next, a case is described in which the moving member 5a is turned to an OFF state. In this case, as depicted in FIG. 27, at the time t43, the current value to be supplied to the coils 43a, 43c, 44a, 44c is decreased so as to be lower than the current value A22 that allows the coils 43a, 44a to generate the magnetic field strength G2 allowing the moving member 5a to be kept in an ON state. As a result, as depicted in FIG. 28(3), the orientation equivalent to the orientation of the magnetic field applied by the coils 43a, 44a cannot be kept in the guiding area 32a, and therefore the rotation is made in an upward direction. Then, the rotationally-moving magnet 6a moves by an attractive force occurring between the fixed magnet 7 and itself toward a fixed magnet 7 side. Accordingly, the moving member 5a connected to the rotationally-moving magnet 6a is retracted toward the inside of the housing 32 of the magnetic actuator 41a, thereby causing an OFF state. Then, as depicted in FIG. 27, at the time t44, the current value to be supplied to the coils 43a, 43c, 44a, 44c is stopped, thereby stopping application of the magnetic field. With this, as depicted in FIG. 28(4), the orientation equivalent to the orientation of the magnetic field applied by the coils 43c, 44c cannot be kept in the guiding area 32b, and therefore the rotation is made in an upward direction. Then, the rotationally-moving magnet 6b moves to a fixed magnet 7 side by an attractive force occurring between the fixed magnet 7 and itself. Accordingly, the moving member 5b connected to the fixed moving magnet 6b is retracted toward the inside of the housing 32 of the magnetic actuator 41a, thereby causing an OFF state.

As described above, by providing the coils 43a, 44a, 43c, 44c that can set the current values to be supplied differently to cause each of the rotationally-moving magnets 6a, 6b to move and by providing an external device that supplies power to the coils 43a, 44a, 43c, 44c, the operation of the moving members 5a, 5b is switched, thereby allowing the magnetic actuator 41a with high operation flexibility to be achieved.

Figure 29:
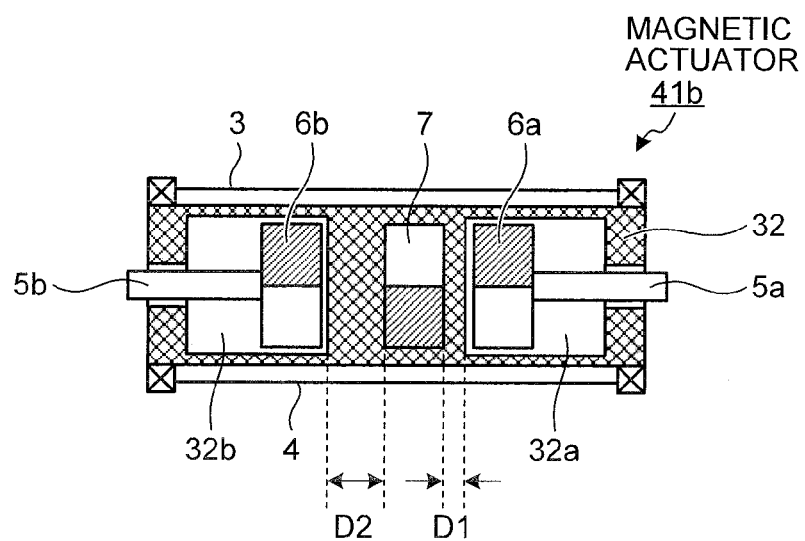
FIG. 29 shows a diagram depicting still another configuration of the magnetic actuator depicted in FIG. 22.

Instead of providing coils with different number of winding, the magnetic field strengths with which each of the rotationally-moving magnets 6a, 6b moves can be differently set so as to switch the operation of the moving members 5a, 5b. For example, as depicted in a magnetic actuator 41b in FIG. 29, distances between the fixed magnet 7 and each of the rotationally-moving magnets 6a, 6b are set to be different so that the magnetic field strengths with which each of the rotationally-moving magnets 6a, 6b move are different. In this case, the rotationally-moving magnet 6a is separated from the fixed magnet 7 by a partition having a thickness D1, and the rotationally-moving magnet 6b is separated from the fixed magnet 7 by a partition having a thickness D2 thicker than D1. Therefore, compared with the rotationally-moving magnet 6a, the rotationally-moving magnet 6b has a low action of the attractive force between the fixed magnet 7 and itself, and is therefore rotatable with application of a magnetic field with a magnetic field strength smaller than that of the rotationally-moving magnet 6a.

Figure 30:
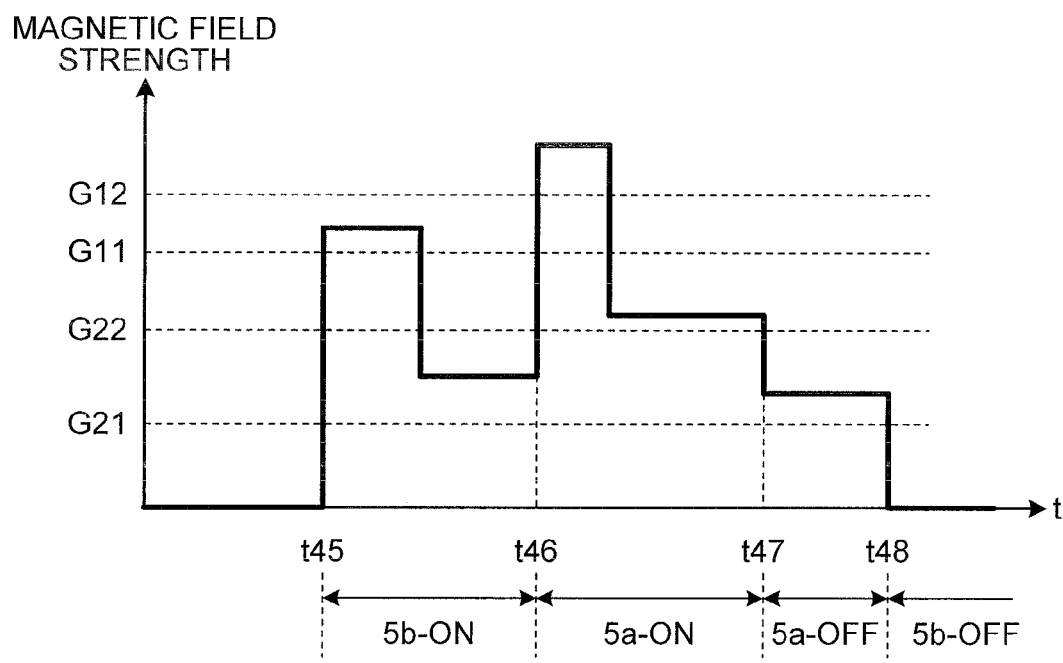
FIG. 30 shows a diagram depicting time dependency of a magnetic field strength supplied by coils depicted in FIG. 29.

Therefore, as depicted in FIG. 30, in the magnetic actuator 41b, at the time t45, the coils 3, 4 apply a magnetic field to the inside of the guiding areas 32a, 32b with a magnetic field strength stronger than a magnetic field strength G11 that allows the rotationally-moving magnet 6b to rotate, thereby causing the rotationally-moving magnet 6b to rotate. Based on a repulsive force between the rotationally-moving magnet 6b and the fixed magnet 7, the rotationally-moving magnet 6b is moved to cause the moving member 5b to be in an ON state. Then, the coils 3, 4 weaken the magnetic field strength with a magnetic field strength G21 as a lower limit, keeping the ON state of the moving member 5b. Next, at the time t46 in FIG. 30, the coils 3, 4 apply a magnetic field to the inside of the guiding areas 32a, 32b with a magnetic field strength stronger than a magnetic field strength G12 that allows the rotationally-moving magnet 6a to rotate, thereby causing the rotationally-moving magnet 6a to rotate. Based on a repulsive force between the rotationally-moving magnet 6a and the fixed magnet 7, the rotationally-moving magnet 6a is moved to cause the moving member 5a to be in an ON state. Then, the coils 3, 4 weaken the magnetic field strength to be applied to the inside of the guiding areas 32a, 32b with a magnetic field strength G22 as a lower limit, thereby keeping the moving member 5a in an ON state. Then, at the time t47 in FIG. 30, the coils 3, 4 weaken the magnetic field strength of the magnetic field to be applied to the inside of the guiding areas 32a, 32b to be equal to or smaller than G22 to cause the rotationally-moving magnet 6a to be moved to the fixed magnet 7 side, thereby causing the moving member 5a to be in an OFF state. Furthermore, at the time t48 in FIG. 30, the coils 3, 4 stop the magnetic field to be applied to the rotationally-moving magnet 6a to cause the rotationally-moving magnet 6b to be moved to the fixed magnet 7 side, thereby causing the moving member 5b to be in an OFF state.

As described above, with the distances between each of the rotationally-moving magnets 6a, 6b and the fixed magnet 7 being changed to change the magnetic field strength that allows the rotationally-moving magnets 6a, 6b to move, the moving members 5a, 5b can be driven separately using one set of coils, and the magnetic actuator 41b with high operation flexibility can be achieved.

Figure 31:
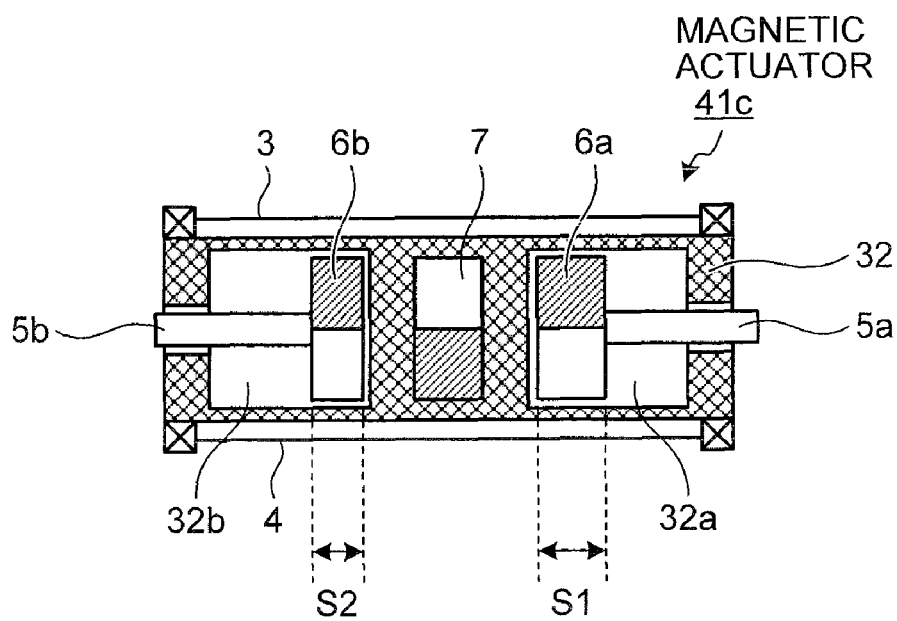
FIG. 31 shows a diagram depicting still another configuration of the magnetic actuator depicted in FIG. 22.
Figure 32:
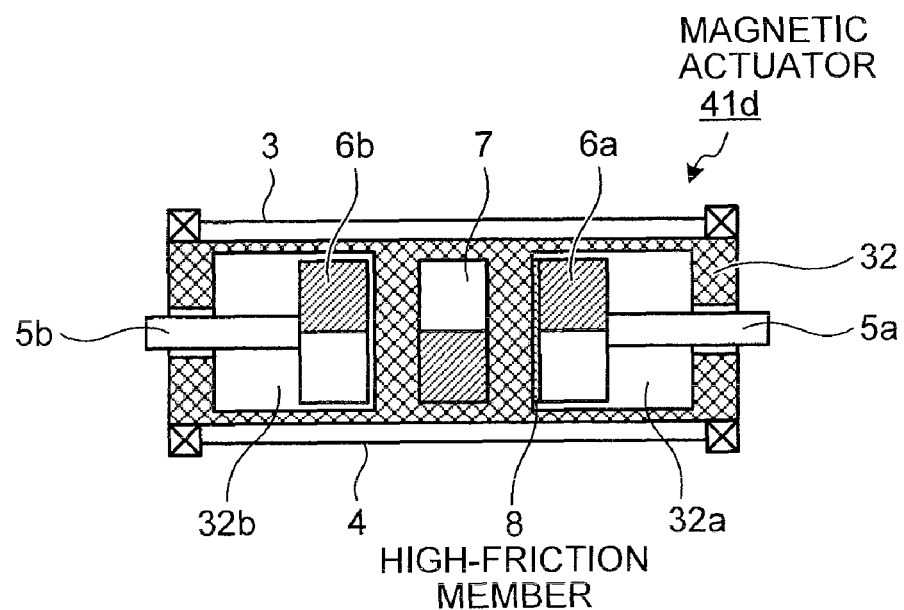
FIG. 32 shows a diagram depicting still another configuration of the magnetic actuator depicted in FIG. 22.

Also, as depicted in a magnetic actuator 41c in FIG. 31, with the rotationally-moving magnets 6a, 6b being changed in size, the magnetic field strengths that allow the rotationally-moving magnets 6a, 6b to move may be changed. In the magnetic actuator 41c, a rotationally-moving magnet 6a with a magnetic size S1 larger than the rotationally-moving magnet 6b with a magnet size S2 is provided, thereby allowing the rotationally-moving magnet 6b to rotate by application of a magnetic field with a magnetic field strength weaker than that of the rotationally-moving magnet 6a. Also, as depicted in a magnetic actuator 41d in FIG. 32, in the rotationally-moving magnet 6a, a high-friction member 8 with a high friction force may be provided on a surface in contact with the partition provided between the fixed magnet 7 and the rotationally-moving magnet 6a, thereby changing the magnetic field strength that allows the rotationally-moving magnets 6a, 6b to move. Since the friction force at the time of rotation is higher compared with the rotationally-moving magnet 6b to suppress the rotation, the rotationally-moving magnet 6a is rotatable with a larger magnetic field strength compared with the rotationally-moving magnet 6b. In the magnetic actuators 41c, 41d, with the magnetic field strength of the magnetic field to be applied to the guiding areas 32a, 32b being changed as depicted in FIG. 30, driving of the moving members 5a, 5b can be controlled in the same manner as the magnetic actuator 41b.

Fourth Modification Example

Figure 33:
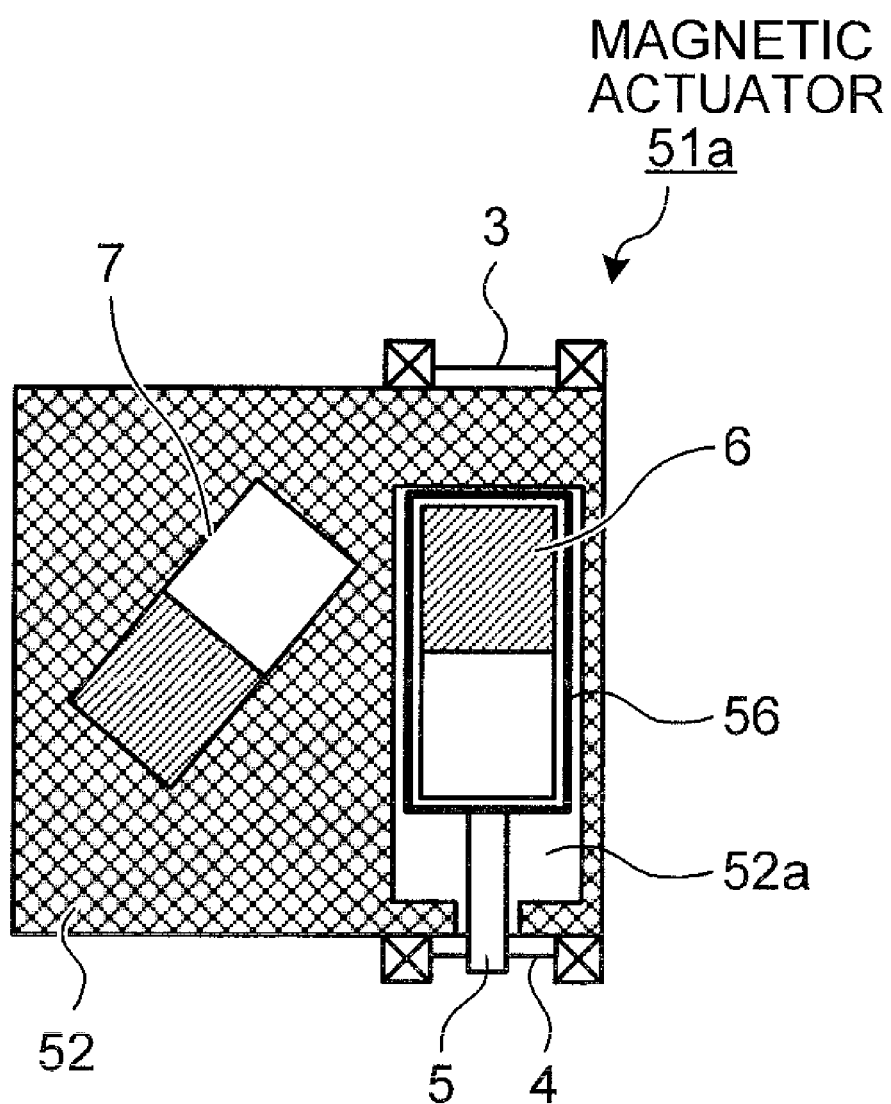
FIG. 33 shows a sectional view of a magnetic actuator according to a fourth modification example in the first embodiment cut along an axial direction.

Next, a fourth modification example in the first embodiment is described. FIG. 33 is a sectional view of a magnetic actuator according to the fourth modification example cut along an axial direction. As depicted in FIG. 33, a magnetic actuator 51a according to the fourth modification example has, in contrast to the magnetic actuator 1, a casing 56 that has accommodated therein the rotationally-moving magnet 6 so as not to inhibit the rotation of the rotationally-moving magnet 6 in a radial direction of the magnetic actuator 51a, and a moving member 5 is connected to a lower end of this casing 56. Also, the rotationally-moving magnet 6 is disposed in a housing 52, and a guiding area 52a is provided, which is an inner space that allows this rotationally-moving magnet 6 to move in a vertical direction in FIG. 33 within the magnetic actuator 51a depicted in FIG. 33. Furthermore, the fixed magnet 7 is fixed in the magnetic actuator 51a at an angle tilted with respect to a central axis of the magnetic actuator 51a.

Figure 34:
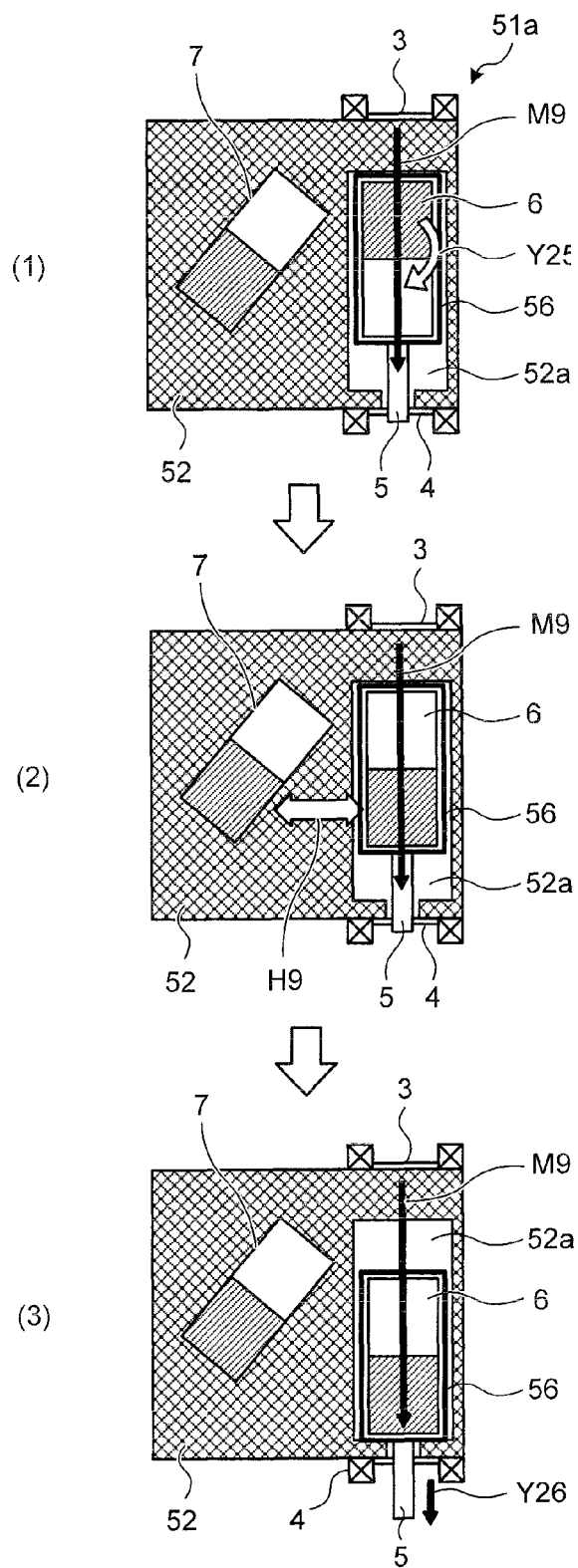
FIG. 34 shows diagrams explaining the operation of the magnetic actuator depicted in FIG. 33.

Next, the operation of the magnetic actuator 51a is described. First, when the magnetic actuator 51a is turned from an OFF state to an ON state, as depicted in FIG. 34(1), coils 3, 4 apply a magnetic field M9 to the inside of the guiding area 52a with a magnetic field strength stronger than a magnetic field strength that allows the rotationally-moving magnet 6 to rotate. As a result, as indicated by an arrow Y25 in FIG. 34(1), the rotationally-moving magnet 6 rotates a half turn in a downward direction in FIG. 34(1) according to the magnetic-field orientation of a magnetic field M9. Then, as depicted in FIG. 34(2), a repulsive force H9 occurs between the rotationally-moving magnet 6 and the fixed magnet 7. With this repulsive force H9, the rotationally-moving magnet 6 moves, as indicated by an arrow Y26 in FIG. 34(3), in a downward direction in FIG. 34 along the guiding area 52a. With this movement of the rotationally-moving magnet 6, the moving member 5 protrudes from the housing 52 of the magnetic actuator 51a, thereby causing the magnetic actuator 51a to be in an ON state. Note that, to keep the magnetic actuator 51a in an ON state, a magnetic field is required to be continuously applied with a magnetic field strength that is weaker than the magnetic field strength that allows the rotationally-moving magnet 6 to rotate and is strong enough to allow a positional state of the rotationally-moving magnet 6 at a lower end of the guiding area 52a to be kept.

As described above, according to the fourth modification example, by changing the posture of the fixed magnet 7 and the moving direction of the rotationally-moving magnet 6 in the guiding area 52a, the moving member 5 can be moved in a radial direction of the magnetic actuator, and a magnetic actuator with higher flexibility in design can be achieved.

Figure 35:
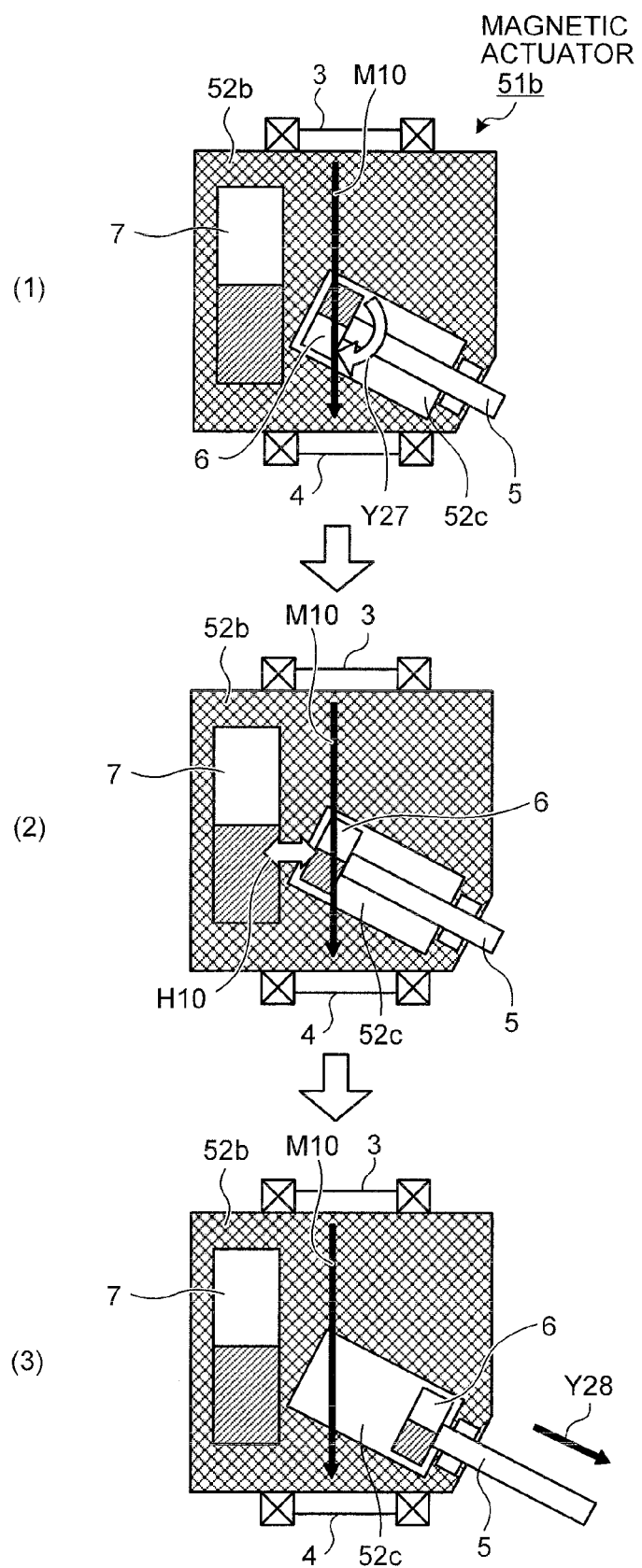
FIG. 35 shows diagrams depicting another configuration of the magnetic actuator depicted in FIG. 33.

Note that, as depicted in a magnetic actuator 51b of FIG. 35, by providing a guiding area 52c in a housing 52b at an angle tilted with respect to the central axis of the magnetic actuator 51b, the moving member 5 can be driven at the angle tilted with respect to the central axis of the magnetic actuator. To change this magnetic actuator 51b from an OFF state to an ON state, as depicted in FIG. 35(1), the coils 3, 4 apply a magnetic field M10 to the inside of the guiding area 52c with a magnetic field strength stronger than the magnetic field strength that allows the rotationally-moving magnet 6 to rotate, thereby causing the rotationally-moving magnet 6 to rotate as indicated by an arrow Y27 in FIG. 35(1). Then, as depicted in FIG. 35(2), a repulsive force H10 occurs between the rotationally-moving magnet 6 and the fixed magnet 7 and, with this repulsive force H10, the rotationally-moving magnet 6 moves, as indicated by an arrow Y28 in FIG. 35(3), along the guiding area 52c at an angle tilted in a downward direction in FIG. 35(3) with respect to the central axis of the magnetic actuator. With this movement of the rotationally-moving magnet 6, the moving member 5 protrudes from the housing 52b of the magnetic actuator 51b, thereby causing the magnetic actuator 51b to be in an ON state. Note that, to keep the magnetic actuator 51b in an ON state, in the same manner as the magnetic actuator 51a, a magnetic field is required to be continuously applied with a magnetic field strength that is weaker than the magnetic field strength that allows the rotationally-moving magnet 6 to rotate and is strong enough to allow a positional state of the rotationally-moving magnet 6 at a lower end of the guiding area 52c to be kept.

Fifth Modification Example

Figure 36:
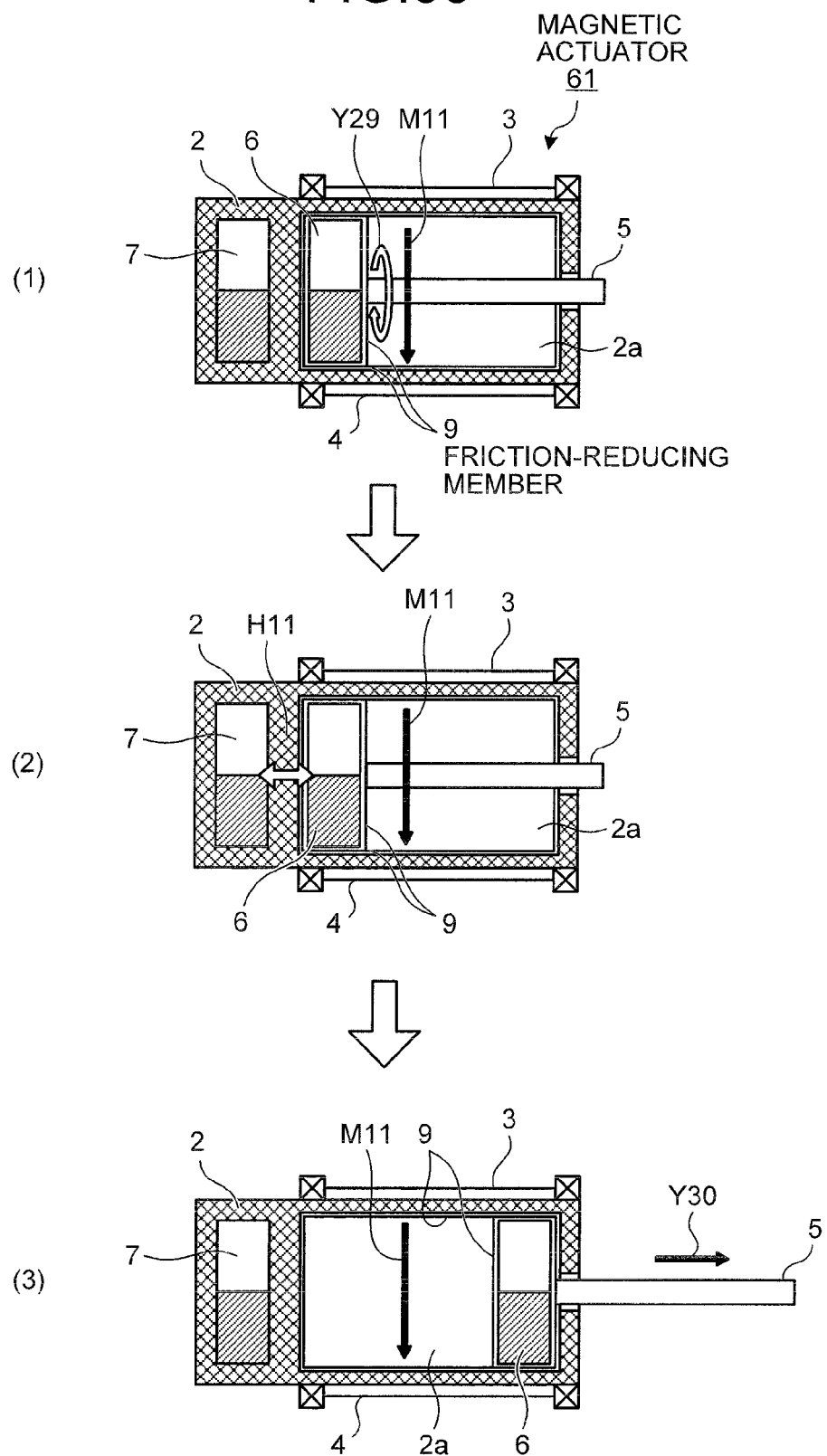
FIG. 36 shows sectional views of a magnetic actuator according to a fifth modification example in the first embodiment cut along an axial direction.

Next, a fifth modification example in the first embodiment is described. FIG. 36 shows sectional views of a magnetic actuator according to the fifth modification example cut along an axial direction. As depicted in FIG. 36(1), a magnetic actuator 61 according to the fifth modification example has, in contrast to the magnetic actuator 1, a friction-reducing member 9 disposed on a surface of the rotationally-moving magnet 6 to reduce friction between the guiding area 2a and the rotationally-moving magnet 6. Furthermore, also on the inner surface of the guiding area 2a, the friction-reducing member 9 is provided to the entire area that is brought into contact with the rotationally-moving magnet 6. For this reason, in the magnetic actuator 61, compared with the case in which no friction-reducing member 9 is provided, the rotationally-moving magnet 6 is rotatable with a weak magnetic field strength.

Therefore, as indicated by an arrow Y29 in FIG. 36(1), the coils 3, 4 apply a magnetic field M11 with a magnetic field strength weaker than the magnetic field strength G1 that allows the rotationally-moving magnet 6 to rotate, thereby allowing the rotationally-moving magnet 6 to rotate. Furthermore, since the friction-reducing member 9 provided on the surface of the rotationally-moving magnet 6 and the friction-reducing member 9 provided on the surface of the guiding area 2a are in contact with each other, as depicted in FIG. 36(2) and FIG. 36(3), a movement due to a repulsive force H11 occurring with the fixed magnet 7 is smoothly made, thereby protruding, as indicated by an arrow Y30 in FIG. 36(3), the moving member 5 outside of the housing 2 of the magnetic actuator 61 to cause an ON state.

As described above, according to the fifth modification example, the friction-reducing members 9 are provided to improve the sliding property of the rotationally-moving magnet 6 at the time of moving. With this, the magnetic field strength of the magnetic field to be applied to the magnetic actuator 61 can be reduced, thereby making it possible to achieve the magnetic actuator 61 with further improved energy efficiency.

Note that, even when the friction-reducing member 9 is provided either on the surface of the rotationally-moving magnet 6 or on the inner surface of the guiding area 2a, compared with the magnetic actuator 1, the sliding property of the rotationally-moving magnet 6 at the time of moving can be improved, and therefore energy efficiency of the magnetic actuator can be improved.

Second Embodiment

Figure 37:
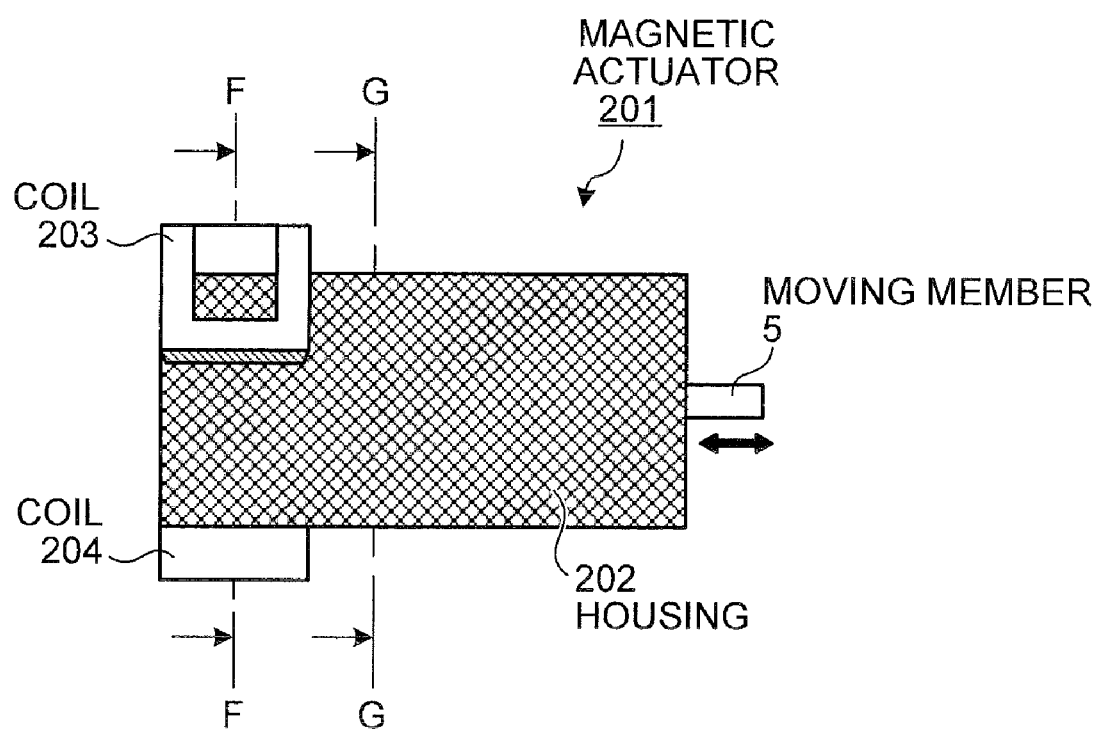
FIG. 37 shows a front view of a magnetic actuator according to a second embodiment.
Figure 38:
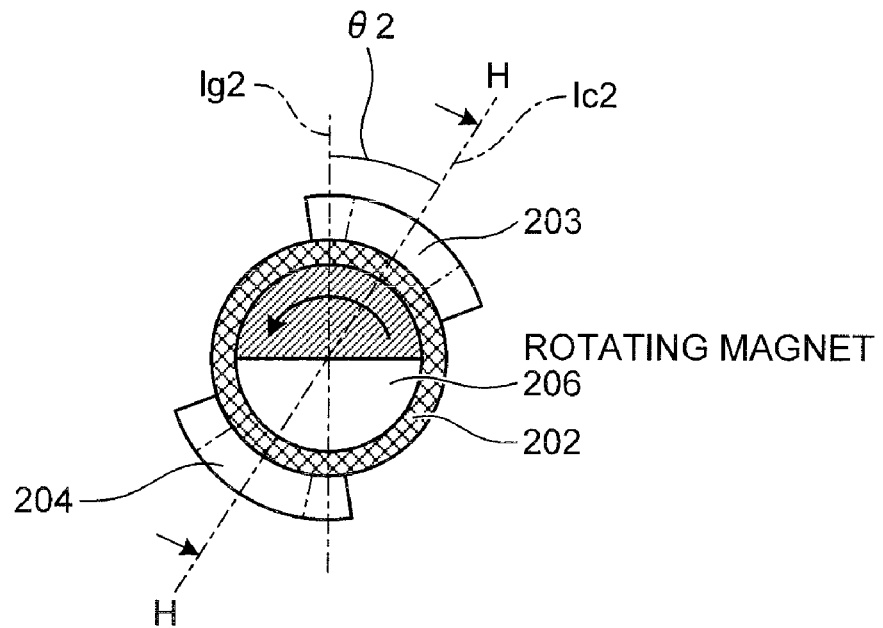
FIG. 38 shows a sectional view of the magnetic actuator depicted in FIG. 37 cut along a radial direction along an F-F line depicted in FIG. 37.
Figure 39:
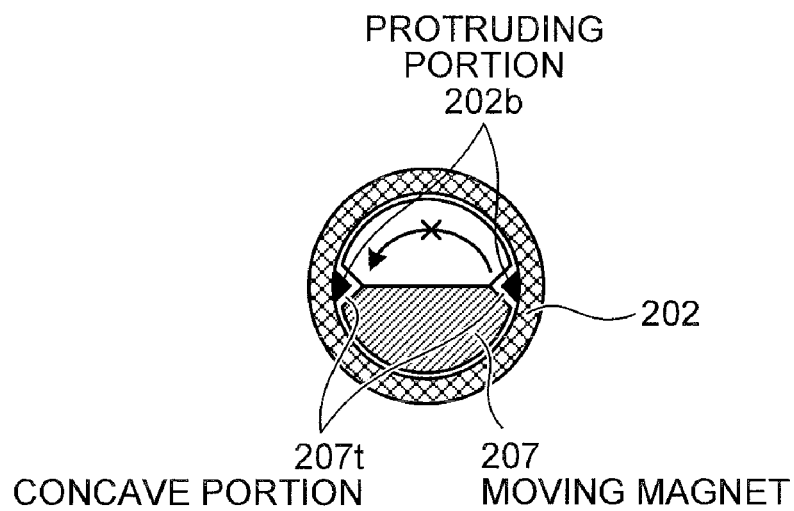
FIG. 39 shows a sectional view of the magnetic actuator depicted in FIG. 37 cut along a G-G line in a radial direction depicted in FIG. 37.
Figure 40:
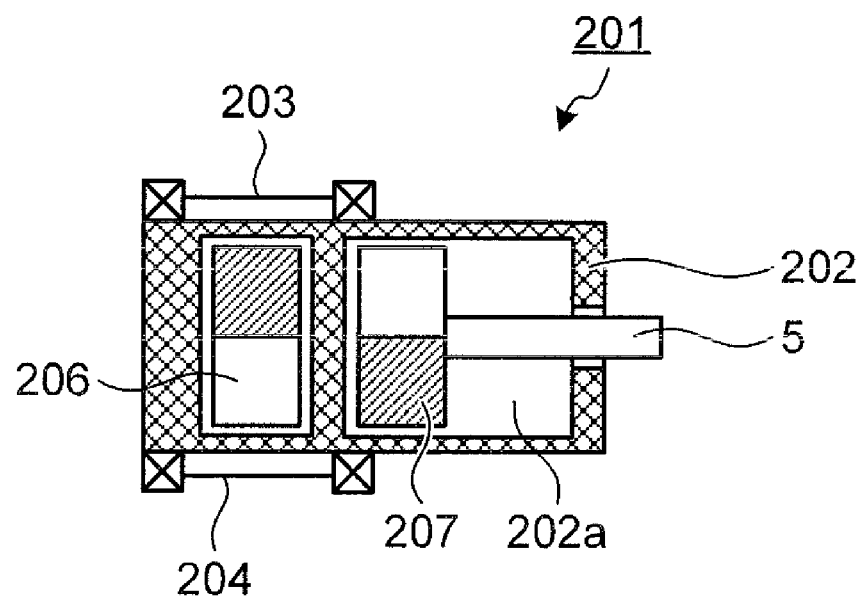
FIG. 40 shows a sectional view of the magnetic actuator depicted in FIG. 37 cut along an H-H line in an axial direction depicted in FIG. 38.

Next, a second embodiment is described. FIG. 37 is a front view of a magnetic actuator according to the second embodiment. FIG. 38 is a sectional view of the magnetic actuator cut along an F-F line in a radial direction depicted in FIG. 37. FIG. 39 is a sectional view of the magnetic actuator cut along a G-G line in the radial direction depicted in FIG. 37. FIG. 40 is a sectional view of the magnetic actuator cut along an H-H line in an axial direction depicted in FIG. 38.

As depicted in FIG. 37, in a magnetic actuator 201 according to the second embodiment, outside of a housing 202, which is an exterior component in an approximately cylindrical shape with its ends closed, a coil 203 and a coil 204 disposed opposite to the coil 203 are fixed. The coils 203, 204 are capable of generating a magnetic field. Also, in the same manner as the magnetic actuator 1, the magnetic actuator 201 has a moving member 5 movable in an axial direction of the housing 202.

Also, as depicted in FIG. 39 and FIG. 40, a rotating magnet 206 is provided in the housing 202 so as to face to a moving magnet 207 via a partition that partitions the inner space. The rotating magnet 206 is rotatable about the central axis of the magnetic actuator 201. That is, the rotating magnet 206 is disposed so as to be rotatable in a plane including a magnetization direction of the rotating magnet 206 with respect to the housing 202 and, with a magnetic field generated in a guiding area 202a by the coils 203, 204 fixedly disposed on the housing 202 correspondingly to the disposed position of the rotating magnet 206, the rotating magnet 206 is rotatable in a radial direction of the magnetic actuator 201 as indicated by an arrow in FIG. 38.

Also, the coils 203, 204 generate, as with the first embodiment, a magnetic field for the rotating magnet 206 is generated with supply of power by a connected external device not shown. As indicated by a straight line lc2, the coils 203, 204 are placed so as to have a predetermined angle θ2 relative to a straight line lg2 indicative of the magnetization direction of the moving magnet 207. As with the first embodiment, the predetermined angle θ2 is required to be equal to or smaller than 60 degrees. In particular, it is preferable that the angle θ2 is equal to or greater than five degrees and equal to or smaller than 40 degrees. Furthermore, by setting the angle θ2 to be equal to or greater than five degrees and equal to or smaller than 30 degrees, it is possible to weaken the magnetic field strength of the magnetic field applied by the coils 203, 204 and also to achieve stable rotation of the rotating magnet 206.

Furthermore, as depicted in FIG. 38 to FIG. 40, the guiding area 202a is provided in the housing 202 as an inner space in the housing 202. The guiding area 202a has an inner diameter corresponding to a diameter size of the moving magnet 207 and a length in an axial direction. The length is set such that a right end of the moving member 5 does not protrude when the moving member 5 is retracted toward the inside of the housing 202 of the magnetic actuator 201. The moving magnet 207 is placed in a state in which its rotation in the guiding area 202a is restrained with respect to the housing 202. Also, the moving magnet 207 is placed in a state in which its magnetization direction is fixed to a radial direction of the housing 202. The moving magnet 207 has a concave portion 207t. On an inner surface of the guiding area 202a, a protruding portion 202b is provided and, with this protruding portion 202b and the concave portion 207t of the moving magnet 207 engaging with each other, the rotation of the moving magnet 207 in a radial direction of the magnetic actuator 201 is restrained as indicated by an arrow in FIG. 39. For this reason, the moving magnet 207 moves in a horizontal direction in FIG. 40 in the guiding area 202a without rotation. Therefore, the moving member 5 connected to the moving magnet 207 also moves in and out relative to the magnetic actuator 201 without rotation.

Figure 41:
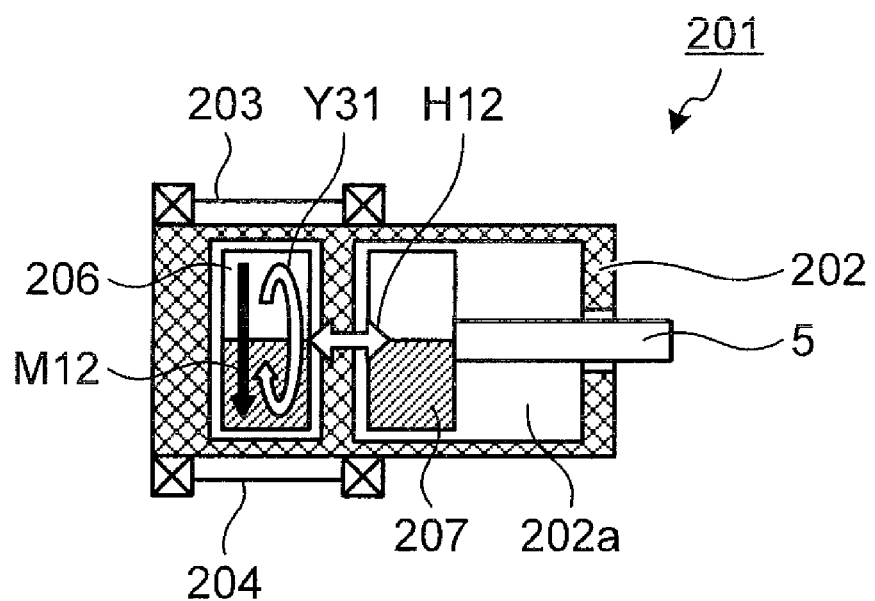
FIG. 41 shows a diagram explaining the operation of the magnetic actuator depicted in FIG. 37.
Figure 42:
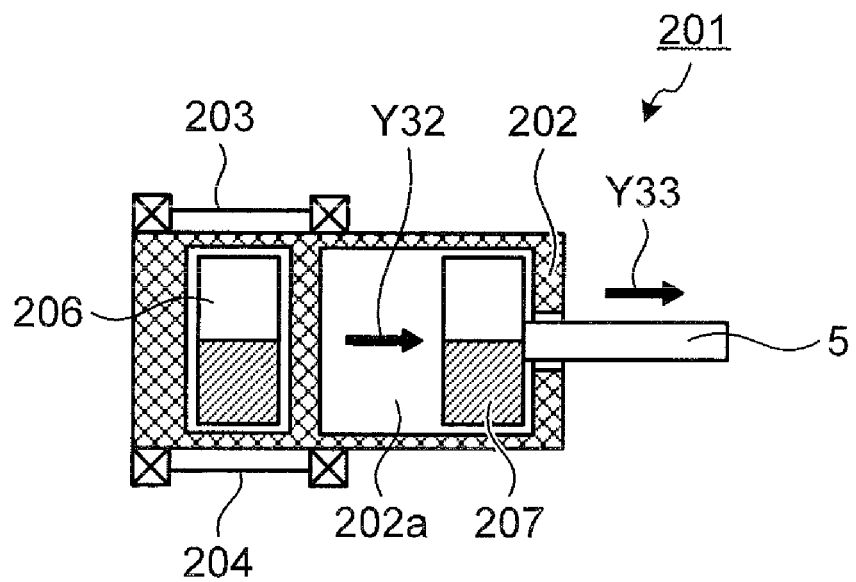
FIG. 42 shows a diagram explaining the operation of the magnetic actuator depicted in FIG. 37.

Next, with reference to FIG. 41 and FIG. 42, the operation of the magnetic actuator 201 is described. First, to turn the magnetic actuator 201 in an OFF state depicted in FIG. 40 to an ON state, as depicted in FIG. 41, the coils 203, 204 apply a magnetic field M12 oriented in a radial direction of the magnetic actuator 201 with a magnetic field strength allowing the rotating magnet 206 to rotate. As a result, with the magnetic field M12, the rotating magnet 206 rotates a half turn in a downward direction in FIG. 41 according to the magnetic-field orientation of the magnetic field M12. As a result, a repulsive force H12 occurs between the rotating magnet 206 and the moving magnet 207.

With the repulsive force H12 occurring between the moving magnet 207 and the rotating magnet 206, the moving magnet 207 moves, as indicated by an arrow Y32 in FIG. 42, in a right direction in FIG. 42 along the guiding area 202a. With the movement of the moving magnet 207 in the right direction, the moving member 5 connected to the moving magnet 207 protrudes as indicated by an arrow Y33 in FIG. 42 in a right direction in FIG. 42 from the right side surface of the magnetic actuator 201. As a result, the magnetic actuator 201 is turned to an ON state. Then, in the magnetic actuator 201, as with the magnetic actuator 1, after the moving member 5 protrudes to cause an ON state, the coils 203, 204 apply a magnetic field strength lower in strength than the magnetic field strength allowing the rotating magnet 206 to rotate and to a degree that the rotating magnet 206 does not rotate a half turn again. With this, the ON state can be kept. Furthermore, in the magnetic actuator 201, as with the magnetic actuator 1, by stopping application of the magnetic field by the coils 203, 204, the ON state can be changed to an OFF state.

As described above, according to the second embodiment, the magnetic actuator 201 is driven by using the repulsive force occurring between the rotating magnet 206 and the moving magnet 207, and therefore effects similar to those in the first embodiment can be achieved. Also, according to the second embodiment, since the moving member 5 does not rotate when the magnetic actuator 201 operates, the magnetic actuator can be applied to the case in which the moving member 5 should not be rotated. This can further improve flexibility in design. Still further, in the magnetic actuator 201, in contrast to the case of the magnetic actuator 1 in which the coils 3, 4 generating a magnetic field are disposed in the entire area corresponding to the guiding area 2a, it is enough to provide the coils 203, 204 only near the rotating magnet 206. Therefore, the coils can be downsized, and energy efficiency can further be improved.

First Modification Example

Figure 43:
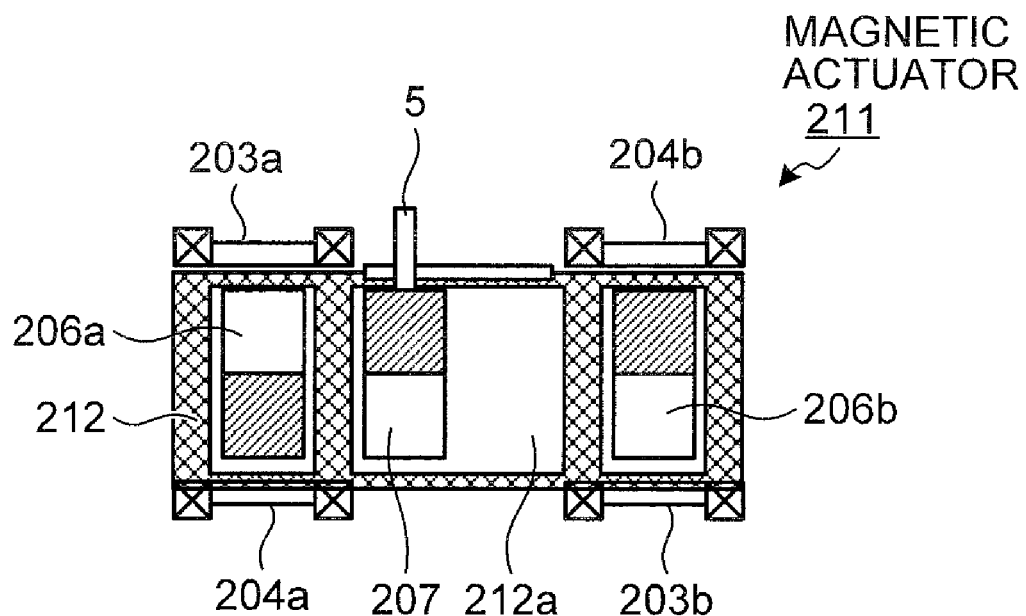
FIG. 43 shows a sectional view of a magnetic actuator according to a first modification example in the second embodiment cut along an axial direction.

Next, a first modification example in the second embodiment is described. FIG. 43 is a sectional view of a magnetic actuator according to a first modification example cut along an axial direction. As depicted in FIG. 43, a magnetic actuator 211 according to the first modification example has, in contrast to the magnetic actuator 201, two rotating magnets: a rotating magnet 206a disposed on a left side of the moving magnet 207 placed in a housing 212 with rotation being restricted and a rotating magnet 206b disposed on a right side of the moving magnet 207 with rotation being restricted. Each of these rotating magnets 206a, 206b is rotatable in a plane including each magnetization direction with respect to the housing 212. Also, outside of the housing 212, coils 203a, 204a that apply a magnetic field to the rotating magnet 206a and coils 203b, 204b that apply a magnetic field to the rotating magnet 206b are placed. The coils 203a, 204a and the coils 203b, 204b are placed, as with the coils 203, 204, so as to have a predetermined angle θ2 equal to or smaller than 60 degrees relative to a straight line lg2 indicative of the magnetization direction of the moving magnet 207. Also, in the magnetic actuator 211, in contrast to the magnetic actuator 201, the moving member 5 is connected to an end in a radial direction of the moving magnet 207, and is movable in a horizontal direction in FIG. 43 in a state of always being protruded outside of the magnetic actuator 211. The magnetic-field generation of coils 203a, 204a is controlled by a first power supply unit not shown. The magnetic-field generation of coils 203b, 204b is controlled by a second power supply unit not shown.

Figure 44:
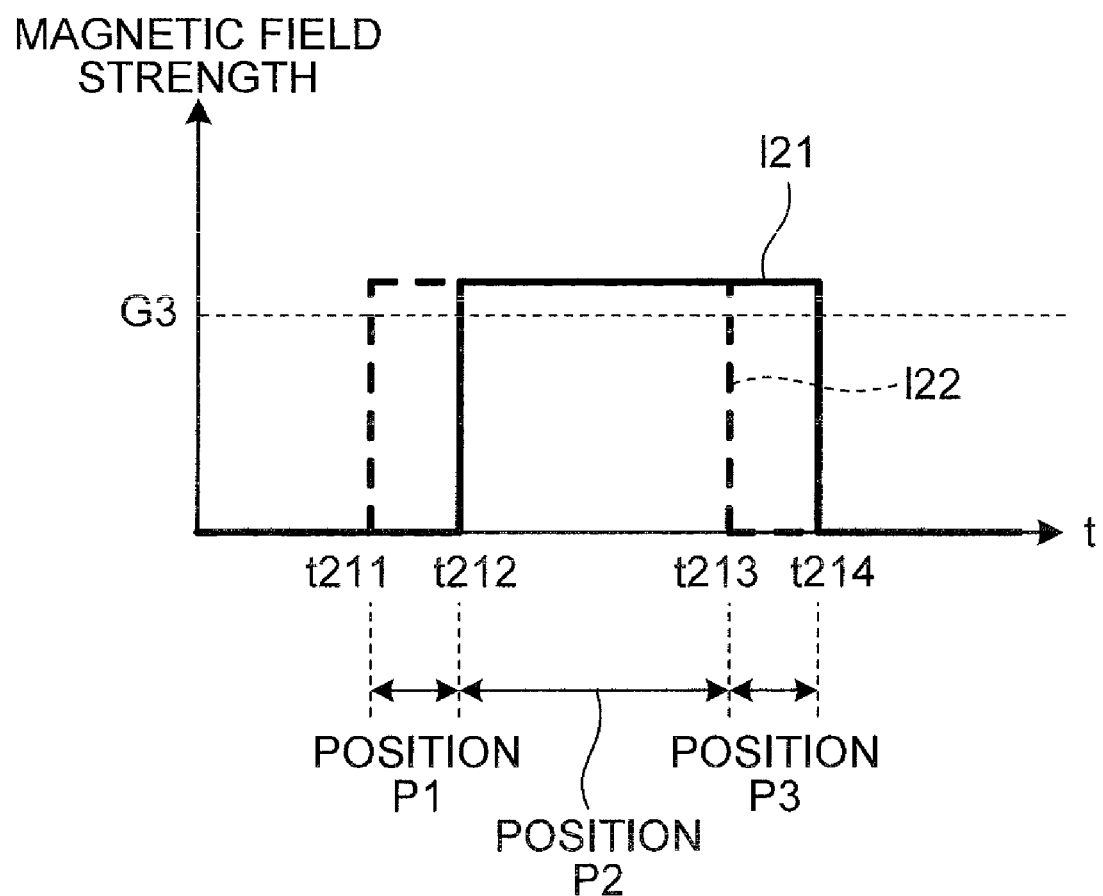
FIG. 44 shows a diagram depicting time dependency of magnetic field strengths applied by coils depicted in FIG. 43.
Figure 45:
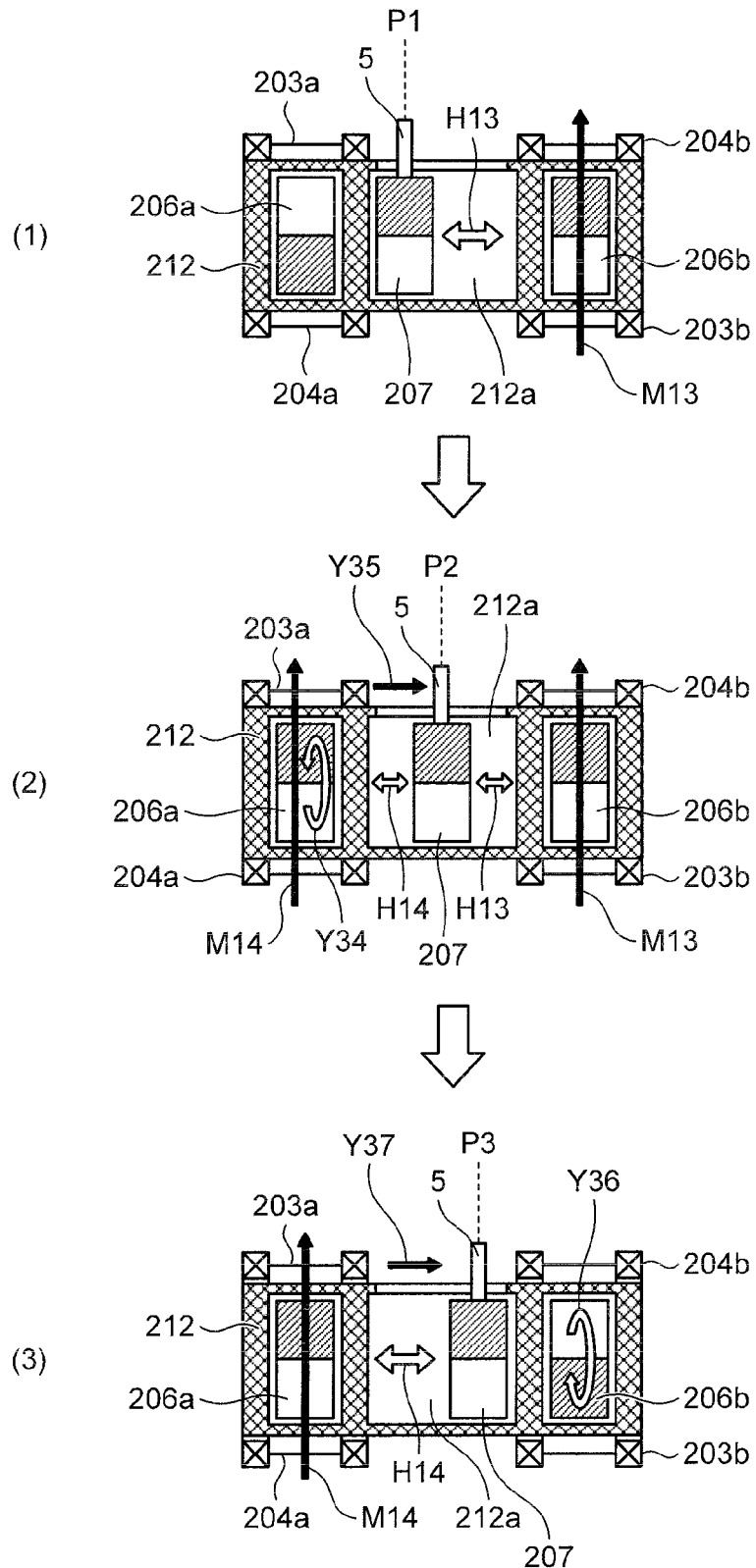
FIG. 45 shows sectional views of the magnetic actuator depicted in FIG. 43 cut along an axial direction.

Next, with reference to FIG. 44 and FIG. 45, the operation of the magnetic actuator 211 is described. FIG. 44 is a diagram depicting time dependency of magnetic field strengths applied by coils 203a, 204a, 203b, 204b, and FIG. 45 shows sectional views of the magnetic actuator 211 depicted in FIG. 43 cut along an axial direction. A curve 121 in FIG. 44 represents a magnetic field strength of a magnetic field to be applied by the coils 203a, 204a, and a curve 122 represents a magnetic field strength of a magnetic field to be applied by the coils 203b, 204b.

First, a case is described in which the moving member 5 is positioned at a position P1 depicted in FIG. 45(1). As indicated by the curve 122 in FIG. 44 and depicted in FIG. 45(1), at a time t211, the coils 203b, 204b apply to the rotating magnet 206b a magnetic field M13 that has a magnetic field strength G3 allowing the rotating magnet 206b to rotate and is oriented the same as the orientation of the magnetic field of the moving magnet 207. For this reason, the rotating magnet 206b is oriented the same as the magnetic-field orientation of the magnetic field M13 as depicted in FIG. 45(1), and a repulsive force H13 occurs between the rotating magnet 206b and the moving magnet 207. With this repulsion H13, the moving magnet 207 moves to the position P1 on a left side of the guiding area 212a. Here, since no magnetic field is applied to the rotating magnet 206a, the rotating magnet 206a rotates such that the magnetic-field orientation thereof becomes the opposite to that of the moving magnet 207. As a result, with attractive force occurring between the moving magnet 207 and the rotating magnet 206a, the moving member 5 connected to the moving magnet 207 can be stably positioned, as depicted in FIG. 45(1), at the position P1 on the left side of the guiding area 212a. As described above, to move the moving member 5 to the position P1 on the left side of the guiding area 212a, the coils 203b, 204b are caused to generate a magnetic field with a predetermined strength.

Next, a case is described in which the moving member 5 is moved to a position P2 depicted in FIG. 45(2). As indicated by the curve 121 in FIG. 44 and depicted in FIG. 45(2), at a time t212, the coils 203a, 204a apply to the rotating magnet 206a a magnetic field M14 equal to or greater than the magnetic field strength G3 allowing the rotating magnet 206a to rotate and is oriented the same as the orientation of the magnetic field of the moving magnet 207. For this reason, the rotating magnet 206a is oriented the same as the magnetic-field orientation of the magnetic field M14 as depicted in FIG. 45(2), and a repulsive force H14 occurs between the rotating magnet 206a and the moving magnet 207. With this repulsion H14, the moving magnet 207 moves in a direction of an arrow Y35 depicted in FIG. 45(2). Furthermore, as depicted in FIG. 44 and FIG. 45(2), since the application of the magnetic field in the coils 203b, 204b continues, the moving member 5 connected to the moving magnet 207 can be positioned at the position P2 at the center of the guiding area 212a with both of the repulsion H14 with the rotating magnet 206a and the repulsive force H13 with the rotating magnet 206b. In this way, to move the moving member 5 to the position P2 at the center of the guiding area 212a, both of the coils 203a, 204a and the coils 203b, 204b are caused to generate a magnetic field with a predetermined strength.

Next, a case is described in which the moving member 5 is positioned at a position P3 depicted in FIG. 45(3). As indicated by the curve 122 in FIG. 44 and depicted in FIG. 45(3), at a time t213, the application of the magnetic field by the coils 203b, 204b is stopped. For this reason, only the rotating magnet 206a is applied with the magnetic field M14 equal to or greater than the magnetic field strength G3 allowing the rotating magnet 206b to rotate and oriented the same as the orientation of the magnetic field of the moving magnet 207. Therefore, as depicted in FIG. 45(3), since the rotating magnet 206a keeps the same orientation as the magnetic-field orientation of the moving magnet 207, the repulsive force H14 between the rotating magnet 206a and the moving magnet 207 remains. As a result, with this repulsive force H14, the moving magnet 207 moves to the position P3 on a right side of the guiding area 212a (refer to an arrow Y37 in FIG. 45(3)). Note that since no magnetic field is applied to the rotating magnet 206b, the rotating magnet 206b rotates such that magnetic-field orientation thereof is opposite to that of the moving magnet 207 (refer to an arrow Y36 in FIG. 45(3)). As a result, with an attractive force occurring between the moving magnet 207 and the rotating magnet 206b, the moving member 5 connected to the moving magnet 207 can be stably positioned, as depicted in FIG. 45(3), at the position P3 on the right side of the guiding area 212a. In this way, to move the moving member 5 to the position P3 on the right side of the guiding area 212a, the coils 203a, 204a are caused to generate a magnetic field with a predetermined strength.

As described above, according to the first modification example, by controlling magnetic-field generation in each coil, three types of position of the moving member 5 can be controlled. With this, a further complex control can be performed on a driven device.

Second Modification Example

Figure 46:
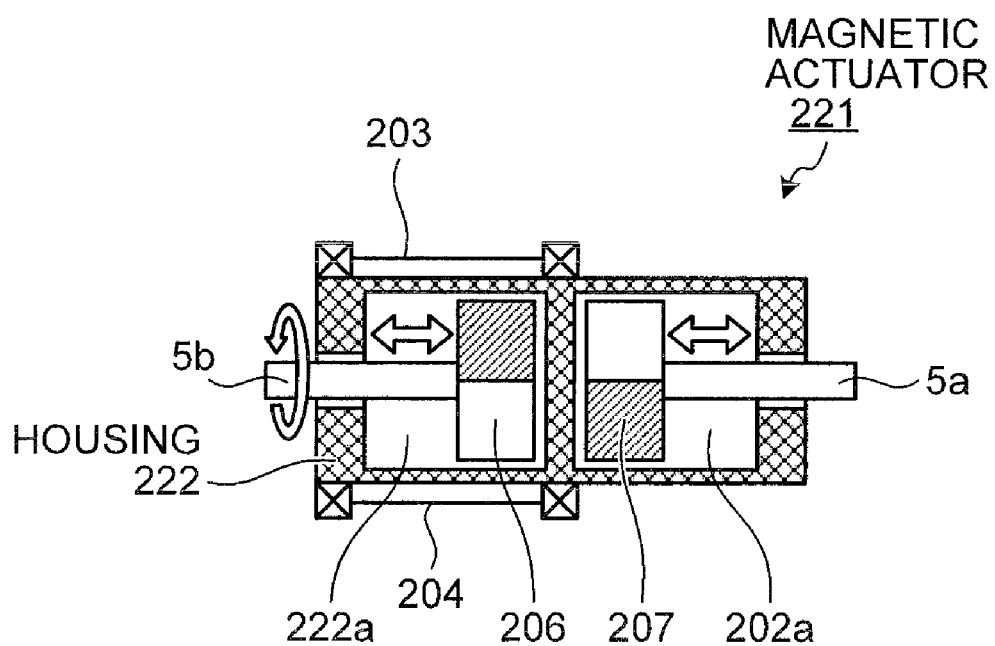
FIG. 46 shows a sectional view of a magnetic actuator according to a second modification example in the second embodiment cut along an axial direction.

Next, a second modification example in the second embodiment is described. FIG. 46 is a sectional view of a magnetic actuator according to the second modification example cut along an axial direction. As depicted in FIG. 46, a magnetic actuator 221 according to the second embodiment has, in contrast to the magnetic actuator 201, a guiding area 222a in a housing 222 in which a rotating magnet 206 is placed. This guiding area 222a regulates the direction of the rotating magnet 206 relatively moving with a repulsive force occurring between the rotating magnet 206 and the moving magnet 207. For this reason, the rotating magnet 206 is movable in an axial direction of the magnetic actuator 221. The magnetic actuator 221 further includes, in addition to the moving member 5a connected to the moving magnet 207, a moving member 5b connected to the rotating magnet 206. The moving member 5b rotates according to the rotation of the rotating magnet 206.

Figure 47:
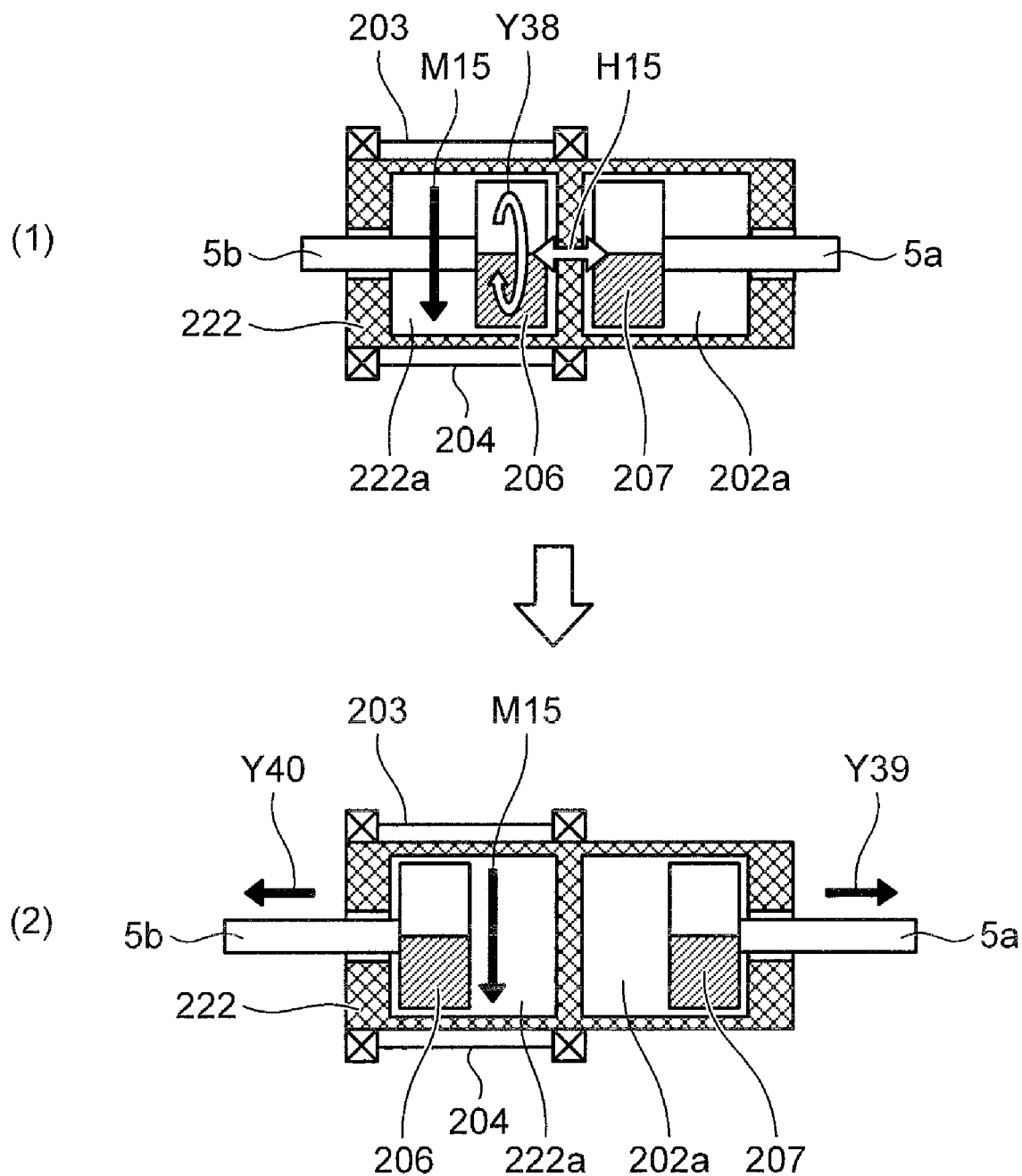
FIG. 47 shows diagrams explaining the operation of the magnetic actuator depicted in FIG. 46.

Next, with reference to FIG. 47, the operation of the magnetic actuator 221 is described. As depicted in FIG. 47(1), the coils 203, 204 apply to the rotating magnet 206 a magnetic field M15 that has a magnetic field strength allowing the rotating magnet 206 to rotate and is oriented the same as the orientation of the magnetic field of the moving magnet. In this case, the rotating magnet 206 rotates, as indicated by an arrow Y38 in FIG. 47(1), a half turn in a downward direction in FIG. 47(1) according to the magnetic field M15. As a result, a repulsive force H15 occurs between the rotating magnet 206 and the moving magnet 207. Then, with the occurring repulsive force H15, the moving magnet 207 moves, as indicated by an arrow Y39 in FIG. 47(2), in a right direction in FIG. 47(2) along the guiding area 202a and, according to the movement of the moving magnet 207 in the right direction, the moving member 5a protrudes in the right direction in FIG. 47(2). Also, with the occurring repulsive force H15, the rotating magnet 206 moves, as indicated by an arrow Y40 in FIG. 47(2), in a left direction in FIG. 47(2) along the guiding area 222a and, according to the movement of the rotating magnet 206, the moving member 5b protrudes in the left direction in FIG. 47(2).

As described above, according to the second modification example, by providing the guiding area 222a also for the rotating magnet 206, simultaneous driving in two directions by the moving members can be achieved. With this, compared with the magnetic actuator 201, space can be saved.

Third Embodiment

Figure 48:
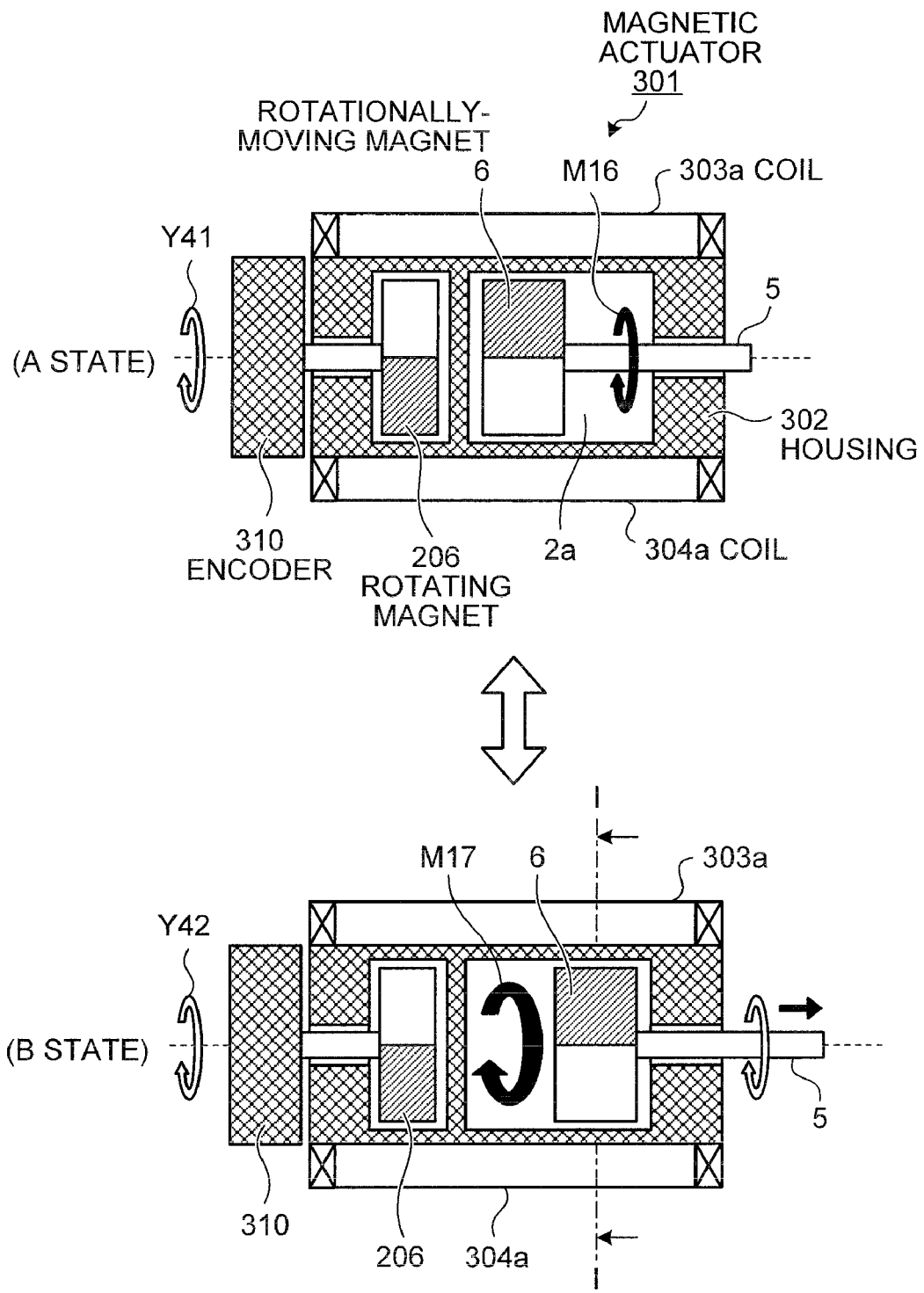
FIG. 48 shows sectional views of a magnetic actuator according to a third embodiment cut along an axial direction.
Figure 49:
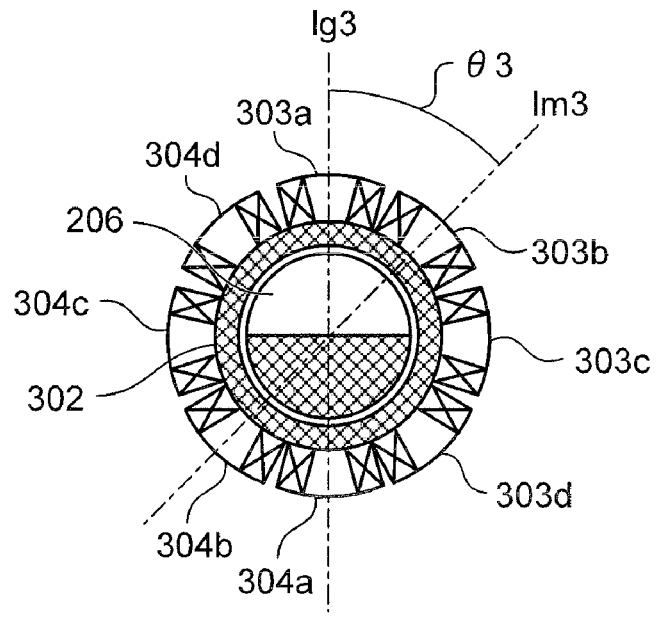
FIG. 49 shows a sectional view of the magnetic actuator depicted in FIG. 48 cut along an I-I line in a radial direction.

Next a third embodiment is described. FIG. 48 shows sectional views of a magnetic actuator according to the third embodiment cut along an axial direction. FIG. 49 is a sectional view of the magnetic actuator depicted in FIG. 48 cut along an I-I line in a radial direction.

As depicted in FIG. 48, a magnetic actuator 301 according to the third embodiment has a rotationally-moving magnet 6 and a rotating magnet 206 that is rotatable. The rotationally-moving magnet 6 is placed in a guiding area 2a for rotation, and is movable in an axial direction of the magnetic actuator 301 in the guiding area 2a. Each of the rotating magnet 206 and the rotationally-moving magnet 6 is rotatable in a plane including a magnetization direction with respect to a housing 302. Also, the rotating magnet 206 is connected to an encoder 310. The encoder 310 rotates according to the rotating operation of the rotating magnet 206. Also, the rotationally-moving magnet 6 is larger in size compared with the rotating magnet 206. In other words, the rotating magnet 206 and the rotationally-moving magnet 6 have different magnetic field strengths. For this reason, the rotationally-moving magnet 6 becomes rotatable by being applied with a magnetic field with a magnetic field strength stronger than a magnetic field strength allowing the rotating magnet 206 to rotate.

As depicted in FIG. 49, the magnetic actuator 301 has four sets of coils: coils 303a, 304a; coils 303b, 304b; coils 303c, 304c; and coils 303d, 304d. Each set of coils sequentially generates a magnetic field to the rotationally-moving magnet 6 and the guiding area 2a. With this, plural magnetic fields can be generated in planes where the rotationally-moving magnet 6 and the rotating magnet 206 are rotatable, and a rotating magnetic field rotating about the central axis of the magnetic actuator 301 can be applied. In the magnetic actuator 301, by changing the magnetic field strength of the magnetic field to be applied to the magnetic actuator 301, the rotating magnet 206 can be caused to rotate in either one of an A state depicted in an upper portion of FIG. 48 and a B state depicted in a lower portion of FIG. 48 to rotate the encoder 310.

Figure 50:
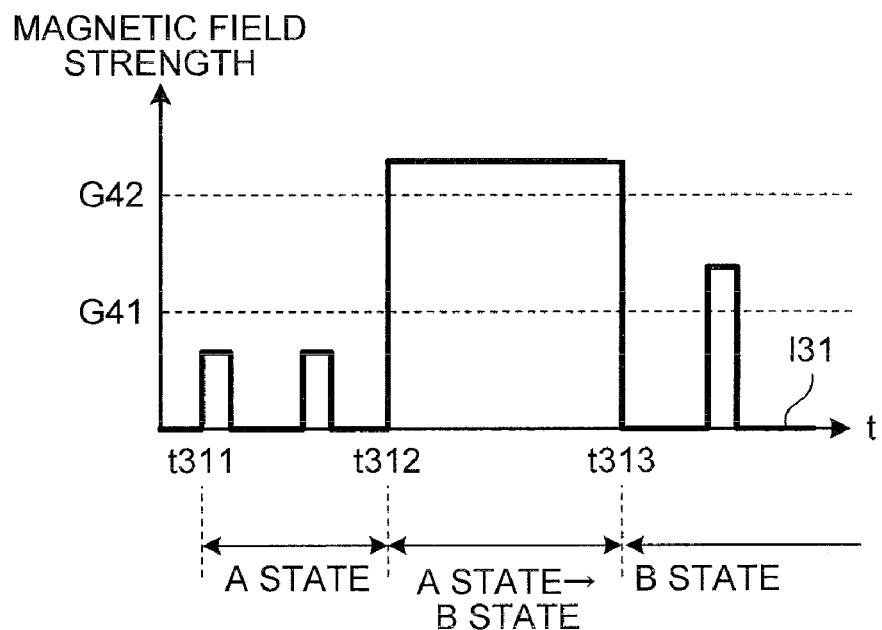
FIG. 50 shows a diagram depicting time dependency of the magnetic field strength applied by coils depicted in FIG. 48.
Figure 51:
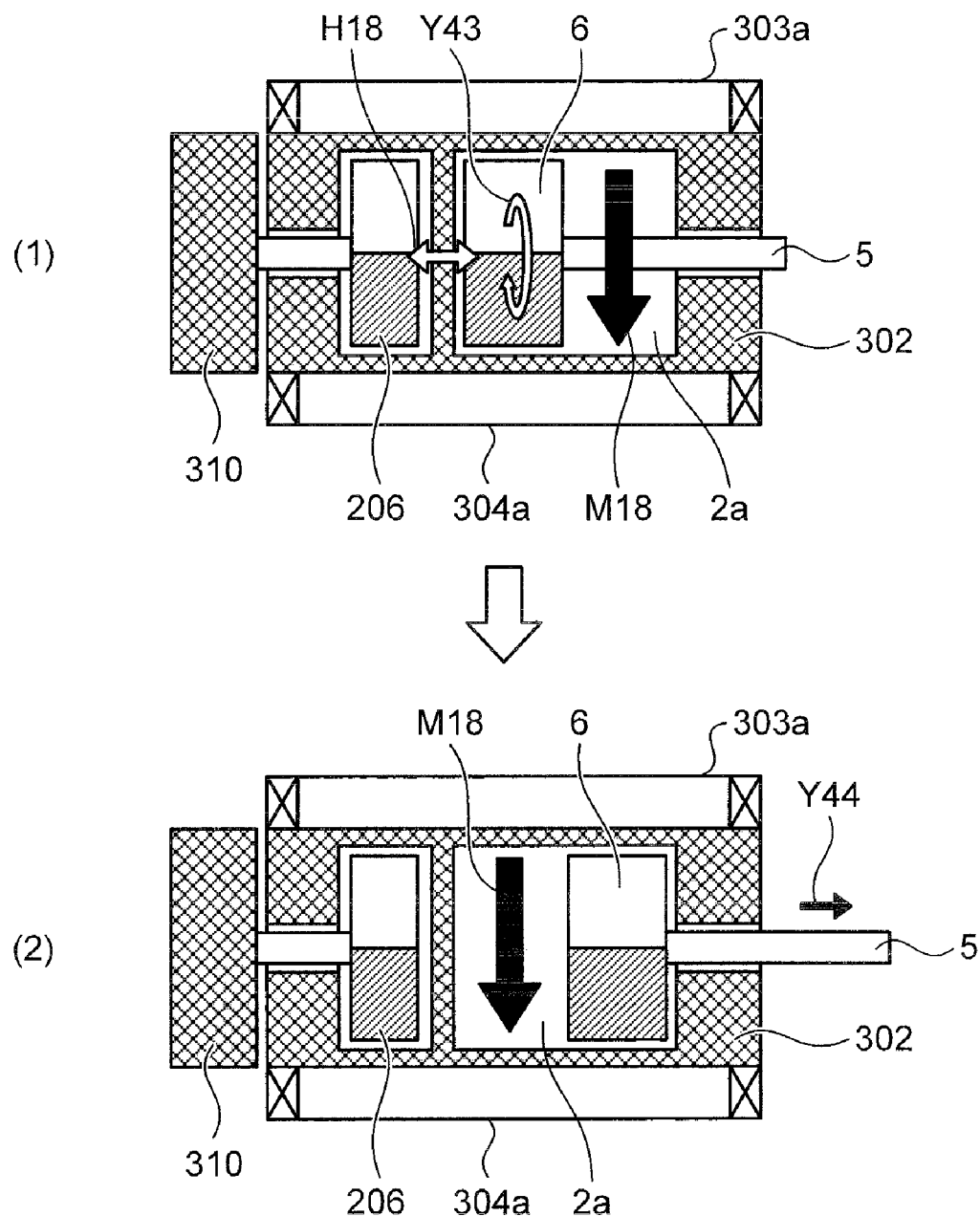
FIG. 51 shows sectional views of the magnetic actuator depicted in FIG. 48 cut along an axial direction.

Next, with reference to FIG. 50 and FIG. 51 together with FIG. 48 and FIG. 49, the operation of the magnetic actuator 301 is described. A curve 131 in FIG. 50 depicts time dependency of the magnetic field to be applied by the coils 303a, 304 out of the coils 303a, 304a, the coils 303b, 304b, the coils 303c, 304c, and the coils 303d, 304d. FIG. 51 shows sectional views of the magnetic actuator 301 cut along an axial direction at times t312 to t313 depicted in FIG. 50.

First, at times t311 to t312 in FIG. 50, as indicated by the curve 131, each set of coils 303a, 304a, coils 303b, 304b, coils 303c, 304c, and coils 303d, 304d is caused to sequentially generate a magnetic field with the magnetic field strength below a magnetic field strength G41 for application of a rotating magnetic field M16 to the magnetic actuator 301. In this case, since the magnetic field strength of the rotating magnetic field M16 to be applied is weak, the rotating magnet 206 and the rotationally-moving magnet 6 integrally rotate via a partition with mutual attractive force. As a result, as indicated by an arrow Y41 in the upper portion of FIG. 48, the encoder 310 connected to the rotating magnet 206 rotates according to the rotation of the rotating magnet 206.

Next, to protrude the moving member 5 to turn the magnetic actuator 301 to an ON state, the magnetization direction of the rotationally-moving magnet 6 and the rotating magnet 206 is detected and, as with the first embodiment, a strong magnetic field is generated so as to form an angular difference within 60 degrees with each detected magnetization direction. For example, when the detected magnetization direction is a straight line lm3 depicted in FIG. 49, the coils 303a, 304a corresponding to a straight line lg3 having an angle Θ3 within 60 degrees relative to this straight line lm3 generate a strong magnetic field. In this case, after it is detected depending on the presence or absence of rotation of the encoder 310 whether the rotating magnet 206 rotates, a magnetic field for protruding the moving member 5 is applied. At the time t312 in FIG. 50, as depicted in FIG. 51(1), the coils 303a, 304a apply in a radial direction in the guiding area 2a a magnetic field M18 with a magnetic field strength exceeding at least a magnetic field strength G42 with which the rotationally-moving magnet 6 is fixed to the same orientation as the orientation of the applied magnetic field. In this case, the rotationally-moving magnet 6 rotates, as indicated by an arrow Y43 in FIG. 51(1), so that the magnetic field is oriented in a downward direction in FIG. 51(1), according to the orientation of the magnetic field M18. As a result, a repulsive force H18 occurs between the rotationally-moving magnet 6 and the rotating magnet 206.

With this repulsive force H18, the rotationally-moving magnet 6 and the rotating magnet 206 repel against each other and, as indicated by an arrow Y44 in FIG. 51(2), the rotationally-moving magnet 6 moves in a right direction in FIG. 51(2) along the guiding area 2a. In this case, also according to the movement of the rotationally-moving magnet 6, the moving member 5 is protruded outside of the housing 302 of the magnetic actuator 301, thereby causing the magnetic actuator 301 to be in an ON state.

Furthermore, a case is described in which the moving member 5 is rotated while the magnetic actuator 301 is kept in an ON state. In this case, at the time t313 in FIG. 50, as depicted in a lower portion of FIG. 48, each set of the coils 303a, 304a, the coils 303b, 304b, the coils 303c, 304c, and the coils 303d, 304d is caused to sequentially generate a magnetic field with a magnetic field strength exceeding the magnetic field strength G41 to apply a rotating magnetic field M17 to the magnetic actuator 301. This magnetic field strength G41 is a threshold for changing to the A state depicted in an upper portion of FIG. 48. By continuously applying this rotating magnetic field M17 with the magnetic field strength exceeding the magnetic field strength G41, the B state depicted in the lower portion of FIG. 48 can be kept. As indicated by an arrow Y42 in the lower portion of FIG. 48, the moving member 5 can be rotated with the magnetic actuator 301 being in an ON state. Also, with the application of the rotating magnetic field M17, the rotating magnet 206 also rotates. Therefore, by detecting the rotation of the encoder 310 connected to the rotating magnet 206, it can be determined whether the rotating operation of the moving member 5 is being normally performed.

As described above, according to the third embodiment, by connecting the encoder 310 to the rotating magnet 206, two types of operation, a rotating operation of the encoder 310 and an operation of protruding the moving member 5, can be performed. With this, a further complex control can be performed on a driving device.

First Modification Example

Figure 52:
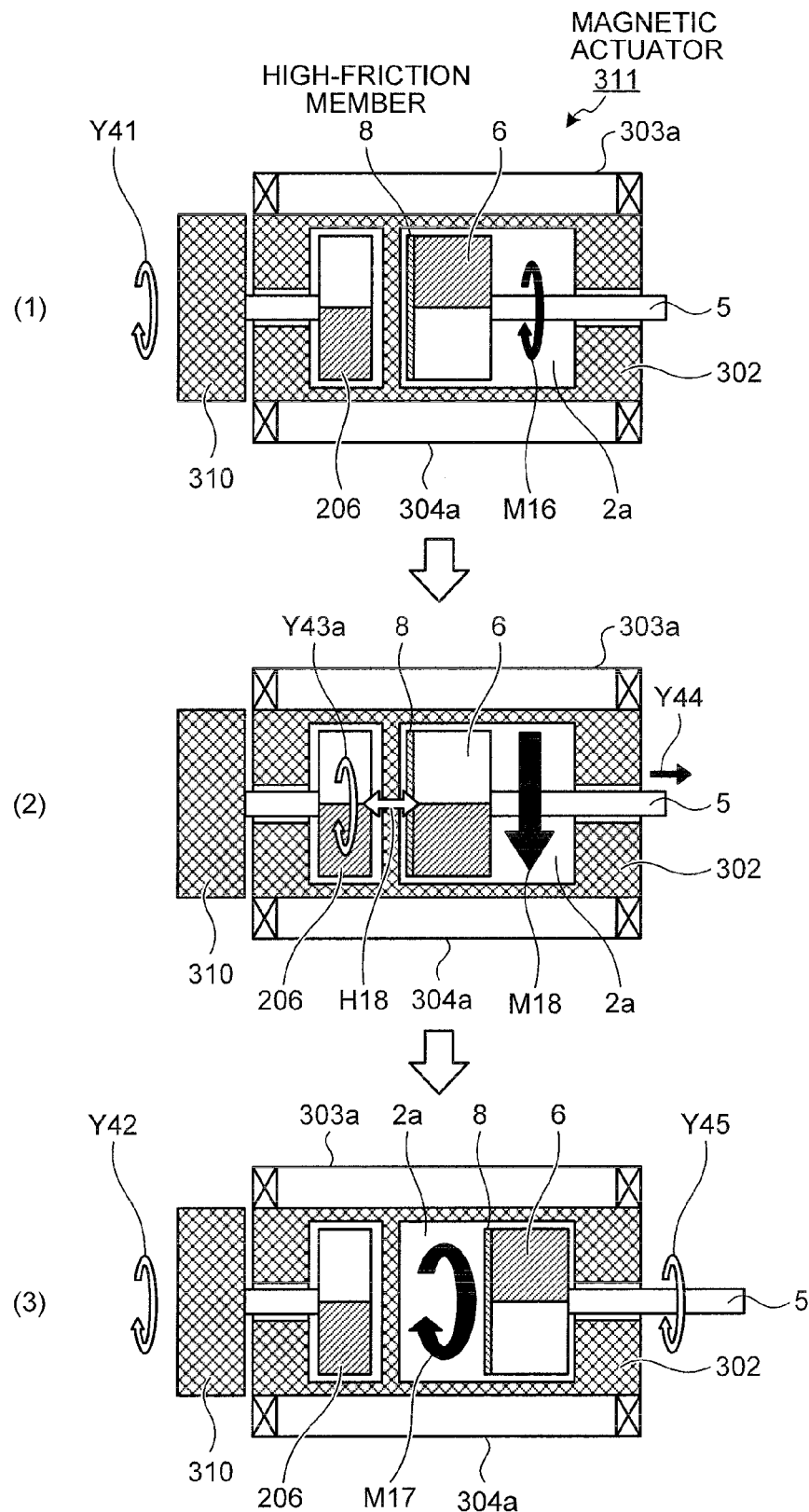
FIG. 52 shows sectional views of a magnetic actuator according to a first modification example in the third embodiment cut along an axial direction.

Next, a first modification example in the third embodiment is described. FIG. 52 shows sectional views of a magnetic actuator according to the first modification example cut along an axial direction. As depicted in FIG. 52, a magnetic actuator 311 according to the first modification example has, in contrast to the magnetic actuator 301, a configuration in which a high-friction member 8 is provided on a surface of the rotationally-moving magnet 6 on a rotating magnet 206 side. When making contact with the partition on the rotating magnet 206 side, the rotation of the rotationally-moving magnet 6 is restrained by the high-friction member 8.

For this reason, as depicted in FIG. 52(1), even when a rotating magnetic field M16 is applied, the rotationally-moving magnet 6 does not rotate. As depicted in FIG. 52(2), with a magnetic field M18, which is a strong magnetic field, being applied, the rotating magnet 206 rotates as indicated by an arrow Y43a according to the magnetic-field orientation of the magnetic field M18, causing the magnetic-field orientation of the rotationally-moving magnet 6 and the magnetic-field orientation of the rotating magnet 206 to be matched. As a result, a repulsive force H18 occurs between the rotationally-moving magnet 6 and the rotating magnet 206 and, as depicted in FIG. 52(3), with the repulsive force H18, the rotationally-moving magnet 6 moves away from the partition on the rotating magnet 206 side to move in a right direction in FIG. 52(3), thereby causing the magnetic actuator 311 to be in an ON state. In this case, since the high-friction member 8 on the surface of the rotationally-moving magnet 6 moves away from the partition on the rotating magnet 206 side, the restraint of the rotation of the rotationally-moving magnet 6 is released to become rotatable. As a result, as depicted in FIG. 52(3), with the rotating magnetic field M17 being applied, the rotationally-moving magnet 6 rotates together with the rotating magnet 206 in a direction, for example, indicated by an arrow Y45 in FIG. 52(3).

As described above, according to the first modification example, with the high-friction member 8 provided to the rotationally-moving magnet 6 on the rotating magnet 206 side, the rotationally-moving magnet 6 can be rotated only when the moving member 5 is protruded to cause the magnetic actuator 311 to be in an ON state.

Figure 53:
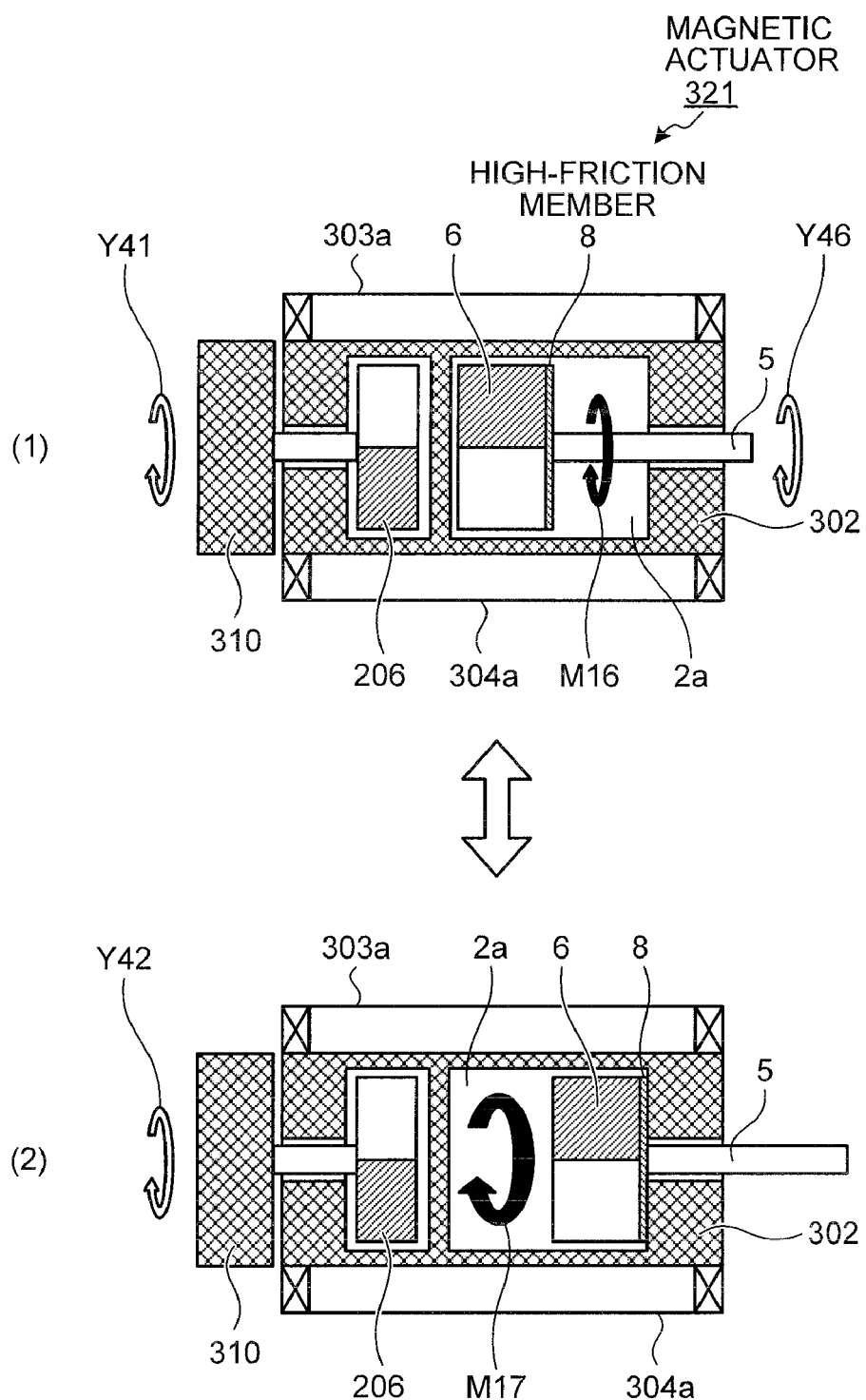
FIG. 53 shows drawings depicting another configuration of the magnetic actuator depicted in FIG. 52.

Also, as depicted in a magnetic actuator 321 of FIG. 53, in the rotationally-moving magnet 6, the high-friction member 8 may be provided on a surface on a side opposite to the rotating magnet 206 side. As depicted in FIG. 53(1), when the rotating magnetic field M16 is applied, the rotationally-moving magnet 6 is positioned on the rotating magnet 206 side, and therefore the high-friction member 8 does not make contact with other members. In this case, since the rotation of the rotationally-moving magnet 6 is not restrained by the high-friction member 8, as indicated by an arrow Y46, the rotationally-moving magnet 6 is rotatable similarly to the rotating magnet 206 rotating as indicated by the arrow Y41. On the other hand, as depicted in FIG. 53(2), when the magnetic actuator 321 is in an ON state, that is, when the moving member 5 is in a state of being protruded outside of the housing 302 of the magnetic actuator 321, the high-friction member 8 on the rotationally-moving magnet 6 and the inner surface of the housing 302 are in a contact state. In this case, when the rotating magnetic field M17 is applied to the magnetic actuator 321, the rotation of the rotationally-moving magnet 6 is restrained, and only the rotating magnet 206 rotates as indicated by an arrow Y42.

According to the magnetic actuator 321, the high-friction member 8 is provided to the rotationally-moving magnet 6 on a side opposite to the rotating magnet 206 side. With this, the rotationally-moving magnet 6 can be rotated only when the moving member 5 is drawn toward the inside of the housing 302 of the magnetic actuator 321 to cause the magnetic actuator 321 to be in an OFF state. In this way, in the situation where the rotationally-moving magnet 6 is in a state of receiving either one of an attractive force and a repulsive force from the rotating magnet 206, the operation with the rotation of the rotationally-moving magnet 6 restrained can be achieved by providing the high-friction member in the guiding area 2a, the high-friction member restraining the rotation of the rotationally-moving magnet 6 in a plane including the magnetization direction of the rotationally-moving magnet 6 relative to the housing.

Fourth Embodiment

Next, a fourth embodiment is described. While the magnetic actuator main body has been described in the first to third embodiments, a case is specifically described in the fourth embodiment in which the magnetic actuator described in the first to third embodiments is applied to a capsule endoscope insertable into a subject to perform medical activities in the subject.

Figure 54:
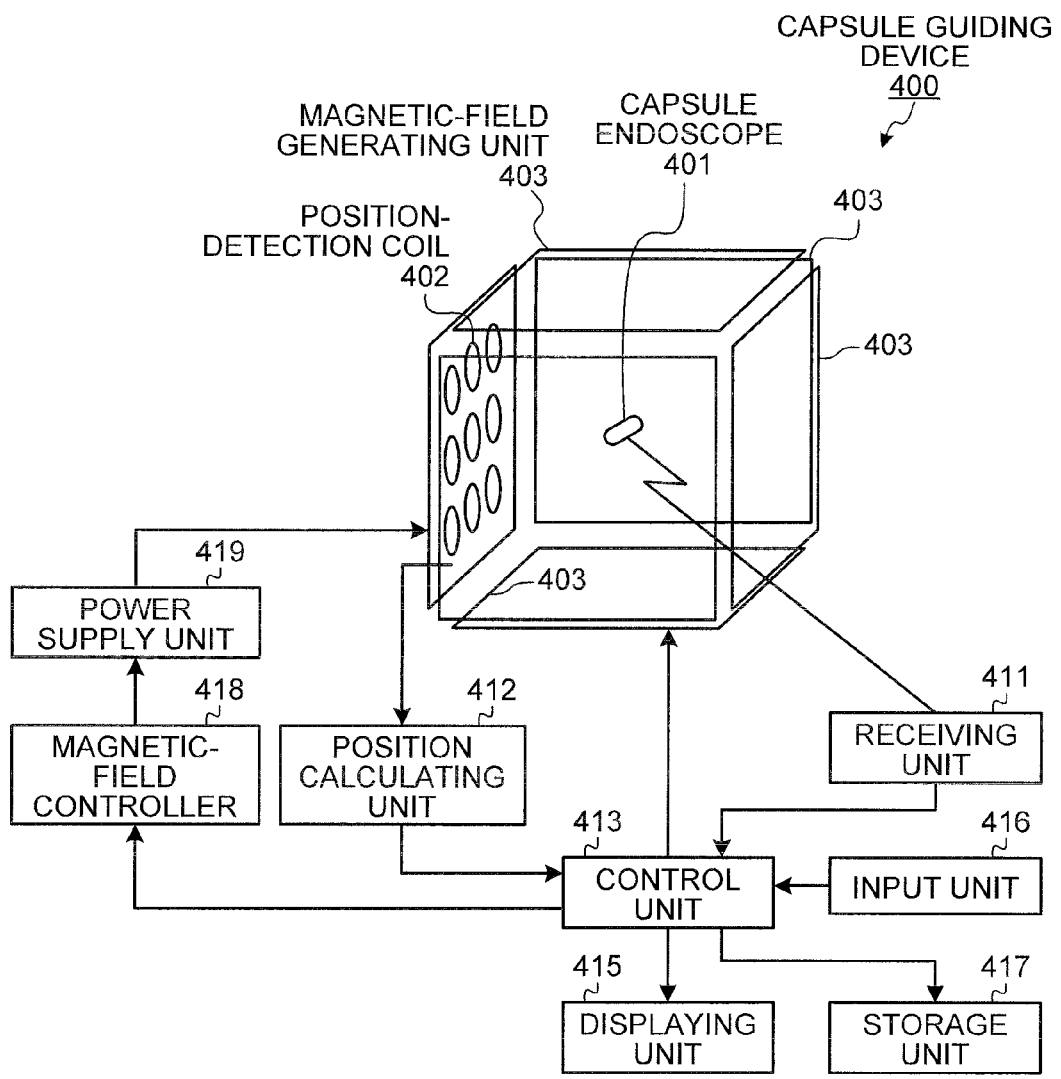
FIG. 54 shows a schematic diagram depicting the configuration of a capsule guiding system according to a fourth embodiment.

FIG. 54 is a schematic diagram depicting the configuration of a capsule guiding system in the fourth embodiment. As depicted in FIG. 54, a capsule guiding system 400 in the fourth embodiment has: a capsule endoscope 401 of a capsule type that is inserted into a body cavity in a subject by being swallowed from the mouse of the subject to communicate with an external device; a position-detection coil 402 fixedly disposed in a matrix manner; a magnetic-field generating unit 403 provided around the subject and capable of generating a three-dimensional rotating magnetic field; a receiving unit 411 that receives a signal corresponding to each piece of information including image information transmitted from the capsule endoscope 401; a position calculating unit 412 that calculates and detects the position and posture of the capsule endoscope 401 with respect to the magnetic-field generating unit 403 based on a voltage induced by the position-detection coil 402; a control unit 413 that controls each component of the capsule guiding system 400; a display unit 415 that displays and outputs an image captured by the capsule endoscope 401; an input unit 416 that inputs instruction information for making various operation instructions in the capsule guiding system 400 to the control unit 413; a storage unit 417 that has stored therein the information about the image captured by the capsule endoscope 401 and the position information of the capsule endoscope 401 calculated by the position calculating unit 412; a magnetic-field controller 418 that controls magnetic fields associated with the position-detection coil 402 and the magnetic-field generating unit 403; and a power supply unit 419 that supplies power according to the control of the magnetic-field controller 418 to the position-detection coil 402 and the magnetic-field generating unit 403.

Figure 55:
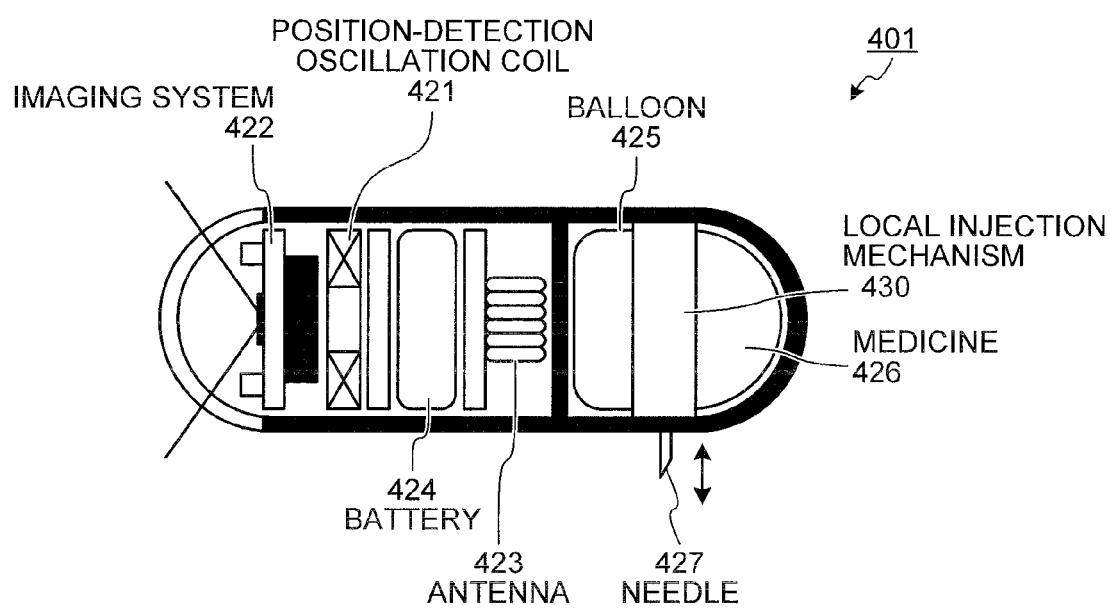
FIG. 55 shows a schematic diagram depicting the inner structure of a capsule endoscope depicted in FIG. 54.

Next, the capsule endoscope 401 according to the fourth embodiment is described. FIG. 55 is a schematic diagram depicting the inner structure of the capsule endoscope 401 depicted in FIG. 54. As depicted in FIG. 55, the capsule endoscope 401 includes: a position-detection oscillation coil 421 that produces a magnetic field for position detection; an imaging system 422 that captures the inside of a predetermined body cavity for position detection; an antenna 423 that transmits a predetermined signal to the receiving unit 411; a battery 424 that supplies power to each component of the capsule endoscope 401; a balloon 425 that preserves a medicine 426; a needle 427 for an injection of the medicine 426 preserved in the balloon 425 into a desired region in the subject; and a local injection mechanism 430 that controls the injection of the medicine by the needle 427. Here, in the local injection mechanism 430, the magnetic actuator 1 described in the first embodiment is applied.

Figure 56:
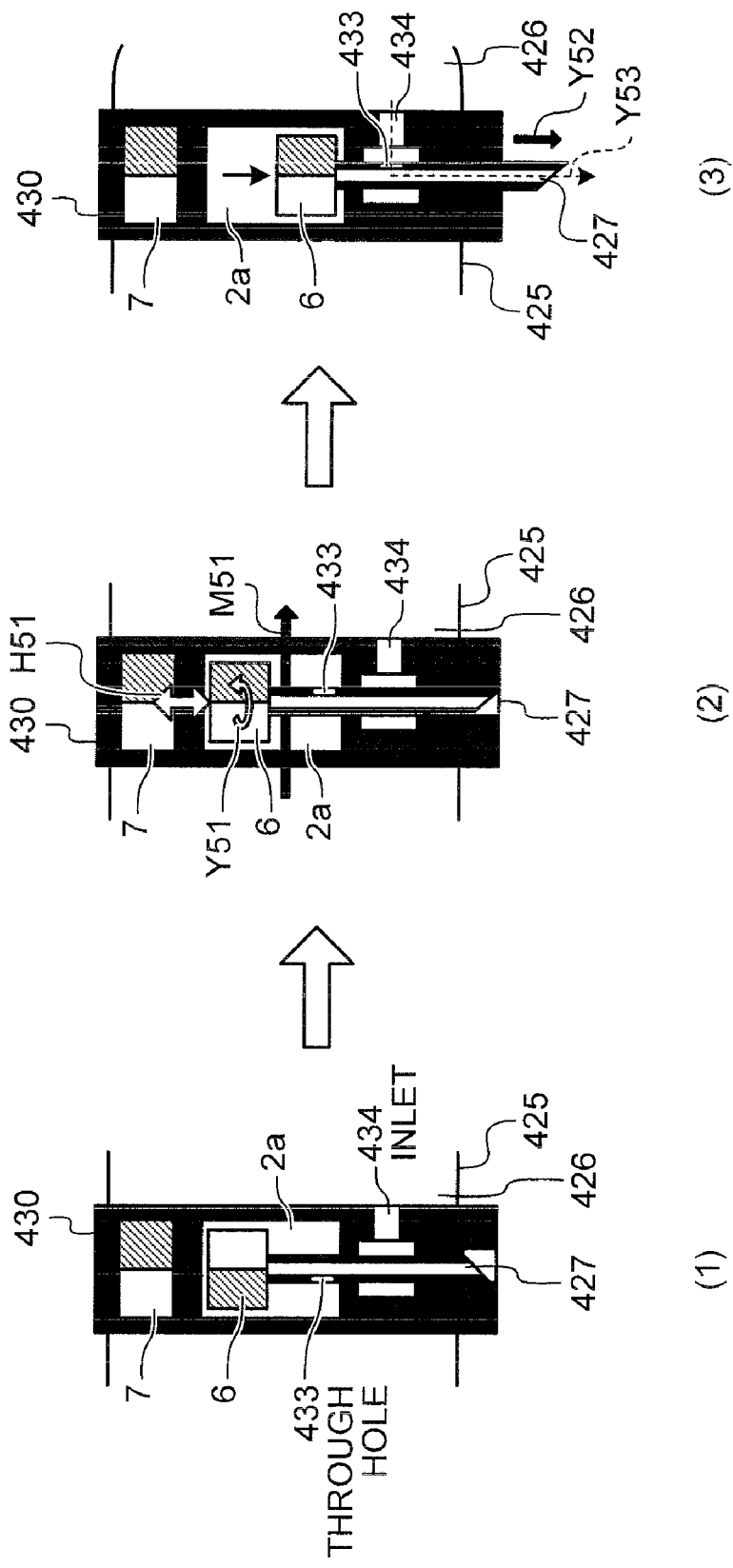
FIG. 56 shows diagrams explaining a local injection mechanism depicted in FIG. 55.

Next, with reference to FIG. 56(1), the local injection mechanism 430 is described. The local injection mechanism 430, having an approximately cylindrical shape has, as depicted in FIG. 56, a rotationally-moving magnet 6, a fixed magnet 7 disposed such that a magnetization direction thereof is in a radial direction relative to the local injection mechanism 430, and the needle 427 having a through hole 433 communicated to an inlet 434 from which the medicine in the balloon 425 is injected when the needle protrudes. The rotationally-moving magnet 6 is rotatable in a radial direction of the local injection mechanism 430, and is movable in a vertical direction inside a guiding area 2a, which is a hollow area provided in the local injection mechanism 430. The fixed magnet 7 is disposed so as to have a magnetic field oriented the same as the radial direction of the local injection mechanism 430. The needle 427 is connected to a lower end of the rotationally-moving magnet 6, and moves in a vertical direction in FIG. 56 according to the movement of the rotationally-moving magnet 6 in the vertical direction in FIG. 56. Also, the local injection mechanism 430 is different from the magnetic actuator 1 in that the magnetic-field generating unit 403 that generates a magnetic field allowing the rotationally-moving magnet 6 to rotate is placed outside of the subject swallowing the capsule endoscope 401 provided with the local injection mechanism 430. Furthermore, the housing 2 of the magnetic actuator 1 corresponds to the main body of the capsule endoscope 401 insertable into a subject to perform medical activities in the subject. Note that since the capsule endoscope 401 moves the body cavity in the subject, the relative position with respect to the magnetic-field generating unit 403 placed outside of the subject can be changed. Since being able to generate a three-dimensional rotating magnetic field under the control of the magnetic-field controller 418, the magnetic-field generating unit 403 can generate magnetic fields in plural directions.

With reference to FIG. 56, the operation of the local injection mechanism 430 is described. In the capsule guiding system 400, when an operator finds a lesion in image information transmitted from the capsule endoscope 401, the operator operates the input unit 416 to make an instruction for injecting the medicine into the lesion part. In this case, in the capsule guiding system 400, power is supplied by the power supply unit 419 to the magnetic-field generating unit 403 under the control of the magnetic-field controller 418, thereby causing a magnetic field M51 to be generated from the magnetic-field generating unit 403. That is, as depicted in FIG. 56(1), to the capsule endoscope 401 with the needle 427 being accommodated in the local injection mechanism 430, the magnetic field M51 depicted in FIG. 56(2) is generated from the magnetic-field generating unit 403. Also, the magnetic-field generating unit 403 generates the magnetic field M51 having an angular difference equal to or smaller than 60 degrees with respect to a magnetization direction of the fixed magnet 7 in the capsule endoscope 401 calculated by the position calculating unit 412. This magnetic field M51 has a magnetic field strength allowing the rotationally-moving magnet 6 to rotate and has an angular difference equal to or smaller than 60 degrees with respect to the right direction of the capsule endoscope 401 in FIG. 56(2).

For this reason, as indicated by an arrow Y51 in FIG. 56(2), the rotationally-moving magnet 6 rotates a half turn in the right direction in FIG. 56(2) according to the magnetic-field orientation of the magnetic field M51. With the rotationally-moving magnet 6 rotating a half turn, the through hole 433 positioned on a left side of the central axis of the local injection mechanism 430 is positioned on a right side of the central axis of the local injection mechanism 430. Then, as depicted in FIG. 56(2), a repulsive force H51 occurs between the rotationally-moving magnet 6 and the fixed magnet 7, and the rotationally-moving magnet 6 moves, as depicted in FIG. 56(3), in a downward direction in FIG. 56(3) along the guiding area 2a. Accordingly, as indicated by an arrow Y52 in FIG. 56(3), the needle 427 connected to the rotationally-moving magnet 6 also moves in the downward direction in FIG. 56(3). With the movement of the needle 427 in the downward direction, the through hole 433 positioned on the right side of the central axis of the local injection mechanism 430 also moves in the downward direction to connect to the inlet 434. As a result, as indicated by an arrow Y53 in FIG. 56(3), the medicine 426 in the balloon 425 is injected via the inlet 434 and the through hole 433 from the inside of the needle 427 to a desired region in the subject.

As described above, according to the fourth embodiment, a complex watertight mechanism is not required, and injection of the medicine 426 by the needle 427 can be controlled with a simple structure with magnets placed in the capsule endoscope 401. Also, according to the fourth embodiment, by using a repulsive force occurring between the rotationally-moving magnet 6 and the fixed magnet 7, the needle 427 protrudes outside of the capsule endoscope 401. Therefore, the battery 424 in the capsule endoscope 401 is not required to be used. For this reason, according to the fourth embodiment, the capacity of the battery 424 in the capsule endoscope 401 is not required to be increased. Therefore, the capsule endoscope 401 can be downsized, and insertability into the subject can be improved.

First Modification Example

Figure 57:
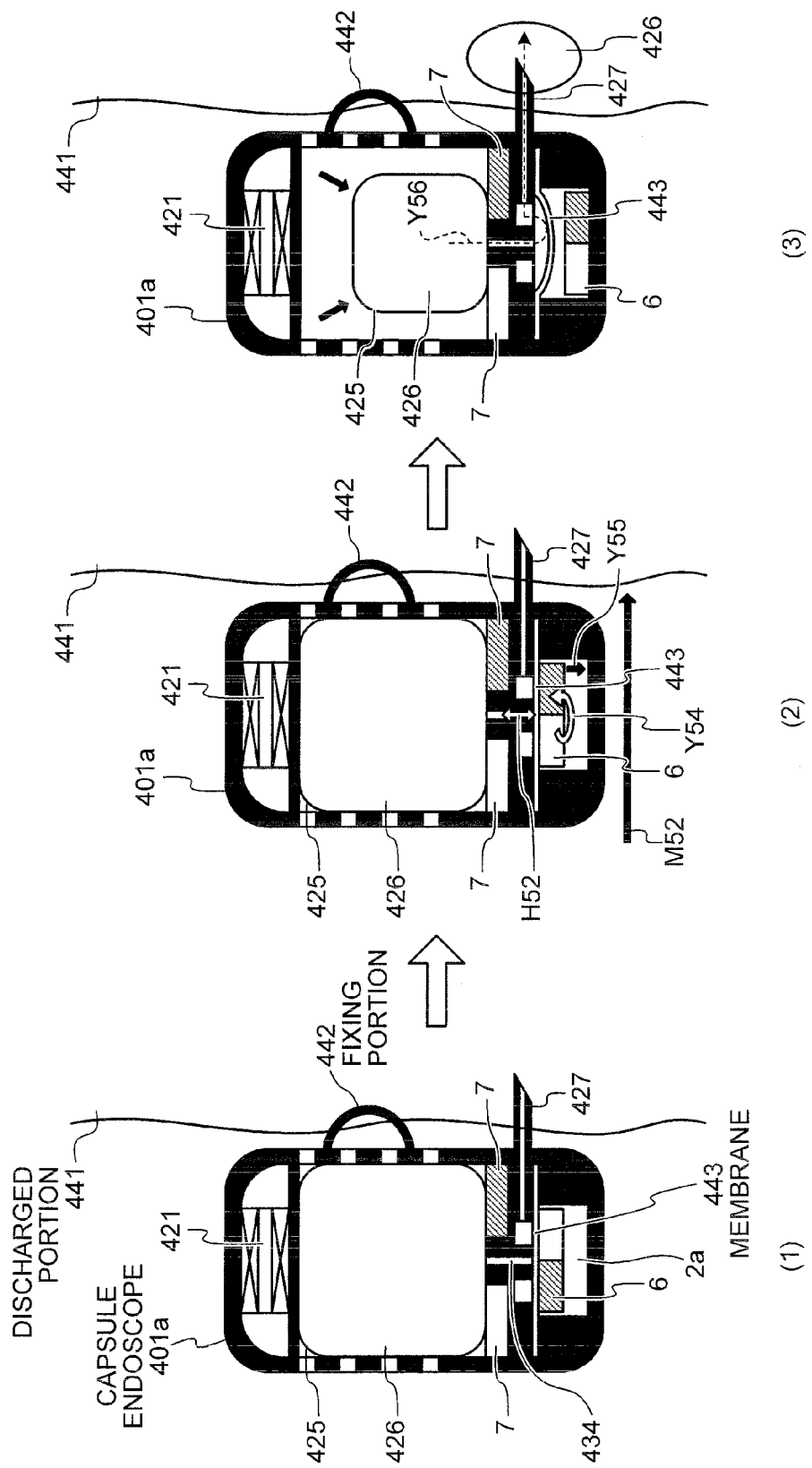
FIG. 57 shows diagrams explaining a capsule endoscope according to a first modification example in the fourth embodiment.

Next, with reference to FIG. 57, a first modification example in the fourth embodiment is described. In the first modification example, a case is described in which the magnetic actuator 1 is applied to medicine discharge in an indwelling capsule.

As depicted in FIG. 57, in a capsule endoscope 401a for indwelling according to the first modification example, a fixing unit 442 for fixing the capsule endoscope 401a to a discharged portion 441 and a membrane 443 that can be open and closed between the inlet 434, from which the medicine 426 in the balloon 425 is injected, and the needle 427 are provided.

When no magnetic field with the magnetic field strength allowing the rotationally-moving magnet 6 to rotate is applied to the capsule endoscope 401a, with an attractive force occurring with the fixed magnet 7 provided between the balloon 425 and the membrane 443 with a magnetization direction being fixed in a radial direction of the capsule endoscope 401a, the rotationally-moving magnet 6 is stably positioned in an upward direction of the guiding area 2a in FIG. 57(1). In this case, the rotationally-moving magnet 6 and the fixed magnet 7 attract each other to cause the rotationally-moving magnet 6 to be positioned in an upward direction of the guiding area 2a. With this, the membrane 443 provided between the rotationally-moving magnet 6 and the inlet 434 seals the inlet 434.

Then, as depicted in FIG. 57(2), the magnetic-field generating unit 403 generates a magnetic field M52 having an angular difference equal to or smaller than 60 degrees with respect to the magnetization direction of the fixed magnet 7 in the capsule endoscope 401a calculated by the position calculating unit 412 and having a magnetic field strength allowing the rotationally-moving magnet 6 to rotate. With this, the rotationally-moving magnet 6 rotates, as indicated by an arrow Y54 in FIG. 57(2), a half turn in a right direction in FIG. 57(2) according to the magnetic-field orientation of the magnetic field M52. As depicted in FIG. 57(2), with the rotationally-moving magnet 6 rotating a half turn, a repulsive force H52 occurs between the rotationally-moving magnet 6 and the fixed magnet 7, and the rotationally-moving magnet 6 moves, as indicated by an arrow Y55 in FIG. 57(2), in a downward direction in FIG. 57(3) along the guiding area 2a. Accordingly, as depicted in FIG. 57(3), the membrane 443 sealing the inlet 434 by the rotationally-moving magnet 6 bends also in the downward direction. As a result, as indicated by an arrow Y56 in FIG. 57(3), the inlet 434 sealed by the membrane 443 is released, and the medicine 426 in the balloon 425 is delivered via the inlet 434 to the needle 427 and is injected to the desired region inside the discharged portion 441 from the needle 427.

Furthermore, by stopping the application of the magnetic field by the magnetic-field generating unit 403, the rotationally-moving magnet 6 moves in an upward direction in FIG. 57 in the guiding area 2a by an attractive force with the fixed magnet 7, causing the membrane 443 to seal the inlet 434 accordingly. As a result, the discharge of the medicine 426 inside the balloon 425 is stopped.

As described above, according to the first modification example, the fixed magnet 7 and the rotationally-moving magnet 6 are provided across the membrane 443 that can open and close the inlet 434, thereby making it possible to open and close the membrane 443 to control discharge of the medicine 426 by the capsule endoscope 401a.

Second Modification Example

Figure 58:
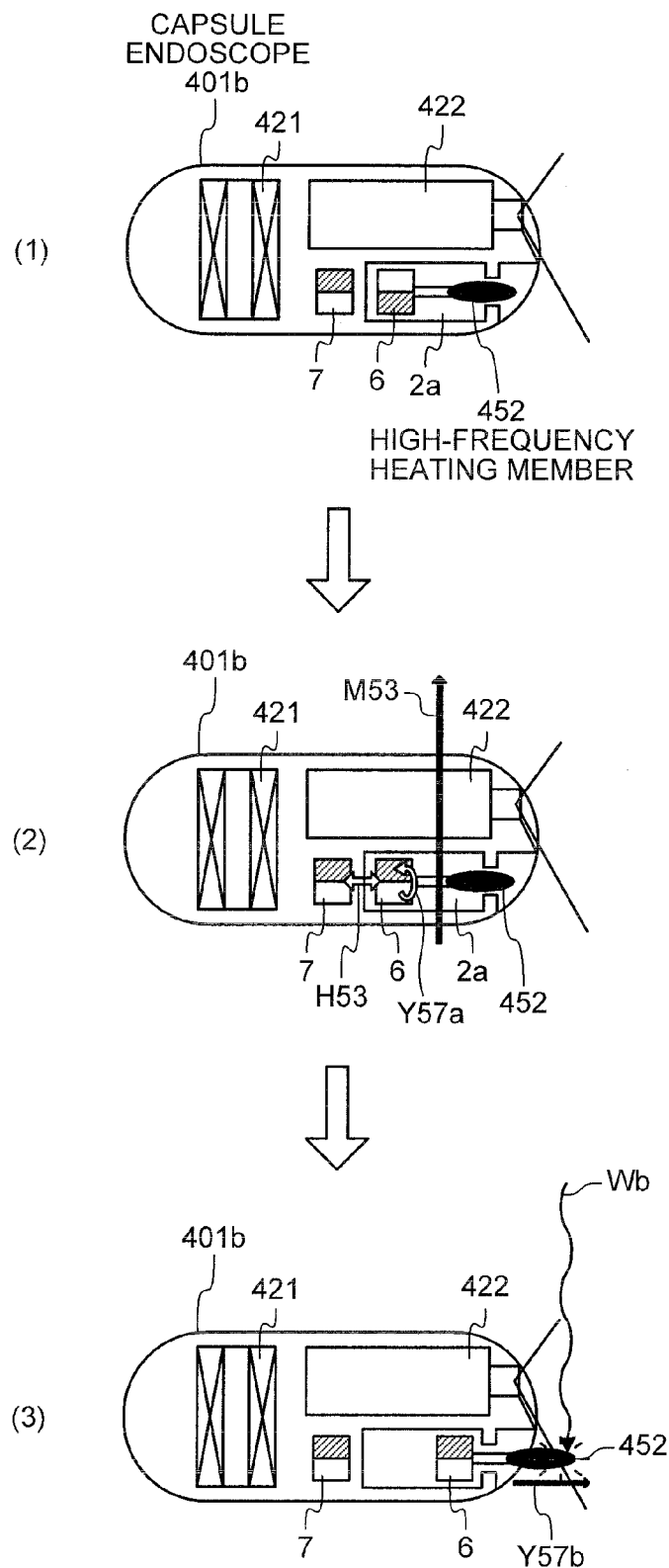
FIG. 58 shows diagrams explaining a capsule endoscope according to a second modification example in the fourth embodiment.

Next, with reference to FIG, 58, a second modification example in the fourth embodiment is described. In the second modification example, as depicted in FIG. 58(1), a case is described in which the magnetic actuator 1 is applied to a high-frequency heating treatment capsule capable of burning a tissue by applying a high-frequency magnetic field. As depicted in FIG. 58, a capsule endoscope 401b, which is a high-frequency heating treatment capsule, according to the second modification example includes a high-frequency heating member 452 connected to the rotationally-moving magnet 6 and capable of heating in a high-frequency magnetic field. A situation of pushing of the high-frequency heating member 452 and a state of the high-frequency heating member 452 burning a tissue can be confirmed by the imaging system 422. Also, the detecting direction of the position-detection oscillation coil 421 is a radial direction of the capsule endoscope 401b, and is matched with the orientation of the magnetic field required for rotating the rotationally-moving magnet 6 rotatable in the radial direction of the capsule endoscope 401b. For this reason, the position calculating unit 412 can determine that the orientation of the magnetic field of the rotationally-moving magnet 6 is the same as that of the position-detection oscillation coil 421.

When it is found through observation by the imaging system 422 in FIG. 58(1) that the capsule endoscope 401b has reached a tissue to be treated, as depicted in FIG. 58(2), the magnetic-field generating unit 403 generates a magnetic field M53 having an angular difference equal to or smaller than 60 degrees with respect to an axial direction of the capsule endoscope 401b calculated by the position calculating unit 412 and having a magnetic field strength allowing the rotationally-moving magnet 6 to rotate. The magnetic field generated by the magnetic-field generating unit 403 is a static magnetic field. As a result, the rotationally-moving magnet 6 rotates, as indicated by an arrow Y57a in FIG. 58(2), a half turn in an upper direction in FIG. 58(2) according to the magnetic-field orientation of the magnetic field M53. Then, as depicted in FIG. 58(2), with the rotationally-moving magnet 6 rotating a half turn, a repulsive force H53 occurs between the rotationally-moving magnet 6 and the fixed magnet 7, and the rotationally-moving magnet 6 moves, as indicated by an arrow Y57b in FIG. 58(3), in a right direction in FIG. 58(3) along the guiding area 2a. Accordingly, as depicted in FIG. 58(3), the high-frequency heating member 452 connected to the rotationally-moving magnet 6 also moves in the right direction in FIG. 58(3) to be pushed outside of the capsule endoscope 401b. Then, the magnetic-field generating unit 403 applies a high-frequency magnetic field Wb to the capsule endoscope 401b to heat the high-frequency heating member 452 and, as a result, a tissue to be treated can be burnt.

As described above, according to the second modification example, the frequency generated by the magnetic-field generating unit 403 is controlled and, according to each frequency generated by the magnetic-field generating unit 403, different operations of pushing the high-frequency heating member connected to the rotationally-moving magnet 6 and heating the high-frequency heating member can be performed.

Figure 59:
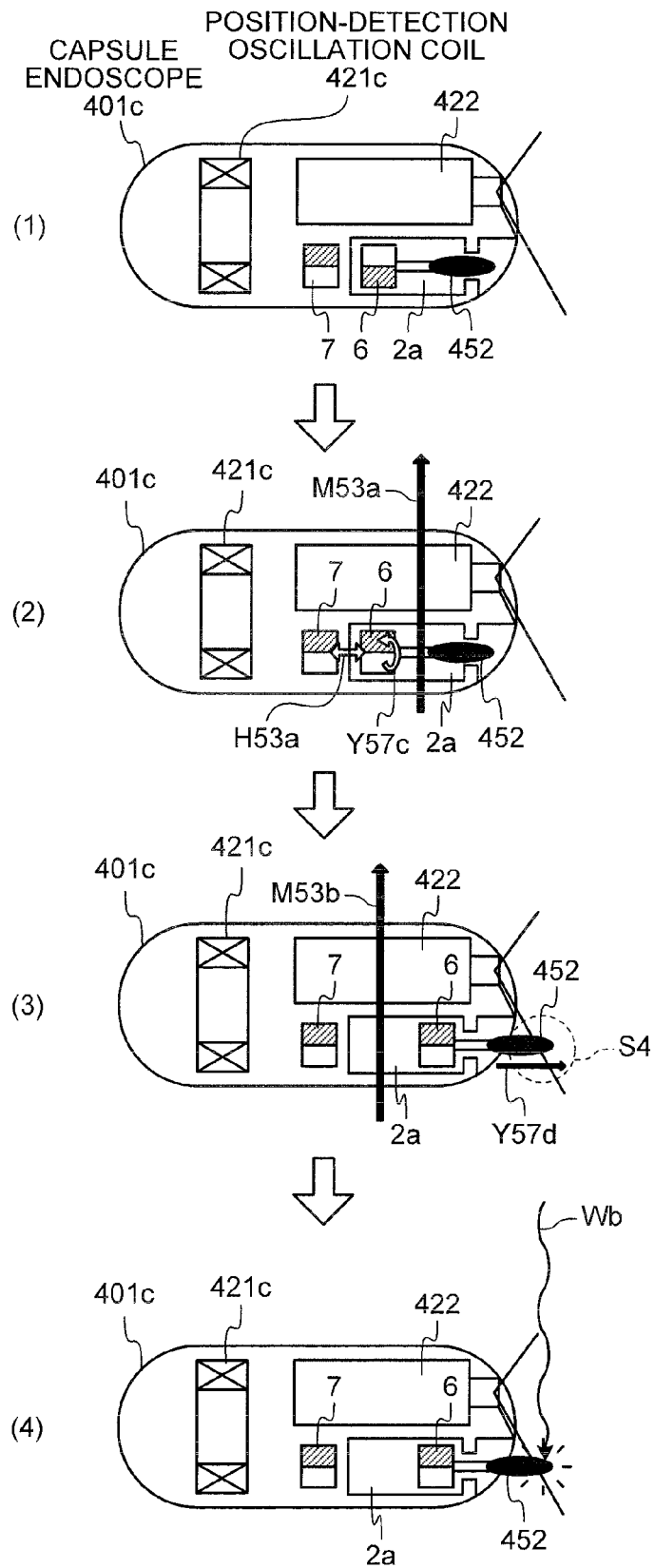
FIG. 59 shows diagrams explaining another example of the capsule endoscope depicted in FIG. 58.

Further, a capsule endoscope 401c as depicted in FIG. 59(1) will be described in which the detecting direction of the position-detection oscillation coil 421c is an axial direction of the capsule endoscope 401c and is not matched with the orientation of the magnetic field required for rotating the rotationally-moving magnet 6 rotatable in a radial direction of the capsule endoscope 401c.

In this case, as depicted in FIG. 59(2), the magnetic-field generating unit 403 generates a rotating magnetic field M53a in a plane perpendicular to the direction of the capsule endoscope 401c calculated by the position calculating unit 412. As a result, the rotationally-moving magnet 6 rotates, as indicated by an arrow Y57c in FIG. 59(2), a half turn in an upper direction in FIG. 59(2) according to the magnetic field of the magnetic field M53a. Then, with a repulsive force H53a depicted in FIG. 59(2) occurring with the rotationally-moving magnet 6 rotating a half turn, the rotationally-moving magnet 6 moves, as indicted by an arrow Y57d in FIG. 59(3), in a right direction in FIG. 59(3) along the guiding area 2a.

Accordingly, as depicted in FIG. 59(3), the high-frequency heating member 452 connected to the rotationally-moving magnet 6 also moves in the right direction in FIG. 59(3) to be pushed to the outside of the capsule endoscope 401c. Then, as depicted in FIG. 59(3), when the high-frequency heating member 452 is pushed to an area S4 in a field of view of the imaging system 422, the pushing of the high-frequency heating member 452 can be confirmed by the imaging system 422. As described above, with the pushing of the high-frequency heating member 452 has been confirmed by the imaging system 422, the magnetic-field generating unit 403 applies a magnetic field M53b with the direction of the magnetic field being fixed to the orientation of the magnetic field of the fixed magnet 7. Thereafter, as depicted in FIG. 59(4), with the application of the high-frequency magnetic field Wb by the magnetic-field generating unit 403, the pushed high-frequency heating member 452 is heated to burn a tissue to be treated. Note that the pushing of the high-frequency heating member 452 may be confirmed by providing in the capsule endoscope 401c, other than the imaging system 422, a sensor capable of confirming the operation of the magnetic actuator, such as a contact sensor or passage detection sensor. In this case, the magnetic-field generating unit 403 controls magnetic-field application based on the detection result of the sensor received by the receiving unit 411.

Third Modification Example

Figure 60:
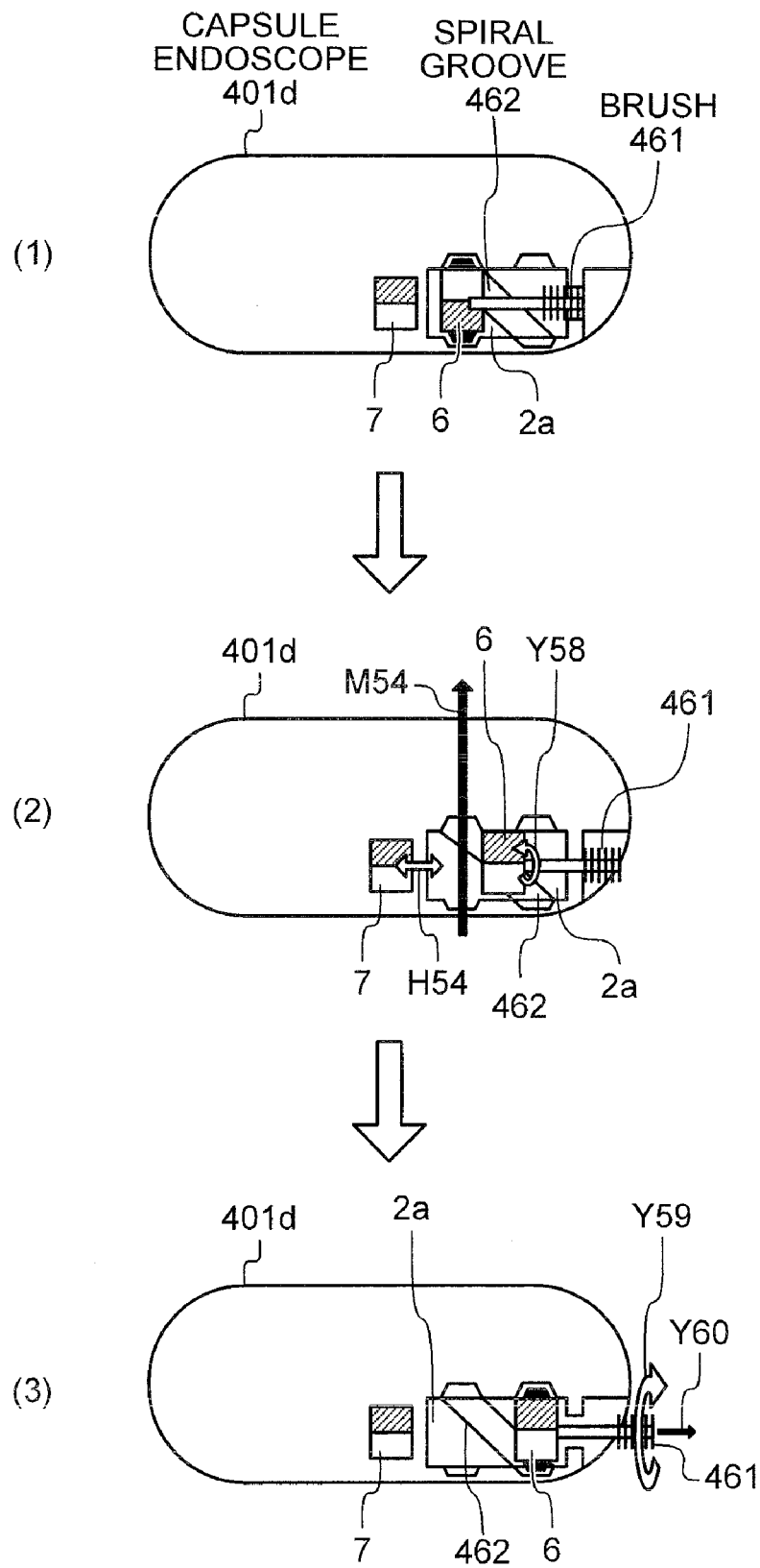
FIG. 60 shows diagrams explaining a capsule endoscope according to a third modification example in the fourth embodiment.

Next, with reference to FIG. 60, a third modification example in the fourth embodiment is described. In the third modification example, as depicted in FIG. 60(1), a case is described in which the magnetic actuator 1 is applied to a brush biopsy capsule obtaining a tissue by a biopsy brush. As depicted in FIG. 60, in a capsule endoscope 401d, which is a biopsy brush capsule, according to the third modification example, with the rotationally-moving magnet 6 rotationally moving along a spiral groove 462 provided in the guiding area 2a, a brush 461 for biopsy connected to the rotationally-moving magnet 6 is pushed outside of the capsule endoscope 401d while rotating.

In FIG. 60(1), when the capsule endoscope 401d reaches the tissue for biopsy, as depicted in FIG. 60(2), the magnetic-field generating unit 403 applies a magnetic field M54 having an angular difference equal to or smaller than 60 degrees with respect to an axial direction of the capsule endoscope 401d and having a magnetic field strength allowing the rotationally-moving magnet 6 to rotate. As a result, the rotationally-moving magnet 6 rotates, as depicted in FIG. 60(2), a half turn according to the magnetic-field orientation of the magnetic field M54 and, with a repulsive force H54 occurring between the rotationally-moving magnet 6 and the fixed magnet 7, as indicated by an arrow Y58 in FIG. 60(2), the rotationally-moving magnet 6 moves in a right direction in FIG. 60(2) along the guiding area 2a while rotating along the spiral groove 462. Accordingly, as indicated by an arrow Y59 in FIG. 60(3), the brush 461 connected to the rotationally-moving magnet 6 also rotates to be pushed outside of the capsule endoscope 401d, as indicated by an arrow Y60. As a result, the tissue to be obtained is scrubbed away from the subject by the pushed brush 461 while rotating.

As described above, according to the third modification example, by rotationally moving the rotationally-moving magnet 6 along the spiral groove 462, the amount of rotation and the amount of pushing of the brush 461 at the time of moving can be controlled. With this, the brush 461 can be pushed while being rotated for accurate biopsy.

Fourth Modification Example

Figure 61:
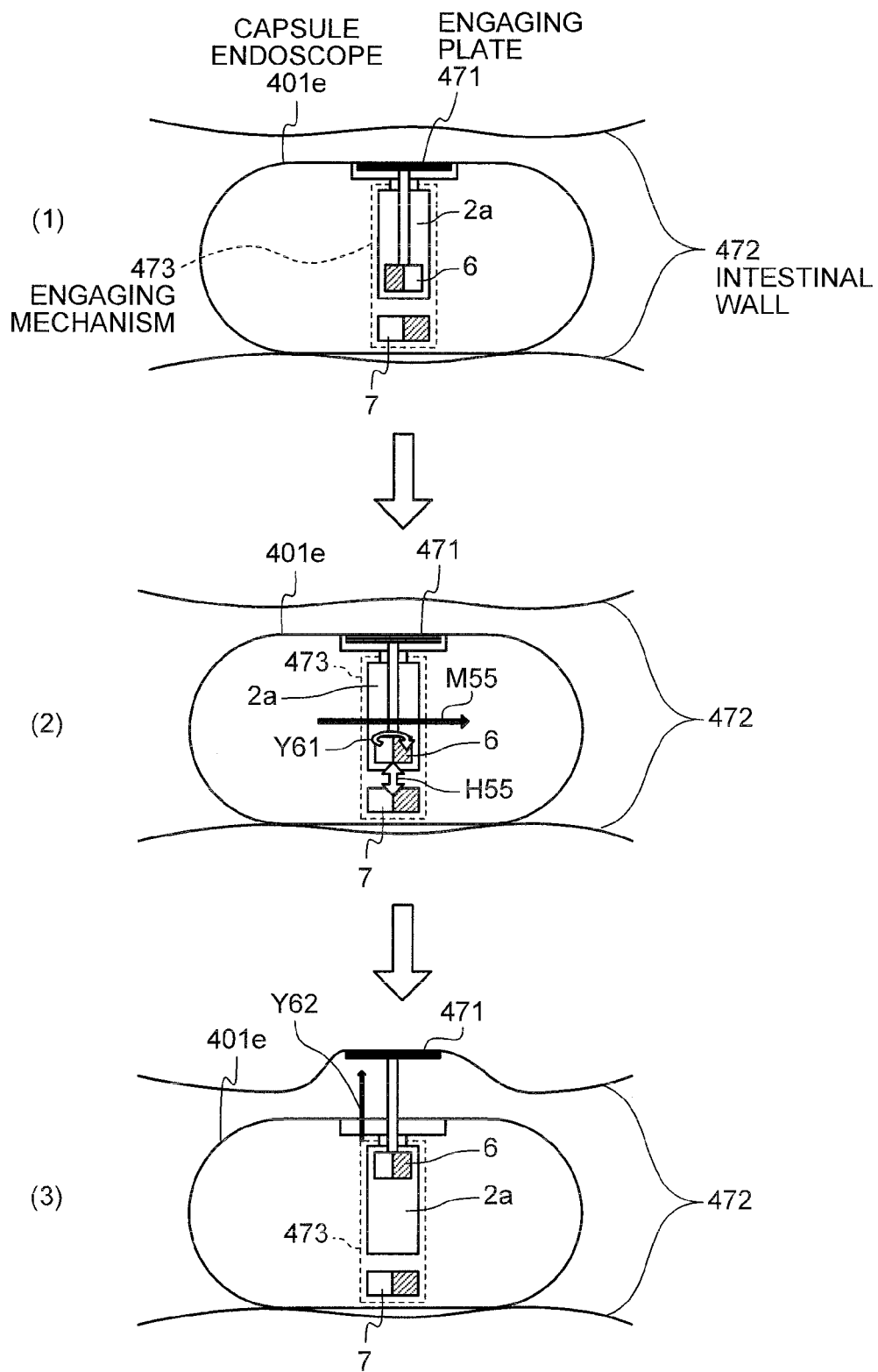
FIG. 61 shows diagrams explaining a capsule endoscope according to a fourth modification example in the fourth embodiment.

Next, with reference to FIG. 61, a fourth modification example in the fourth embodiment is described. As depicted in FIG. 61(1), a capsule endoscope 401e according to the fourth modification example pushes an engaging plate 471 by using an engaging mechanism 473 to which the magnetic actuator 1 is applied, thereby making it possible to engage the capsule endoscope in an intestinal wall 472.

In FIG. 61(1), when the capsule endoscope 401e reaches an engaging area, as depicted in FIG. 61(2), the magnetic-field generating unit 403 applies a magnetic field M55 having an angular difference equal to or smaller than 60 degrees with respect to an axial direction of the capsule endoscope 401e and having a magnetic field strength allowing the rotationally-moving magnet 6 to rotate. As a result, the rotationally-moving magnet 6 rotates, as indicated by an arrow Y61 in FIG. 61(2), a half turn according to the magnetic-field orientation of the magnetic field M55 and, with a repulsive force H55 occurring between the rotationally-moving magnet 6 and the fixed magnet 7, the rotationally-moving magnet 6 moves in an upper direction in FIG. 61(3) along the guiding area 2a. Accordingly, as indicated by an arrow Y62 in FIG. 61(3), the engaging plate 471 connected to the rotationally-moving magnet 6 is pushed outside of the capsule endoscope 401e. As a result, the capsule endoscope 401e can engage with the inside of a predetermined body cavity, such as the intestinal wall 472, thereby making it possible to stably performing each process, such as biopsy.

Fifth Modification Example

Figure 62:
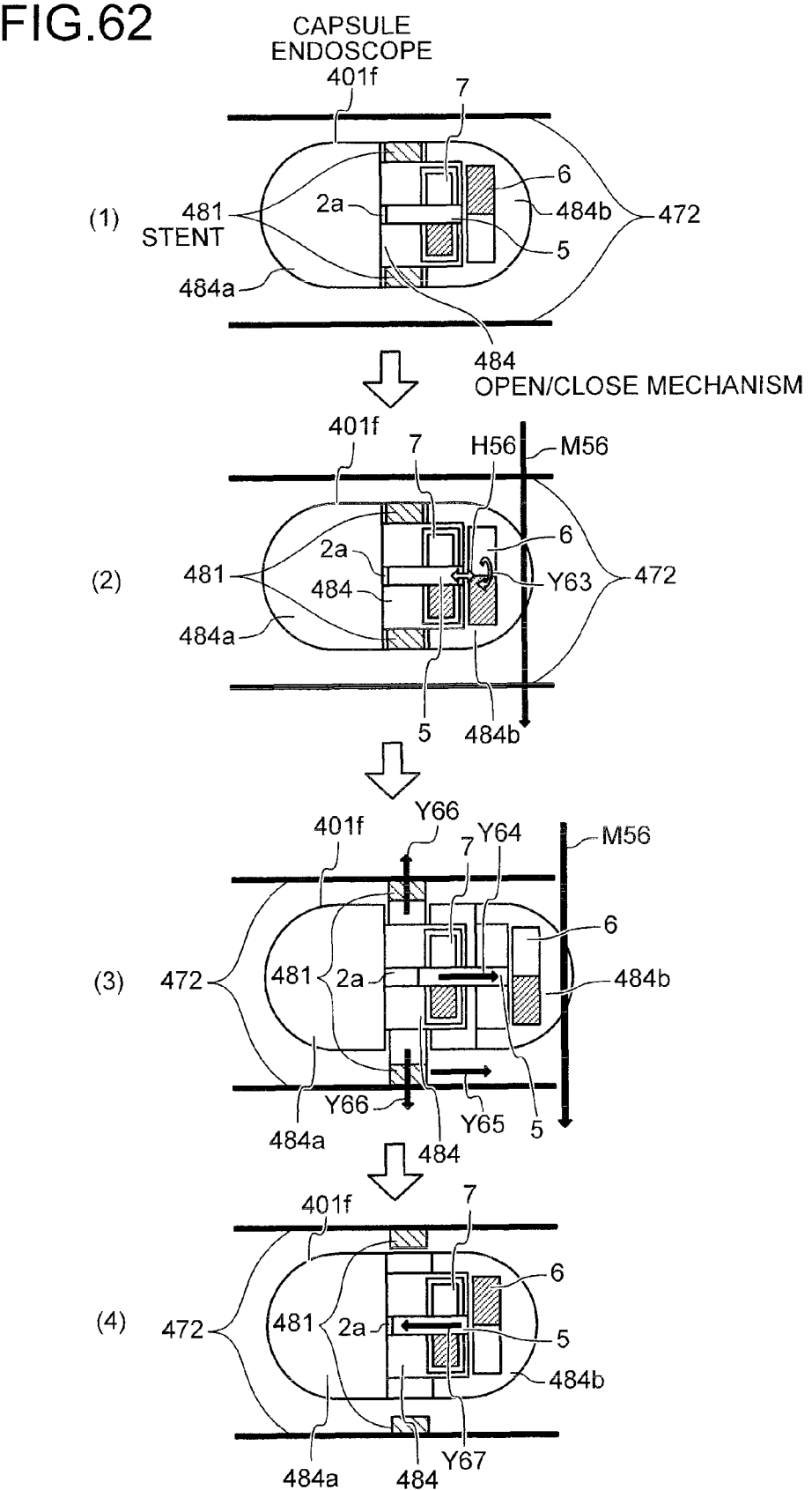
FIG. 62 shows diagrams explaining a capsule endoscope according to a fifth modification example in the fourth embodiment.

Next, with reference to FIG. 62, a fifth modification example in the fourth embodiment is described. As depicted in FIG. 62(1), in a capsule endoscope 401f according to the fifth modification example, the magnetic actuator 1 is applied to open and close the casing of the capsule endoscope 401f to release a stent 481 accommodated in the casing for marking. The fixed magnet 7 is fixedly provided in an open/close mechanism 484 connected to a casing 484a forming a left-side part of the capsule endoscope 401f to control opening and closing of the casing of the capsule endoscope 401f. The rotationally-moving magnet 6 is rotatable in a radial direction of the capsule endoscope 401f in a casing 484b forming a left side part of the capsule endoscope 401f. At a central axis of the fixed magnet 7, the moving member 5 connected to the casing 484b is inserted so as to be movable in a horizontal direction of the guiding area 2a. For this reason, according to the movement of the casing 484b in the right direction of the rotationally-moving magnet 6, the moving member 5 passes the central axis of the fixed magnet 7 along the guiding area 2a for movement.

In FIG. 62(1), when the capsule endoscope 401f reaches an area in which marking is desired, as depicted in FIG. 62(2), the magnetic-field generating unit 403 applies a magnetic field M56 having an angular difference equal to or smaller than 60 degrees with respect to a radial direction of the capsule endoscope 401f and having the magnetic field strength allowing the rotationally-moving magnet 6 to rotate. In this case, the rotationally-moving magnet 6 rotates, as indicated by an arrow Y63 in FIG. 62(2), a half turn according to the magnetic-field orientation of the magnetic field M56. Then, as indicated by an arrow Y64 in FIG. 62(3), with a repulsive force H56 occurring with the fixed magnet 7, the rotationally-moving magnet 6 moves in a right direction in FIG. 62(3) along the guiding area 2a. Accordingly, the moving member 5 also passes the central axis of the fixed magnet 7 to move in the right direction in FIG. 62(3) along the guiding area 2a. As a result, as depicted in FIG. 62(3), with the movement of the moving member 5 in the right direction, the entire casing 484b connected to the moving member 5 also moves in the right direction (refer to an arrow Y65 in FIG. 62(3)) to open the capsule endoscope 401f. Then, the stent 481 is released outside of the capsule endoscope 401f to be widened (refer to an arrow Y66 in FIG. 62(3)), thereby being indwelt in a region desired for marking as depicted in FIG. 62(4). Then, by stopping the application of the magnetic field by the magnetic-field generating unit 403, as depicted in FIG. 62(4), with an attractive force between the fixed magnet 7 and the rotationally-moving magnet 6, the moving member 5 moves in the left direction along the guiding area 2a (refer to an arrow Y67 in FIG. 62(4)) to bring the casing 484a and the casing 484b in contact with each other to close the capsule endoscope 401f. As described above, by using the magnetic actuator 1, the stent 481 can be smoothly released.

Sixth Modification Example

Figure 63:
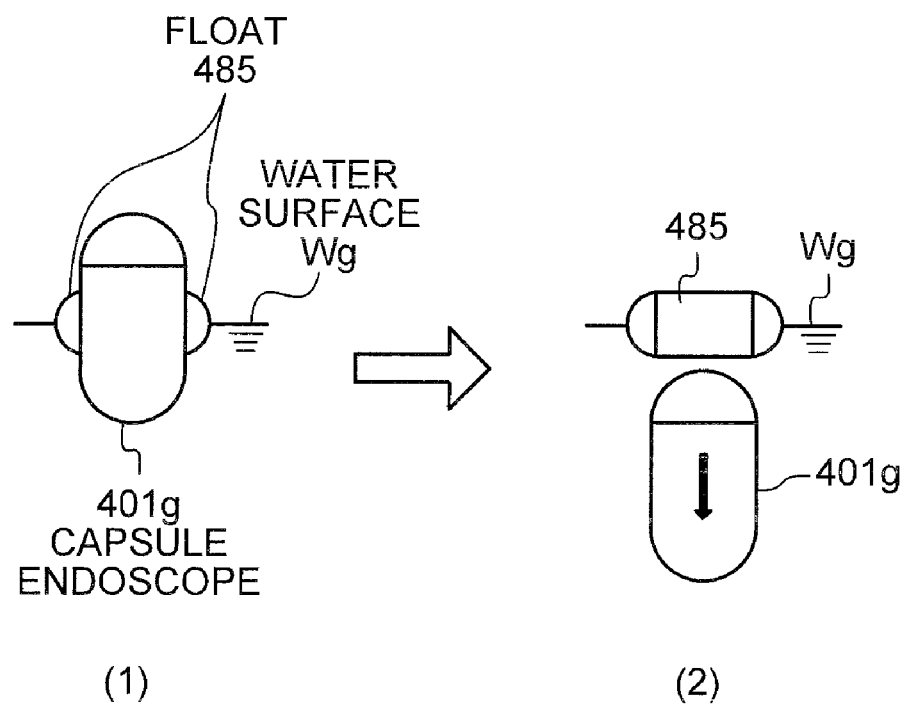
FIG. 63 shows diagrams explaining a capsule endoscope according to a sixth modification example in the fourth embodiment.
Figure 64:
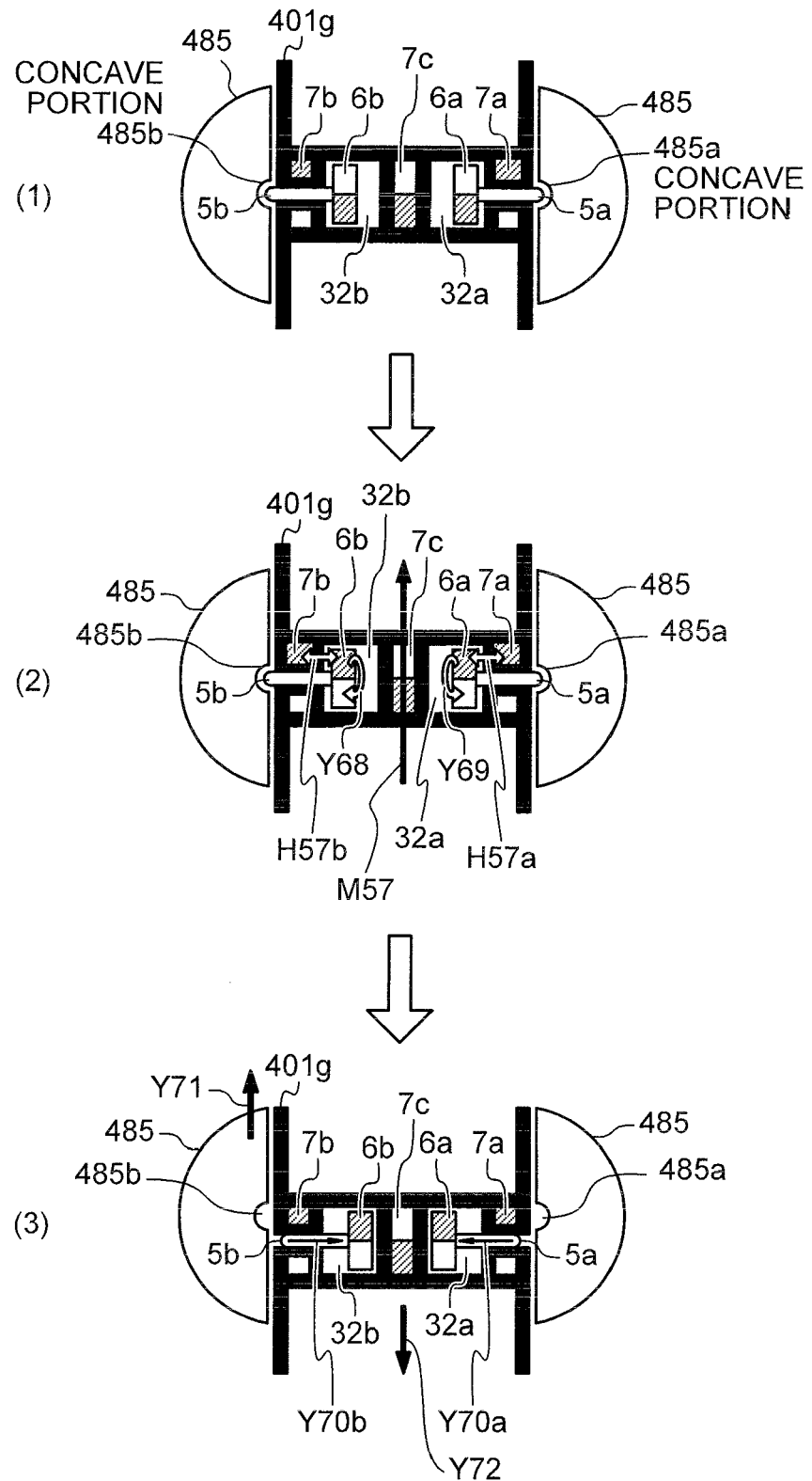
FIG. 64 shows diagrams explaining the operation of the capsule endoscope depicted in FIG. 63.

Next, with reference to FIG. 63 and FIG. 64, a sixth modification example in the fourth embodiment is described. As depicted in FIG. 63(1), a capsule endoscope 401g according to the sixth modification example in a state of having a float 485 attached thereon can float near a water surface Wg. And, the capsule endoscope 401g in a state of being separated from the float 485 sinks into the water as depicted in FIG. 63(2), because the specific gravity of the capsule endoscope 401g is changed. In the capsule endoscope 401g, as depicted in FIG. 63(1), after observing in a state of floating in the water with the float 485 attached, the float 485 is detached, as depicted in FIG. 63(2), thereby allowing observation from the bottom of the water.

Next, an operation is described in which the float 485 is detached from the capsule endoscope 401g. As depicted in FIG. 64(1), the capsule endoscope 401g has fixed magnets 7a, 7b with the same magnetic-field orientation and a fixed magnet 7c provided between the fixed magnets 7a, 7b with its magnetic-field orientation opposite to that of the fixed magnets 7a, 7b. The capsule endoscope 401g has rotationally-moving magnets 6a, 6b placed in guiding areas 32a, 32b, respectively, provided among the fixed magnets 7a, 7b, 7c. The rotationally-moving magnets 6a, 6b have connected thereto moving members 5a, 5b, respectively. The moving member 5a can move the central axis of the fixed magnet 7a in a horizontal direction in FIG. 64(1) according to the movement of the rotationally-moving magnet 6a, and the moving member 5b can move the central axis of the fixed magnet 7b in a horizontal direction in FIG. 64(1) according to the movement of the rotationally-moving magnet 6b. With the moving members 5a, 5b engagingly attached to concave portions 485a, 485b, respectively, provided to the float 485, the float 485 is attached to the capsule endoscope 401g.

Then, when the float 485 is detached from the capsule endoscope 401g, as depicted in FIG. 64(2), the magnetic-field generating unit 403 applies a magnetic field M57 having an angular difference equal to or smaller than 60 degrees with respect to an axial direction of the capsule endoscope 401g and having a magnetic field strength allowing the rotationally-moving magnets 6a, 6b to rotate. As a result, the rotationally-moving magnets 6a, 6b rotate, as indicated by arrows Y68, Y69, respectively, in FIG. 64(2), a half turn according to the magnetic-field orientation of the magnetic field M57 and, with repulsive forces H57a, H57b occurring between the rotationally-moving magnets 6a, 6b and their corresponding fixed magnets 7a, 7b respectively, move to the inside of the capsule endoscope 401g along the guiding areas 32a, 32b. For this reason, the moving member 5a connected to the rotationally-moving magnet 6a, as indicated by an arrow Y70a in FIG. 64(3), passes the central axis of the fixed magnet 7a to move in a left direction to be accommodated in the capsule endoscope 401g. Also, the moving member 5b connected to the rotationally-moving magnet 6b, as indicated by an arrow Y70b in FIG. 64(3), passes the central axis of the fixed magnet 7b to move in a right direction to be accommodated in the capsule endoscope 401g. That is, the moving members 5a, 5b engagingly attached to the concave portions 485a, 485b, respectively, of the float 485 are detached from the concave portions 485a, 485b to be accommodated in the capsule endoscope 401g.

For this reason, as indicated by an arrow Y71 in FIG. 64(3), the float 485 is detached from the capsule endoscope 401g to move upward toward the water surface, and the capsule endoscope 401g sinks into the water, as indicated by an arrow Y72. The rotationally-moving magnets 6a, 6b moving to the inside of the capsule endoscope 401g with the repulsive forces H57a, 57b keep a state adjacent to the fixed magnet 7c by an attractive force occurring with the fixed magnet 7c. As a result, the moving members 5a, 5b also keep a state of being accommodated in the capsule endoscope 401g and are not pushed outside of the capsule endoscope 401g.

As described above, in the capsule endoscope 401g, the float 485 can be detached by primarily applying a magnetic field, thereby allowing smooth observation of a wide range with high energy efficiency.

Seventh Modification Example

Figure 65:
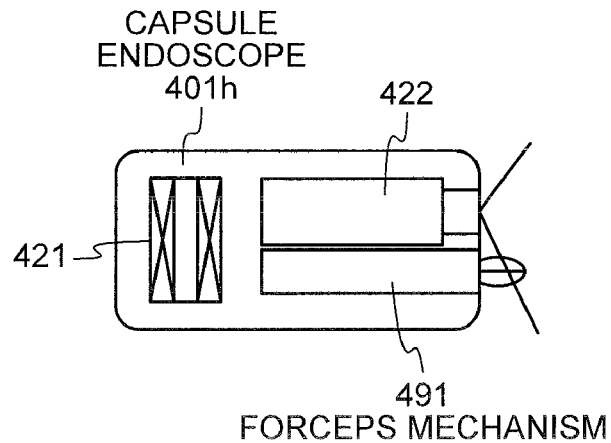
FIG. 65 shows a diagram explaining a capsule endoscope according to a seventh modification example in the fourth embodiment.

Next, a seventh modification example in the fourth embodiment is described. As depicted in FIG. 65, a capsule endoscope 401h according to the seventh modification example uses a forceps mechanism 491 to which the magnetic actuator 201 is applied to perform biopsy when it is found through observation by the imaging system 422 that the capsule endoscope 401h has reached a tissue for biopsy.

Figure 66:
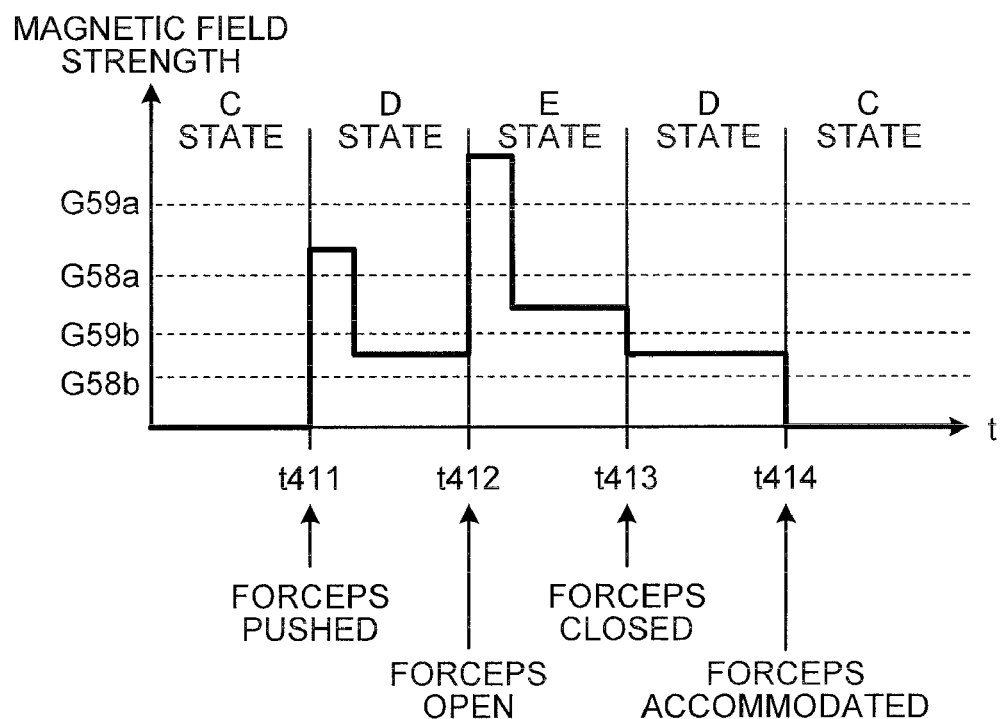
FIG. 66 shows a diagram depicting time dependency of the magnetic field strength of a magnetic field to be applied to the capsule endoscope depicted in FIG. 65.
Figure 67:
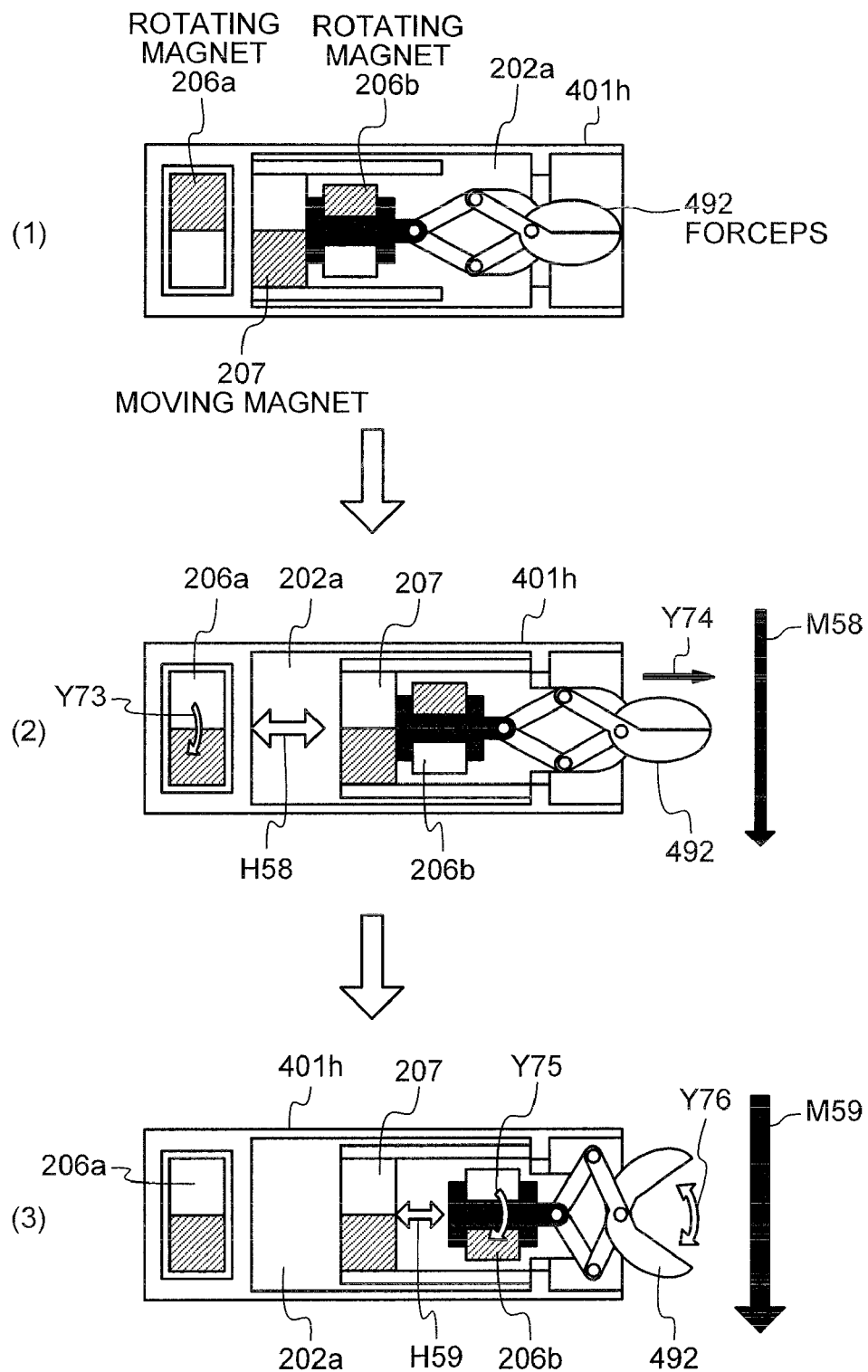
FIG. 67 shows sectional views of the capsule endoscope depicted in FIG. 65 cut along an axial direction.

Next, with reference to FIG. 66 and FIG. 67, the operation of the forceps mechanism 491 in the capsule endoscope 401h is described. FIG. 66 is a diagram depicting time dependency of the magnetic field strength of a magnetic field to be applied by the magnetic-field generating unit 403, and FIG. 67 shows sectional views of the capsule endoscope 401h cut along an axial direction at times t411 to t414 depicted in FIG. 66. The capsule endoscope 401h includes, as depicted in FIG. 67(1), in addition to a rotating magnet 206a, a rotating magnet 206b with which a member inserted in the central axis of the moving magnet 207 is brought into contact at the time of accommodating a forceps 492 in the capsule endoscope 401h. The capsule endoscope 401h moves in the body cavity in a C state depicted in FIG. 67(1) in which the forceps 492 is accommodated in the capsule endoscope 401h. When the capsule endoscope 401h is in a C state, as depicted in FIG. 66, the magnetic-field generating unit 403 stops magnetic-field generation.

First, at the time t411 in FIG. 66, when the capsule endoscope 401h moves in the C state depicted in FIG. 67(1) and the capsule endoscope 401h reaches a tissue for biopsy, the magnetic-field generating unit 403 generates, as depicted in FIG. 67(2), a magnetic field M58 with a magnetic field strength stronger than a magnetic field strength G58a so as to push the forceps 492. This magnetic field strength G58a is a magnetic field strength allowing the rotating magnet 206a in the C state to rotate in the same orientation as the orientation of the magnetic field of the moving magnet 207. For this reason, as indicated by an arrow Y73 in FIG. 67(2), the rotating magnet 206a rotates in the same orientation as the orientation of the magnetic field M58, thereby causing a repulsive force H58 between the rotating magnet 206a and the moving magnet 207. With this repulsive force H58, the moving magnet 207 moves in a right direction in FIG. 67(2). In this case, according to the movement of the moving magnet 207, the rotating magnet 206b and the forceps 492 connected to the rotating magnet 206b also move in the right direction in FIG. 67(2). Therefore, as indicated by an arrow Y74 in FIG. 67(2), the state is changed to a D state in which a blade portion of the forceps 492 is pushed from the capsule endoscope 401h. Note that, between t411 and t412 in FIG. 66, after the forceps 492 is pushed, the D state depicted in FIG. 67(2) can be kept by applying a magnetic field with a magnetic field strength stronger than the magnetic field strength G58b allowing the orientation of the magnetic field of the rotating magnet 206a to be kept the same as the orientation of the magnetic field of the moving magnet 207.

Next, at the time t412 in FIG. 66, when the forceps 492 is opened, as depicted in FIG. 67(3), the magnetic-field generating unit 403 generates a magnetic field M59 with a magnetic field strength stronger than the magnetic field strength G59a. This magnetic field strength G59a is a magnetic field strength allowing the rotating magnet 206b adjacent to the moving magnet 207 in the D state to rotate in the same orientation as the orientation of the magnetic field of the moving magnet 207. For this reason, as indicated by an arrow Y75 in FIG. 67(3), the rotating magnet 206b rotates in the same orientation as the orientation of the magnetic field M59, thereby causing a repulsive force H59 between the rotating magnet 206b and the moving magnet 207. With this repulsive force H59, the rotating magnet 206b moves in a right direction in FIG. 67(3). In this case, by moving in the right direction in FIG. 67(3), the rotating magnet 206b adds a pressure to a leg portion of the forceps 492. With this, as indicated by an arrow Y76 in FIG. 67(3), the state is changed to an E state in which the leg portion of the forceps 492 is contracted to open the blade portion. Note that, between t412 and t413 in FIG. 66, after the blade portion of the forceps 492 is open, the E state depicted in FIG. 67(3) can be kept by applying a magnetic field with a magnetic field strength stronger than the magnetic field strength G59b allowing the orientation of the magnetic field of the rotating magnet 206b to be kept the same as the orientation of the magnetic field of the moving magnet 207.

Then, at the time t413 in FIG. 66, when the blade portion of the forceps 492 is closed for biopsy, the magnetic field strength of the magnetic field to be applied by the magnetic-field generating unit 403 is made weaker than G59b, thereby releasing the rotational restraint on the rotating magnet 206b. As a result, the rotating magnet 206b rotates and attracts the moving magnet 207, and therefore the capsule endoscope 401h is changed to a D state depicted in FIG. 67(2). Then, at the time t414 in FIG. 66, when the forceps 492 is to be accommodated in the capsule endoscope 401h, the application of the magnetic field by the magnetic-field generating unit 403 is stopped, thereby releasing the rotational restraint on the rotating magnet 206a. As a result, the rotating magnet 206b rotates to attract the moving magnet 207, thereby causing the capsule endoscope 401h to be changed to a C state depicted in FIG. 67(1). As described above, according to the seventh modification example, by changing the magnetic field strength generated by the magnetic-field generating unit 403, biopsy can be performed by changing each state of the forceps 492. Fifth Embodiment Next, a fifth embodiment is described. In the fifth embodiment, a capsule endoscope is described in which plural magnetic actuators described in the first and second embodiments are used to control the operation of plural components. Note that a capsule guiding system in the fifth embodiment has a configuration similar to that of the capsule guiding system 400 in the fourth embodiment.

Figure 68:
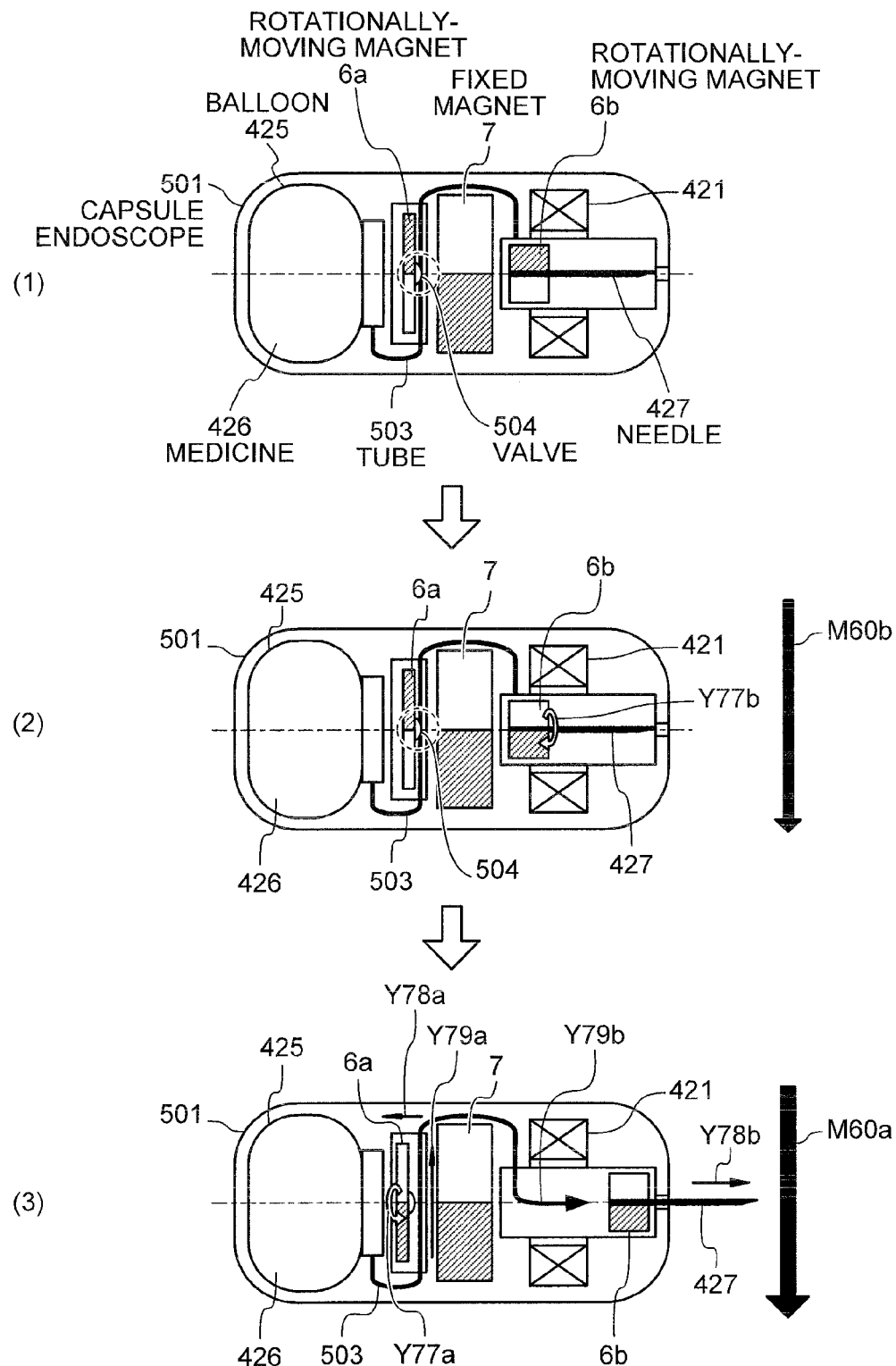
FIG. 68 shows sectional views of a capsule endoscope according to a fifth embodiment cut along an axial direction.

FIG. 68 is a sectional view of the capsule endoscope according to the fifth embodiment cut along an axial direction. As depicted in FIG. 68(1), a capsule endoscope 501 according to the fifth embodiment applies plural magnetic actuators 1 to perform a process of opening and closing a medicine valve and a process of piercing with a needle.

In the capsule endoscope 501, when no magnetic field is applied by the magnetic-field generating unit 403, as depicted in FIG. 68(1), with an attractive force between the rotationally-moving magnet 6a and the fixed magnet 7, a valve 504 connected to the rotationally-moving magnet 6a to press a tube 503 to stop the flowing of the medicine 426 is closed. Also, as depicted in FIG. 68(1), with the attractive force between the rotationally-moving magnet 6b and the fixed magnet 7, the rotationally-moving magnet 6b is positioned on a side of the fixed magnet 7 fixedly disposed on a back side of the capsule endoscope 501. Therefore, the needle 427 connected to the rotationally-moving magnet 6b is accommodated in the capsule endoscope 501.

Also, as with the magnetic actuator configured of the rotationally-moving magnet 6a and the fixed magnet 7 and any of the magnetic actuators 41a to 41d in the first embodiment, in a magnetic actuator configured of the rotationally-moving magnet 6b and the fixed magnet 7, a magnet size or a gap between the rotationally-moving magnet 6a, 6b and the fixed magnet 7 is set so that the magnetic actuator is driven with different magnetic field strengths. In the capsule endoscope 501, to locally inject the medicine without wasting, the valve 504 is desirably controlled so that the valve 504 is open after the piercing with the needle 427. That is, the rotationally-moving magnet 6b that controls the needle 427 is desirably rotatable with a magnetic field strength weaker than that of the rotationally-moving magnet 6a that controls the valve 504. For this reason, the magnet size of the rotationally-moving magnet 6b is made smaller than the magnet size of the rotationally-moving magnet 6a, or a gap between the rotationally-moving magnet 6b and the fixed magnet 7 is made larger than a gap between the rotationally-moving magnet 6a and the fixed magnet 7.

Next, the operation of the capsule endoscope 501 is described. In FIG. 68(1), when the capsule endoscope 501 reaches the local-injection target area, as depicted in FIG. 68(2), the magnetic-field generating unit 403 applies a magnetic field M60b with a magnetic field strength allowing the rotationally-moving magnet 6b to rotate to the capsule endoscope 501. As a result, the rotationally-moving magnet 6b rotates, as indicated by an arrow Y77b in FIG. 68(2), a half turn according to the magnetic-field orientation of the magnetic field M60b and, as depicted in FIG. 68(3), with a repulsive force occurring between the rotationally-moving magnet 6b and the fixed magnet 7, the rotationally-moving magnet 6b moves in a right direction in FIG. 68(3). Accordingly, as indicated by an arrow Y78b in FIG. 68(3), the needle 427 connected to the rotationally-moving magnet 6b is pushed outside of the capsule endoscope 501.

Next, as depicted in FIG. 68(3), the magnetic-field generating unit 403 applies a magnetic field M60a with a magnetic field strength allowing the rotationally-moving magnet 6b to rotate to the capsule endoscope 501 and stronger than the magnetic field strength allowing the rotationally-moving magnet 6b to rotate to the capsule endoscope 501. As a result, the rotationally-moving magnet 6a rotates, as indicated by an arrow Y77a in FIG. 68(3), a half turn according to the magnetic-field orientation of the magnetic field M60a and, as indicated by an arrow Y78a, with a repulsive force occurring between the rotationally-moving magnet 6a and the fixed magnet 7, the rotationally-moving magnet 6a moves in the right direction in FIG. 68(3). Accordingly, the valve 504 connected to the rotationally-moving magnet 6b opens. As a result, as indicated by arrows Y79a, Y79b in FIG. 68(3), the medicine 426 in the balloon 425 is injected from the needle 427 via a tube into a desired region in the subject.

As described above, according to the fifth embodiment, the medical-agent valve is released after the piercing of the needle, thereby making it possible to locally inject the medicine without wasting. Also, according to the fifth embodiment, plural operations can be controlled by the same driving source by changing the magnetic field strength, thereby making it possible to simplify and downsize the capsule guiding system. Furthermore, according to the fifth embodiment, plural operations can be controlled by an actuator with a simple structure, thereby making it possible to include plural functions in the limited space of the capsule endoscope.

The case is described in FIG. 68 in which the operation of piercing with the needle 427 and the operation of opening the valve 504 are sequentially performed, but these operations may be driven simultaneously. In this case, simultaneous driving is achieved by equalizing the magnet sizes of the rotationally-moving magnets 6a, 6b or by approximately equalizing a gap between the rotationally-moving magnet 6a and the fixed magnet 7 and a gap between the rotationally-moving magnet 6b and the fixed magnet 7. Or, simultaneous driving can be achieved by applying a magnetic field with a magnetic field strength allowing the rotationally-moving magnet 6a to rotate, thereby operating, together with the rotationally-moving magnet 6a, the rotationally-moving magnet 6b that is operable with magnetization with a magnetic field strength weaker than that of the rotationally-moving magnet 6a.

First Modification Example

Figure 69:
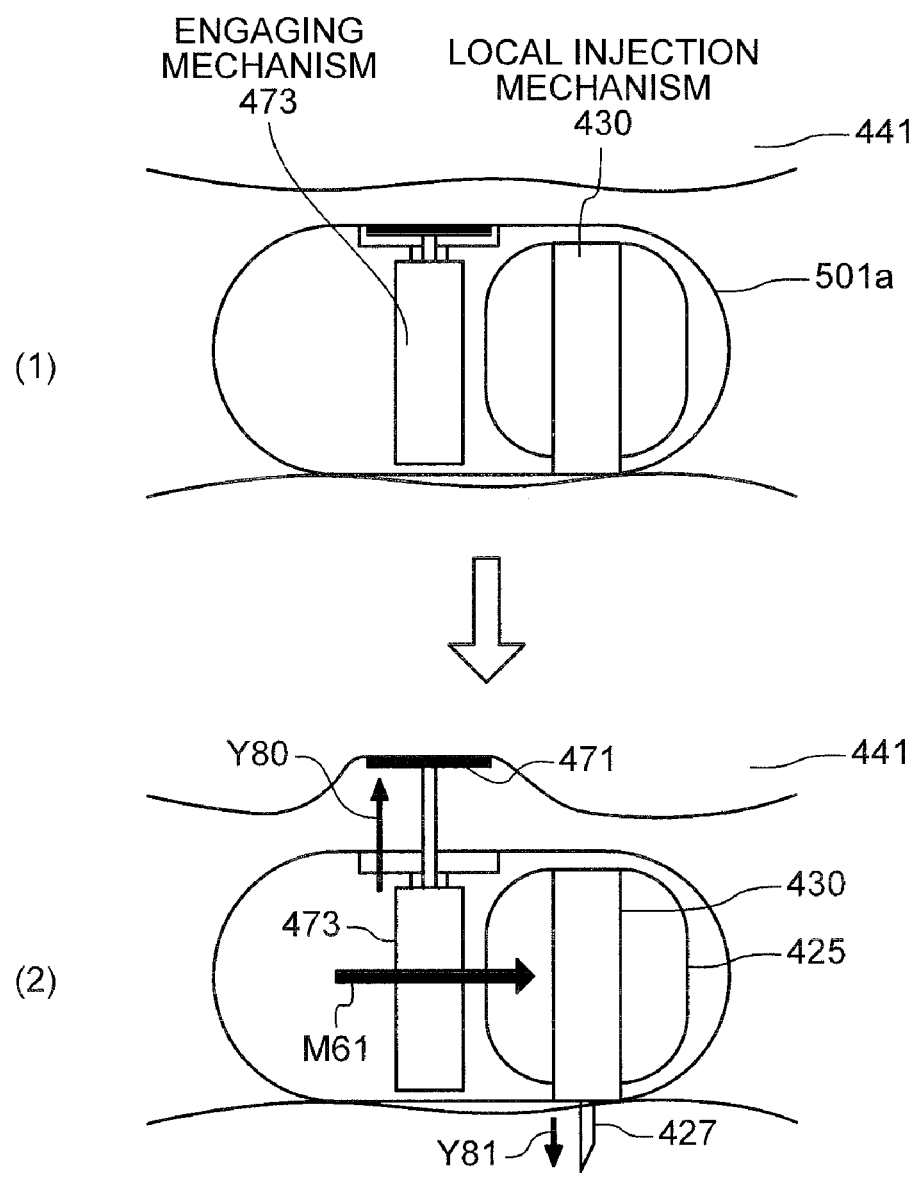
FIG. 69 shows diagrams explaining a capsule endoscope according to a first modification example in the fifth embodiment.

Next, with reference to FIG. 69, a first modification example in the fifth embodiment is described. As depicted in FIG. 69(1), a capsule endoscope 501a according to the first modification example includes both of the local injection mechanism 430 described with reference to FIG. 55 and FIG. 56 and an engaging mechanism 470 described with reference to FIG. 61. In the capsule endoscope 501a, a magnetic actuator that configures the local injection mechanism 430 and a magnetic actuator that configures the engaging mechanism 473 have their magnetic size or a gap between the rotationally-moving magnet 6 and the fixed magnet 7 set so that the engaging mechanism 473 operates earlier than the local injection mechanism 430.

For this reason, as indicated by an arrow Y80 in FIG. 69(2), the magnetic-field generating unit 403 first applies a magnetic field M61 with a magnetic field strength allowing the magnetic actuator that configures the engaging mechanism 473 to operate, thereby engaging with the engaging plate 471. Thereafter, the magnetic-field generating unit 403 applies, as indicated by an arrow Y81 in FIG. 69(2), a magnetic field with a magnetic field strength allowing the magnetic actuator that configures the local injection mechanism 430 to operate to pierce with the needle 427 for local injection processing. As described above, according to the first modification example, the medicine can be locally injected with the capsule endoscope 501a being engaged, thereby making it possible to reliably pierce without receiving an influence of counterforce at the time of piercing.

Sixth Embodiment

Figure 70:
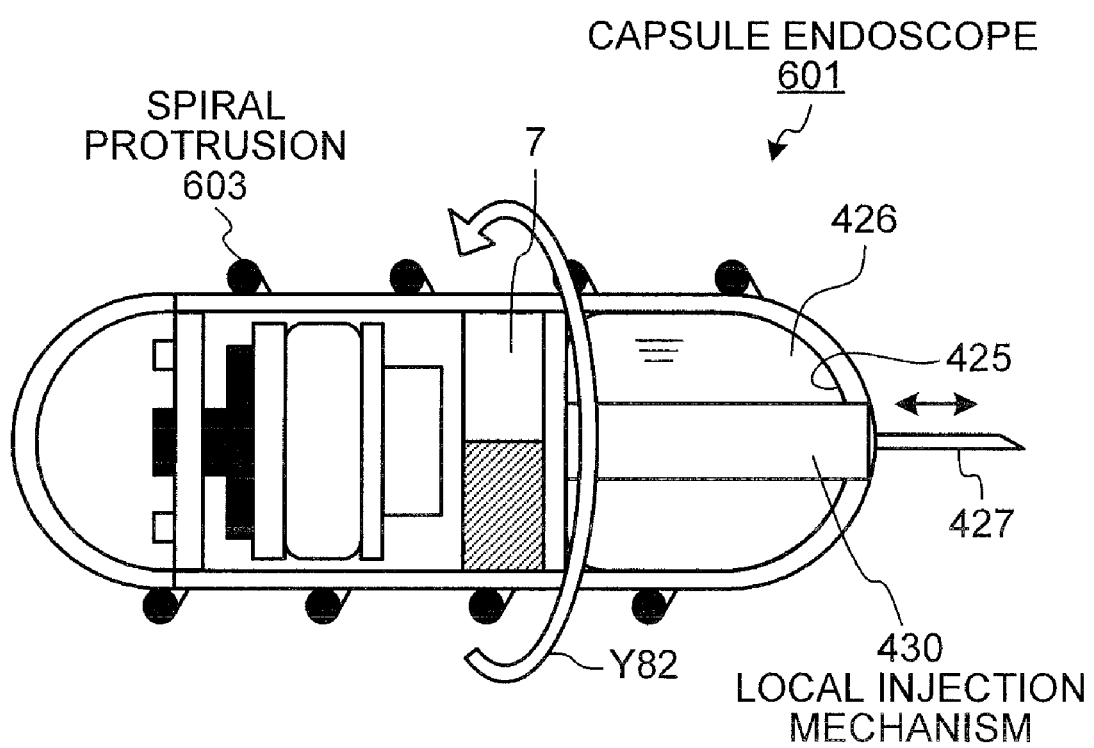
FIG. 70 shows a sectional view of the capsule endoscope according to a sixth embodiment cut along an axial direction.
Figure 71:
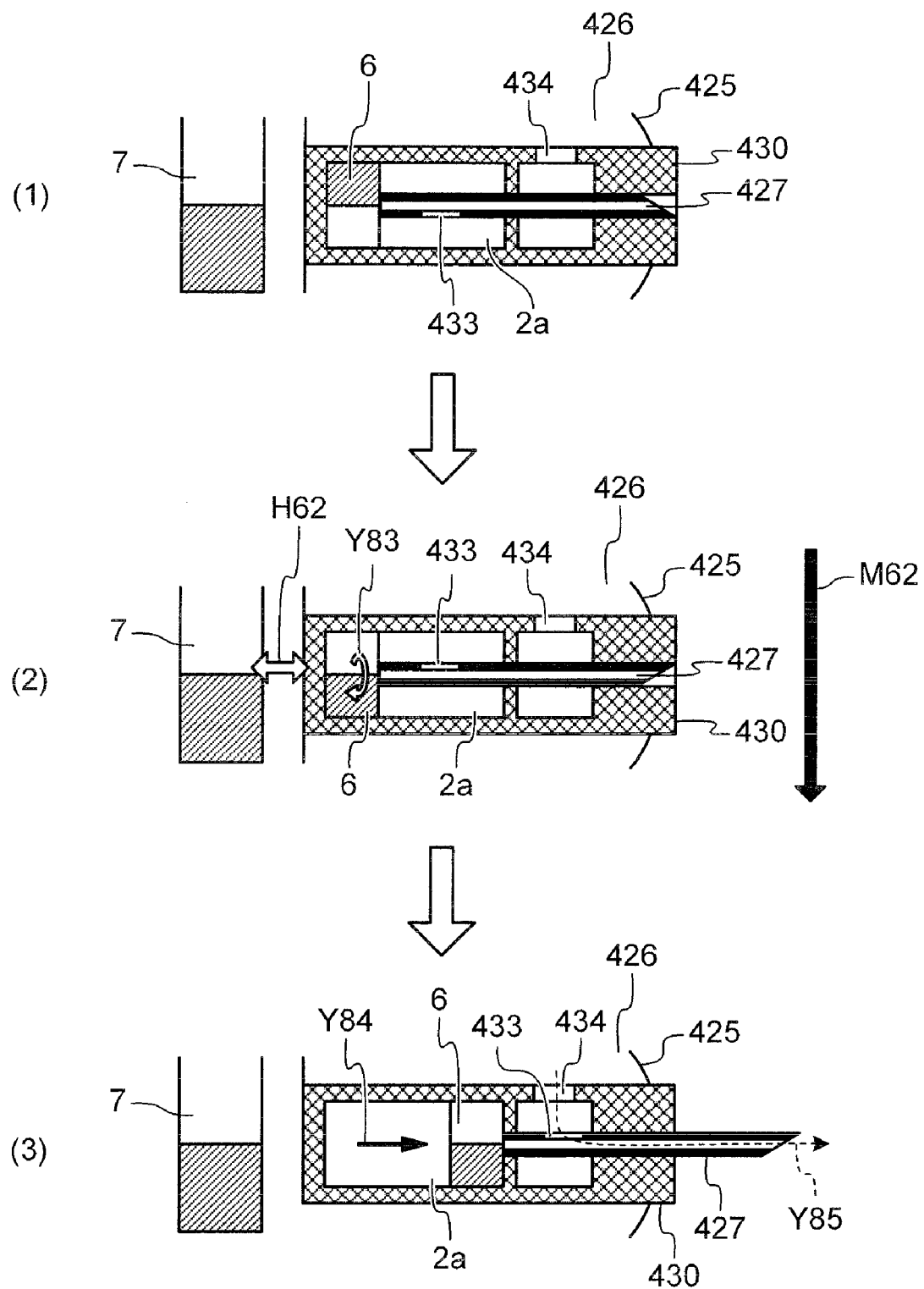
FIG. 71 shows diagrams depicting a section configuration of a local injection mechanism depicted in FIG. 70.
Figure 72:
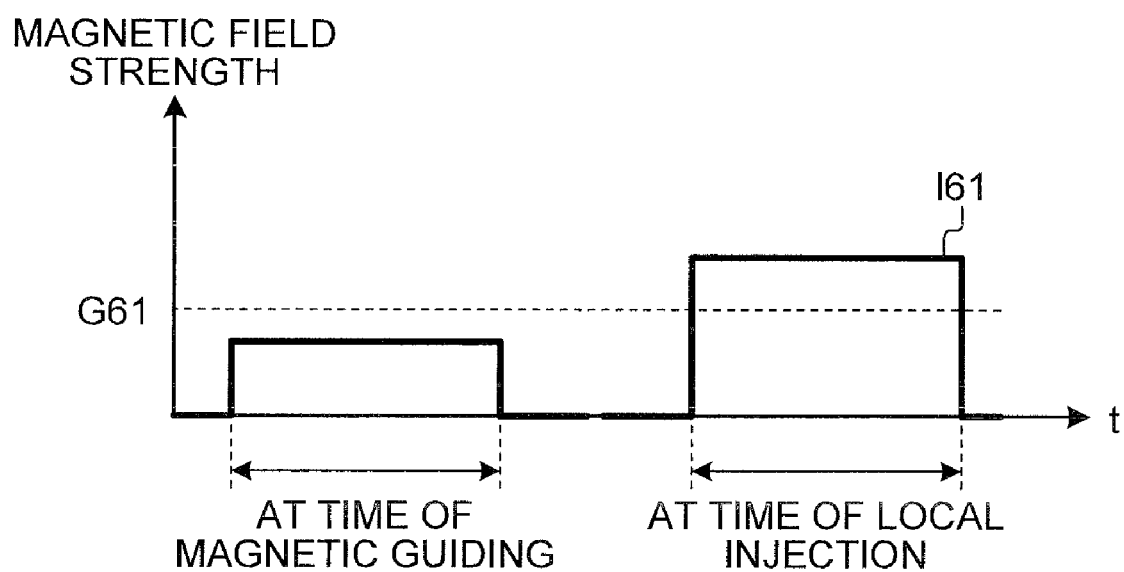
FIG. 72 shows a diagram explaining a magnetic field strength required for the capsule endoscope depicted in FIG. 70 to perform a predetermined operation.

Next, a sixth embodiment is described. FIG. 70 is a sectional view of a capsule endoscope according to the sixth embodiment in an axial direction. FIG. 71 shows diagrams depicting a section configuration of a local injection mechanism depicted in FIG. 70, and FIG. 72 is a diagram explaining a magnetic field strength required for performing a predetermined operation. Note that a capsule guiding system in the sixth embodiment has a configuration similar to that of the capsule guiding system 400 in the fourth embodiment.

As depicted in FIG. 70, a capsule endoscope 601 according to the sixth embodiment includes a fixed magnet 7 with a volume larger than that of the rotationally-moving magnet 6 in the local injection mechanism 430 depicted in FIG. 71(1). The orientation of the magnetic field of the fixed magnet 7 is in a radial direction of the capsule endoscope 601. With a rotating magnetic field exerted about the axis of the capsule endoscope 601 (for example, in a direction indicated by an arrow Y82 in FIG. 70), the capsule endoscope 601 rotates. A spiral protrusion 603 is formed about a cylindrical portion of the capsule endoscope 601. When the capsule endoscope 601 rotates, the spiral protrusion 603 hits in an in-vivo alimentary canal wall, thereby allowing the capsule endoscope 601 to move in an axial direction as a screw.

Here, since the fixed magnet 7 has a volume larger than that of the rotationally-moving magnet 6 in the local injection mechanism 430, as depicted in FIG. 72, by applying a rotating magnetic field with a magnetic field strength weaker than a magnetic field strength G61 allowing the local injection mechanism 430 to operate, the capsule endoscope 601 can be rotated by magnetic guiding.

Also, as depicted in FIG. 71(1) and indicated by a curve 161 in FIG. 72, at the time of local injection, a magnetic field M62 is applied that has a magnetic field with a magnetic field strength stronger than the magnetic field strength G61 allowing the rotationally-moving magnet 6 in the local injection mechanism 430 to rotate and has an angular difference equal to or smaller than 60 degrees relative to the magnetization direction of the fixed magnet 7. As a result, the rotationally-moving magnet 6 rotates as indicated by an arrow Y83 in FIG. 71(2) and, as indicated by an arrow Y84 in FIG. 71(3), with a repulsive force H62 occurring between the fixed magnet 7 and the rotationally-moving magnet 6, moves in a left direction in FIG. 71(3). Accordingly, as indicated by an arrow Y85 in FIG. 71(3), the needle 427 is pushed outside of the capsule endoscope 601 while rotating, thereby injecting the medicine 426. Since the needle 427 is pushed while rotating, reliable piercing can be achieved. The magnetic field M62 applied for operating the local injection mechanism 430 may vibrate the tilt of the magnetic field near a generated magnetic filed direction when the magnetization direction of the fixed magnet 7 is controlled. As a result, an angular difference between the generated magnetic field when the magnetization direction of the fixed magnet 7 is controlled and the magnetization direction of the fixed magnet can be absorbed.

As described above, according to the sixth embodiment, by applying the rotating magnetic field to the capsule endoscope 601, the capsule endoscope 601 can be guided, thereby achieving improvement in observation efficiency and making it possible to accurately control the local injection position.

In the capsule endoscope 601, the case is described in which the size of the fixed magnet 7 is made larger than the rotationally-moving magnet 6 in the local injection mechanism 430 and the fixed magnet 7 is used for magnetic guiding. Alternatively, the size of the rotationally-moving magnet 6 in the local injection mechanism 430 may be made larger than the fixed magnet 7 and the rotationally-moving magnet 6 may be used for magnetic guiding. In this case, with application of the strong magnetic field M62 for operating the local injection mechanism 430, not the rotationally-moving magnet but the fixed magnet 7 rotates, thereby pushing the needle 427 while the main body of the capsule endoscope 601 having the fixed magnet 7 fixed thereto is rotating. As described above, with the rotation of the main body of the capsule endoscope 601, a propulsion force is generated in a piercing direction, thereby allowing a reliable piercing operation.

Figure 73:
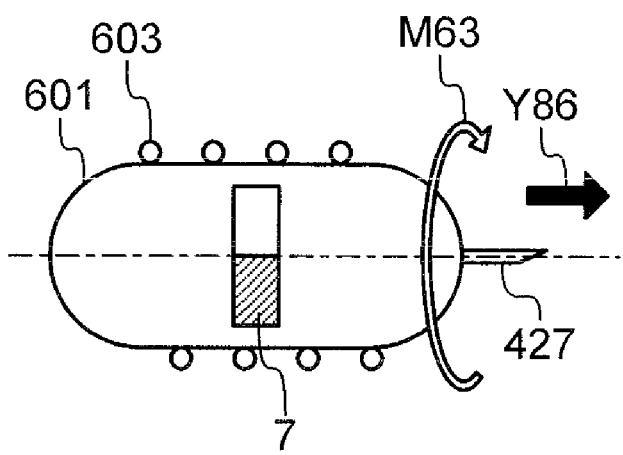
FIG. 73 shows a diagram explaining a magnetic field applied to the capsule endoscope depicted in FIG. 70.

Also, in the capsule endoscope 601, as depicted in FIG. 73, a rotating magnetic field M63 may be set as a magnetic field to be generated at the time of local injection, thereby strongly pressing the needle 427 onto the tube wall with spiral propulsion. In this case, as indicated by an arrow Y86 in FIG. 73, the pressing force can be generated in the piercing direction, thereby allowing reliable piercing.

Figure 74:
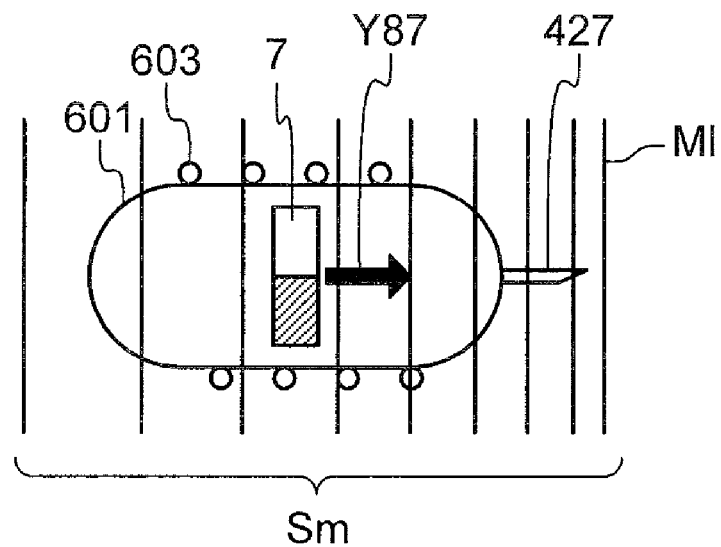
FIG. 74 shows a diagram explaining a magnetic field applied to the capsule endoscope depicted in FIG. 70.

Furthermore, in the capsule endoscope 601, as depicted in FIG. 74, an inclined magnetic field Sm may be applied in which spaces between magnetic lines of force M1 become narrower as heading for a direction of pushing the needle 427, thereby guiding the capsule endoscope 601 with a magnetic attractive force occurring as indicated by an arrow Y87. Still further, in the capsule endoscope 601, the magnetic attractive force may be generated at the time of local injection and the needle may be strongly pressed onto the tube wall with the magnetic attractive force.

First Modification Example

Figure 75:
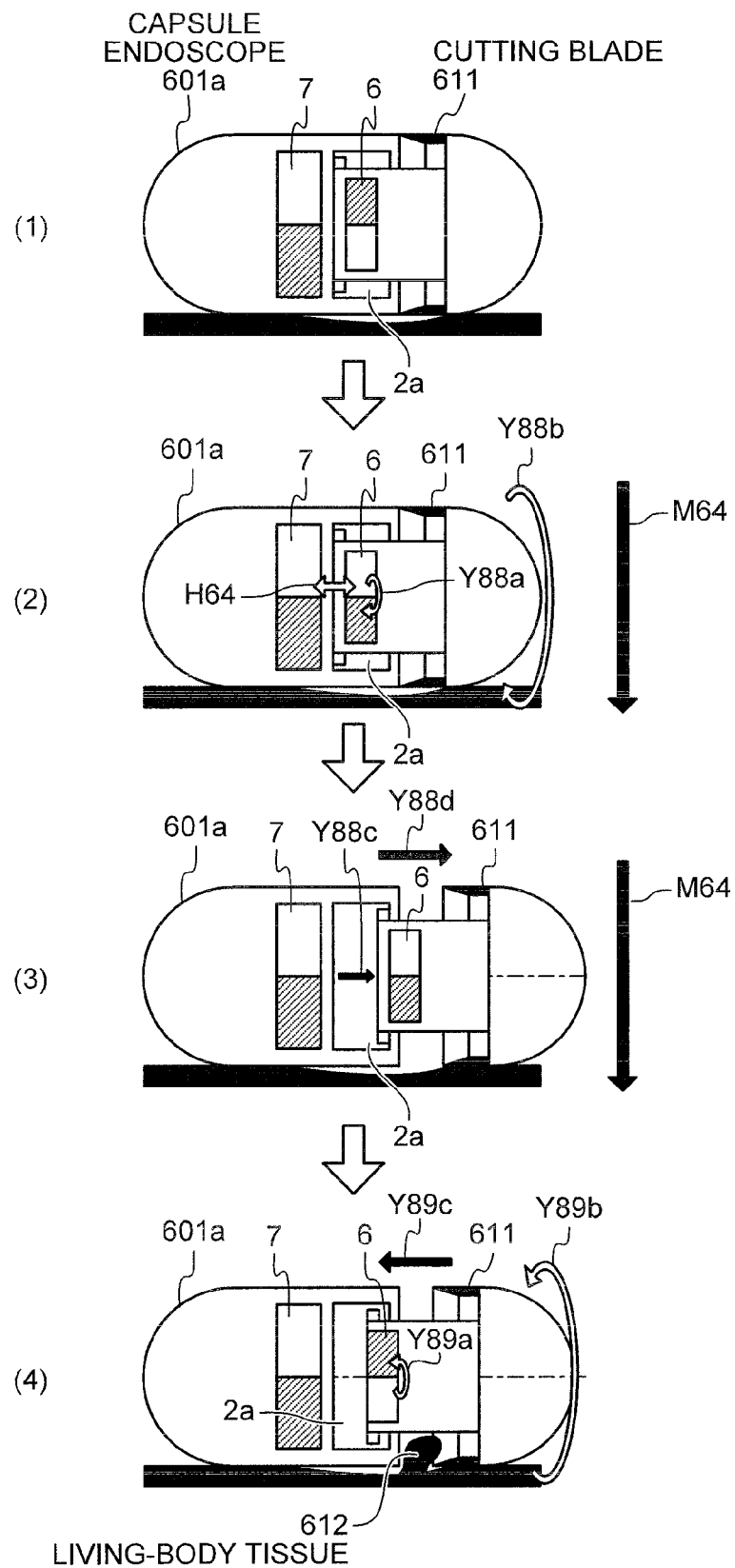
FIG. 75 shows sectional views of a capsule endoscope according to a first modification example in a sixth embodiment cut along an axial direction.

Next, with reference to FIG. 75, a first modification example in the sixth embodiment is described. As depicted in FIG. 75(1), a capsule endoscope 601a according to the first modification example applies the magnetic actuator 1 to widen a biopsy mechanism having a cutting blade 611 in the capsule endoscope 601a to collect a desired tissue. The biopsy mechanism having the cutting blade 611 is connected to the rotationally-moving magnet 6, and rotates or moves integrally with the rotationally-moving magnet 6.

As indicated by an arrow Y88a in FIG. 75(2), with application of a magnetic field M64 with a magnetic field strength allowing the rotationally-moving magnet 6 to rotate, the rotationally-moving magnet 6 rotates. Accordingly, as indicated by an arrow Y88b in FIG. 75(2), the biopsy mechanism that configures a right side portion of the capsule endoscope 601a having the cutting blade 611 also rotates.

With a repulsive force H64 occurring between the rotationally-moving magnet 6 and the fixed magnet 7 depicted in FIG. 75(2), as indicated by an arrow Y88c in FIG. 75(3), the rotationally-moving magnet 6 moves in a right direction in FIG. 75(3) inside the guiding area 2a. Accordingly, as indicated by an arrow Y88d in FIG. 75(3), the biopsy mechanism to which the rotationally-moving magnet 6 is connected also moves in the right direction in FIG. 75(3), thereby widening the biopsy mechanism. Then, as depicted in FIG. 75(4), when a living-body tissue 612 to be collected is present, the magnetic-field generating unit 403 weakens the magnetic field strength of the magnetic field M64. As a result, the repulsive force H64 occurring between the rotationally-moving magnet 6 and the fixed magnet 7 disappears, and the rotationally-moving magnet 6 moves, as indicated by an arrow 89b in FIG. 75(4), to the fixed magnet 7 side while rotating. Accordingly, the biopsy mechanism connected to the rotationally-moving magnet 6 also moves, as indicated by an arrow Y89a and an arrow Y89c, to the fixed magnet 7 side, that is, to a direction of closing the biopsy mechanism, while rotating. In this case, the living-body tissue 612 to be collected is cut out by the cutting blade 611 and is accommodated into the biopsy mechanism. Note that, when a tissue cannot be collected with the biopsy mechanism being closed, a rotating magnetic field is applied to rotate the main body of the capsule endoscope, thereby cutting and collecting a living-body tissue to be collected.

As described above, according to the first modification example, the main body of the capsule endoscope 601a is rotated, thereby allowing the cutting blade 611 to rotate to close the biopsy mechanism. With this, the capability of cutting the living-body tissue 612 to be collected is improved, and the tissue can be reliably collected. Also, according to the first modification example, the magnet of the magnetic actuator is used to rotate the main body of the capsule endoscope 601a, thereby making it possible to improve energy efficiency. Still further, according to the first modification example, no mechanism for rotating the main body of the capsule endoscope is required. With this, the main body of the capsule endoscope can be downsized, and insertability into the subject can be improved.

Figure 76:
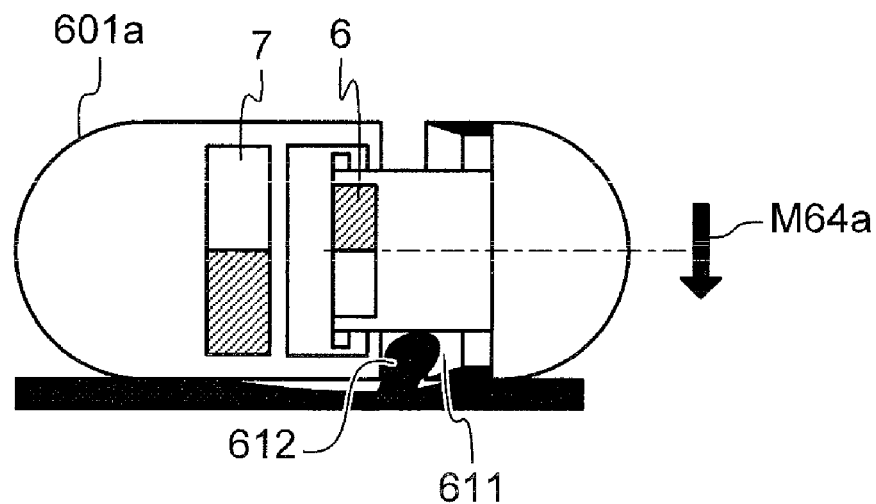
FIG. 76 shows a diagram explaining the operation of the capsule endoscope depicted in FIG. 75.

Still further, as depicted in FIG. 76, with a magnetic attractive force M64a pressing the cutting blade 611 in the capsule endoscope 601a onto the living-body tissue, the living-body tissue can be further reliably cut out and collected.

Seventh Embodiment

Figure 77:
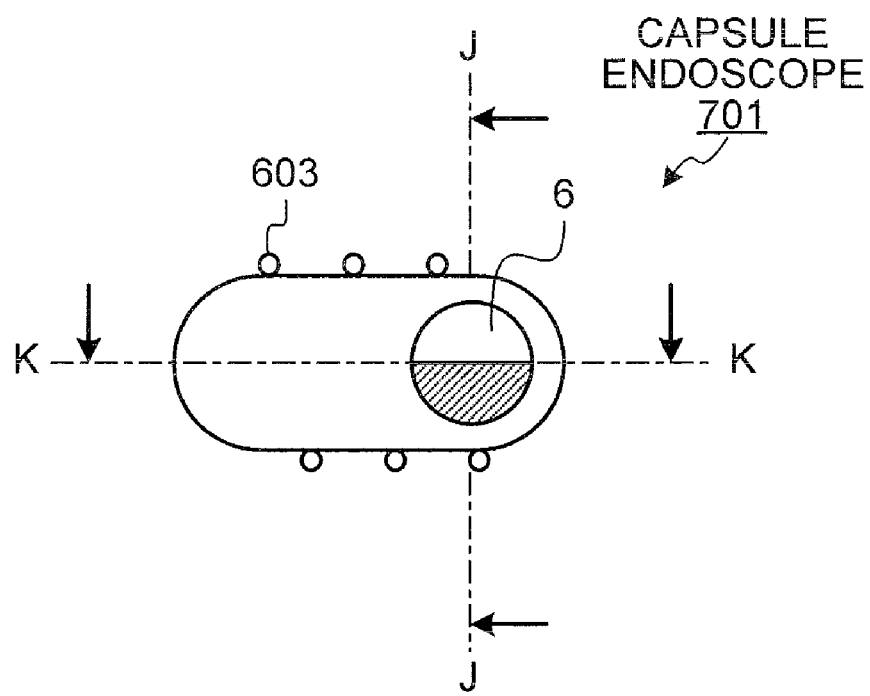
FIG. 77 shows a sectional view of the capsule endoscope according to a seventh embodiment cut along a predetermined plane in an axial direction.
Figure 78:
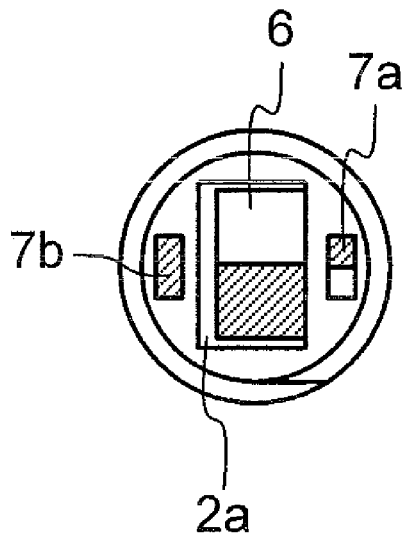
FIG. 78 shows a sectional view of a magnetic actuator depicted in FIG. 77 cut along a J-J line in a radial direction in FIG. 77.
Figure 79:
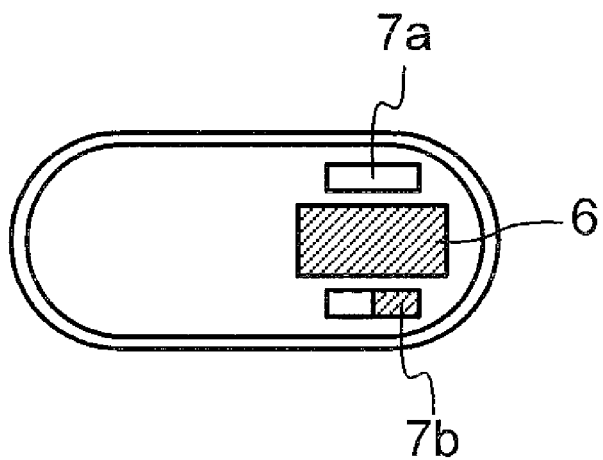
FIG. 79 shows a sectional view of the magnetic actuator depicted in FIG. 77 cut along a K-K line in an axial direction in FIG. 77.

Next, a seventh embodiment is described. In the seventh embodiment, a magnetic field with a different magnetic field strength is applied to a magnet for magnetic guiding, thereby performing magnetic guiding of the capsule endoscope or directional control over the capsule endoscope. FIG. 77 is a sectional view of the capsule endoscope according to the seventh embodiment cut along a predetermined plane in an axial direction, FIG. 78 is a sectional view of a magnetic actuator cut along a J-J line in a radial direction in FIG. 77, and FIG. 79 is a sectional view of the magnetic actuator cut along a K-K line in an axial direction in FIG. 77. Note that a capsule guiding system in the seventh embodiment has a configuration similar to that of the capsule guiding system 400 in the fourth embodiment.

As depicted in FIG. 77, in a capsule endoscope 701 according to the seventh embodiment, the rotationally-moving magnet 6 for magnetic guidance using the spiral protrusion 603 is provided which is rotatable in an axial direction of the capsule endoscope 701. This rotationally-moving magnet 6 of the capsule endoscope 701 can move in a horizontal direction in FIG. 78, that is, in a radial direction of the capsule endoscope 701, inside the guiding area 2a depicted in FIG. 78. Also, as depicted in FIG. 78 and FIG. 79, in the radial direction of the capsule endoscope 701, fixed magnets 7a, 7b are provided on both sides of the rotationally-moving magnet 6, the fixed magnets 7a, 7b having a volume and magnetic force both smaller than those of the rotationally-moving magnet 6. The fixed magnet 7a is fixedly disposed inside the capsule endoscope 701 so that the orientation of the fixed magnet 7a is matched with the radial direction of the capsule endoscope 701. Also, the fixed magnet 7b is fixedly disposed inside the capsule endoscope 701 so that the orientation of the fixed magnet 7b is matched with the axial direction of the capsule endoscope 701.

Although not particularly shown, as with the capsule endoscope 401 according to the fourth embodiment described above, this capsule endoscope 701 according to the seventh embodiment includes, in a capsule casing, the position-detection oscillation coil 421, the imaging system 422, a wireless system that wireless transmits an image signal and the like to the external receiving unit 411 via the antenna 423, the battery 424, and a control unit that controls each component of the capsule endoscope 701 (the position-detection oscillation coil 421, the imaging system 422, and the wireless system). Also, as exemplarily described in the fourth to sixth embodiments or each modification example, this capsule endoscope 701 may include, as appropriate, a local injection mechanism that injects a medicine and a treatment mechanism (a forceps, a high-frequency heating member, etc.) that performs a medical treatment, such as collecting a living-body tissue or burning process onto the inside of the living body.

Figure 80:
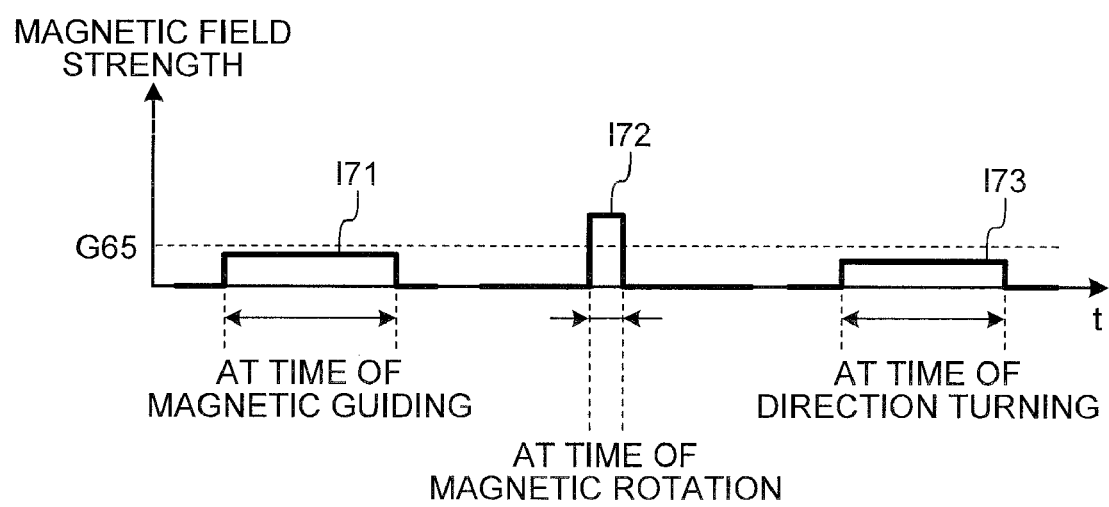
FIG. 80 shows a diagram depicting the magnetic field strength of a magnetic field to be applied in each predetermined state of the capsule endoscope depicted in FIG. 77.
Figure 81:
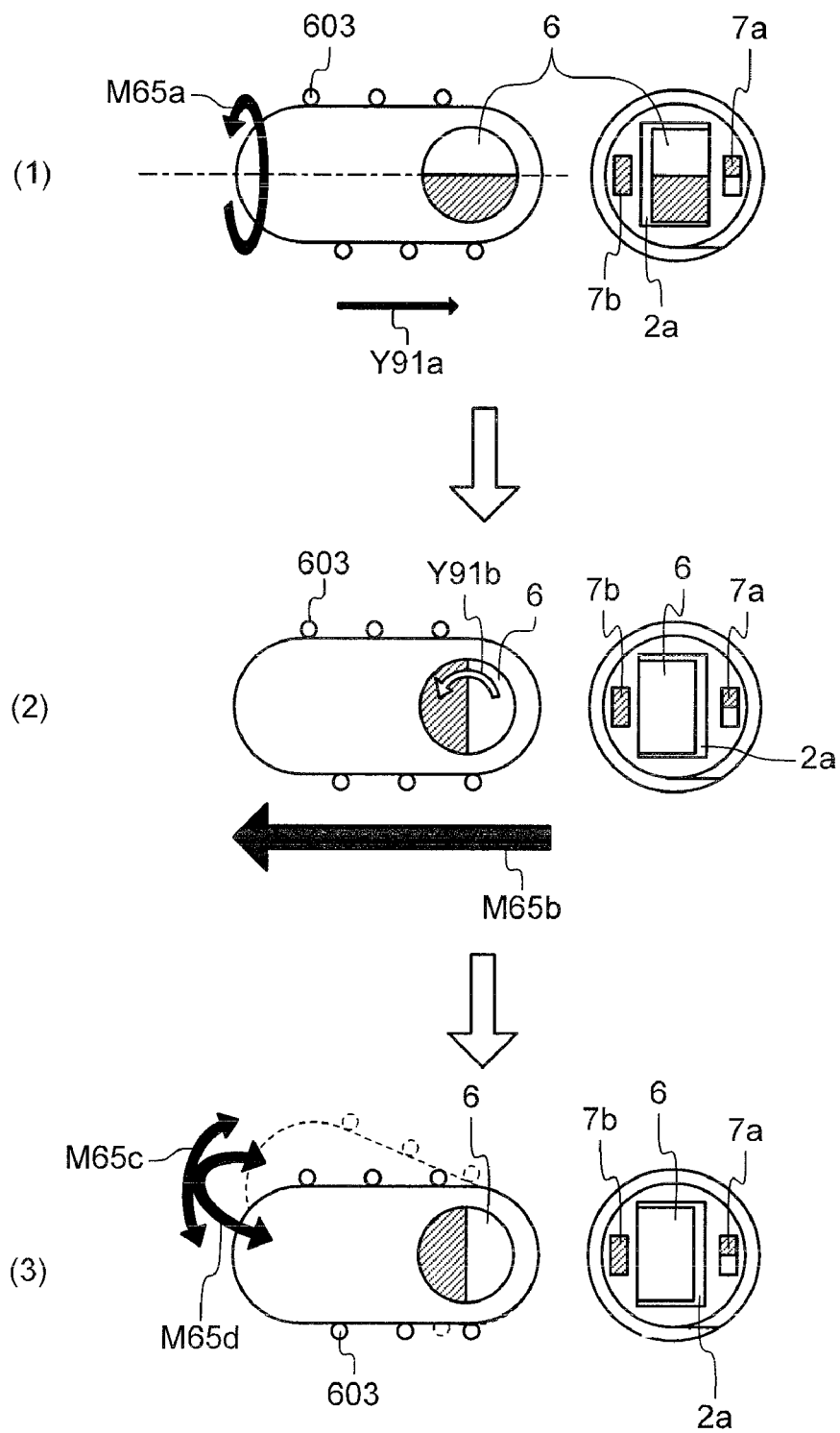
FIG. 81 shows sectional views of the capsule endoscope depicted in FIG. 77 cut along an axial direction.

In this capsule endoscope 701, the rotationally-moving magnet 6 for magnetic guiding is provided which is rotatable in an axial direction of the capsule endoscope 701. For this reason, with rotation according to the magnetic field applied, the magnetization direction of the rotationally-moving magnet 6 can be switched to a radial direction of the capsule endoscope 701 as depicted in FIG. 77 or an axial direction of the capsule endoscope 701. In the capsule endoscope 701 having an approximately cylindrical shape, the magnetization direction of the rotationally-moving magnet 6 can be changed from the radial direction of the capsule endoscope 701 to the axial direction of the capsule endoscope 701, and the magnetization direction changed to the axial direction of the capsule endoscope 701 can be kept. Here, the operation regarding switching the magnetization direction of the rotationally-moving magnet 6 in the capsule endoscope 701 is described. FIG. 80 is a diagram depicting the magnetic field strength to be applied by the magnetic-field generating unit 403 in each predetermined state of the capsule endoscope 701. FIG. 81 shows sectional views of the capsule endoscope 701 depicted in FIG. 77 cut along an axial direction.

When magnetic guiding is performed on the capsule endoscope 701 by using the spiral protrusion 603, as indicated by a curve 171 in FIG. 80, the magnetic-field generating unit 403 applies a rotating magnetic field M65a about a longitudinal axis of the capsule endoscope 701, the rotating magnetic field M65a having a magnetic field strength weaker than a magnetic field strength G65 allowing the rotationally-moving magnet 6 to rotate in the capsule endoscope 701. In this case, as depicted in a left drawing of FIG. 81(1), since the magnetic field strength of the applied rotating magnetic field M65a is weaker than the magnetic field strength allowing rotation, the rotationally-moving magnet 6 is attracted to the fixed magnet 7a to be continuously positioned on the fixed magnet 7a side in the guiding area 2a. For this reason, as depicted in a left drawing of FIG. 81(1), while keeping a state of keeping the magnetization direction in the radial direction of the capsule endoscope 701, that is, while keeping a state of not rotating in the capsule endoscope 701, the rotationally-moving magnet 6 rotates according to the rotating magnetic field M65a applied about the longitudinal axis of the capsule endoscope 701. As a result, the capsule endoscope 701 becomes in a magnetic guiding state of making spiral propulsion in a direction indicated by an arrow Y91a in the left drawing of FIG. 81(1) while rotating.

Next, a case is described in which the magnetization direction of the rotationally-moving magnet 6 is switched from the radial direction of the capsule endoscope 701 to the axial direction thereof. In this case, the magnetic-field generating unit 403 applies, as indicated by a curve 172 in FIG. 80, a magnetic field M65b having a magnetic field strength stronger than the magnetic field strength G65 allowing the rotationally-moving magnet 6 to rotate in the capsule endoscope 701 and having an angular difference equal to or smaller than 60 degrees in the magnetization direction of the fixed magnet 7a. In this case, as indicated by an arrow Y91b in a left drawing of FIG. 81(2), the rotationally-moving magnet 6 rotates according to the magnetic field M65b. As a result, as depicted in a left drawing of FIG. 81(2), the rotationally-moving magnet 6 receives an influence of a repulsive force occurring between the fixed magnet 7a and itself to move to the fixed magnet 7b side in the guiding area 2a and, with an attractive force occurring between the fixed magnet 7b and itself, is continuously positioned on the fixed magnet 7b side in the guiding area 2a. As described above, the magnetization direction of the rotationally-moving magnet 6 can be switched from the radial direction of the capsule endoscope 701 to the axial direction thereof.

Then, as indicated by a curve 173 in FIG. 80, the magnetic-field generating unit 403 applies a magnetic field having a magnetic field strength weaker than the magnetic field strength G65 allowing the rotationally-moving magnet 6 to rotate in the capsule endoscope 701 and corresponding to a turning direction. In this case, as depicted in a left drawing of FIG. 81(3), the magnetic field strength of the applied rotating magnetic field is weaker than the magnetic field strength allowing rotation, the rotationally-moving magnet 6 is attracted to the fixed magnet 7b to be continuously positioned on the fixed magnet 7b side in the guiding area 2a. Then, the rotationally-moving magnet 6 operates so as to achieve a magnetization direction according to the magnetic field applied to the capsule endoscope 701. Therefore, the capsule endoscope 701 can integrally turn the direction according to the orientation of the applied magnetic field. For example, as depicted in a left drawing of FIG. 81(3), when a magnetic field M65c is applied, the capsule endoscope 701 can turn the direction in a vertical direction. When a magnetic field M65d is applied, the capsule endoscope 701 can turn the direction to a depth direction or a front direction.

As described above, according to the seventh embodiment, by applying the magnetic actuator 1, the orientation of the guiding magnet in the capsule endoscope 701 can be changed. As a result, in the capsule endoscope 701, two operations, spiral propulsion and direction turning, can be separately performed, thereby allowing more sophisticated and efficient guiding. Furthermore, in the capsule endoscope 701, the rotationally-moving magnet 6 can be shared for use in these two operations, spiral propulsion and direction turning. With this, the main body of the capsule endoscope can be downsized, and a capsule guiding system excellent in insertability into the subject can be achieved.

First Modification Example

Figure 82:
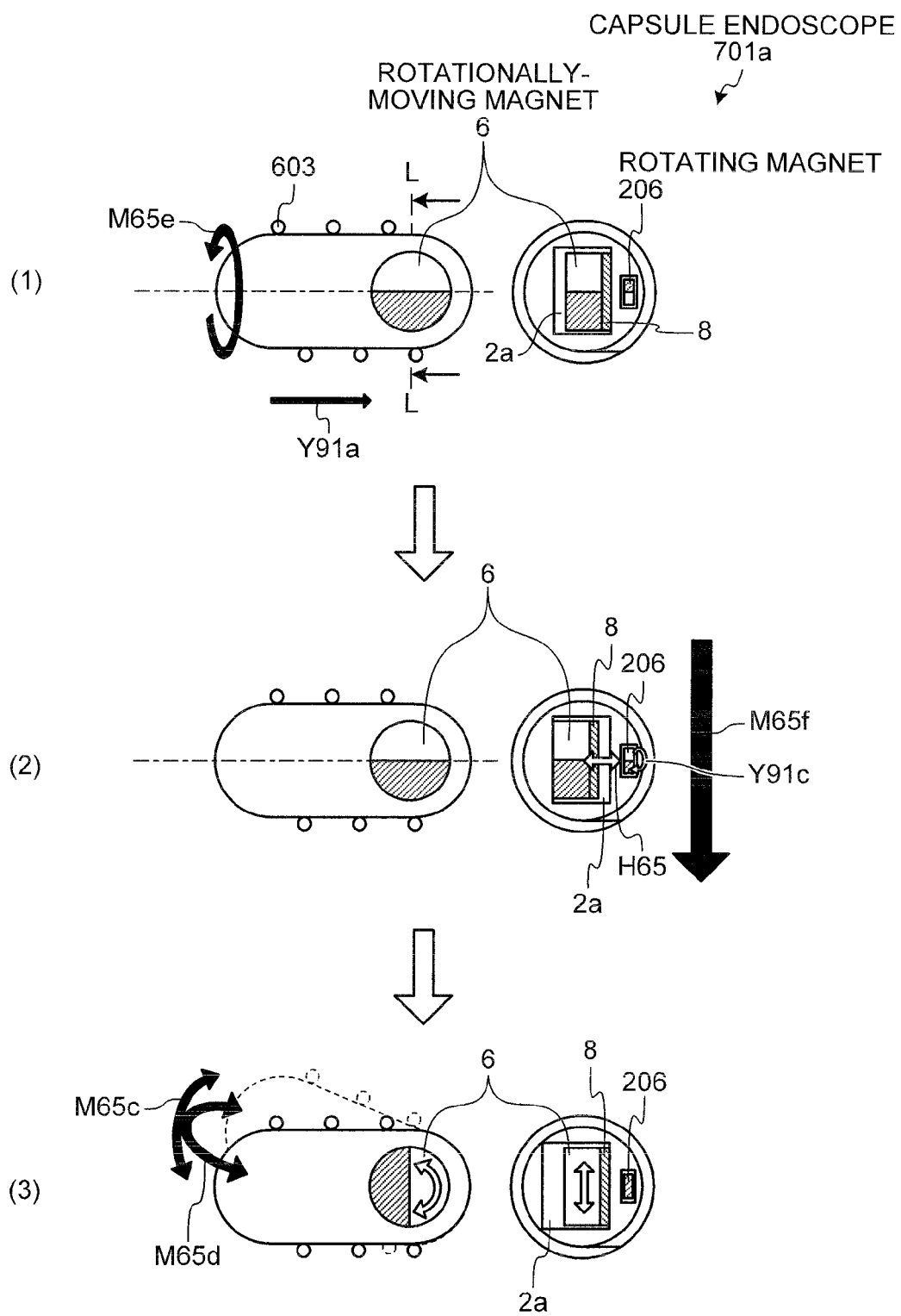
FIG. 82 shows sectional views of a capsule endoscope according to a first modification example in the seventh embodiment.
Figure 83:
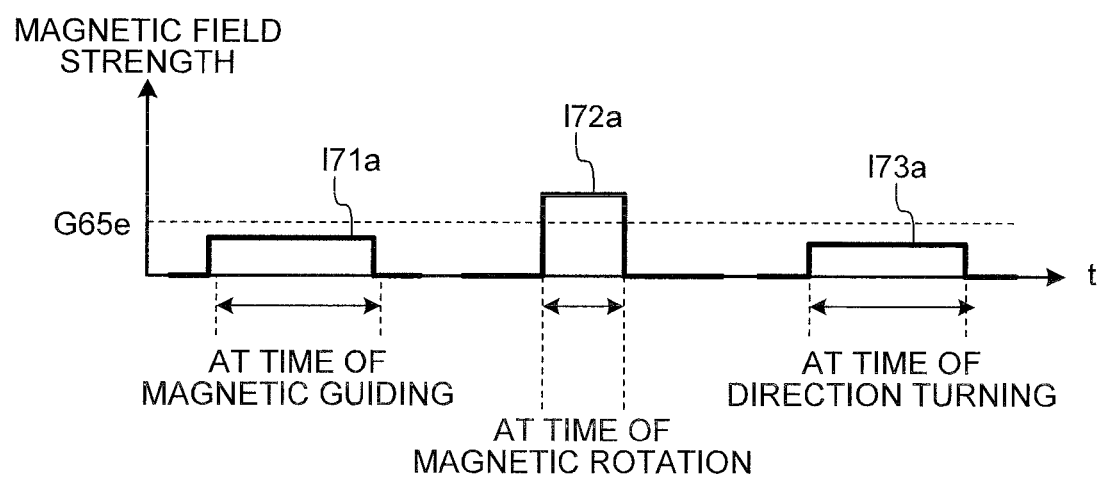
FIG. 83 shows a diagram depicting the magnetic field strength of a magnetic field applied in each predetermined state of the capsule endoscope depicted in FIG. 82.

Next, with reference to FIG. 82 and FIG. 83, a first modification example in the seventh embodiment is described. FIG. 82 shows sectional views of a capsule endoscope according to the first modification example. A left drawing of FIG. 82 shows sectional views of the capsule endoscope according to the first modification example cut along an axial direction, and a right drawing of FIG. 82 shows sectional views of the capsule endoscope cut along an L-L line in the left drawing of FIG. 82. FIG. 83 is a diagram depicting the magnetic field strength of a magnetic field applied by the magnetic-field generating unit 403 in each predetermined state of the capsule endoscope according to the first modification example. As depicted in FIG. 82, a capsule endoscope 701a according to the first modification example has a configuration in which, in contrast to the capsule endoscope 701, the rotating magnet 206 in place of the fixed magnet 7a and the rotationally-moving magnet 6 having the high-friction member 8 provided on a surface on the rotating magnet 206 side in place of the rotationally-moving magnet 6 are included and the fixed magnet 7b is eliminated. Other structure is similar to that of the capsule endoscope 701 according to the seventh embodiment described above. Also, a capsule guiding system according to this first modification example of the seventh embodiment is approximately similar to the capsule guiding system 400 according to the fourth embodiment described above, and has a configuration in which the capsule endoscope 701a is included in place of the capsule endoscope 401 of the capsule guiding system.

First, when the spiral protrusion 603 is used for the capsule endoscope 701a for magnetic guiding, as indicated by a curve 171a in FIG. 83, the magnetic-field generating unit 403 applies a rotating magnetic field M65e about a longitudinal axis of the capsule endoscope 701a, the rotating magnetic field M65e having a magnetic field strength weaker than a magnetic field strength G65e allowing the rotating magnet 206 to rotate in the capsule endoscope 701a. In this case, as depicted in the right drawing of FIG. 82(1), the rotationally-moving magnet 6 is attracted to the rotating magnet 206, with rotation being restrained by the high-friction member 8, to be continuously positioned on the rotating magnet 206 side in the guiding area 2a. As depicted in the left drawing of FIG. 82(1), according to the rotating magnetic field M65e, the rotationally-moving magnet 6 rotates according to the rotating magnetic field M65e applied about the longitudinal axis of the capsule endoscope 701a while keeping the state of not rotating in the capsule endoscope 701a. Therefore, the capsule endoscope 701a becomes in a magnetic guiding state of spiral propulsion in a direction indicated by an arrow Y91a while rotating.

Then, the magnetic-field generating unit 403 applies, as indicated by a curve 172a in FIG. 83, a magnetic field M65e having a magnetic field strength stronger than the magnetic field strength G65e and having an angular difference equal to or smaller than 60 degrees in the magnetization direction of the rotationally-moving magnet 6 in the state depicted in the left drawing of FIG. 82(1). In this case, as indicated by an arrow Y91c in the right drawing of FIG. 82(2), the rotating magnet 206 rotates according to the magnetic field M65e. As a result, as depicted in the right drawing of FIG. 82(2), the rotationally-moving magnet 6 receives an influence of a repulsive force H65 occurring between the rotating magnet 206 and itself to move in the guiding area 2a, and becomes rotatable with a rotation restraint of the high-friction member 8 being released. Then, the magnetization direction of the rotationally-moving magnet 6 is oriented the same as the orientation of the magnetic field M65f, and the rotating magnet 206 having a volume smaller than that of the rotationally-moving magnet 6 rotates so that the magnetization direction becomes the opposite to the rotationally-moving magnet 6. As a result, as depicted in the right drawing of FIG. 82(3), with an attractive force occurring between the rotationally-moving magnet 6 and the rotating magnet 206, the rotationally-moving magnet 6 moves to the rotating magnet 206 side in the guiding area 2a, with rotation being restrained again by the high-friction member 8. As described above, the magnetization direction of the rotationally-moving magnet 6 can be switched from the radial direction of the capsule endoscope 701a to the axial direction thereof.

Then, when direction turning of the capsule endoscope 701a is performed, as with the capsule endoscope 701, as indicated by a curve 173a in FIG. 83, the magnetic-field generating unit 403 applies a magnetic field having a magnetic field strength weaker than the magnetic field strength G65e and being oriented correspondingly to the turning direction, such as the magnetic field M65c or 65d.

In this capsule endoscope 701a, with the magnetic actuator according to the present invention being incorporated, as with the capsule endoscope 701 according to the seventh embodiment, the main body of the capsule endoscope can be downsized. As a result, a capsule guiding system excellent in insertability into the subject can be achieved.

Second Modification Example

Figure 84:
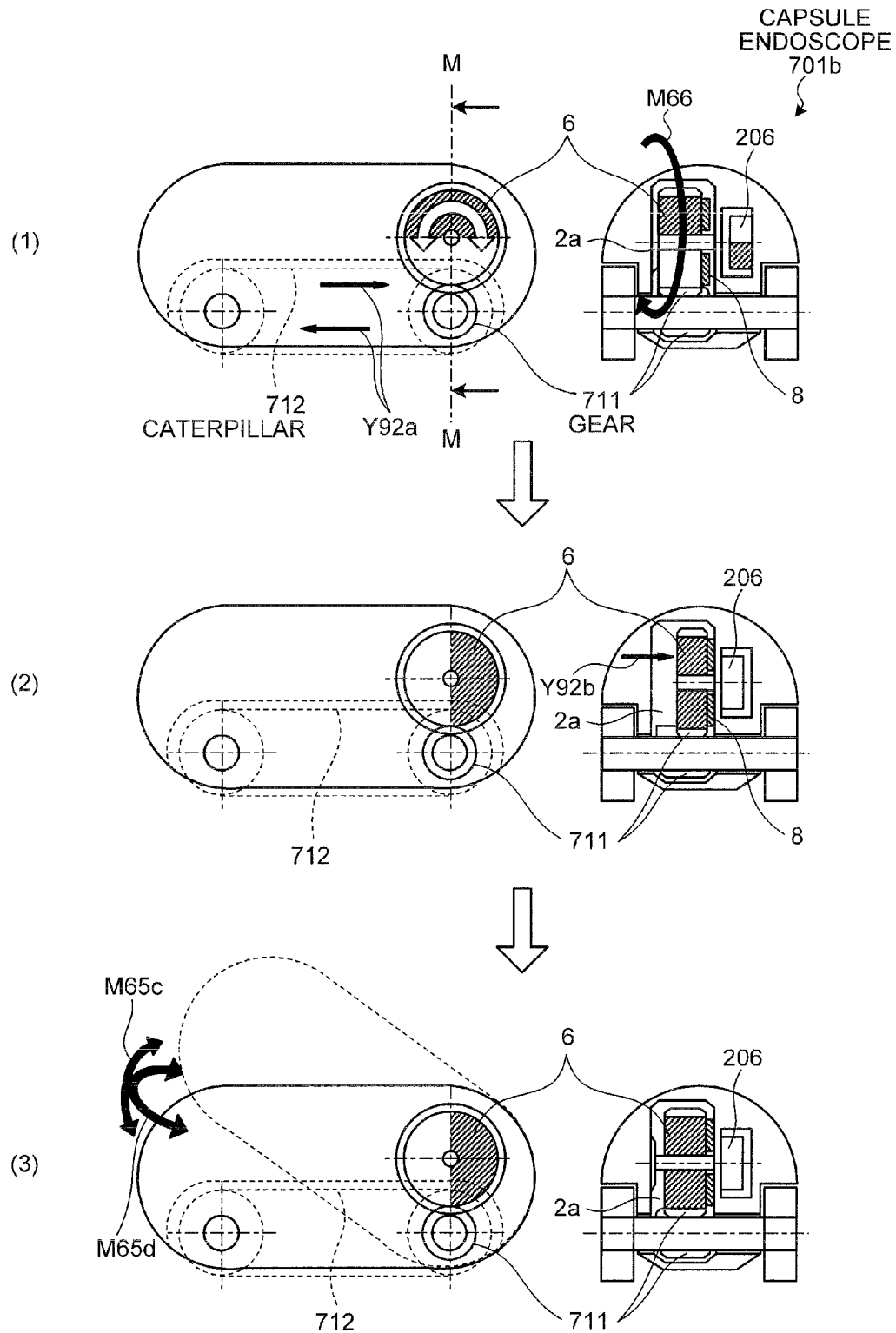
FIG. 84 shows sectional views of a capsule endoscope according to a second modification example in the seventh embodiment.
Figure 85:
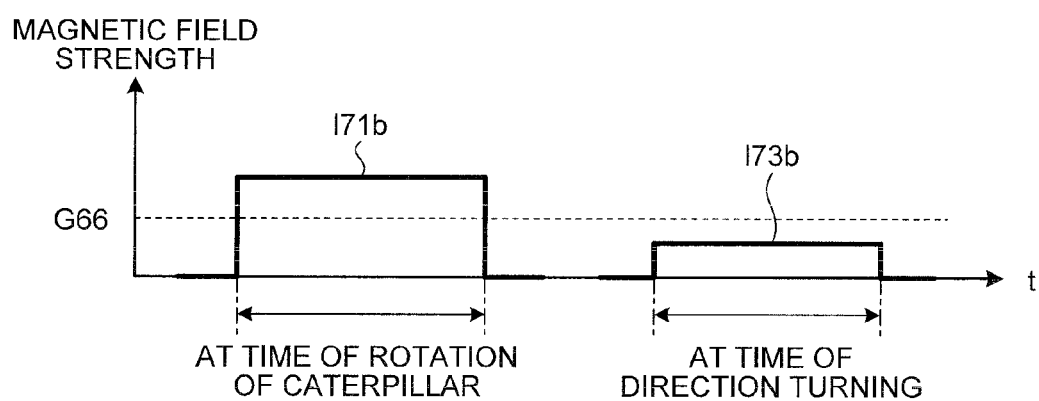
FIG. 85 shows a diagram of the magnetic field strength of a magnetic field applied in each predetermined state of the capsule endoscope depicted in FIG. 84.

Next, with reference to FIG. 84 and FIG. 85, a second modification example in the seventh embodiment is described. FIG. 84 shows sectional views of a capsule endoscope according to the second modification example. A left drawing of FIG. 84 shows sectional views of the capsule endoscope according to the second modification example cut along an axial direction, a right drawing of FIG. 84 shows sectional views of the capsule endoscope cut along an M-M line in the left drawing of FIG. 84. FIG. 85 is a diagram of the magnetic field strength of a magnetic field applied by the magnetic-field generating unit 403 in each predetermined state of the capsule endoscope according to the second modification example. As depicted in FIG. 84, a capsule endoscope 701b according to the second modification example further includes, in contrast to the capsule endoscope 701a, a caterpillar 712 that rotates as indicated by an arrow Y92a to move the capsule endoscope 701b and a gear 711 that controls rotation of the caterpillar 712, and does not include the spiral protrusion 603 described above. Other structure is similar to that in the seventh embodiment described above. The rotationally-moving magnet 6 is a magnet large in size (volume) compared with the rotating magnet 206 as described above, meshing with the gear 711. This gear 711 rotates according to the rotation of this rotationally-moving magnet 6 and, as a result, the caterpillar 712 rotates.

Note that a capsule guiding system according to this second modification example of the seventh embodiment is approximately similar to the capsule guiding system 400 according to the fourth embodiment described above, and has a configuration in which the capsule endoscope 701b is included in place of the capsule endoscope 401 of the capsule guiding system.

When the caterpillar 712 rotates, as indicated by a curve 171b in FIG. 85, the magnetic-field generating unit 403 applies a rotating magnetic field M66 about the axis in a radial direction perpendicular to the longitudinal axis direction of the capsule endoscope 701b, the rotating magnetic field M66 having a magnetic field strength stronger than a magnetic field strength G66 allowing the rotationally-moving magnet 6 to rotate in the capsule endoscope 701b. In this case, as depicted in the right drawing of FIG. 84(1), with the rotating magnetic field M66, which is a strong magnetic field, the rotationally-moving magnet 6 is released from the rotation restraint by the high-friction member 8 and becomes rotatable. Then, with the rotationally-moving magnet 6 rotating, the gear 711 also rotates, and the caterpillar 712 performs a rotating operation, thereby allowing the capsule endoscope 701b to move.

Then, at the time of direction turning, as indicated by a curve 173b in FIG. 85, the magnetic-field generating unit 403 applies a magnetic field oriented correspondingly to the turning direction, the magnetic field having a magnetic field strength weaker than the magnetic field strength G66 allowing the rotationally-moving magnet 6 to rotate in the guiding area 2a of the capsule endoscope 701b. As a result, as depicted in the right drawing of FIG. 84(2), with an attractive force occurring between the rotationally-moving magnet 6 and the rotating magnet 206, the rotationally-moving magnet 6 moves to the rotating magnet 206 side in the guiding area 2a to become in a state in which rotation is restrained again by the high-friction member 8. As described above, the magnetization direction of the rotationally-moving magnet 6 can be switched from the radial direction of the capsule endoscope 701b to the longitudinal axis direction thereof.

Specifically, the magnetic-field generating unit 403 stops the rotating magnetic field M66 at a point where the magnetization direction of the rotationally-moving magnet 6 is matched with the longitudinal axis direction of the capsule endoscope 701b (for example, an imaging view direction of the capsule endoscope 701b) to weaken the magnetic field strength of this rotating magnetic field M66 to a strength smaller than the magnetic field strength G66 described above (refer to FIG. 85). As a result, as depicted in the left drawing of FIG. 84(2), the rotationally-moving magnet 6 stops rotating in the guiding area 2a and, as indicated by an arrow Y92b in the right drawing of FIG. 84(2), therefore moves to the rotating magnet 206 side of the guiding area 2a. Then, as depicted in the right drawing of FIG. 84(3), with an attractive force occurring between the rotating magnet 206 and itself, the rotationally-moving magnet 6 becomes in a state of making contact with a partition on the rotating magnet 206 side, with rotation being restrained by the high-friction member 8. Since the rotationally-moving magnet 6 is in a state of being fixed to the capsule endoscope 701b, as indicated by a curve 173b of FIG. 83 and the left drawing of FIG. 84(3), as with the capsule endoscope 701 described above, the direction turning operation of the capsule endoscope 701b is controlled by the magnetic fields M65c, 65d applied with the magnetic field strength weaker than the magnetic field strength G66. In this case, the capsule endoscope 701b turns the direction by following the magnetization directions of the magnetic fields M65c, 65d changed by the magnetic-field generating unit 403 described above.

Note in this second modification example of the seventh embodiment that, although the magnetic fields M65c, M65d are applied to the capsule endoscope 701b with the longitudinal axis direction of the capsule endoscope 701*b* and the magnetization direction of the rotationally-moving magnet 6 are matched and the magnetic-field directions of these magnetic fields M65*c*, M65*d* are controlled to control direction turning of the capsule endoscope 701*b*, this is not meant to be restrictive. The capsule endoscope 701*b* may be rotated about the longitudinal axis direction by controlling the magnetic field strength and magnetic-field direction of the rotating magnetic field M66 so that the radial direction of the capsule endoscope 701*b* and the magnetization direction of the rotationally-moving magnet 6 are matched, and by forming a rotating magnetic field rotating about the longitudinal axis of the capsule endoscope 701*b* in this state.

As described above, according to the second modification example, effects similar to those of the capsule endoscope 701 can be achieved. Also, with an external magnetic field, the state of the rotationally-moving magnet 6 (specifically, rotatable state and fixed state in the housing) can be switched. With this, propulsion and direction turning of the capsule endoscope by the caterpillar can be made, and more sophisticated and efficient guiding of the capsule endoscope can be achieved.

Also, since the same rotationally-moving magnet 6 can be shared for use in two operations, propulsion and direction turning of the capsule endoscope, a magnetic actuator is not required to be disposed for each operation. As a result, the main body of the capsule endoscope can be downsized, and a capsule guiding system excellent in insertability of the capsule endoscope into the subject can be achieved.

Furthermore, the rotating shaft of the rotationally-moving magnet 6 propelling the capsule endoscope 701*b* (forward or backward) with the rotation of the caterpillar 712 is approximately perpendicular to the longitudinal axis of the capsule endoscope 701*b*. With this, a torque sufficient to topple the capsule endoscope 701*b* about an axis in a radial direction can be increased. With this, it is possible to prevent the capsule endoscope 701*b* from toppling with such an external rotating magnetic field M66 causing the rotationally-moving magnet 6 to rotate. As a result, magnetic-force energy of this rotating magnetic field M66 is not wasted for a topple torque of the capsule endoscope 701*b*, and the rotationally-moving magnet 6 can be efficiently rotated. With this rotating magnetic field M66, the capsule endoscope 701*b* can be reliably propelled.

Still further, the rotationally-moving magnet 6 is rotated relatively to the casing of the capsule endoscope 701*b*, and the caterpillar 712 that rotates relatively with respect to the casing of the capsule endoscope 701 is rotated by following the rotating operation of the rotationally-moving magnet 6. Therefore, these rotationally-moving magnet 6 and the caterpillar 712 can be independently rotated with respect to the casing of the capsule endoscope 701*b*. With this, the capsule endoscope 701*b* can go forward or backward without causing its casing to be rotated about the longitudinal axis or an axis in the radial direction. As a result, it is possible to prevent occurrence of image blurring in an image captured by the imaging system of the capsule endoscope 701*b* due to the rotation of the casing of the capsule endoscope 701*b*. That is, this capsule endoscope 701*b* can go forward and backward in the subject, and can clearly capture an in-vivo image of the subject.

Third Modification Example

Figure 86:
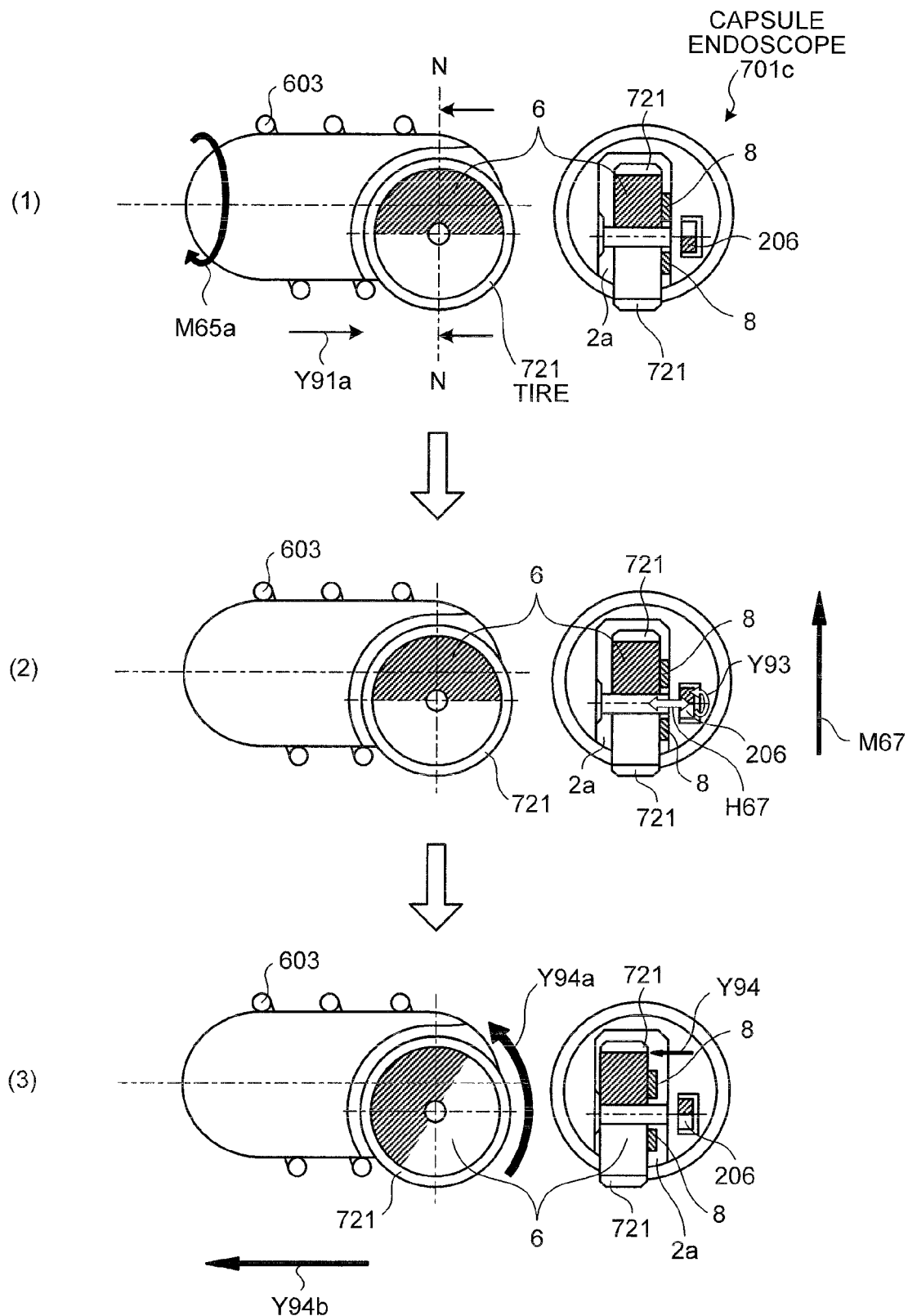
FIG. 86 shows sectional views of a capsule endoscope according to a third modification example in the seventh embodiment.
Figure 87:
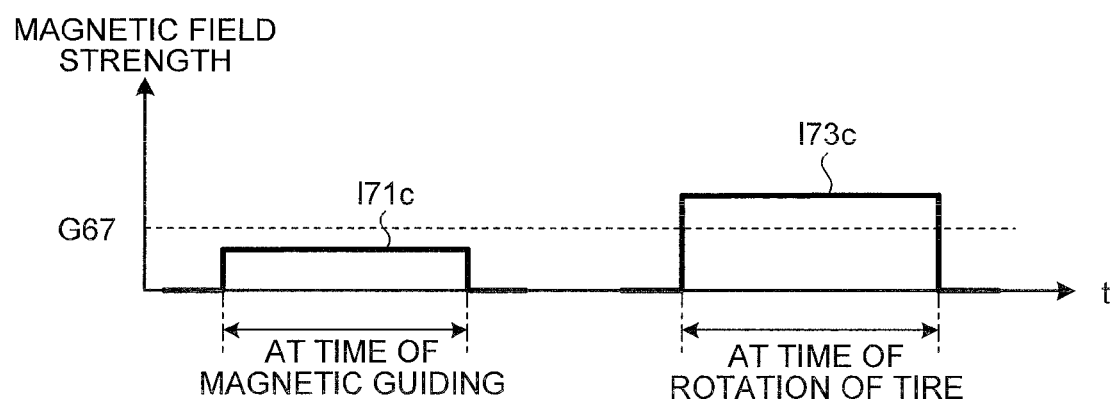
FIG. 87 shows a diagram of the magnetic field strength of a magnetic field applied in each predetermined state of the capsule endoscope depicted in FIG. 86.

Next, with reference to FIG. 86 and FIG. 87, a third modification example according to the seventh embodiment is described. FIG. 86 shows sectional views of a capsule endoscope according to the third modification example. A left drawing of FIG. 86 shows sectional views of the capsule endoscope according to the third modification example cut along an axial direction, and a right drawing of FIG. 86 shows sectional views of the capsule endoscope cut along an N-N line in the left drawing of FIG. 86. FIG. 87 is a diagram of the magnetic field strength of a magnetic field applied by the magnetic-field generating unit 403 in each predetermined state of the capsule endoscope according to the third modification example. As depicted in FIG. 86, in a capsule endoscope 701*c* according to the third modification example, in contrast to the capsule endoscope 701*b*, the rotationally-moving magnet 6 configures a tire 721 that moves the capsule endoscope 701*c*. Then, the capsule endoscope 701*c* includes the spiral protrusion 603 and, as indicated by an arrow Y91*a*, spiral propulsion can be made by magnetic guiding. Other structure is identical to that of the capsule endoscope 701*b* according to the second modification example of the seventh embodiment, and the same configuration portions are provided with the same reference numerals. Also, a capsule guiding system according to this third modification example of the seventh embodiment is approximately similar to the capsule guiding system 400 according to the fourth embodiment described above, and has a configuration including the capsule endoscope 701*b* in place of the capsule endoscope 401 of the capsule guiding system.

First, as indicated in a curve 171*c* of FIG. 87, the magnetic-field generating unit 403 applies a rotating magnetic field M65*a* about a longitudinal axis of the capsule endoscope 701*c*, the rotating magnetic field M65*a* having a magnetic field strength weaker than a magnetic field strength G67 allowing the rotationally-moving magnet 6 greater in volume than the rotating magnet 206 to rotate in the guiding area 2*a*. In this case, as depicted in the right drawing of FIG. 86(1), the rotationally-moving magnet 6 is in a state such that rotation is restrained by the high-friction member 8 and the magnetization direction is fixed so as to be a radial direction of the capsule endoscope 701*c*. Therefore, as depicted in the left drawing of FIG. 86(1), the capsule endoscope 701*c* makes spiral propulsion in a direction indicated by an arrow Y91*a* while rotating about the longitudinal axis according to the rotating magnetic field M65*a* about the longitudinal axis of the capsule endoscope 701*c*. Note in the capsule endoscope 701*c* that, when the magnetization direction of the rotationally-moving magnet 6 is fixed so as to be the longitudinal axis direction of the capsule endoscope 701*c*, the direction is controlled by the magnetic field in a magnetization direction parallel to the longitudinal axis direction of the capsule endoscope 701*c*.

Then, when the tire rotates, as indicated by a curve 173*c* in FIG. 87, the magnetic-field generating unit 403 applies a magnetic field M67 having a magnetic field strength stronger than the magnetic field strength G67 allowing the rotationally-moving magnet 6 to rotate in the capsule endoscope 701*c*. In this case, as depicted in the right drawing of FIG. 86(2), with the rotating magnetic field M67, which is a strong magnetic field, the rotationally-moving magnet 6 and the rotating magnet 206 rotate in the same orientation (direction indicated by an arrow Y93 in FIG. 86(2)) according to the magnetic field M67, thereby causing a repulsive force H67. Then, as indicated by an arrow Y94 in the right drawing of FIG. 86(3), with this repulsive force H67, the rotationally-moving magnet 6 moves in the guiding area 2*a* so as to go away from the rotating magnet 206, and therefore becomes rotatable with restraint of rotation by the high-friction member 8 being released. Then, the rotationally-moving magnet 6 rotates with a rotating magnetic field having a magnetic field strength stronger than the magnetic field strength G67, and the tire 721 also rotates accordingly in a direction of an arrow Y94a depicted in FIG. 86(3), and therefore the capsule endoscope 701c becomes movable as indicated by an arrow Y94b of FIG. 86(3).

In this manner, according to the third modification example, effects similar to those of the capsule endoscope 701 can be achieved. Also, with an external magnetic field, the state of the rotationally-moving magnet 6 (specifically, rotatable state and fixed state in the housing) can be switched. With this, propulsion of the capsule endoscope by the tire and propulsion of the capsule endoscope by the spiral protrusion can be selectively made. Furthermore, by changing the magnetization direction of the rotationally-moving magnet 6 in a fixed state with the external magnetic field, direction turning of the capsule endoscope can be made. As a result, more sophisticated and efficient guiding of the capsule endoscope can be achieved.

Also, the rotationally-moving magnet 6 can be temporarily fixed to the casing of the capsule endoscope 701c in a state such that the magnetization direction is parallel to (or desirably is matched) a capturing direction of the imaging system held by the capsule endoscope 701c. By controlling the magnetization direction of the external magnetic field applied to the rotationally-moving magnet 6 in this fixed state, the capturing direction of the imaging system of the capsule endoscope 701c whose direction is turned by following this rotationally-moving magnet 6 can be controlled in a desired direction. As a result, the capsule endoscope 701c can easily capture an image in the desired direction in the subject.

Furthermore, since the same rotationally-moving magnet 6 can be shared for use in two operations, propulsion and direction turning of the capsule endoscope, a magnetic actuator is not required to be disposed for each operation. As a result, the main body of the capsule endoscope can be downsized, and a capsule guiding system excellent in insertability of the capsule endoscope into the subject can be achieved.

Still further, the rotating shaft of the rotationally-moving magnet 6 for propelling the capsule endoscope 701c (forward or backward) with the rotation of the tire 721 is approximately perpendicular to the longitudinal axis of the capsule endoscope 701c. With this, a torque sufficient to topple the capsule endoscope 701c about an axis in a radial direction can be increased. With this, it is possible to prevent the capsule endoscope 701c from toppling with such an external rotating magnetic field M67 causing the rotationally-moving magnet 6 to rotate. As a result, magnetic-force energy of this magnetic field M67 is not wasted for a topple torque of the capsule endoscope 701c, and the rotationally-moving magnet 6 can be efficiently rotated. With this magnetic field M67, the capsule endoscope 701c can be reliably propelled.

Still further, since the rotationally-moving magnet 6 is rotated relatively to the casing of the capsule endoscope 701c, the tire 721 disposed in the rim of this rotationally-moving magnet 6 can be independently rotated with respect to the casing of the capsule endoscope 701c. With this, the capsule endoscope 701c can go forward or backward without causing its casing to be rotated about the longitudinal axis or an axis in the radial direction. As a result, it is possible to prevent occurrence of image blurring in an image captured by the imaging system of the capsule endoscope 701c due to the rotation of the casing of the capsule endoscope 701c. That is, this capsule endoscope 701c can go forward and backward in the subject, and can clearly capture an in-vivo image of the subject.

Note in the third modification example of the seventh embodiment that the magnetization direction and the magnetic field strength of the external magnetic field to be applied to the rotationally-moving magnet 6 and the rotating magnet 206 are controlled to cause the capsule endoscope 701c to selectively make spiral propulsion by the spiral protrusion 603 and propulsion by the tire 721, this is not meant to be restrictive, and the capsule endoscope 701c may not include the spiral protrusion 603 described above, and may go forward or backward by the tire 721 rotating together with the rotationally-moving magnet 6 rotating by following the external magnetic field.

Also, in the third modification example of the seventh embodiment, the magnetization direction and the magnetic field strength of the external magnetic field to be applied to the rotationally-moving magnet 6 and the rotating magnet 206 are controlled to cause this rotationally-moving magnet 6 to be in a relatively fixed state with respect to the casing of the capsule endoscope 701c. This is not meant to be restrictive, and the rotating magnet 206 and the high-friction member 8 may not be provided, and the rotationally-moving magnet 6 may be rotatably supported with respect to the casing of the capsule endoscope 701c. In this case, the rotationally-moving magnet 6 in this capsule endoscope 701c rotates by following the rotating magnetic field rotating about an axis in the radial direction of the casing of the capsule endoscope 701c and also causes the tire 721 to rotate, thereby generating a propulsion force of the capsule endoscope 701c. This capsule endoscope 701c having a structure in which the rotationally-moving magnet 6 is supported in the casing can go forward or backward with the rotating magnetic field with a weak magnetic field strength compared with the magnetic field strength G67 described above. As a result, consumed energy when this capsule endoscope 701 goes forward or backward can be reduced. Also, a watertight structure of the casing of this capsule endoscope 701c can be achieved in a simple manner.

Fourth Modification Example

Figure 88:
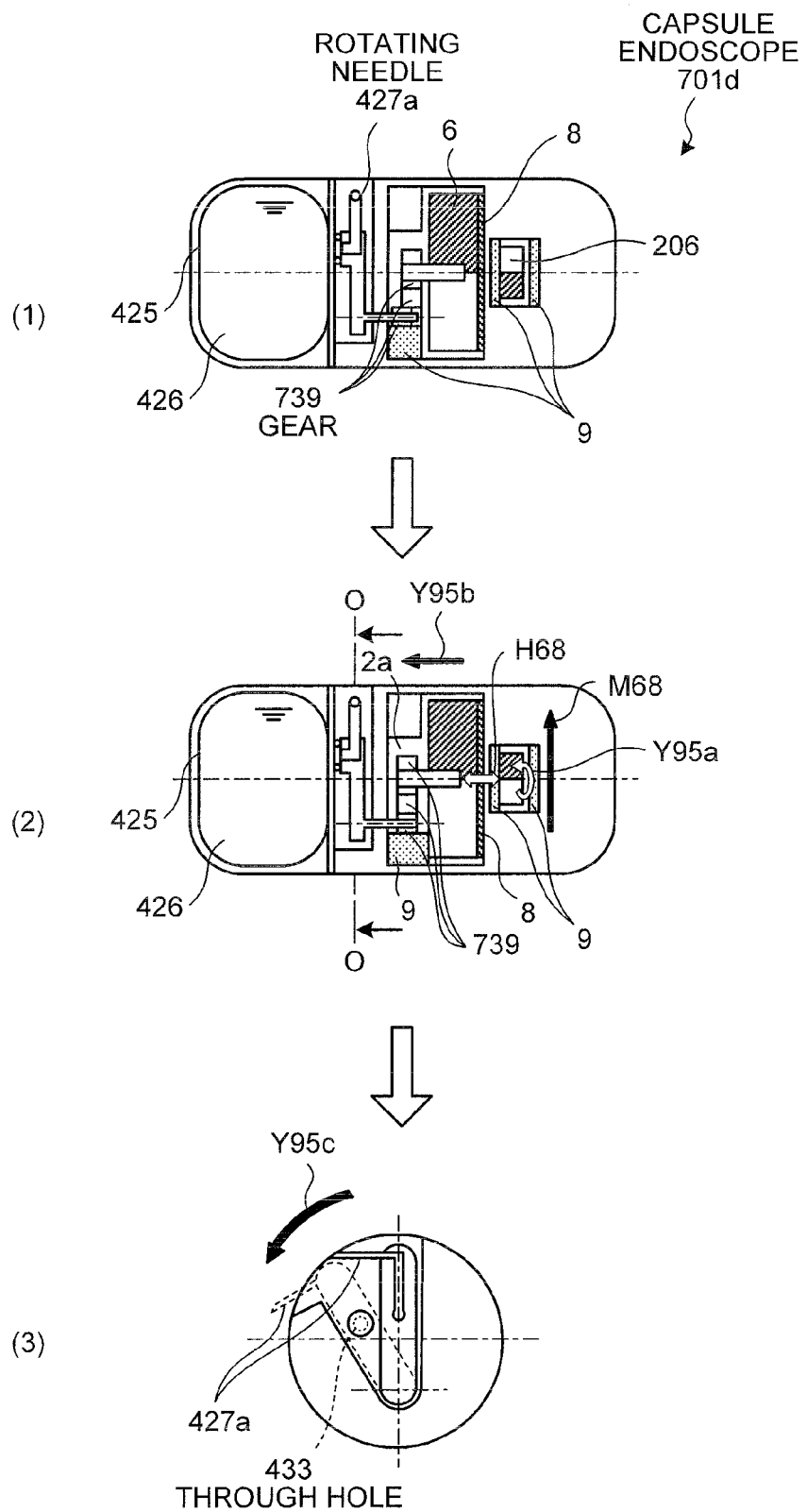
FIG. 88 shows sectional views of a capsule endoscope according to a fourth modification example in the seventh embodiment.
Figure 89:
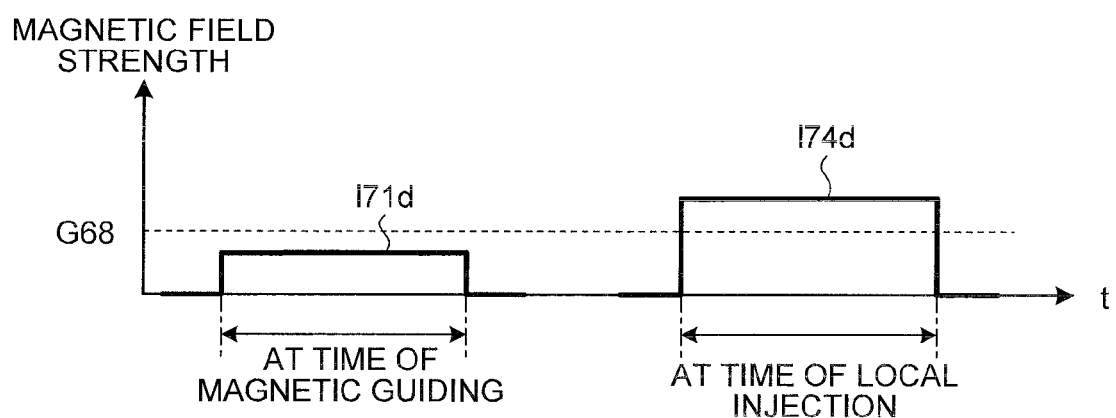
FIG. 89 shows a diagram of the magnetic field strength of a magnetic field applied in each predetermined state of the capsule endoscope depicted in FIG. 88.

Next, with reference to FIG. 88 and FIG. 89, a fourth modification example according to the seventh embodiment is described. FIG. 88 shows sectional views of a capsule endoscope according to the fourth modification example. FIG. 88(1) and FIG. 88(2) are sectional views of the capsule endoscope according to the fourth modification example cut along an axial direction, and FIG. 88(3) is a sectional view of the capsule endoscope cut along an O-O line in FIG. 88(2). FIG. 89 is a diagram of the magnetic field strength of a magnetic field applied by the magnetic field generating unit 403 in each predetermined state of the capsule endoscope according to the fourth modification example. As depicted in FIG. 88, in a capsule endoscope 701d according to the fourth modification example, the friction-reducing member 9 is provided on a contact surface of the rotating magnet 206 so that the rotating magnet 206 smoothly rotates. Also, in the capsule endoscope 701d, the high-friction member 8 is provided on a surface on the rotating magnet 206 side of the rotationally-moving magnet 6 so that rotation is restrained when the rotationally-moving magnet 6 makes contact with the partition on a rotating magnet 206 side. Also, the capsule endoscope 701d has a gear 739 disposed in the guiding area 2a. The gear 739 controls the rotating operation of a rotating needle 427a and meshes with the rotationally-moving magnet 6 when the rotationally-moving magnet 6 rotates.

First, as indicated by a curve 171d in FIG. 89, the magnetic-field generating unit 403 applies a rotating magnetic field about a longitudinal axis of the capsule endoscope 701d, the rotating magnetic field having a magnetic field strength weaker than a magnetic field strength G68 allowing the rotationally-moving magnet 6 greater in volume than the rotating magnet 206 to rotate in the guiding area 2a. In this case, as depicted in FIG. 88(1), the rotationally-moving magnet 6 is in a state in which rotation is restricted by the high-friction member 8. Therefore, the capsule endoscope 701d makes propulsion according to the rotating magnetic field about the longitudinal axis of the capsule endoscope 701d. Note in the capsule endoscope 701d that spiral propulsion may be promoted by providing the spiral protrusion 603.

When the medicine 426 in the balloon 425 is locally injected, as indicated by a curve 174d in FIG. 89, the magnetic-field generating unit 403 applies a magnetic field M68 having a magnetic field strength stronger than the magnetic field strength G68 allowing the rotationally-moving magnet 6 to rotate in the capsule endoscope 701d. In this case, as indicated by an arrow Y95 in FIG. 88(2), with the magnetic field M68, the rotationally-moving magnet 6 and the rotating magnet 206 rotate in the same orientation according to the magnetic field M68, thereby causing a repulsive force H68. Then, as indicated by an arrow Y95b in FIG. 88(2), with this repulsive force H68, the rotationally-moving magnet 6 moves in the guiding area 2a so as to go away from the rotating magnet 206 to mesh with the gear 739. Also, the rotationally-moving magnet 6 is released from the rotation restraint by the high-friction member 8, and therefore becomes movable. Then, by being applied with a magnetic field that has a magnetic field strength stronger than the magnetic field strength G68 and is oriented correspondingly to the rotating direction of the rotating needle 427a, the capsule endoscope 701d rotates and the gear 739 also rotates accordingly. As a result, as depicted in FIG. 88(3), with the rotation of the gear 739, the rotating needle 427a rotates as indicated by an arrow Y95c to be pushed outside of the capsule endoscope 701d. Then, when the rotating needle 427a makes contact with a rotation stop surface, the main body of the capsule endoscope 701d rotates, and the rotating needle 427a pierces along a perimeter direction of an enteric canal or the like. Furthermore, the through hole 433 of the balloon 425 and a through hole not shown of the rotating needle 427a are coupled, and therefore the medicine 426 in the balloon 425 is injected to a desired region via the rotating needle 427a.

Then, by making the orientation of the magnetic field in reverse as keeping the magnetic field strength stronger than the magnetic field strength G68, the rotating needle 427a is accommodated in the capsule endoscope 701d. Furthermore, by weakening the magnetic field strength more than the magnetic field strength G68 of the applied magnetic field, the rotationally-moving magnet 6 is fixed to the capsule endoscope 701d as depicted in FIG. 88(1).

As described above, according to the fourth modification example, effects similar to those of the capsule endoscope 701 can be achieved. Also, by switching the state of the rotationally-moving magnet 6, more sophisticated and efficient propelling operation and local injecting operation of the capsule endoscope can be achieved.

Fifth Modification Example

Next, a fifth modification example of the seventh embodiment of the present invention is described. In the second modification example of the seventh embodiment described above, by controlling the magnetization direction and the magnetic field strength of the external magnetic field, the rotationally-moving magnet 6 is switched to a rotatable state or a fixed state. According to the rotation of the rotationally-moving magnet 6, the gear 711 and also the caterpillar 712 are rotated to generate a propulsion force of the capsule endoscope 701b. In this fifth modification example of the seventh embodiment, with an axle shaft being taken as a rotating magnetic field rotatably disposed with respect to the casing of the capsule endoscope, this rotating magnetic field and the caterpillar 712 are rotated with an external rotating magnetic field to generate a propulsion force of the capsule endoscope.

FIGS. 90A and 90B are schematic diagrams depicting a configuration example of a capsule endoscope according to the fifth modification example in the seventh embodiment. Note in FIGS. 90A and 90B that a side view and a P-P line sectional view of a capsule endoscope 701e according to this fifth modification example of the seventh embodiment are depicted.

The capsule endoscope 701e according to this fifth modification example of the seventh embodiment has a configuration approximately similar to that of the capsule endoscope 701b according to the second modification example of the seventh embodiment described above, the configuration of being able to going forward or backward by the caterpillar 712 driven for rotation by a magnetic actuator. Specifically, as depicted in FIG. 90A, the capsule endoscope 701e includes a capsule casing 731 formed in dimension for easy insertion into the body of a subject, the caterpillar 712 as described above, wheels 732, 733 that rotate the caterpillar 712 in an endless manner, an axle shaft 734 that rotatably supports one wheel (for example, on a front side) 732, and an axle-shaft-like rotating magnet 735 that rotatably supports the other wheel (for example, on a rear side) 733. Also, as with the capsule endoscope 401 according to the fourth embodiment described above, the capsule endoscope 701e includes, in the casing 731, the position-detection oscillation coil 421, the imaging system 422, the wireless system that wireless transmits an image signal and the like to the external receiving unit 411 via the antenna 423, the battery 424, and the control unit that controls each component of the capsule endoscope 401 (the position-detection oscillation coil 421, the imaging system 422, and the wireless system).

Note that, although not particularly shown, as exemplarily depicted in the fourth to sixth embodiments or each modification example, this capsule endoscope 701e may include, as appropriate, a local injection mechanism that injects a medicine and a treatment mechanism (a forceps, a high-frequency heating member, etc.) that performs a medical treatment, such as collecting a living-body tissue or burning process onto the inside of the living body. Also, a capsule guiding system according to this fifth modification example of the seventh embodiment is approximately similar to the capsule guiding system 400 according to the fourth embodiment described above, and has a configuration in which the capsule endoscope 701e is included in place of the capsule endoscope 401 of the capsule guiding system.

A pair of wheels 732 is mounted at both ends of the axle shaft 734 on a front side (the side where the imaging system 422 is disposed) of the casing 731, and rotatably supported by this axle shaft 734. Also, a pair of wheels 733 is mounted at both ends of the rotating magnet 735 serving as an axle shaft on a rear side of the casing 731, and rotatably supported by this rotating magnet 735. These wheels 732, 733 rotate according to the rotation of the rotating magnet 735 to rotate the caterpillar 712 that causes the capsule endoscope 701e to go forward or backward, in an endless manner.

The axle shaft 734 is rotatably inserted in a though hole formed on the front side of the casing 731, and has a pair of wheels 732 described above at both ends. This axle shaft 734 inserted through the through hole is a rotating shaft perpendicular to a longitudinal axis CL1 (that is, parallel to a radial direction of the casing 731), which is a center axis in a longitudinal direction of the casing 731, and rotates independently from the casing 731.

The rotating magnet 735 is rotatably inserted in a through hole formed on the rear side of the casing 731, and has a pair of wheels 733 described above at both ends. This rotating magnet 735 inserted through the through hole is a rotating shaft perpendicular to the longitudinal axis CL1 of the casing 731 (that is, in the radial direction of the casing 731) and, by following an external rotating magnetic field (rotating magnetic field formed by the magnetic-field generating unit 403 described above), rotates independently from the casing 731. This rotating magnet 735 functions as an axle shaft that causes the wheels 733 to rotate about an axis perpendicular to the longitudinal axis CL1 and also functions as a magnetic actuator that causes the caterpillar 712 to rotate by the action of the external rotating magnetic field rotating about the axis in the radial direction of the casing 731. Note that the surface of this rotating magnet 735 is covered with a biocompatible material.

Here, each of the through holes of the casing 731 in which the wheels 734 or the rotating magnet 735 are inserted are through holes formed along a direction perpendicular to the longitudinal axis CL1 of the casing 731 (that is, the radial direction of the casing 731), and is separated from an inner space of the casing 731 where inner components, such as the imaging system 422, the wireless system, and the battery 424 described above, are disposed. Therefore, the casing 731 with these through holes can ensure water-tightness of the inner space, where the inner components of the capsule endoscope 701e are disposed, in a simple structure, and also includes the caterpillar mechanism for causing the capsule endoscope 701e to go forward or backward, that is, the wheels 732, 733, the axle shaft 734 and the rotating magnet 735, and the caterpillar 712, in a state of being separated from this inner space.

A barycenter GP of the capsule endoscope 701e having the configuration as described above is set at a predetermined position in the casing 731 by adjusting the arrangement of the components described above (the inner components, such as the imaging system 422 and the battery 424, the wheels 732, 733, the axle shaft 734, the rotating magnet 735, the caterpillar 712, etc). Specifically, as depicted in FIG. 90A, the barycenter GP is set on a center axis CL2, which is an axis in a radial direction of the casing 731 and passes through a center CP of the inner space of the casing 731, and is further desirably set at a position away from the center CP to a bottom side of the casing 731 (the side where the caterpillar mechanism, such as the wheels 732, 733, is disposed).

Note that the position-detection oscillation coil 421 (not shown) for detecting at least one of the position and direction of this capsule endoscope 701e by the position calculating unit 412 described above is disposed in the casing 731 such that the rotating shaft of the rotating magnet 735 described above and a coil axis are parallel to each other. This position-detection oscillation coil 421 forms a magnetic field in a direction perpendicular to the magnetization direction of the rotating magnet 735.

Next, the operation of the caterpillar mechanism that causes the capsule endoscope 701 to go forward or backward with a external rotating magnetic field is described. FIGS. 91A and 91B are schematic diagrams depicting a state in which the caterpillar mechanism of the capsule endoscope operates with the external rotating magnetic field. Note in FIGS. 91A and 91B that a side view of the capsule endoscope 701e according to this fifth modification example of the seventh embodiment and a P-P line sectional view thereof are depicted.

As depicted in FIG. 91B, to the rotating magnet 735 rotatably inserted in a through hole of the casing 731, a rotating magnetic field M70 rotating about an axis in a radial direction of this casing 731 is applied by the magnetic-field generating unit 403. In this case, the rotating magnet 735 rotates about the axis in the radial direction of the casing 731 by following this rotating magnetic field M70, and also causes the wheels 733 at both ends to rotate.

By the action of this rotating magnet 735, the caterpillar 712 rotates in the same direction as that of the rotating magnet 735 to generate a propulsion force of the capsule endoscope 701e. That is, the caterpillar 712 converts the rotary force of the rotating magnet 735 following this rotating magnetic field M70 to a propulsion force of the capsule endoscope 701e. Note that the axle shaft 734 rotatably inserted in the through hole of the casing 731 and the wheels 732 at its both ends rotate by following this caterpillar 712 without hindering the rotation of the caterpillar 712 by the action of this rotating magnet 735. With this rotation of the caterpillar 712, the capsule endoscope 701e can go forward or backward in the body of the subject without causing the casing 731 to rotate.

Here, the rotating magnet 735 functioning as a magnetic actuator for the caterpillar mechanism of this capsule endoscope 701e smoothly rotates by following the external rotating magnetic field M70 without being hindered by the high-friction member 8 or others, such as the rotating magnet 206. For this reason, even if this rotating magnetic field M70 to be applied to the rotating magnet 735 has a smaller magnetic field strength compared with the magnetic field strength G66 of the rotating magnetic field M66 in the second modification example of the seventh embodiment described above, the rotating magnet 735 can be rotated about the axis in the radial direction of the casing 731. As a result, consumption energy required for generating the rotating magnetic field M70 that causes this rotating magnet 735 to rotate can be reduced.

As described above, the configuration in the fifth modification example of the seventh embodiment is as follows. On a portion of the casing separated from the inner space of the capsule casing where inner components, such as an imaging system, a wireless system, a battery, etc., are disposed, a through hole is formed in a direction perpendicular to a longitudinal direction of the casing. Through this through hole, a rotating magnet, which is an axle shaft of the caterpillar mechanism of the capsule endoscope and functions as a magnetic actuator, is rotatably inserted. To this rotating magnet, an external rotating magnetic field rotating about the axis in the radial direction of the casing is applied, thereby causing this rotating magnet to rotate independently from the casing and about the axis in the radial direction of the casing. By this action of the rotating magnet, the caterpillar is rotated to cause the capsule endoscope to go forward or backward. Therefore, a capsule endoscope can be achieved that can easily go forward or backward in the subject with the external rotating magnetic field and can ensure water-tightness of the inner space (that is, a space where inner components of the capsule endoscope, such as an imaging system, a wireless system, and a battery, are disposed) of the capsule casing including a caterpillar mechanism for such going forward or backward with a simple casing structure.

Also, the position-detection oscillation coil that forms a magnetic field in a direction perpendicular to the magnetization direction of this rotating magnet is provided. Therefore, the position of the capsule endoscope in the subject can be detected, and also the rotation-axis direction of the rotating magnet, which is a direction always perpendicular to the magnetization direction of this rotating magnet, can be detected. By applying a rotating magnetic field perpendicular to this rotation-axis direction to the rotating magnet, the position and direction of the capsule endoscope can be more accurately guided.

Furthermore, one of the axle shafts of the caterpillar mechanism is formed by the rotating magnet functioning as a magnetic actuator for this caterpillar mechanism. Therefore, this caterpillar mechanism can be downsized and, as a result, downsizing of the main body of the capsule endoscope can be prompted, and also a capsule guiding system excellent in insertability of the capsule endoscope into the subject can be achieved.

Still further, the rotating shaft of this rotating magnet is approximately perpendicular to the longitudinal axis of the capsule endoscope. With this, a torque sufficient to topple the capsule endoscope about an axis in a radial direction can be increased. With this, it is possible to prevent the capsule endoscope from toppling with such an external rotating magnetic field causing the rotating magnet to rotate. As a result, magnetic-force energy of this external rotating magnetic field is not wasted for a topple torque of the capsule endoscope, and the rotating magnet can be efficiently rotated. With this rotating magnetic field, the capsule endoscope can be reliably propelled.

Still further, the barycenter of the capsule endoscope is set on a center axis, which is an axis in a radial direction of the capsule casing and passes through the center of the casing. Therefore, caterpillar traveling of the capsule endoscope with the caterpillar mechanism can be stabilized. Also, by setting the barycenter of the capsule endoscope at a position on the center axis in the radial direction of this casing and away from the center position of the casing to the bottom side of the casing (caterpillar mechanism side) (that is, by lowering the barycenter), this caterpillar traveling of the capsule endoscope with the caterpillar mechanism can be further stabilized. Even in caterpillar traveling on an inclined plane, the capsule endoscope can be stably guided without toppling or the like.

Still further, since the rotating magnet rotatably inserted in the through hole of the casing is rotated with the external rotating magnetic field, the rotating magnet can be smoothly rotated by following the external rotating magnetic field. For this reason, the magnetic field strength of the external magnetic field to be applied to the rotating magnet can be lowered and, as a result, consumption energy required for generating the external rotating magnetic field that causes this rotating magnet to rotate can be reduced.

Still further, with the rotating magnet relatively rotated with respect to the capsule casing, the caterpillar is rotated independently from the casing. Therefore, the capsule endoscope can be caused to go forward or backward without causing this casing to rotate about the longitudinal axis or about the axis in the radial direction. As a result, it is possible to prevent occurrence of image blurring in an image captured by the imaging system of the capsule endoscope due to the rotation of the casing. That is, this capsule endoscope can go forward and backward in the subject, and can clearly capture an in-vivo image of the subject.

Note in the fifth modification example of the seventh embodiment that the position-detection oscillation coil for detecting at least one of the position and direction of the capsule endoscope in the subject is provided to the capsule endoscope. This is not meant to be restrictive. In place of this position-detection oscillation coil, an LC marker may be provided to the capsule endoscope. This LC marker is disposed in the capsule endoscope such that its coil axis and the rotating shaft of the rotating magnet are approximately parallel to each other, and may be disposed, for example, on an axle shaft (the axle shaft 734 described above) paired with the rotating magnet in the caterpillar mechanism. In this case, it is sufficient for the position calculating unit 412 described above to calculate (detect) at least one of the position and direction of the capsule endoscope in the subject based on an LC marker scheme.

Still further, in the fifth modification example of the seventh embodiment described above, the barycenter GP of the capsule endoscope 701*e* is set on the center axis CL2 in the radial direction of the casing 731 by adjusting the arrangement of the inner components, such as the imaging system 422 and the battery 424, the wheels 732, 733, the axle shaft 734, the rotating magnet 735, the caterpillar 712, etc. This is not meant to be restrictive. A counter weight having a weight equivalent to that of the rotating magnet 735 may be provided at a position on the rotating magnet 735 symmetrical to the center axis CL2 in the radial direction of the casing 731 to correct the deviation of weight due to the rotating magnet 735, and the barycenter GP of the capsule endoscope 701*e* may be set on the center axis CL2 in the radial direction of the casing 731 (further, at a position de-centered to a bottom side of the casing 731). In this case, such a counter weight may be any of a battery, a super-capacitor, a position-detection oscillation coil, a weight, and others, or may be a combination of these as appropriate.

Sixth Modification Example

Next, a sixth modification example of the seventh embodiment of the present invention is described. In the fifth modification example of the seventh embodiment described above, the rotating magnet 735 functioning as a magnetic actuator for the caterpillar mechanism is used as an axle shaft of the caterpillar mechanism. In this sixth modification example of the seventh embodiment, the rotating magnet functioning as a magnetic actuator for the caterpillar mechanism is disposed on the center axis of the casing in a radial direction, thereby lowering the barycenter of the capsule endoscope.

Figure 92:
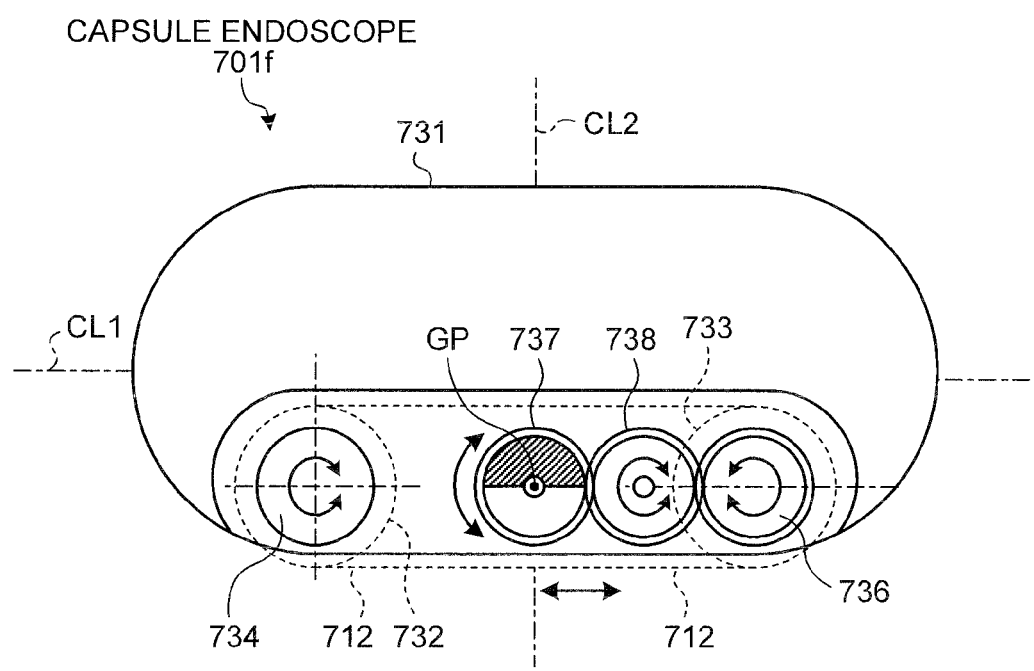
FIG. 92 shows a schematic longitudinal sectional view depicting a configuration example of a capsule endoscope according to a sixth modification example of the seventh embodiment of the present invention.

FIG. 92 is a schematic longitudinal sectional view depicting a configuration example of a capsule endoscope according to the sixth modification example of the seventh embodiment of the present invention. Note in FIG. 92 that the capsule casing 731 and the caterpillar mechanism are depicted. As depicted in FIG. 92, a capsule endoscope 701*f* according to this sixth modification example of the seventh embodiment includes an axle shaft 736 in place of the rotating magnet 735 of the capsule endoscope 701*e* according to the fifth modification example of the seventh embodiment described above, and further includes a gear 738 that rotates by meshing with a gear unit of this axle shaft 736 and a rotating magnet 737 having a gear unit meshing with this gear 738 in the perimeter. Other structure is similar to that of the fifth modification example of the seventh embodiment described above, and the same components are provided with the same reference numerals. Also, a capsule guiding system according to this sixth modification example of the seventh embodiment is approximately similar to the capsule guiding system 400 according to the fourth embodiment described above, and has a configuration in which the capsule endoscope 701*f* is included in place of the capsule endoscope 401 of the capsule guiding system.

Note that, although not particularly shown, as with the capsule endoscope 701*e* according to the fifth modification example of the seventh embodiment described above, the capsule endoscope 701f includes, in the casing 731, the position-detection oscillation coil 421, the imaging system 422, the wireless system that wireless transmits an image signal and the like to the external receiving unit 411 via the antenna 423, the battery 424, and the control unit that controls each component (the position-detection oscillation coil 421, the imaging system 422, and the wireless system). Also, as exemplarily depicted in the fourth to sixth embodiments or each modification example described above, the capsule endoscope 701f may include, as appropriate, a local injection mechanism that injects a medicine and a treatment mechanism (a forceps, a high-frequency heating member, etc.) that performs a medical treatment, such as collecting a living-body tissue or burning process onto the inside of the living body.

The axle shaft 736 is rotatably inserted in a through hole formed on a rear side of the casing 731, and has a pair of wheels 733 at both ends. This axle shaft 736 inserted through the through hole is a rotating shaft perpendicular to the longitudinal axis CL1 of the casing 731 (that is, parallel to a radial direction of the casing 731), and rotates independently from the casing 731.

The rotating magnet 737 functions as a magnetic actuator that causes the caterpillar 712 to rotate by the action of the external rotating magnetic field M70 rotating about an axis in a radial direction of the casing 731. Specifically, the rotating magnet 737 is rotatably supported by the rotating shaft perpendicular to the longitudinal axis CL1 of the casing 731, and rotates about the axis in the radial direction of the casing 731 by following the external rotating magnetic field M70 described above. In this case, the rotating magnet 737 rotates independently from the casing 731. This rotating magnet 737 has a gear unit meshing with the gear 738, and causes the axle shaft 736 to rotate via this gear 738. The gear 738 meshes with the gear unit of the rotating magnet 737 and the gear unit of the axle shaft 736 to transfer the rotating operation of the rotating magnet 737 to the axle shaft 736.

A barycenter GP of the capsule endoscope 701f having the configuration described above is set at a predetermined position in the casing 731 by adjusting the arrangement of the rotating magnet 737 with the heaviest weight among the components described above (the inner components, such as the imaging system 422 and the battery 424, the wheels 732, 733, the axle shafts 734, 736, the rotating magnet 737, the gear 738, the caterpillar 712, etc). Specifically, as depicted in FIG. 92, the barycenter GP is set by disposing the rotating magnet 737 at a position on a center axis CL2 in the radial direction of the casing 731 and de-centered to a bottom side of the casing 731 (the side where the caterpillar mechanism, such as the wheels 732, 733, is disposed). This barycenter GP is positioned at a point of intersection of the rotating shaft of the rotating magnet 737 and the center axis CL2 in the radial direction.

As described above, in the sixth modification example of the seventh embodiment, the rotating magnet is disposed at a position on the center axis in the radial direction of the capsule casing and de-centered to the bottom side of the casing (the side where the caterpillar mechanism is disposed). With this, the barycenter of the capsule endoscope is set at the point of intersection of the rotating shaft of this rotating magnet and the center axis in the radial direction of the casing. The rotating operation of this rotating magnet is transferred to the axle shaft of the caterpillar mechanism via the gear, and others are similar to those in the fifth modification example of the seventh embodiment described above. Therefore, operations and effects similar to those in the fifth modification example of the seventh embodiment can be enjoyed. Also, the barycenter of the capsule endoscope can be easily set at the position de-centered from the center of the casing to the bottom side (the side where the caterpillar mechanism is disposed). With this, lowering the barycenter of the capsule endoscope, which is advantageous in stabilizing caterpillar traveling by the caterpillar mechanism, can be achieved in a simple manner.

Seventh Modification Example

Next, a seventh modification example of the seventh embodiment in the present invention is described. In the fifth modification example of the seventh embodiment described above, the caterpillar mechanism is provided on one side (bottom side) of the casing 731. In this seventh modification example of the seventh embodiment, a caterpillar mechanism is provided to each of casing portions symmetrical with respect to a longitudinal axis of the capsule casing (that is, on the bottom and the top of the casing).

Figure 93B:
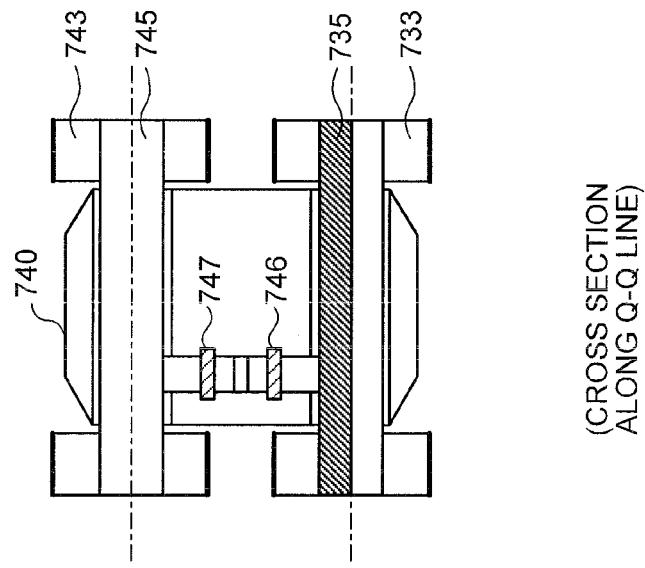
FIGS. 93A and 93B show schematic diagrams depicting a configuration example of a capsule endoscope according to a seventh modification example of the seventh embodiment.
Figure 93A:
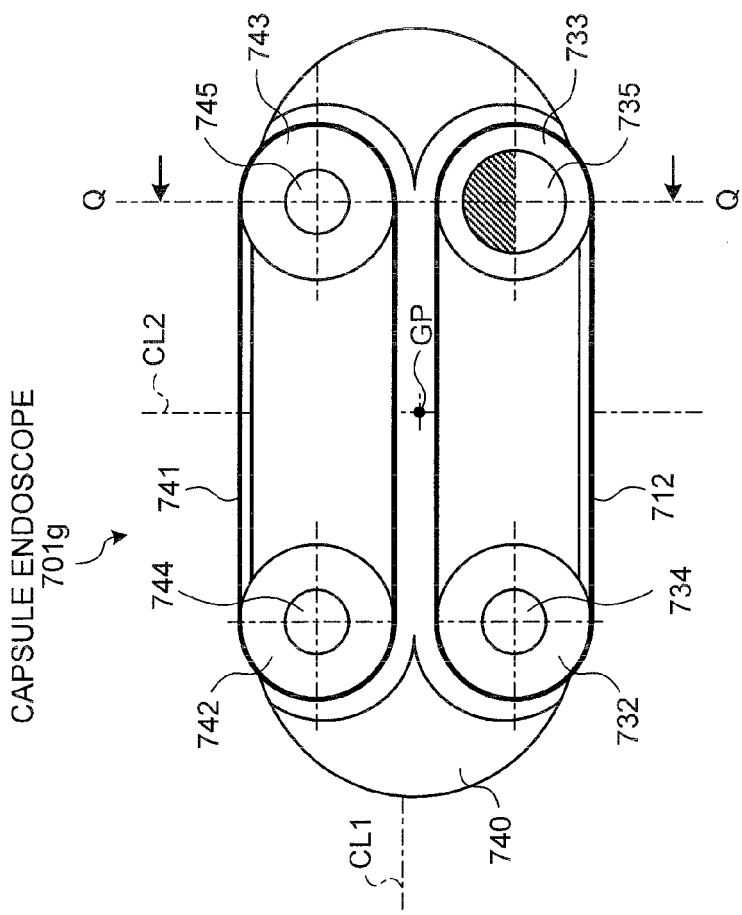

FIGS. 93A and 93B are schematic diagrams depicting a configuration example of a capsule endoscope according to the seventh modification example of the seventh embodiment. Note in FIGS. 93A and 93B that a side view of the capsule endoscope according to the seventh modification example of the seventh embodiment and a Q-Q line sectional view thereof are depicted.

As depicted in FIG. 93A, a capsule endoscope 701g according to this seventh modification example of the seventh embodiment includes, in place of the casing 731 of the capsule endoscope 701e according to the fifth modification example of the seventh embodiment described above, a capsule casing 740 having a structure in which two caterpillar mechanisms can be disposed symmetrically with respect to the longitudinal axis CL1. Also, the capsule endoscope 701g includes, on the bottom side of this casing 740, a caterpillar mechanism (the caterpillar 712, the wheels 732, 733, the axle shaft 734, and the rotating magnet 735) similar to that of the capsule endoscope 701e according to the fifth modification example of the seventh embodiment described above and, on the top side of this casing 740, a caterpillar mechanism symmetrical to this caterpillar mechanism on the bottom side, that is, a caterpillar 741, wheels 742, 743, and axle shafts 744 and 745. Furthermore, the capsule endoscope 701g includes, in this casing 740, gears 746, 747 for interlocking the caterpillar mechanism on the bottom side and the on the top side. Note in the seventh modification example of the seventh embodiment that the rotating magnet 735 includes a gear unit that meshes with this gear 746. Other structure is identical to that of the fifth modification example of the seventh embodiment, and the same component portions are provided with the same reference numerals. Also, a capsule guiding system according to this seventh modification example of the seventh embodiment is approximately similar to the capsule guiding system 400 according to the fourth embodiment described above, and has a configuration including the capsule endoscope 701g in place of the capsule endoscope 401 of the capsule guiding system.

Note that, although not particularly shown, as with the capsule endoscope 701e according to the fifth modification example of the seventh embodiment described above, the capsule endoscope 701g includes, in the casing 740, the position-detection oscillation coil 421, the imaging system 422, the wireless system that wireless transmits an image signal and the like to the external receiving unit 411 via the antenna 423, the battery 424, and the control unit that controls each of these component (the position-detection oscillation coil 421, the imaging system 422, and the wireless system). Also, as exemplarily depicted in the fourth to sixth embodiments or each modification example, the capsule endoscope 701g may include, as appropriate, a local injection mechanism that injects a medicine and a treatment mechanism (a forceps, a high-frequency heating member, etc.) that performs a medical treatment, such as collecting a living-body tissue or burning process onto the inside of the living body.

The casing 740 is a capsule casing formed with a size easy for insertion into the body of the subject and, as described above, has a structure in which two caterpillar mechanisms can be disposed symmetrically with respect to the longitudinal axis CL1. Specifically, as with the casing 731 of the capsule endoscope 701e according to the fifth modification example of the seventh embodiment described above, the casing 740 has a through hole through which the axle shaft 734 is rotatably inserted and a through hole through which the rotating magnet 735 is rotatably inserted. Also, the casing 740 has through holes through which the axle shafts 744, 755 are rotatably inserted, among the caterpillar mechanism on the top side. The through holes on the top side of the casing 740 and the through holes on the bottom side thereof are symmetrical with respect to the longitudinal axis CL1, and are formed along a direction perpendicular to the longitudinal axis CL1 of the casing 740 (that is, the radial direction of the casing 740). Furthermore, the through holes on the top side of the casing 740 and the through holes on the bottom side thereof are each separated from an inner space of the casing 740 where the inner components, such as the imaging system 422, the wireless system, the battery 424, etc., as described above, are disposed.

A pair of wheels 742 is mounted at both ends of the axle shaft 744 on a front side (the side where the imaging system 422 is disposed) on the top side of the casing 740, and rotatably supported by this axle shaft 744. Also, a pair of wheels 743 is mounted at both ends of the axle shaft 745 on a rear side on the top side of the casing 740, and rotatably supported by this axle shaft 745. These wheels 742, 743 support the caterpillar 741 in the caterpillar mechanism on the top side of the casing 740 and also rotate in an interlocking manner with the operation of the caterpillar mechanism on the bottom side of the casing (in detail, the rotation of the rotating magnet 735) and, as a result, rotate the caterpillar 741 in an endless manner. In this case, the caterpillar 741 converts the rotary force of the rotating magnet 735 transferred from the caterpillar mechanism on the bottom side via the gears 746, 747 to a propulsion force of the capsule endoscope 701g.

The axle shaft 744 is rotatably inserted in a through hole formed on the front side among the through holes formed on the top side of the casing 740, and has a pair of wheels 742 described above at both ends. On the other hand, the axle shaft 745 is rotatably inserted in a through hole formed on the rear side among the through holes formed on the top side of the casing 740, and has a pair of wheels described above at both ends. These axle shafts 744, inserted through the respective through holes are rotating shafts perpendicular to the longitudinal axis CL1 of the casing 740 (that is, parallel to a radial direction of the casing 740), and rotate independently from the casing 740.

Also, the axle shaft 745 on rear side has a gear unit meshing with the gear 747, and rotates, in an interlocking manner with the rotating operation of the rotating magnet 735 transferred by two gears 746, 747, meshing to this rotating magnet 735. The gears 746, 747 are paired gears rotating while meshing, and are supported by a rotating shaft rotatable with respect to the casing 740. While meshing with the gear unit of the rotating magnet 735, the gear 746 rotates in reverse to the rotating magnet 735 according to the rotating operation of this rotating magnet 735. This gear 746 transfers the rotating operation of this rotating magnet 735 to the gear 747. While meshing with the gear 746 and the gear unit of the axle shaft 745, the gear 747 rotates in the same direction as that of the rotating magnet 735 according to the rotating operation of this gear 746. This gear 747 causes the axle shaft 745 to rotate in reverse to this rotating magnet 735 according to the rotating operation transferred from the rotating magnet 735 via this gear 746.

A barycenter GP of the capsule endoscope 701g having the configuration as described above is set at a predetermined position in the casing 740 by adjusting the arrangement of the components described above (the inner components, such as the imaging system 422 and the battery 424, the caterpillar mechanism on the top side, the caterpillar mechanism on the bottom side, etc). Specifically, as depicted in FIG. 93A, the barycenter GP is set on the longitudinal axis CL1 of the casing 740, and is further desirably set at a point of intersection of the center axis CL2 in the radial direction of the casing 740 and the longitudinal axis CL1 (that is, at the center position of the casing 740).

Next, the operation of each caterpillar mechanism provided on both sides (the bottom side and the top side) of the casing 740 is described. FIGS. 94A and 94B are schematic diagrams depicting a state in which the caterpillar mechanisms on both sides of the capsule endoscope operate with an external rotating magnetic field. Note in FIGS. 94A and 94B that a side view of the capsule endoscope 701g according to the seventh modification example of the seventh embodiment and a Q-Q line sectional view thereof are depicted.

As depicted in FIG. 94B, as with the fifth modification example of the seventh embodiment, to the rotating magnet 735 rotatably inserted in the through hole on the bottom side of the casing 740, the rotating magnetic field M70 rotating about an axis in a radial direction of the casing 740 is applied by the magnetic-field generating unit 403. By following this applied rotating magnetic field M70, the rotating magnet 735 rotates about the axis in the radial direction of the casing 740. As a result, as with the fifth modification example of the seventh embodiment, the caterpillar 712, the axle shaft 734, and the wheels 732, 733 of the caterpillar mechanism on the bottom side rotate in the same direction as that of this rotating magnet 735.

On the other hand, the caterpillar 741, the wheels 742, 743, and the axle shaft 744, 745 forming the caterpillar mechanism on the top side of the casing 740 operate in an interlocking manner with the operation of the caterpillar mechanism on the bottom side (in detail, the rotating operation of the rotating magnet 735). That is, the axle shaft 745 rotates in reverse to this rotating magnet 735 in an interlocking manner with the rotating operation of the rotating magnet 735 transferred by the gears 746, 747. The wheels 743 supported by this axle shaft 745 rotate together with the axle shaft 745 to cause the caterpillar 741 to rotate in reverse to the caterpillar 712 of the caterpillar mechanism on the bottom side described above. Note that, while supporting the front side of the caterpillar 741, the wheels 742, 744 rotate according to the rotation of the caterpillar 741.

Here, while catching an inner wall of an organ facing the bottom portion of the casing 740, the caterpillar 712 of the caterpillar mechanism on the bottom side rotates in the same direction as that of the rotating magnet 735 with the rotary force of the rotating magnet 735 rotating by following the external rotating magnetic field M70. On the other hand, while catching the inner wall of the organ facing the top portion of the casing 740, the caterpillar 741 of the caterpillar mechanism on the top side rotates in reverse to that of the rotating magnet 735 in an interlocking manner with the rotating operation of the rotating magnet 735 described above. With these caterpillars 712, 741 rotating in reverse to each other, a larger propulsion force can be generated, compared with a propulsion force by a caterpillar on only one side.

Even when the inner diameter dimension of the organ is small compared with the outer diameter dimension of the casing 740 because the inside of the organ is not sufficiently expanded, the capsule endoscope 701g including these caterpillars 712, 741 can go forward or backward while expanding the inside of the organ according to the outer shape of the casing 740 by the action of the caterpillars 712, 741 that perform a rotating operation in an interlocking manner and in reverse to each other as described. Also, the caterpillar mechanism on the bottom side (the caterpillar 712, the wheels 732, 733, the axle shaft 734, and the rotating magnet 735) and the caterpillar mechanism on the top side (the caterpillar 741, the wheels 742, 743, and the axle shaft 744, 745) perform a rotating operation independently from the casing 740. Therefore, the capsule endoscope 701g can go forward and backward in the subject without causing the casing 740 to rotate according to the rotating operation of each of the caterpillar mechanisms on the bottom side and the top side.

As described above, in the seventh modification example of the seventh embodiment, the caterpillar mechanism on the bottom side having the rotating magnet as a magnetic actuator and the caterpillar mechanism on the top side interlocking with the rotating operation of the caterpillar mechanism on the bottom side via the gear are disposed symmetrically with respect to the longitudinal axis of the capsule casing. To this rotating magnet, an external rotating magnetic field is applied, and the caterpillar mechanism on the bottom side is caused to perform a rotating operation by rotating this rotating magnet by following the applied external rotating magnetic field. Also, by interlocking manner with the rotating operation of this rotating magnet, the caterpillar mechanism on the top side is caused to perform a rotating operation in reverse to that of the caterpillar mechanism on the bottom side. Other structure is configured similarly to that of the fifth modification example of the seventh embodiment. Therefore, operations and effects similar to those in the fifth modification example of the seventh embodiment can be enjoyed. Also, a strong propulsion force can be generated, compared with a propulsion force by a caterpillar mechanism on only one side. Even when the inside of the organ is not sufficiently expanded, it can go forward or backward in the body of the subject without propulsion being hindered by a pressure from an organ's inner wall side.

Note in the seventh modification example of the seventh embodiment that the position-detection oscillation coil 421 for detecting at least one of the position and direction of the capsule endoscope in the subject is disposed in parallel to the rotating shaft of the rotating magnet 735. This is not meant to be restrictive and, in place of this position-detection oscillation coil, an LC marker may be provided to the capsule endoscope. This LC marker is disposed in the capsule endoscope so that its coil axis and the rotating shaft of the rotating magnet are approximately parallel to each other, and is disposed to, for example, any one of the axle shafts 734, 744, 745 of the caterpillar mechanism except the rotating magnet 735. In this case, it is sufficient for the position calculating unit 412 described above to calculate (detect) at least one of the position and direction of the capsule endoscope in the subject based on an LC marker scheme.

Also, in the seventh modification example of the seventh embodiment, the barycenter GP of the capsule endoscope 701g is set on the longitudinal axis CL1 of the casing 740 by adjusting the arrangement of the inner components, such as the imaging system 422 and the battery 424, the caterpillar mechanism on the top side, the caterpillar mechanism on the bottom side, and others. This is not meant to be restrictive. A counter weight having a weight equivalent to that of the rotating magnet 735 may be provided at a position on the rotating magnet 735 symmetrical to the center position in the casing 740 to correct the deviation of weight due to the rotating magnet 735, and the barycenter GP of the capsule endoscope 701g may be set on the longitudinal axis CL1 of the casing 740 (further, at the center position of the casing 740). In this case, such a counter weight may be any of a battery, a super-capacitor, a position-detection oscillation coil, a weight, and others, or may be a combination of these as appropriate.

Eighth Modification Example

Next, an eighth modification example of the seventh embodiment is described. In the fifth modification example of the seventh embodiment described above, a propulsion force of the capsule endoscope is obtained by the caterpillar mechanism including the rotating magnet 735 rotating about the axis perpendicular to the longitudinal axis CL1 of the capsule casing 731 as a magnetic actuator. In this eighth modification example of the seventh embodiment, by a propelling mechanism including a rotating magnet rotating about the longitudinal axis CL1 of the capsule casing as a magnetic actuator, the capsule endoscope is caused to go forward or backward in a longitudinal axis direction.

Figure 95:
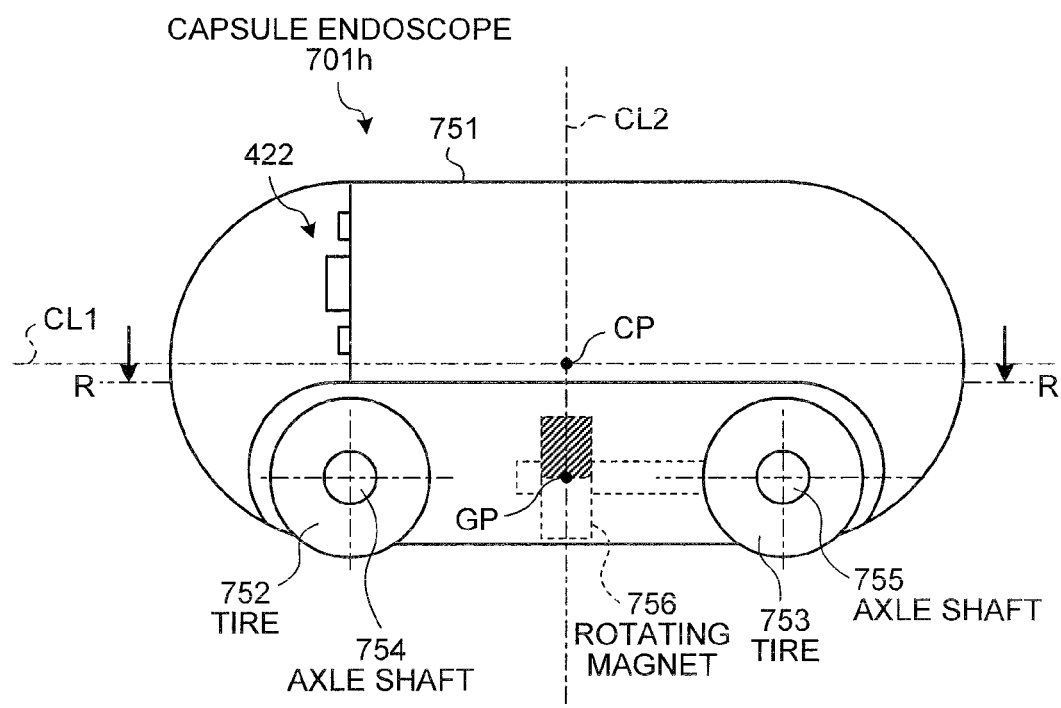
FIG. 95 shows a schematic diagram depicting a configuration example of a capsule endoscope according to an eighth modification example of the seventh embodiment.
Figure 96:
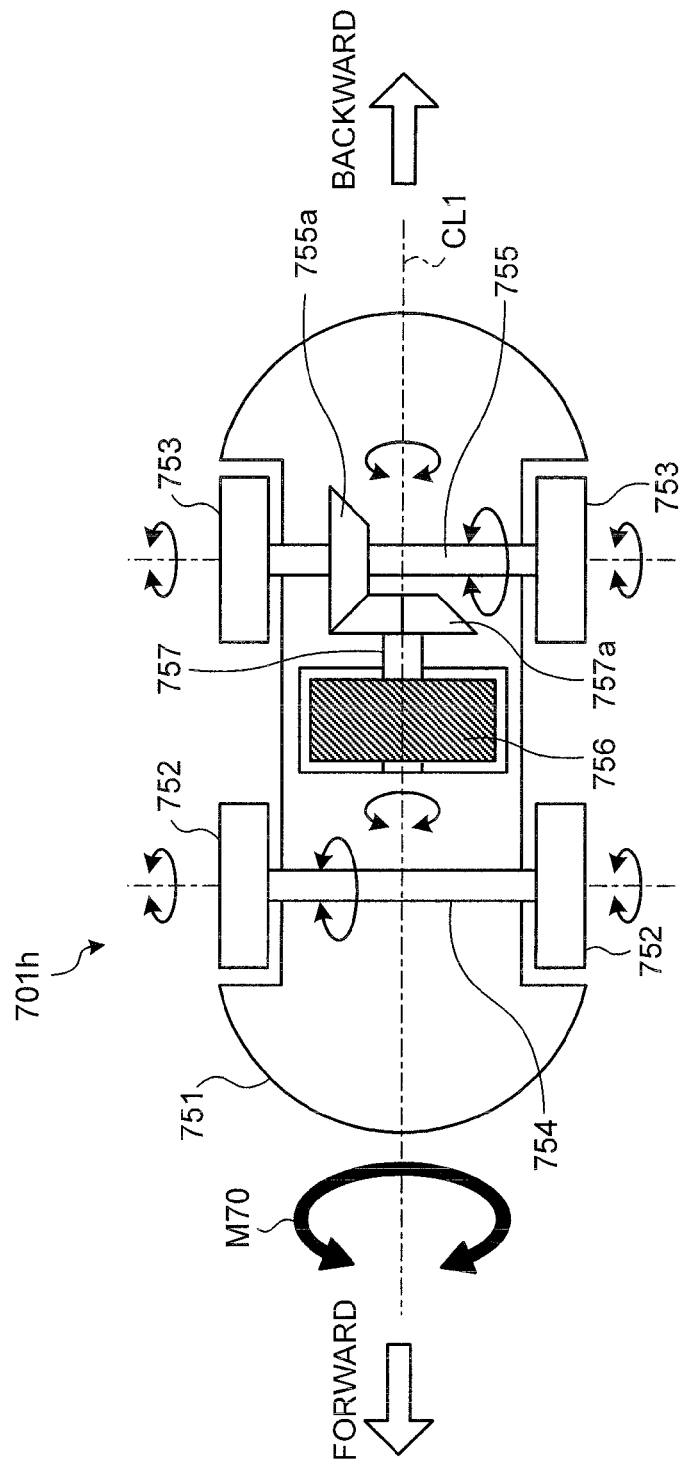
FIG. 96 shows sectional view of the capsule endoscope cut along an R-R line depicted in FIG. 95.

FIG. 95 is a schematic diagram depicting a configuration example of a capsule endoscope according to the eighth modification example of the seventh embodiment. FIG. 96 is a R-R line sectional view of the capsule endoscope depicted in FIG. 95. Note in FIG. 96 that a casing of a capsule endoscope 701h according to the eighth modification example of the seventh embodiment and a propelling mechanism thereof are schematically depicted.

The capsule endoscope 701h according to the eighth modification example of the seventh embodiment includes, in place of the caterpillar mechanism of the capsule endoscope 701e according to the fifth modification example of the seventh embodiment, a propelling mechanism is provided using four wheel tires. That is, as depicted in FIGS. 95 and 96, the capsule endoscope 701h includes a capsule casing 751 formed with a size easy for insertion into the body of a subject, a pair of tires 752 disposed on a front side of the casing 751, a pair of tires 753 disposed on a rear side of the casing 751, an axel shaft 754 that supports the pair of tires 752 on the front side, an axel shaft 755 that supports the pair of tires 753 on the rear side, a rotating magnet 756 as a magnetic actuator performing a rotating operation by following an external rotating magnetic field, a rotating shaft 757 that rotatably supports the rotating magnet 756 about the longitudinal axis CL1 of the casing 751, and gears 757a, 755a that convert the rotation of this rotating magnet 756 to rotation about the axle shaft 755. The other structure is identical to that of the fifth modification example of the seventh embodiment, and the same component portions are provided with the same reference numerals. Also, a capsule guiding system according to this eighth modification example of the seventh embodiment is approximately similar to the capsule guiding system 400 according to the fourth embodiment described above, and has a configuration in which the capsule endoscope 701h is included in place of the capsule endoscope 401 of the capsule guiding system.

Note that, as with the capsule endoscope 701e according to the fifth modification example of the seventh embodiment, the capsule endoscope 701h includes, in the casing 751, the position-detection oscillation coil 421, the imaging system 422, the wireless system that wireless transmits an image signal and the like to the external receiving unit 411 via the antenna 423, the battery 424, and the control unit that controls each component (the position-detection oscillation coil 421, the imaging system 422, and the wireless system). Also, as exemplarily depicted in the fourth to sixth embodiments or each modification example described above, the capsule endoscope 701h may include, as appropriate, a local injection mechanism that injects a medicine and a treatment mechanism (a forceps, a high-frequency heating member, etc.) that performs a medical treatment, such as collecting a living-body tissue or burning process onto the inside of the living body.

A pair of tires 752 is mounted at both ends of the axle shaft 754 on a front side of the casing 751 (the side where the imaging system 422 is disposed), and rotatably supported by this axle shaft 754. Also, a pair of tires 753 is mounted at both ends of the axle shaft 755 on a rear side of the casing 751, and rotatably supported by this axle shaft 755. These tires 752, 753 rotate according to the rotation of the rotating magnet 756 to generate a propulsion force of the capsule endoscope 701h.

The axle shaft 754 is rotatably inserted in a through hole formed on a front side of the casing 751, and has a pair of tires 752 at both ends. On the other hand, the axle shaft 755 is rotatably inserted in a through hole formed on a rear side of the casing 751, and has a pair of tires 753 at both ends. These axle shafts 754, 755 inserted through the respective through holes are rotating shafts perpendicular to the longitudinal axis CL1 of the casing 751 (that is, parallel to a radial direction of the casing 751), and rotate independently from the casing 751.

The rotating magnet 756 is supported by the rotating shaft 757 rotatably disposed in the casing 751, and rotates with the external rotating magnetic field M70 to generate a rotary force as a source of a propulsion force of the capsule endoscope 701h. Here, the rotating shaft 757 is parallel to the longitudinal axis CL1 of the casing 751. The rotating magnet 756 rotatably supported by this rotating shaft 757 follows the external rotating magnetic field M70 to rotate about the longitudinal axis CL1 of the casing 751. In this case, the rotating magnet 756 rotates independently from the casing 751 without the rotation of the casing 751.

The gears 757a, 755a are achieved by using bevel gears or the like, converting the rotating operation of this rotating magnet 756 to a rotating operation of the axle shaft 755 (that is, a rotating operation about the axis in a radial direction perpendicular to the longitudinal axis CL1 of the casing 751). Specifically, the gear 757a is provided at an end of the rotating shaft 757 of the rotating magnet 756, and rotates together with this rotating shaft 757. On the other hand, the gear 755a is provided to the axle shaft 755 so that the axle shaft 755 and the rotating shaft are matched. By interlocking with the rotation of this gear 757a, the axle shaft 755 is rotated about the axis in the radial direction of the casing 751. With these gears 757a and 755a meshing each other and rotating, the rotating operation about the longitudinal axis CL1 by the rotating magnet 756 is converted to a rotating operation about the axle shaft 755.

Note that the four tires 752, 753, the axle shafts 754, 755, the rotating magnet 756, the rotating shaft 757, and the gears 757a, 755a form a propelling mechanism of the capsule endoscope 701h according to this eighth modification example of the seventh embodiment to go forward or backward in the longitudinal axis CL1 direction. Also, the rotating magnet 756 and the rotating shaft 757 form a magnetic actuator in the propelling mechanism of this capsule endoscope 701h.

Also, as with the capsule endoscope 701e according to the fifth modification example of the seventh embodiment, a barycenter GP of this capsule endoscope 701h is set at a predetermined position in the casing 751 by adjusting the arrangement of the components described above (the inner components, such as the imaging system 422 and the battery 424, the propelling mechanism described above, etc). In this case, the barycenter GP is desirably set on the center axis CL2 in a radial direction of the casing 751 and, furthermore, as depicted in FIG. 95, is desirably set at a position de-centered from a center CP of the casing 751 to a bottom side of the casing 751 (the side where the propelling mechanism, such as the tires 752, 753, etc. are disposed).

Note that the position-detection oscillation coil 421 (not shown) for detecting at least one of the position and direction of this capsule endoscope 701h by the position calculating unit 412 described above is disposed in the casing 751 so that the rotating shaft 757 of the rotating magnet 756 described above and a coil axis are parallel to each other. This position-detection oscillation coil 421 forms a magnetic field in a direction perpendicular to the magnetization direction of the rotating magnet 756.

Next, with reference to FIG. 96, the operation of the propelling mechanism of the capsule endoscope 701h is described. As depicted in FIG. 96, to the rotating magnet 756 rotatably supported by the rotating shaft 757 about the longitudinal axis CL1 of the casing 751, the rotating magnetic field M70 rotating about the longitudinal axis CL1 of this casing 751 is applied by the magnetic-field generating unit 403. In this case, the rotating magnet 756 follows this rotating magnetic field M70 to rotate about the longitudinal axis CL1 of the casing 751 together with the rotating shaft 757, and also causes the gear 757a at the end of this rotating shaft 757 to rotate about the longitudinal axis CL1.

This gear 757a rotates while meshing with the gear 755a of the axle shaft 755, thereby transferring the rotating operation of the rotating magnet 756 described above to the axle shaft 755 via the gear 755a. In this case, the gear 755a converts the rotating operation about the rotating shaft 757 (that is, the longitudinal axis CL1 of the casing 751) transferred from the rotating magnet 756 via this gear 757a to a rotating operation about the axis in the radial direction of the casing 751 to cause the axel shaft 755 to rotate about the axis in the radial direction of the casing 751.

The axle shaft 755 rotating about the axis in the radial direction of the casing 751 together with this gear 755a causes the pair of tires 753 to rotate about the axis in the radial direction of the casing 751. This pair of tires 753 rotates about the axle shaft 755, and also converts the rotary force of the rotating magnet 756 described above to the propulsion force of the capsule endoscope 701h. The capsule endoscope 701h uses the propulsion force generated with the rotating operation of this pair of tires 753 to go forward or backward in the direction of the longitudinal axis CL1 in the body of the subject. Note that the axle shaft 754 and the pair of tires 752 on the front side of the casing 751 rotate in the same direction as that of the tires 753 independently from the casing 751 without hindering the capsule endoscope 701h from going forward and backward.

As described above, in the eighth modification example of the seventh embodiment, a propelling mechanism is provided that causes the tires to rotate about the axle shaft in the radial direction of the casing in an interlocking manner with the rotating operation of the rotating magnet that rotates about the longitudinal axis of the capsule casing. By following an external rotating magnetic field applied to this rotating magnet, the rotating magnet is rotated about the longitudinal axis of the casing. The rotating operation of this rotating magnet is converted to a rotating operation about the axle shaft by the gear to cause the tires of the propelling mechanism to perform a rotating operation. Other structure is configured similarly to that of the fifth modification example of the seventh embodiment. Therefore, operations and effects similar to those in the fifth embodiments of the seventh embodiment can be enjoyed. Also, energy required for propulsion of the capsule endoscope is not required to be preserved in the casing, and a propelling mechanism of the capsule endoscope can be achieved with a simple structure. As a result, downsizing of the capsule endoscope can be promoted, and a capsule guiding system excellent in insertability of the capsule endoscope into the subject can be achieved.

Note in the eighth modification example of the seventh embodiment that the position-detection oscillation coil for detecting at least one of the position and direction of the capsule endoscope in the subject is disposed in parallel to the rotating shaft 757 of the rotating magnet 756. This is not meant to be restrictive, and the position-detection oscillation coil may be disposed perpendicularly to this rotating shaft 757. Also, in place of this position-detection oscillation coil, an LC marker may be provided to the capsule endoscope. This LC marker is disposed in the capsule endoscope so that its coil axis and the rotating shaft of the rotating magnet are approximately perpendicular or parallel to each other. In this case, it is sufficient for the position calculating unit 412 described above to calculate (detect) at least one of the position and direction of the capsule endoscope in the subject based on an LC marker scheme.

Also, in the eighth modification example of the seventh embodiment, a barycenter GP of the capsule endoscope 701*h* is set on the center axis CL2 in the radial direction of the casing 751 by adjusting the arrangement of the inner components, such as the imaging system 422 and the battery 424, and the propelling mechanism, such as the rotating magnet 756 and the tires 752, 753 (for example, the rotating magnet 756, which is the heaviest, is disposed on the center axis CL2 in the radial direction of the casing 751). This is not meant to be restrictive. A counter weight having a weight equivalent to that of the rotating magnet 756 may be provided at a position on the rotating magnet 756 symmetrical to the center axis CL2 in the radial direction of the casing 751 to correct the deviation of weight due to the rotating magnet 756, and the barycenter GP of the capsule endoscope 701*h* may be set on the center axis CL2 in the radial direction of the casing 751 (further, at a position de-centered to a bottom side of the casing 751). In this case, such a counter weight may be any of a battery, a super-capacitor, a position-detection oscillation coil, a weight, and others, or may be a combination of these as appropriate.

Ninth Modification Example

Next, a ninth modification example of the seventh embodiment of the present invention is described. In the fifth modification example of the seventh embodiment, the caterpillar 712 is rotated in an interlocking manner with the rotating operation of the rotating magnet 735 rotating about the axis in the radial direction of the casing 731 by following the external rotating magnetic field, thereby propelling the capsule endoscope 701*e*. In the ninth modification example of the seventh embodiment, rotating units each having its external surface provided with a spiral protrusion are rotated by a rotating magnet to propel the capsule endoscope.

FIGS. 97A and 97B are schematic diagrams depicting a configuration example of the capsule endoscope according to the ninth modification example of the seventh embodiment. Note in FIGS. 97A and 97B that a side view of a capsule endoscope 701*i* according to the ninth modification example of the seventh embodiment and an S-S line sectional view thereof are depicted.

This capsule endoscope 701*i* according to the ninth modification example of the seventh embodiment includes, in place of the caterpillar mechanism of the capsule endoscope 701*e* according to the fifth modification example of the seventh embodiment described above, a propelling mechanism that causes the rotating units each having its external surface provided with a spiral protrusion to rotate about the axis in a longitudinal direction to obtain a propulsion force. That is, as depicted in FIGS. 97A and 97B, the capsule endoscope 701*i* includes a capsule casing 761 formed with a size easy for insertion into the body of a subject, rotating units 762*a* to 762*d* each having its external surface with a spiral protrusion 763, a rotating magnet 764 that follows the external rotating magnetic field M70 to cause the rotating unit 762*a* to rotate, and a gear 765 that causes the remaining rotating units 762*b* to 762*d* to rotate in an interlocking manner with the rotating operation of this rotating unit 762*a*. Other structure is identical to that of the fifth modification example of the seventh embodiment, and the same component portions are provided with the same reference numerals. Also, a capsule guiding system according to this ninth modification example of the seventh embodiment is approximately similar to the capsule guiding system 400 according to the fourth embodiment described above, and has a configuration including the capsule endoscope 701*i* in place of the capsule endoscope 401 of the capsule guiding system.

Note that, as with the capsule endoscope 701*e* according to the fifth modification example of the seventh embodiment described above, the capsule endoscope 701*i* includes, in the casing 761, the position-detection oscillation coil 421, the imaging system 422, the wireless system that wireless transmits an image signal and the like to the external receiving unit 411 via the antenna 423, the battery 424, and the control unit that controls each component (the position-detection oscillation coil 421, the imaging system 422, and the wireless system). Also, as exemplarily depicted in the fourth to sixth embodiments or each modification example described above, the capsule endoscope 701*i* may include, as appropriate, a local injection mechanism that injects a medicine and a treatment mechanism (a forceps, a high-frequency heating member, etc.) that performs a medical treatment, such as collecting a living-body tissue or burning process onto the inside of the living body.

The casing 761 is a capsule casing formed with a size easy for insertion into an organ of the subject, and has concave portions for disposing four rotating units 762*a* to 762*d* that propels the capsule endoscope 701*a*. This casing 761 rotatably supports four rotating units 762*a* to 762*d* in a manner such that at least the spiral protrusion 763 is exposed outside of the concave portion. Note that, among the rotating units 762*a* to 762*d* supported by this casing 761, the rotating unit 762*a* and a rotating unit 762*c* are symmetrical with respect to the longitudinal axis CL1 of the casing 761, and the rotating unit 762*b* and the rotating unit 762*d* are symmetrical with respect to the longitudinal axis CL1 of the casing 761. Also, the casing 761 has included therein the gear 765 that interlocks these four rotating units 762*a* to 762*d*, and rotatably supports this gear 765 about the longitudinal axis CL1.

The rotating units 762a to 762d are capsule-shaped members each having the spiral protrusion 763 formed in a spiral shape on its external surface, and rotate about the axis in the longitudinal direction (that is, about an axis parallel to the longitudinal axis CL1) in a manner such that they are supported by the casing 761, thereby generating a propulsion force of the capsule endoscope 701i. Also, the rotating units 762a to 762d each has a gear unit that meshes with the gear 765, and rotate in the same direction while meshing with this gear 765. That is, these rotating units 762a to 762d interlock with each other via this gear 765.

The rotating magnet 764 functions as a magnetic actuator that causes these rotating units 762a to 762d to rotate. Specifically, the rotating magnet 764 has a magnetization direction in a radial direction perpendicular to the longitudinal axis CL1 of the casing 761, and is fixedly disposed in any one of these four rotating units 762a to 762d, for example, the rotating unit 762a. When the external rotating magnetic field M70 rotating about an axis parallel to the longitudinal axis CL1 is applied, this rotating magnet 764 causes the rotating unit 762a to rotate about an axis parallel to the longitudinal axis CL1.

The four rotating units 762a to 762d, the rotating magnet 764, and the gear 765 having the spiral protrusion 763 on the external surface described above forms a propelling mechanism that causes the capsule endoscope 701i according to this ninth modification example of the seventh embodiment to go forward or backward in the longitudinal axis CL1 direction.

On the other hand, the position-detection oscillation coil 421 (not shown) for detecting at least one of the position and direction of this capsule endoscope 701i by the position calculating unit 412 described above is disposed in the casing 761 so that the rotating shaft of the rotating magnet 764 described above and a coil axis are parallel to each other. This position-detection oscillation coil 421 forms a magnetic field in a direction perpendicular to the magnetization direction of the rotating magnet 764.

Next, with reference to FIGS. 97A and 97B, the operation of the propelling mechanism of the capsule endoscope 701i is described. As depicted in FIG. 97A, to the rotating magnet 764 rotatable about the axis parallel to the longitudinal axis CL1, the external rotating magnetic field M70 rotating about a rotation axis of the rotating unit 762a containing this rotating magnet 764 is applied by the magnetic-field generating unit 403 described above. In this case, the rotating magnet 764 follows this rotating magnetic field M70 to rotate, and also causes the rotating unit 762a to rotate about the axis parallel to the longitudinal axis CL1.

This rotating unit 762a rotates together with this rotating magnet 764 about an axis parallel to the longitudinal axis CL1, and also causes the gear 765 in the casing 761 to rotate. The gear 765 rotates while meshing with each gear unit of four rotating units 762a to 762d to transfer the rotating operation of the rotating magnet 764 to the rotating units 762b to 762d. That is, the rotating units 762b to 762d interlocks with the rotating operation of the rotating unit 762a transferred via this gear 765 to rotate about the axis parallel to the longitudinal axis CL1. In this case, while each bringing the spiral protrusion 763 into contact with the inner wall of the organ in the subject, four rotating units 762a to 762d rotate in the same direction as that of the rotating magnet 764 independently from the casing 761, thereby generating a propulsion force of the capsule endoscope 701i. With this action of each spiral protrusion 763 of the rotating units 762a to 762d rotating in this manner, the capsule endoscope 701i goes forward or backward in the direction of the longitudinal axis CL1 in the organ of the subject without causing the casing 761 to rotate about the longitudinal axis CL1.

As described above, in the ninth modification example of the seventh embodiment, the propelling mechanism is provided that includes the rotating magnet rotating about the axis in the longitudinal direction of the capsule casing as a magnetic actuator and causes the plurality of rotating units each having its external surface with a spiral protrusion to rotate about the axis in the longitudinal direction to generate a propulsion force. This rotating magnet is rotated by following the external rotating magnetic field, and the plurality of rotating units are caused to perform a rotating operation in the same direction as that of this rotating magnet in an interlocking manner with the rotating operation of this rotating magnet. With this, the spiral protrusions rotating together with these plurality of rotating units are brought into contact with the inner wall of the organ. Other structure is configured similarly to that of the fifth modification example of the seventh embodiment. Therefore, operations and effects similar to those in the fifth modification example of the seventh embodiment can be enjoyed. Also, a propulsion force sufficient to go forward or backward to the inside of the narrow organ can be obtained. Even when the inside of the organ is not sufficiently expanded, it can easily go forward or backward in the subject.

Also, energy required for propulsion of the capsule endoscope is not required to be preserved. Therefore, downsizing of the capsule endoscope can be promoted in a simple manner, and a capsule guiding system excellent in insertability of the capsule endoscope into the subject can be achieved.

Note in the ninth modification example of the seventh embodiment described above that the position-detection oscillation coil for detecting at least one of the position and direction of the capsule endoscope in the subject is disposed in parallel to the rotating shaft of the rotating magnet 764. This is not meant to be restrictive, and the position-detection oscillation coil may be disposed perpendicularly to this rotating shaft 764. Also, in place of this position-detection oscillation coil, an LC marker may be provided to the capsule endoscope. This LC marker is disposed in the capsule endoscope so that its coil axis and the rotating shaft of the rotating magnet are approximately perpendicular or parallel to each other. In this case, it is sufficient for the position calculating unit 412 described above to calculate (detect) at least one of the position and direction of the capsule endoscope in the subject based on an LC marker scheme.

Also, in the ninth modification example of the seventh embodiment described above, the barycenter of the capsule endoscope 701i is set on the longitudinal axis CL1 of the casing 761 by adjusting the arrangement of the inner components, such as the imaging system 422 and the battery 424, and the propelling mechanism, such as the rotating magnet 764 and the rotating units 762a to 762d. This is not meant to be restrictive. A counter weight having a weight equivalent to that of the rotating magnet 764 may be provided at a position on the rotating magnet 764 symmetrical to the longitudinal axis CL1 of the casing 761 (for example, in the rotating unit 762c) to correct the deviation of weight due to the rotating magnet 764, and the barycenter of the capsule endoscope 701i may be set on the longitudinal axis CL1 of the casing 761 (further, at the center position of the casing 761). In this case, such a counter weight may be any of a battery, a supercapacitor, a position-detection oscillation coil, a weight, and others, or may be a combination of these as appropriate.

Note in the fourth to seventh embodiments that the case is described in which the magnetic actuator according to the first to third embodiments is applied to a so-called capsule endoscope. Similar effects can also be achieved when the magnetic actuator is applied to a medical device having an inserting unit for insertion into the subject, as with an endoscope or catheter.

Eighth Embodiment

Figure 98:
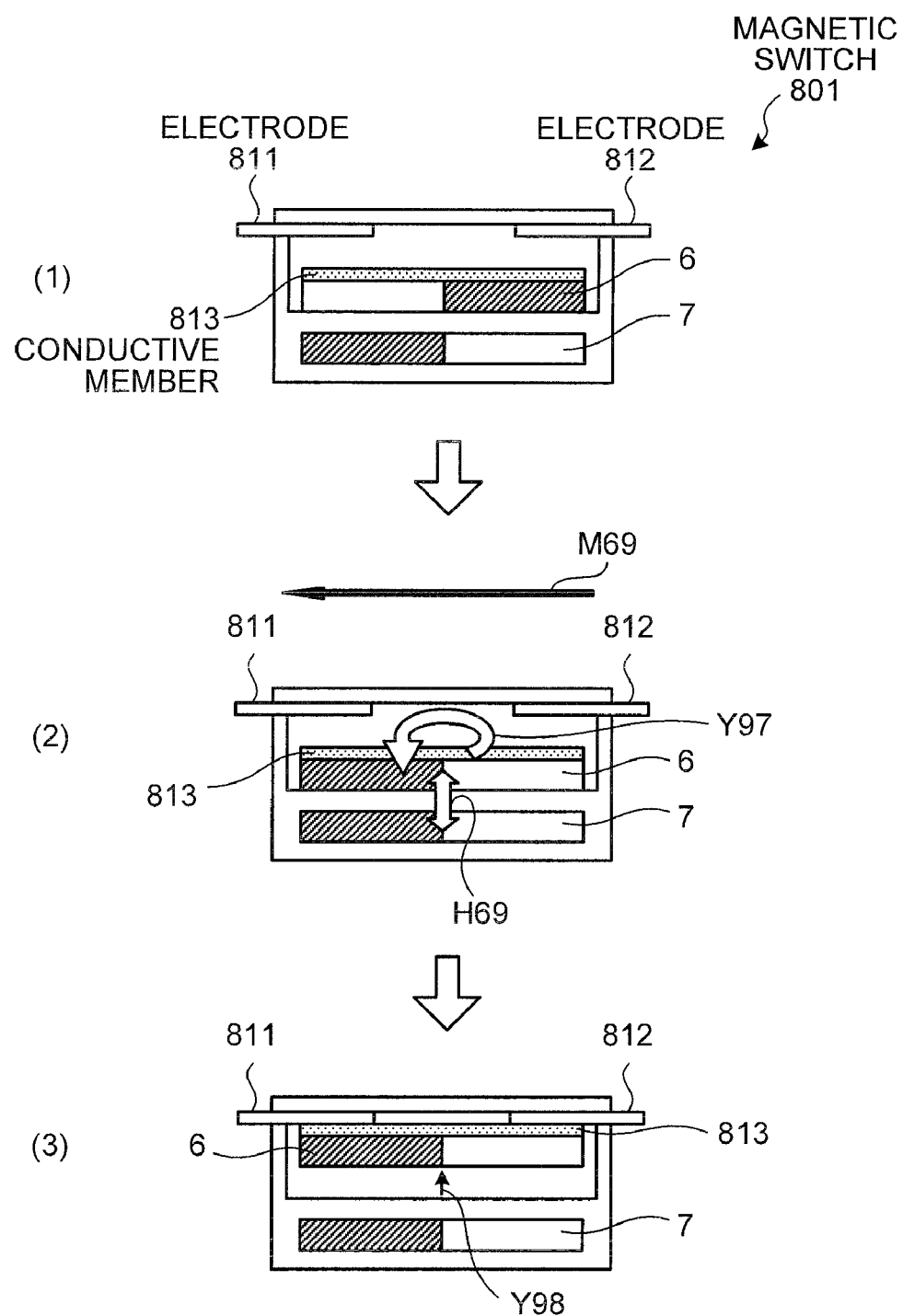
FIG. 98 shows sectional views of a magnetic switch according to an eighth embodiment.

Next, with reference to FIG. 98, an eighth embodiment is described. In the eighth embodiment, a case is described in which the magnetic actuator 1 is applied to a magnetic switch. FIG. 98 is a sectional view of a magnetic switch according to the eighth embodiment.

As depicted in FIG. 98, a magnetic switch 801 according to the eighth embodiment has a configuration in which a conductive member 813 is provided on a surface of the rotationally-moving magnet 6 on electrodes 811, 812 side. As depicted in FIG. 98(1), when the magnetic switch 801 in an OFF state is changed to an ON state, as depicted in FIG. 98(2), a magnetic field M69 is applied having a magnetic field strength allowing the rotationally-moving magnet 6 to rotate and having an angular difference equal to or smaller than 60 degrees with respect to the magnetization direction of the rotationally-moving magnet 6. In this case, as indicated by an arrow Y97 in FIG. 98(2), the rotationally-moving magnet 6 rotates according to the magnetic field M69, and a repulsive force H69 occurs between the fixed magnet 7 and itself. With this repulsive force H69, as indicated by an arrow Y98 in FIG. 98(3), the rotationally-moving magnet 6 moves to the electrodes 811, 8112 side, thereby bringing the electrodes 811, 812 and the conductive member 813 on the rotationally-moving magnet 6 into contact to cause the magnetic switch 801 to become in an ON state. Note that the magnetic switch 801 can be kept in an ON state by continuing application of the magnetic field M69, and the magnetic switch 801 can be kept in an OFF state by stopping application of the magnetic field M69.

As described above, according to the magnetic switch 801 according to the eighth embodiment, unlike a conventionally-used lead switch, no vacuum tube is required, thereby making it possible to downsize the switch and improve flexibility in designing the shape.

As described above, an aspect of the present invention includes: a first permanent magnet and a second permanent magnet being relatively rotatable in a plane including a magnetization direction in a housing; a magnetic-field generating unit that generates a magnetic field that causes the first permanent magnet and/or the second permanent magnet to relatively rotate in a direction so that the first permanent magnet and the second permanent magnet mutually generate a repulsive force; and a first guiding portion that regulates a direction in which the first permanent magnet and the second permanent magnet relatively move by the generated repulsive force. With this, a high-energy-efficiency magnetic actuator with ensured flexibility in design can be achieved.

Also, by using the magnetic actuator according to the present invention, the capsule inner structure of a capsule endoscope that performs various operations by the magnetic actuator can be simplified. With this, effects can be achieved such that downsizing of the capsule endoscope having the magnetic actuator can be promoted and also the capsule endoscope operated by the magnetic actuator can be easily inserted into the body of the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic actuator comprising:
a housing;
a first permanent magnet and a second permanent magnet placed in the housing and being relatively rotatable in a plane including a magnetization direction;
a magnetic-field generating unit outside of the housing, the magnetic-field generating unit generating a magnetic field that relatively rotates the first permanent magnet and/or the second permanent magnet so that switching between a first arrangement in which the first permanent magnet and the second permanent magnet do not generate a repulsive force against each other and a second arrangement in which the first permanent magnet and the second permanent magnet generate a repulsive force against each other is performed; and
a first guiding portion provided in the housing to regulate a direction in which the first permanent magnet and the second permanent magnet relatively move by the generated repulsive force, wherein
the first permanent magnet is fixed to the housing,
the second permanent magnet is placed in the first guiding portion and is rotatable in the plane including the magnetization direction of the second permanent magnet, and
the magnetic-field generating unit generates a magnetic field in the first guiding portion.

2. The magnetic actuator according to claim 1, wherein the first and the second permanent magnets have different magnetic forces.

3. A magnetic actuator comprising:
a housing;
a first permanent magnet and a second permanent magnet placed in the housing and being relatively rotatable in a plane including a magnetization direction;
a magnetic-field generating unit outside of the housing, the magnetic-field generating unit generating a magnetic field that relatively rotates the first permanent magnet and/or the second permanent magnet so that switching between a first arrangement in which the first permanent magnet and the second permanent magnet do not generate a repulsive force against each other and a second arrangement in which the first permanent magnet and the second permanent magnet generate a repulsive force against each other is performed; and
a first guiding portion provided in the housing to regulate a direction in which the first permanent magnet and the second permanent magnet relatively move by the generated repulsive force, wherein
the first permanent magnet is placed with its rotation being restrained with respect to the housing in the first guiding portion,
the second permanent magnet is rotatable in the plane including the magnetization direction of the second permanent magnet with respect to the housing, and
the magnetic-field generating unit generates the magnetic field for the second permanent magnet.

4. A magnetic actuator comprising:
a housing;
a first permanent magnet and a second permanent magnet placed in the housing and being relatively rotatable in a plane including a magnetization direction;
a magnetic-field generating unit outside of the housing, the magnetic-field generating unit generating a magnetic field that relatively rotates the first permanent magnet and/or the second permanent magnet so that switching between a first arrangement in which the first permanent magnet and the second permanent magnet do not generate a repulsive force against each other and a second arrangement in which the first permanent magnet and the second permanent magnet generate a repulsive force against each other is performed; and a first guiding portion provided in the housing to regulate a direction in which the first permanent magnet and the second permanent magnet relatively move by the generated repulsive force, wherein each of the first and the second permanent magnets is rotatable in the plane including the magnetization direction with respect to the housing, and the first and second permanent magnets have different magnetic-field strengths, the second permanent magnet is placed in the first guiding portion, the magnetic-field generating unit generates the magnetic field for the first permanent magnet and in the first guiding portion, and the magnetic actuator further comprises a magnetic-field-direction changing unit that controls the magnetic-field generating unit so as to generate a plurality of magnetic fields in the planes in which the first permanent magnet and the second permanent magnet are rotatable.

5. A magnetic actuator comprising:

a housing;

a first permanent magnet and a second permanent magnet placed in the housing and being relatively rotatable in a plane including a magnetization direction;

a magnetic-field generating unit outside of the housing, the magnetic-field generating unit generating a magnetic field that relatively rotates the first permanent magnet and/or the second permanent magnet so that switching between a first arrangement in which the first permanent magnet and the second permanent magnet do not generate a repulsive force against each other and a second arrangement in which the first permanent magnet and the second permanent magnet generate a repulsive force against each other is performed;

a first guiding portion provided in the housing to regulate a direction in which the first permanent magnet and the second permanent magnet relatively move by the generated repulsive force; and a third permanent magnet provided in the housing, wherein the second permanent magnet is placed in the first guiding portion, and the first guiding portion is placed between the first permanent magnet and the third permanent magnet.

6. A capsule endoscope comprising:

a capsule-shaped casing insertable into a subject;

a permanent magnet rotatable independently from the casing; and a propulsion-force converting unit that converts a rotary force of the permanent magnet rotating by following an external rotating magnetic field to a propulsion force for propelling the capsule endoscope in the subject;

wherein the permanent magnet rotates about an axis approximately parallel to an axis in the longitudinal direction of the casing, and the propulsion-force converting unit converts the rotary force of the permanent magnet to a propulsion force in the longitudinal direction of the casing.

7. The capsule endoscope according to claim 6, wherein a barycenter of the capsule endoscope is set on a center axis in a radial direction perpendicular to the longitudinal direction of the casing.

8. The capsule endoscope according to claim 6, wherein a barycenter of the capsule endoscope is set on a center axis in the longitudinal direction of the casing.

9. The capsule endoscope according to claim 6, further comprising a magnetic-field generating unit that generates, outside of the casing, a magnetic field in a fixed magnetization direction with respect to a rotating shaft of the permanent magnet.

10. The capsule endoscope according to claim 6, wherein the casing contains a function executing unit in a fluid-tight manner, the function executing unit executing a function of capturing an in-vivo image of the subject, and the permanent magnet and the propulsion-force converting unit are disposed outside of an inner space of the casing containing the function executing unit in a fluid-tight manner.

11. The capsule endoscope according to claim 6, further comprising a state changing unit that changes a state in which the permanent magnet is relatively rotatable with respect to the casing to a state in which the permanent magnet is relatively fixed with respect to the casing.

12. A method of operating a magnetic actuator including, in a housing, a first permanent magnet, a second permanent magnet, and a third permanent magnet that contribute to operations, the method comprising:

changing a magnetic field to be applied to the first permanent magnet and the second permanent magnet;

relatively rotating the first permanent magnet and the second permanent magnet so that a first state in which an attractive force occurs between the first and second permanent magnets is shifted to a second state in which a repulsive force occurs between the first and second permanent magnets or the second state is shifted to the first state;

changing a relative distance between the first permanent magnet and the second permanent magnet;

changing a magnetic field to be applied to the second permanent magnet and the third permanent magnet;

relatively rotating the second permanent magnet and the third permanent magnet so that a third state in which an attractive force occurs between the second and third permanent magnets is shifted to a fourth state in which a repulsive force occurs between the second and third permanent magnets or the fourth state is shifted to the third state; and changing a relative distance between the second permanent magnet and the third permanent magnet.

* * * * *